(12) United States Patent
Hook et al.

(10) Patent No.: US 8,993,785 B2
(45) Date of Patent: Mar. 31, 2015

(54) PROCESS FOR PREPARING 5-BIPHENYL-4-AMINO-2-METHYL PENTANOIC ACID

(71) Applicants: David Hook, Rheinfelden (CH);
Thomas Ruch, Frenkendorf (CH);
Bernard Riss, Huningue (FR);
Bernhard Wietfeld, Efringen-Kirchen (DE); Gottfried Sedelmeier, Schallstadt (DE); Matthias Napp, Lörrach (CH);
Markus Bänziger, Bubendorf (CH);
Steven Hawker, Hertfordshire (GB);
Lech Ciszewski, Morristown, NJ (US);
Liladhar Murlidhar Waykole, Succasunna, NJ (US)

(72) Inventors: David Hook, Rheinfelden (CH);
Thomas Ruch, Frenkendorf (CH);
Bernard Riss, Huningue (FR);
Bernhard Wietfeld, Efringen-Kirchen (DE); Gottfried Sedelmeier, Schallstadt (DE); Matthias Napp, Lörrach (CH);
Markus Bänziger, Bubendorf (CH);
Steven Hawker, Hertfordshire (GB);
Lech Ciszewski, Morristown, NJ (US);
Liladhar Murlidhar Waykole, Succasunna, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/224,700

(22) Filed: Mar. 25, 2014

(65) Prior Publication Data
US 2014/0249320 A1 Sep. 4, 2014

Related U.S. Application Data

(62) Division of application No. 13/333,437, filed on Dec. 21, 2011, now Pat. No. 8,716,495, which is a division of application No. 12/522,767, filed as application No. PCT/EP2008/000142 on Jan. 10, 2008, now Pat. No. 8,115,016.

(30) Foreign Application Priority Data

Jan. 12, 2007 (EP) .................................. 07100451

(51) Int. Cl.
*C07D 207/38* (2006.01)
(Continued)

(52) U.S. Cl.
CPC ............. *C07C 269/04* (2013.01); *C07C 227/16* (2013.01); *C07C 227/22* (2013.01); *C07C 227/32* (2013.01); *C07C 229/34* (2013.01); *C07C 231/02* (2013.01); *C07C 233/47* (2013.01); *C07C 271/22* (2013.01); *C07D 207/24* (2013.01); *C07D 207/26* (2013.01); *C07D 207/267* (2013.01); *C07D 207/27* (2013.01); *C07D 207/273* (2013.01); *C07D 207/277* (2013.01); *C07D 207/40* (2013.01); *C07D 207/44* (2013.01); *C07F 7/10* (2013.01); *C07C 219/18* (2013.01); *C07D 207/12* (2013.01); *C07C 227/20* (2013.01); *C07C 231/12* (2013.01); *C07D 207/404* (2013.01); *C07D 403/06* (2013.01)
USPC .......................................................... 548/543

(58) Field of Classification Search
None
See application file for complete search history.

(56) References Cited

U.S. PATENT DOCUMENTS

| 3,896,149 A | 7/1975 | Kotone |
| 5,102,882 A | 4/1992 | Kimura |

(Continued)

FOREIGN PATENT DOCUMENTS

| EP | 257602 A1 | 2/1988 |
| EP | 055175 | 8/1993 |

(Continued)

OTHER PUBLICATIONS

Vicario et al., Aziridine Ring-Opening Reaction with Chiral Enolates. Stereocontrolled Synthesis of 5-substituted-3-methyl-pyrrolidin-2-ones. J. Org. Chem., 66, pp. 5801-5807 (2001).

(Continued)

*Primary Examiner* — Michael Barker
(74) *Attorney, Agent, or Firm* — Matthew Mulkeen; David R. Kulandsky

(57) ABSTRACT

The present invention relates to pyrrolidin-2-ones according to the formula (1), or salts thereof,

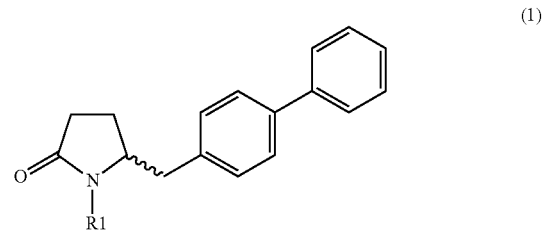

(1)

wherein R1 is hydrogen or a nitrogen protecting group, methods for their preparation and their use in the preparation of NEP-inhibitors, particularly in the preparation of N-(3-carboxyl-1-oxopropyl)-(4S)-(p-phenylphenylmethyl)-4-amino-(2R)-methyl butanoic acid ethyl ester or salt thereof.

15 Claims, 12 Drawing Sheets

(51) Int. Cl.

| | | |
|---|---|---|
| *C07D 207/267* | (2006.01) | |
| *C07D 207/44* | (2006.01) | |
| *C07C 269/04* | (2006.01) | |
| *C07C 227/16* | (2006.01) | |
| *C07C 227/22* | (2006.01) | |
| *C07C 227/32* | (2006.01) | |
| *C07C 229/34* | (2006.01) | |
| *C07C 231/02* | (2006.01) | |
| *C07C 233/47* | (2006.01) | |
| *C07C 271/22* | (2006.01) | |
| *C07D 207/24* | (2006.01) | |
| *C07D 207/26* | (2006.01) | |
| *C07D 207/27* | (2006.01) | |
| *C07D 207/273* | (2006.01) | |
| *C07D 207/277* | (2006.01) | |
| *C07D 207/40* | (2006.01) | |
| *C07F 7/10* | (2006.01) | |
| *C07C 219/18* | (2006.01) | |
| *C07D 207/12* | (2006.01) | |
| *C07C 227/20* | (2006.01) | |
| *C07C 231/12* | (2006.01) | |
| *C07D 207/404* | (2006.01) | |
| *C07D 403/06* | (2006.01) | |

(56) References Cited

U.S. PATENT DOCUMENTS

| 5,217,996 A | 6/1993 | Ksander |
|---|---|---|
| 5,250,522 A | 10/1993 | De Lomaert |
| 5,273,990 A | 12/1993 | De Lombaert |
| 5,354,892 A | 10/1994 | Ksander |
| 5,424,306 A | 6/1995 | Kawamoto et al. |
| 5,550,119 A | 8/1996 | Jeng |
| 5,965,592 A | 10/1999 | Buehlmayer |
| 6,420,415 B1 | 7/2002 | Yamashita |
| 7,618,981 B2 | 11/2009 | Duke |

FOREIGN PATENT DOCUMENTS

| EP | 0 885 869 | 12/1998 |
|---|---|---|
| EP | 1 903 027 | 3/2008 |
| JP | 3056461 | 3/1991 |
| RU | 93046500 | 4/1996 |
| WO | WO 03/059345 | 7/2003 |
| WO | WO 03/082837 | 10/2003 |
| WO | WO 2005/108409 | 11/2005 |
| WO | WO 2006/016178 | 2/2006 |
| WO | WO 2006/086456 | 8/2006 |

OTHER PUBLICATIONS

De Lombaert, S. et al: Biorganic & Medicinal Chemistry Letters (1993) 5(2), pp. 145-150.
Knox JE et al: Journal of Medicinal Chemistry (2006) 49(22), pp. 6585-6590 (English).
Yin Z et al: bioorganic & Medicinal Chemistry Letters (2006) 16(1), pp. 40-43 (English).
Ksander et al: "Dicarboxylic acid dipeptide neutral endopeptidase inhibitors", J. Med. Chem. vol. 38, pp. 1689-1700 (1995).
Database Caplus, XP 002438102, Preparation of pyroglutamic acid amides a sprolyl endopeptidase inhibitors, Database accession No. 115:23284(DN) abstract & JP 03 056461, (1991).
Clayton D.W. et al: "Condensation of the y-Curboxyl Group of a Glutam yl Peptides with the Peptide Chain", Journal of the Chemical Society, Peptides Part V, pp. 371-380, 1956.
Knuiants et al: "Amides", Soviet Encyclopedia, 1988, vol. 1, p. 127.

Figure 1: X-ray structure of (S)-5-biphenyl-4-ylmethylpyrrolidin-2-one (1-a, R1 = H)
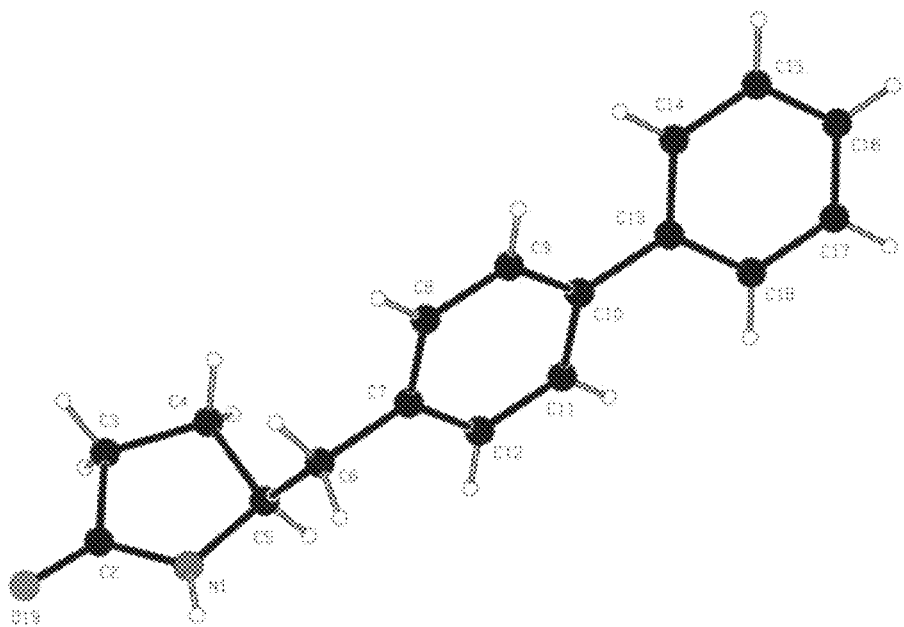

Figure 2: X-ray structure of (3R, 5S)-5-biphenyl-4-ylmethyl-1-(2,2-dimethylpropionyl)-3-methylpyrrolidin-2-one (2-a, R1 = Piv)
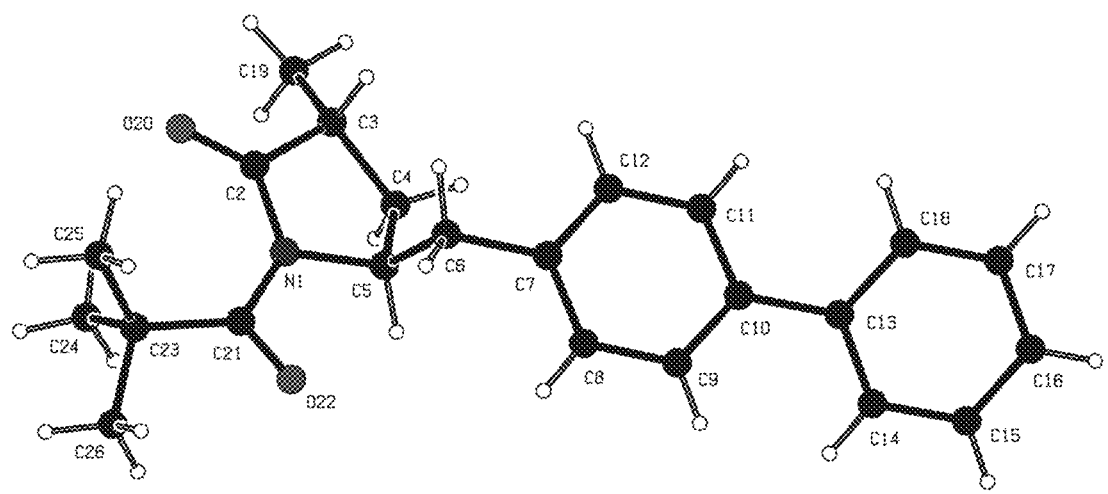

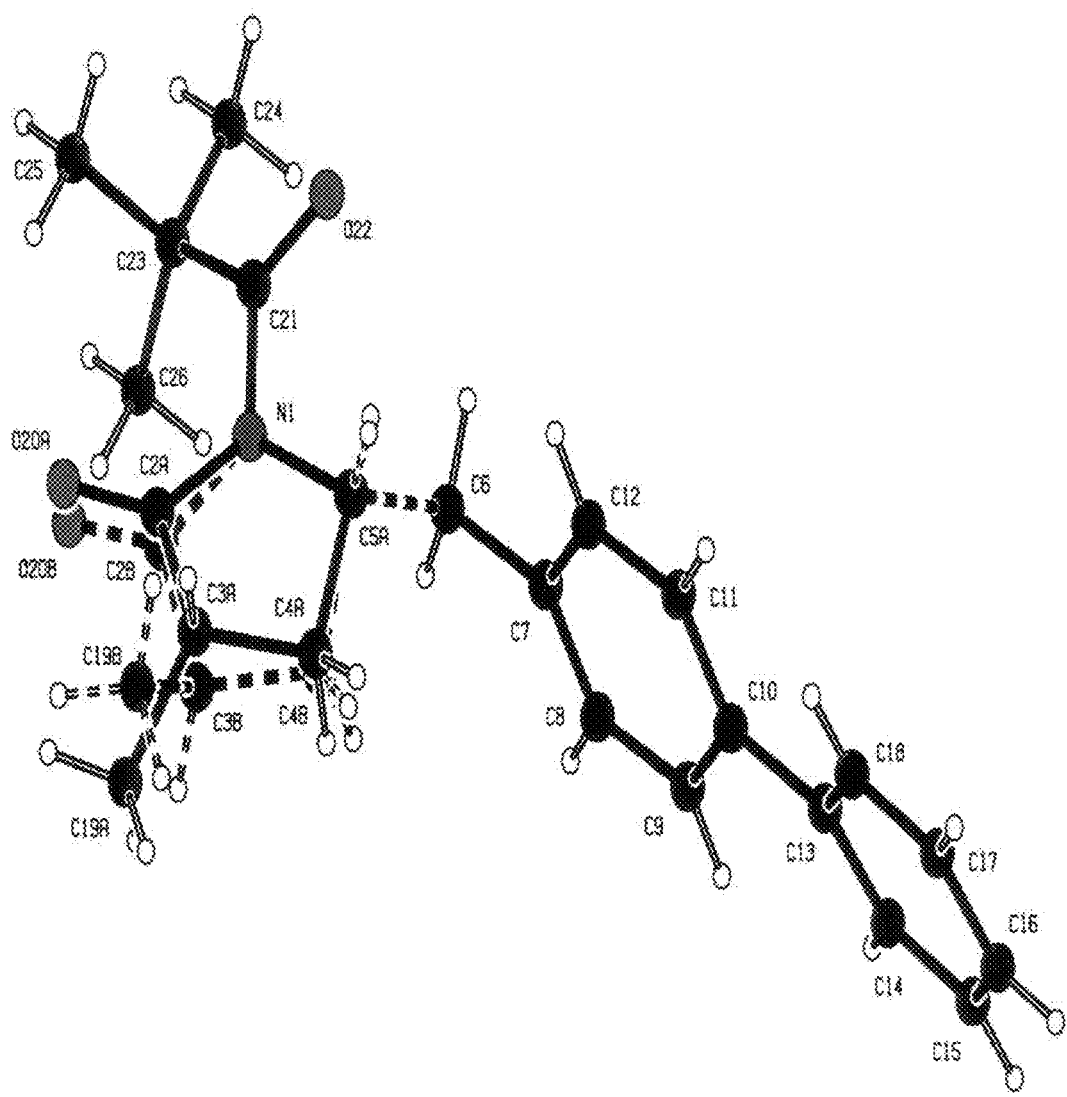
Figure 3: X-ray structure of (3S, 5S)-5-biphenyl-4-ylmethyl-1-(2,2-dimethylpropionyl)3-methylpyrrolidin-2-one (2-b, R1 = Piv)

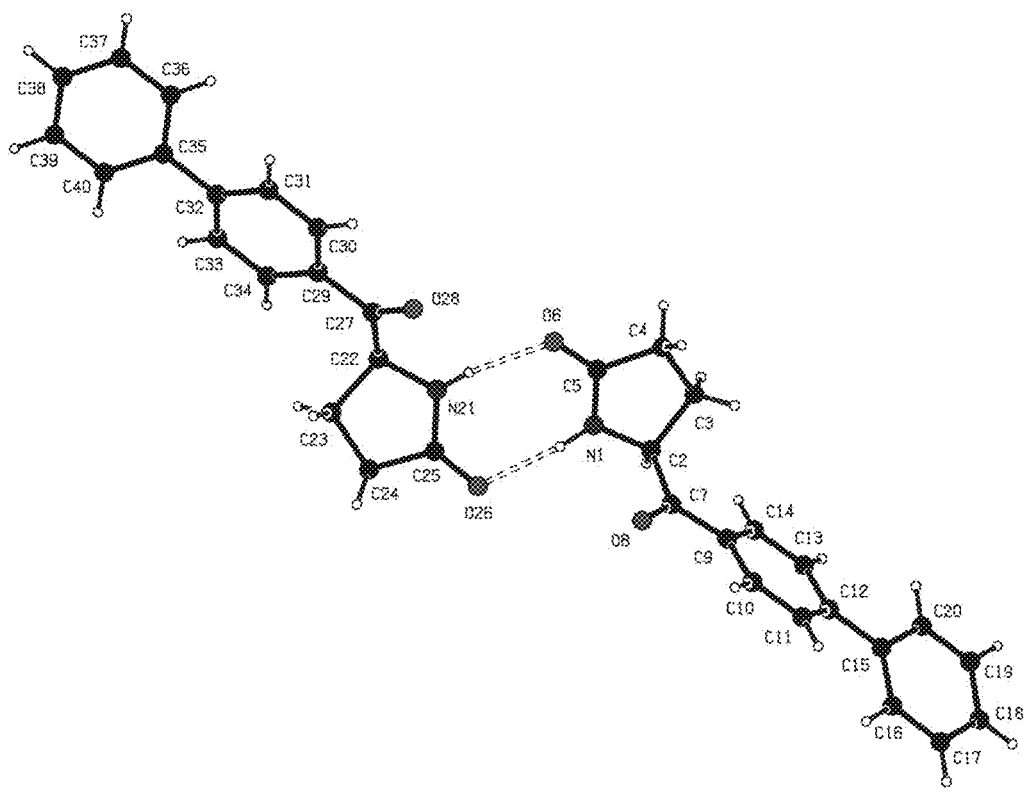
Figure 4: X-ray structure of (S)-5-(biphenyl-4-carbonyl)pyrrolidin-2-one (5-a, R1 = H)

Figure 5: X-ray structure of (2R, 4S)-4-amino-5-biphenyl-4-yl-2-methylpentanoic acid hydrochloride (3-a, R1 = R2 = R3 = H)
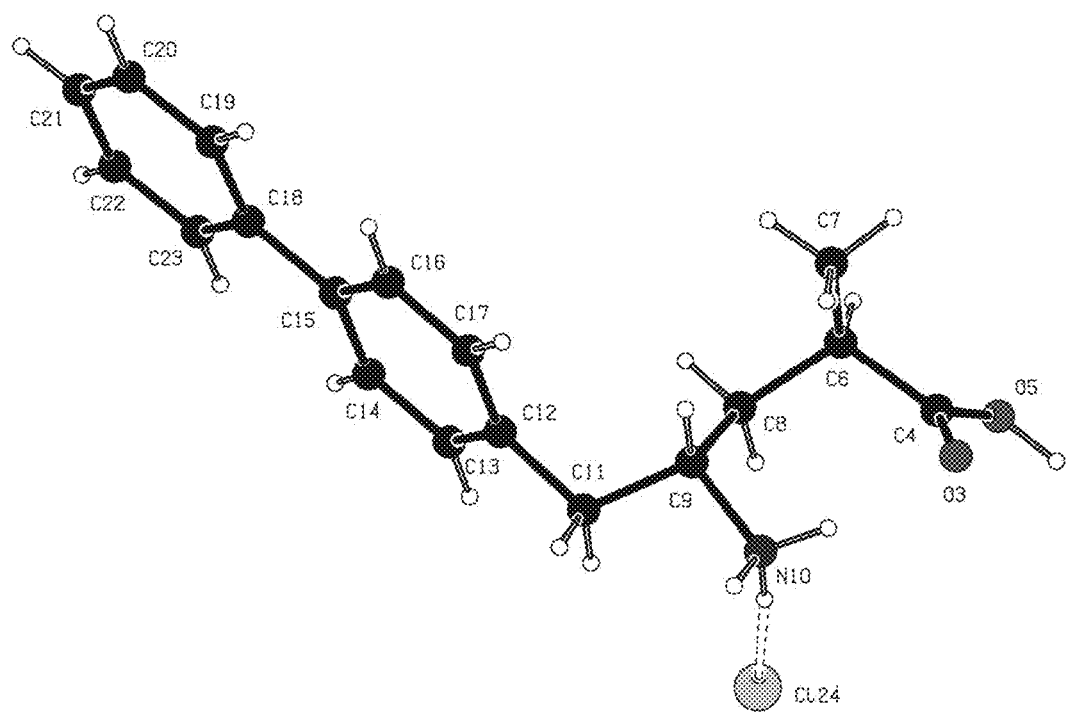

Figure 6a: X-ray structure of (2R, 4S)-4-amino-5-biphenyl-4-yl-2-methylpentanoic acid ethyl ester hydrochloride (3-a, R1 = R2 = H, R3 = Et)
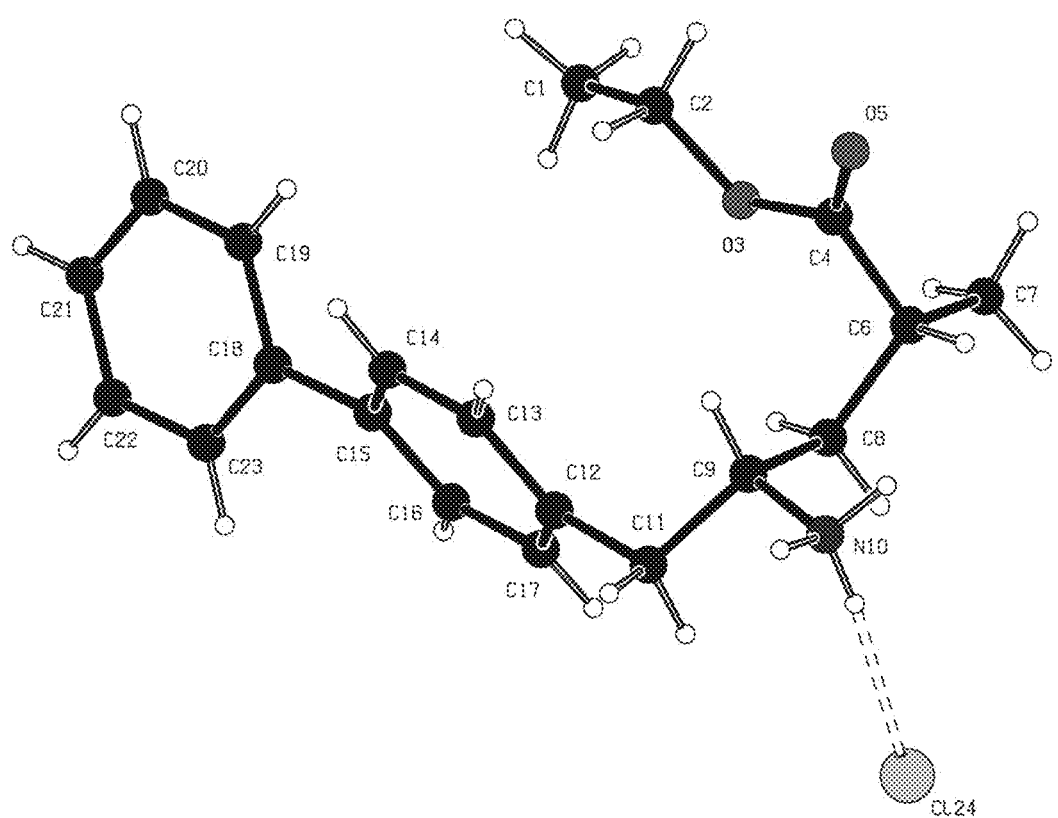

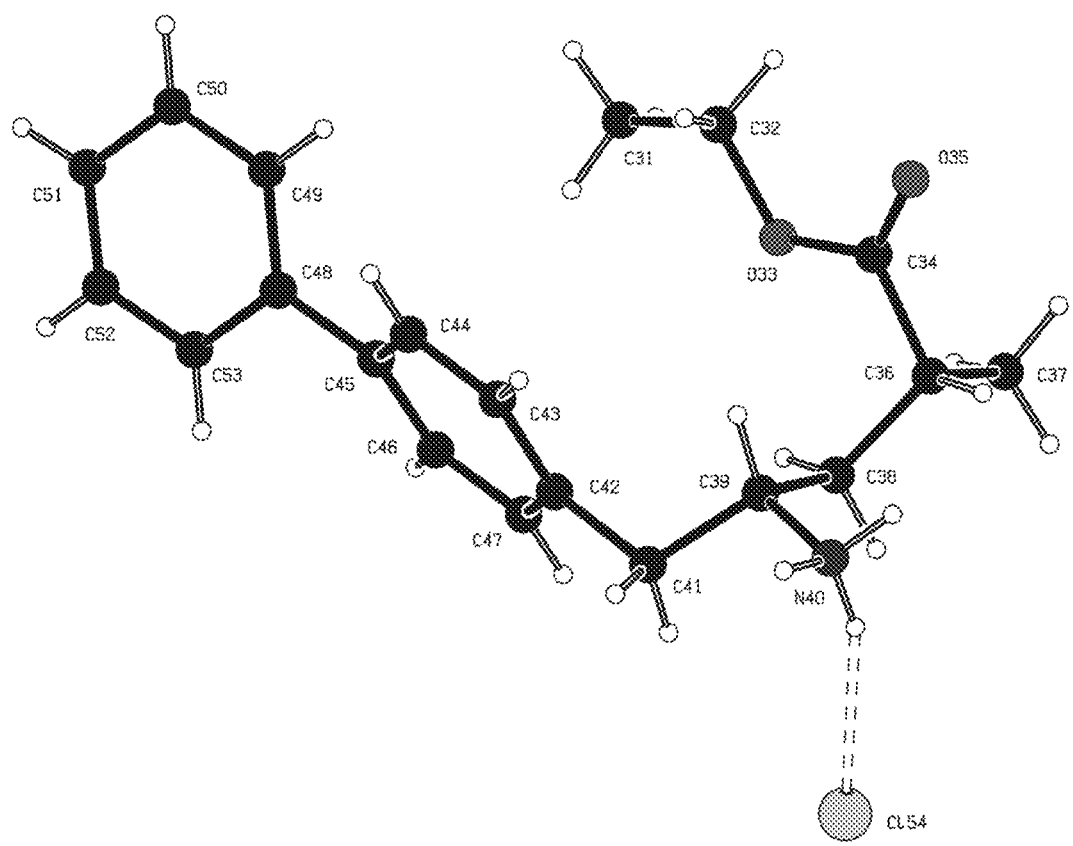
Figure 6b: X-ray structure of (2R, 4S)-4-amino-5-biphenyl-4-yl-2-methylpentanoic acid ethyl ester hydrochloride (3-a, R1 = R2 = H, R3 = Et)

Figure 7: X-ray structure of (3R, 5S)-5-biphenyl-4-ylmethyl-3-methylpyrrolidin-2-one (2-a, R1 = H)
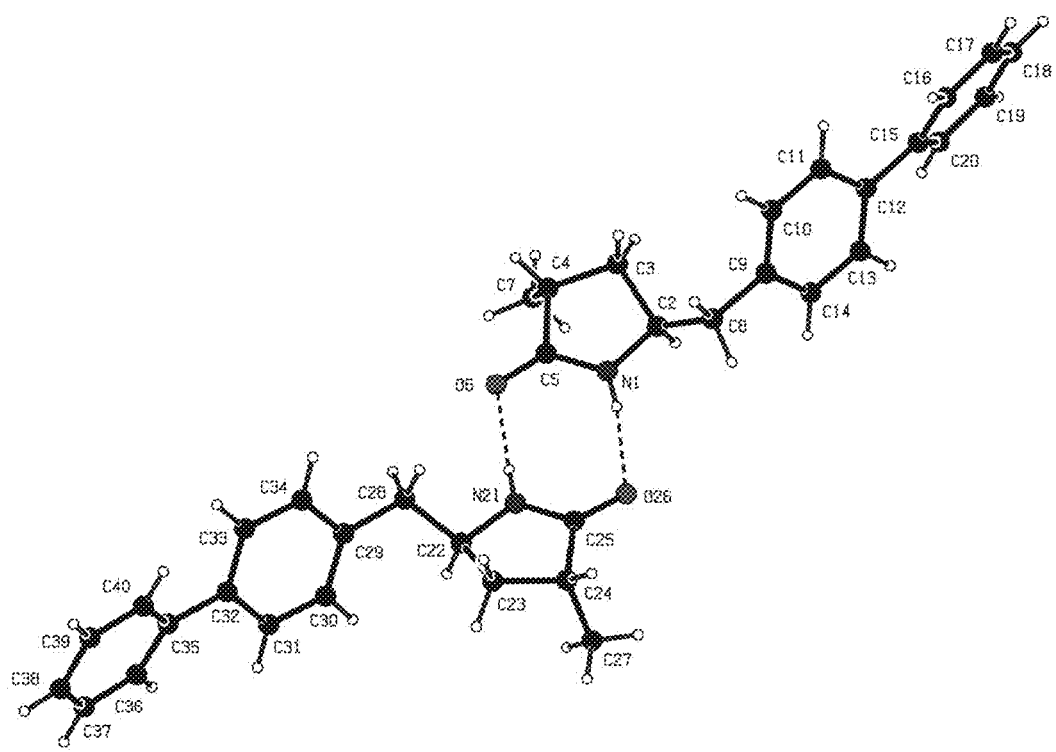

Figure 8: X-ray structure of (3R, 5S)-5-biphenyl-4-ylmethyl-3-methyl-2-oxo-pyrrolidine-1-carboxylic acid tert-butyl ester (2-a, R1 = BOC)
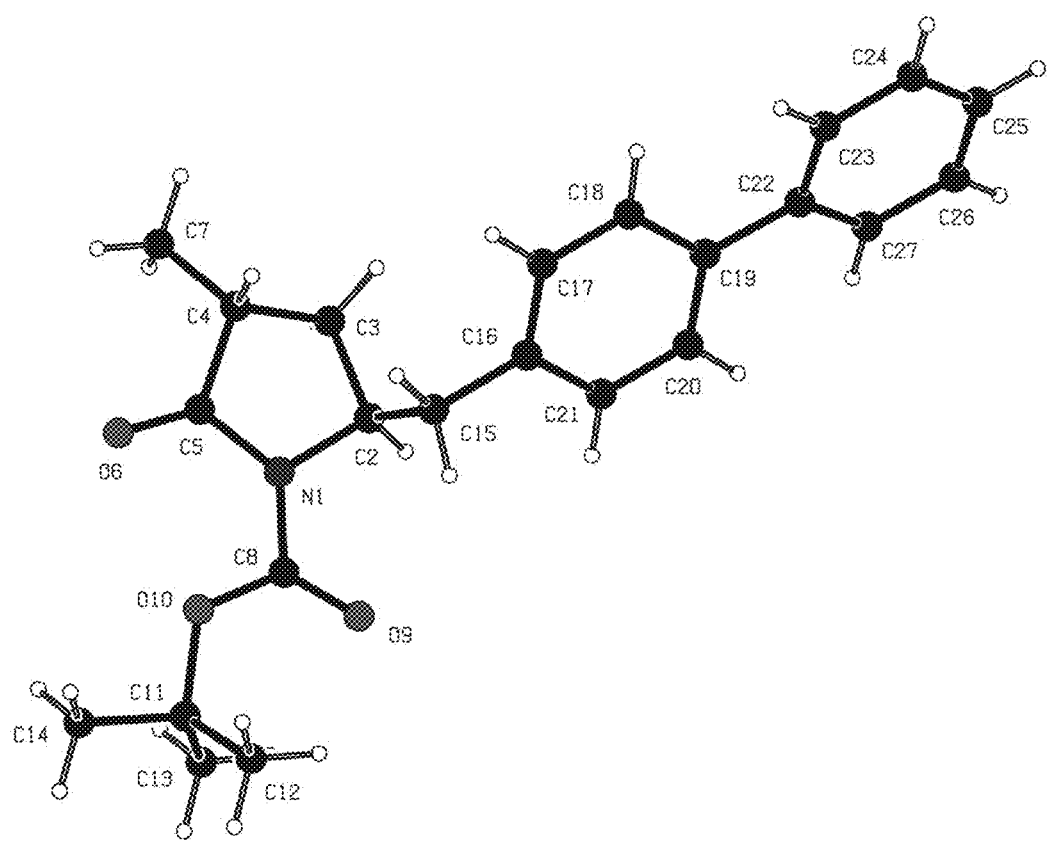

Figure 9: X-ray structure of (S)-5-biphenyl-4-ylmethyl-1-(2,2-dimethylpropionyl)pyrrolidin-2-one (1-a, R1 = pivaloyl)
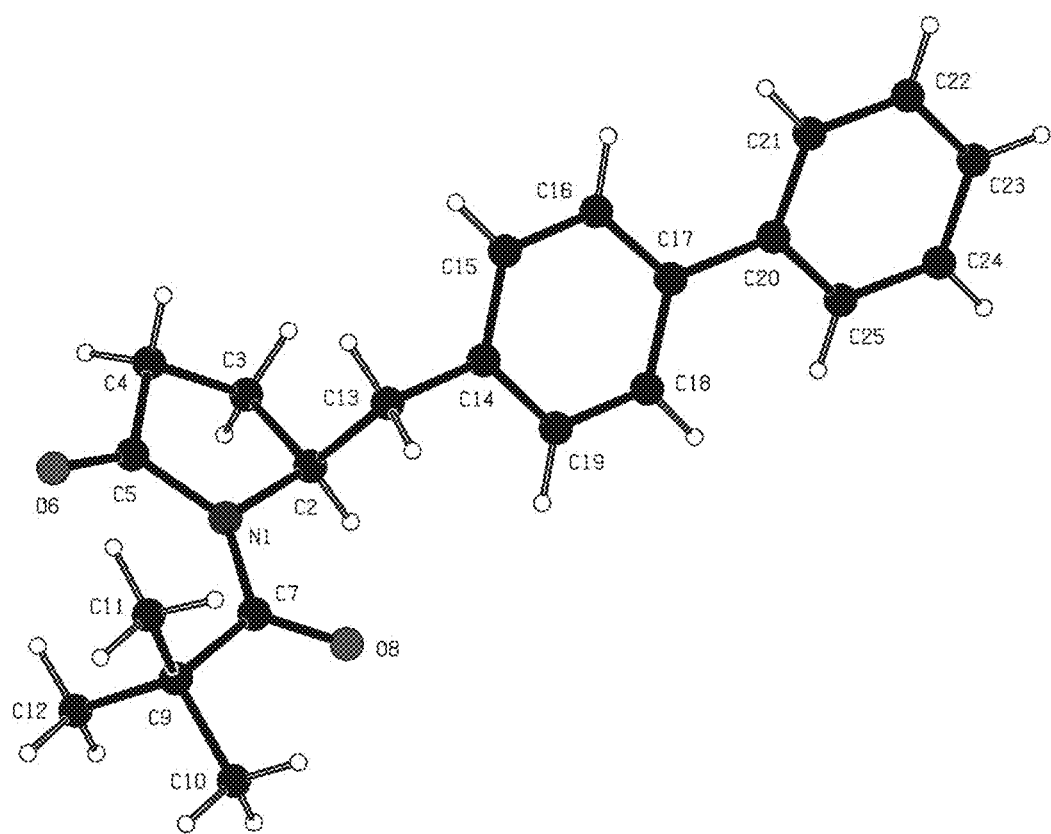

Figure 10: X-ray structure of (S)-5-biphenyl-4-ylmethyl-2-oxo-pyrrolidine-1-carboxylic acid tert-butyl ester (1-a, R1 = BOC)
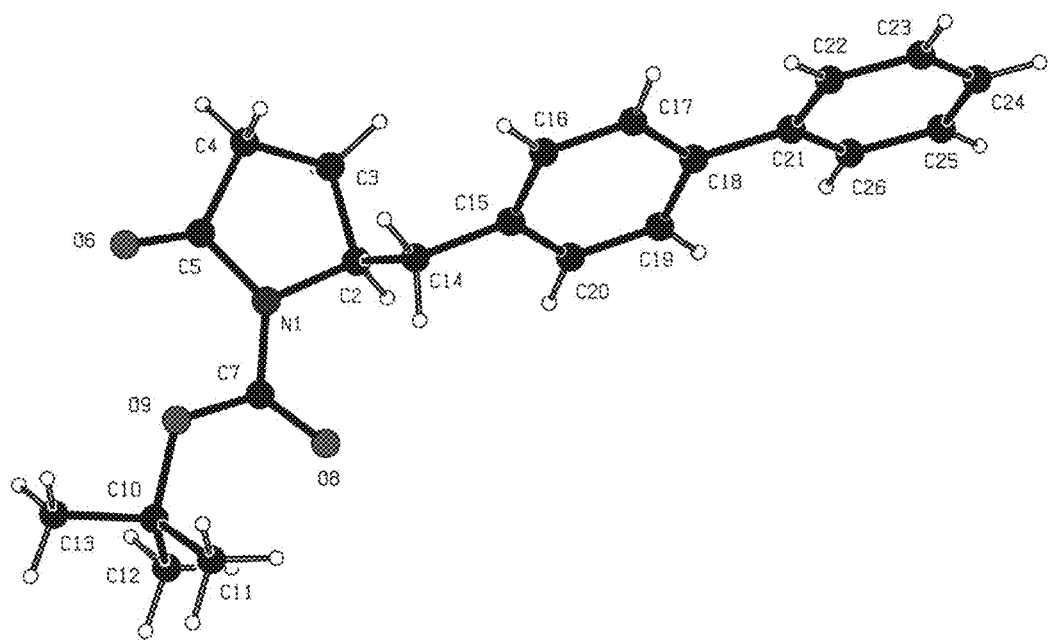

Figure 11: X-ray structure of (S)-4-Amino-5-biphenyl-4-yl-pentanoic acid ethyl ester hydrochloride [10-a, R5 = Et]
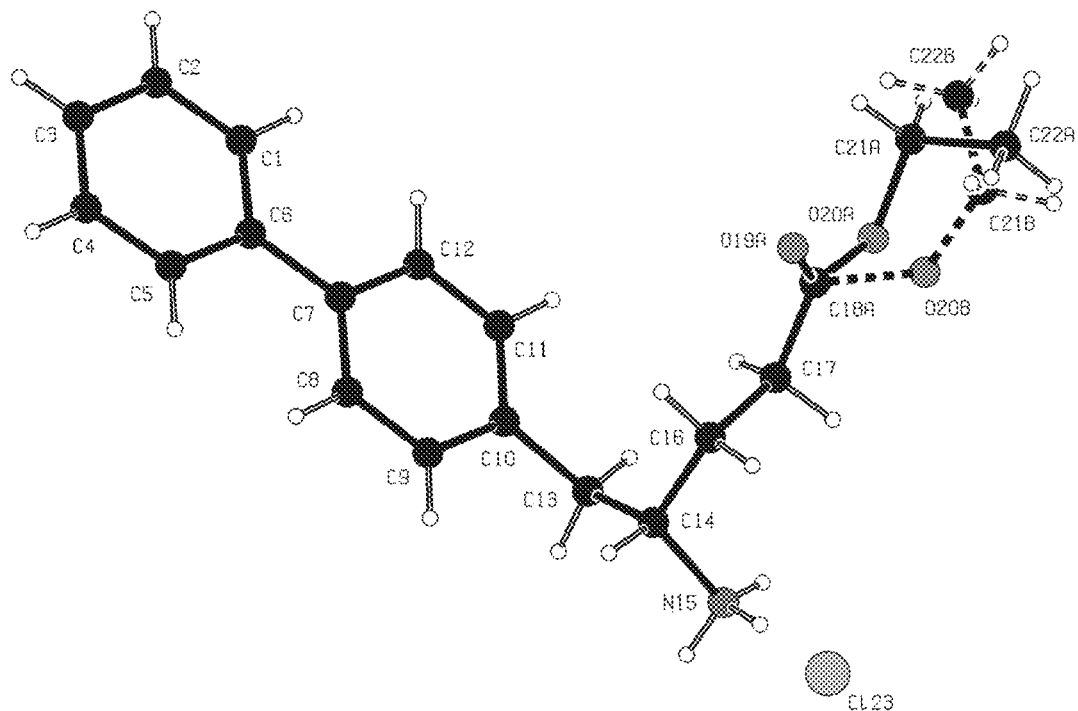

PROCESS FOR PREPARING 5-BIPHENYL-4-AMINO-2-METHYL PENTANOIC ACID

This application is a Divisional application of Ser. No. 13/333,437, filed Dec. 21, 2011, which is a Divisional application of Ser. No. 12/522,767, filed Jul. 10, 2009, which is a National Phase Application of PCT/EP2008/000142, filed Jan. 10, 2008, which claims benefit of EP 07/100,451.9, filed Jan. 10, 2008.

The present invention relates to pyrrolidin-2-ones according to formula (1), or salts thereof,

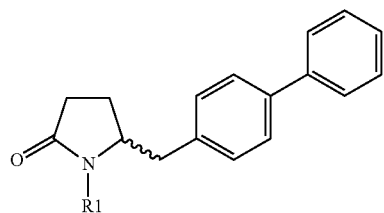

(1)

wherein R1 is hydrogen or a nitrogen protecting group, as defined herein, methods for their preparation and their use in the preparation of NEP-inhibitors, particularly in the preparation of N-(3-carboxyl-1-oxopropyl)-(4S)-(p-phenylphenylmethyl)-4-amino-(2R)-methyl butanoic acid ethyl ester, or salt thereof.

Endogenous atrial natriuretic peptides (ANP), also called atrial natriuretic factors (ANF), have diuretic, natriuretic and vasorelaxant functions in mammals. The natural ANF peptides are metabolically inactivated, in particular by a degrading enzyme which has been recognized to correspond to the enzyme neutral endopeptidase (NEP, EC 3.4.24.11), which is also responsible for e.g. the metabolic inactivation of enkephalins.

In the art biaryl substituted phosphonic acid derivatives are known which are useful as neutral endopeptidase (NEP) inhibitors, e.g. as inhibitors of the ANF-degrading enzyme in mammals so as to prolong and potentiate the diuretic, natriuretic and vasodilator properties of ANF in mammals by inhibiting the degradation thereof to less active metabolites. NEP inhibitors are thus particularly useful for the treatment of conditions and disorders responsive to the inhibition of neutral endopeptidase (EC 3.4.24.11), particularly cardiovascular disorders such as hypertension, renal insufficiency including edema and salt retention, pulmonary edema and congestive heart failure.

Processes for preparing NEP-inhibitors are known.

U.S. Pat. No. 5,217,996 describes biaryl substituted 4-amino-butyric acid amide derivatives which are useful as neutral endopeptidase (NEP) inhibitors, e.g. as inhibitors of the ANF-degrading enzyme in mammals. As a preferred embodiment U.S. Pat. No. 5,217,996 discloses N-(3-carboxyl-1-oxopropyl)-(4S)-(p-phenylphenylmethyl)-4-amino-(2R)-methyl butanoic acid ethyl ester and a method for its preparation.

Several dicarboxylic acid dipeptide neutral endopeptidase (NEP) inhibitors are further described in G. M. Ksander et al., J. Med. Chem. 1995, 38, 1689-1700, "Dicarboxylic Acid Dipeptide Neutral Endopeptidase Inhibitors". Among others, N-(3-carboxyl-1-oxopropyl)-(4S)-(p-phenylphenylmethyl)-4-amino-(2R)-methyl butanoic acid ethyl ester and a method for its preparation are disclosed.

It was an object of the present invention to provide an alternative reaction route in a process for producing NEP inhibitors or prodrugs thereof, in particular it was an object to provide an alternative reaction route in a process for producing N-(3-carboxyl-1-oxopropyl)-(4S)-(p-phenylphenylmethyl)-4-amino-(2R)-methyl butanoic acid ethyl ester, or salt thereof.

U.S. Pat. No. 5,217,996 discloses the preparation of N-(3-carboxyl-1-oxopropyl)-(4S)-(p-phenylphenylmethyl)-4-amino-(2R)-methyl butanoic acid ethyl ester. In the preparation of said compound N-t-butoxycarbonyl-(4R)-(p-phenylphenylmethyl)-4-amino-2-methyl-2-butenoic acid ethyl ester is hydrogenated in the presence of palladium on charcoal. A major drawback of said process is that such a hydrogenation step is not very selective and yields N-t-butoxycarbonyl-(4S)-(p-phenylphenylmethyl)-4-amino-2-methylbutanoic acid ethyl ester as a 80:20 mixture of diastereomers. Moreover, the process for preparing N-t-butoxycarbonyl-(4R)-(p-phenylphenylmethyl)-4-amino-(2)-methyl(2)-butenoic acid ethyl ester requires D-tyrosine as starting material, which is an unnatural amino acid and is not readily available.

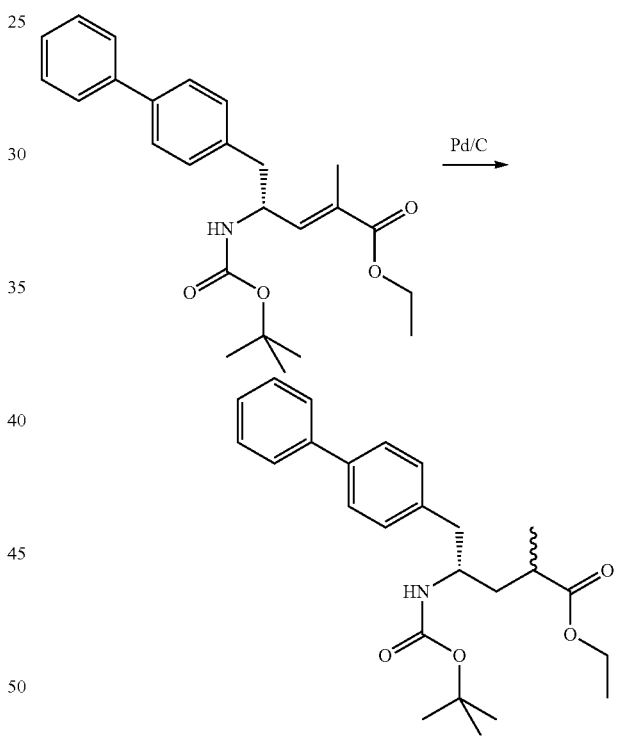

It was hence an object of the present invention to provide an alternative reaction route for preparing compound N-t-butoxycarbonyl(4S)-(p-phenylphenylmethyl)-4-amino-2-methylbutanoic acid ethyl ester, or salt thereof, preferably a reaction route which avoids the above-mentioned drawbacks of the prior art process. In particular, it was an object of the present invention to provide a process for preparing compound N-t-butoxycarbonyl-(4S)-(p-phenylphenylmethyl)-4-amino-(2R)-methylbutanoic acid ethyl ester, or salt thereof, wherein the above-mentioned hydrogenation step is avoided.

It was a still further object to provide a process for producing compound N-t-butoxycarbonyl-(4S)-(p-phenylphenylmethyl)-4-amino-2-methylbutanoic acid ethyl ester, or salt thereof, having a high diastereomeric ratio, wherein the (2R,4S)-configuration according to formula (3-a) is preferred. In particular, the diastereomeric ratio is desirably more than 60:40, preferably more than 70:30, particularly preferred more than 80:20. More preferred the diastereomeric ratio is more than 90:10. The diastereomeric ratio can be up to 99:1, preferably 100:0. Preferred diasteromeric ratios refer to the ratio of diasteromers (3-a) to (3-b), or salts thereof, (3-a)

(3-b)

wherein R1 is H, R2 is t-butoxycarbonyl and R3 is ethyl. The conversion of a compound of formula (3), (3)

wherein R1 is H, R2 is t-butoxycarbonyl and R3 is ethyl, into a NEP inhibitor or prodrug thereof, in particular into N-(3-carboxyl-1-oxopropyl)-(4S)-(p-phenylphenylmethyl)-4-amino-(2R)-methyl butanoic acid ethyl ester, or salt thereof, has been described, for example in the Journal of Medicinal Chemistry, 1995, 38, 1689.

It was also an object to provide an alternative process, wherein the resulting compound N-t-butoxycarbonyl(4S)-(p-phenylphenylmethyl)-4-amino-(2R)methyl-butanoic acid ethyl ester, or salt thereof, can be provided in pure or even in crystalline form.

Furthermore, it was an object of the present invention to provide a process wherein readily available starting compounds, e.g. natural amino acids or derivatives thereof, can be used and unnatural amino acids as starting material are avoided. Preferably it was an object of the present invention to provide a process wherein the starting materials are available from the chiral pool.

The objects of the present invention can be achieved by providing a specific lactam as a key intermediate. Starting from that specific lactam, advantageous reaction routes producing the desired NEP-inhibitors and prodrugs thereof are possible.

BRIEF DESCRIPTION OF THE DRAWING

FIG. 1 shows a X-ray structure of (S)-5-biphenyl-4-ylmethylpyrrolidin-2-one.
FIG. 2 shows a X-ray structure of (3R,5S)-5-biphenyl-4-ylmethyl-1-(2,2-dimethylpropionyl)-3-methylpyrrolidin-2-one.
FIG. 3 shows a X-ray structure of (3S,5S)-5-biphenyl-4-ylmethyl-1-(2,2-dimethylpropionyl)-3-methylpyrrolidin-2-one.
FIG. 4 shows a X-ray structure of (S)-5-(biphenyl-4-carbonyl)pyrrolidin-2-one.
FIG. 5 shows a X-ray structure of (2R,4S)-4-amino-5-biphenyl-4-yl-2-methylpentanoic acid hydrochloride.
FIG. 6a shows a X-ray structure of (2R,4S)-4-amino-5-biphenyl-4-yl-2-methylpentanoic acid ethyl ester hydrochloride.
FIG. 6b shows a X-ray structure of (2R,4S)-4-amino-5-biphenyl-4-yl-2-methylpentanoic acid ethyl ester hydrochloride.
FIG. 7 shows a X-ray structure of (3R,5S)-5-biphenyl-4-ylmethyl-3-methylpyrrolidin-2-one.
FIG. 8 shows a X-ray structure of (3R,5S)-5-biphenyl-4-ylmethyl-3-methyl-2-oxo-pyrrolidine-1-carboxylic acid tert-butyl ester.
FIG. 9 shows a X-ray structure of (S)-5-biphenyl-4-ylmethyl-1-(2,2-dimethylpropionyl)pyrrolidin-2-one.
FIG. 10 shows a X-ray structure of (S)-5-biphenyl-4-ylmethyl-2-oxo-pyrrolidine-1-carboxylic acid tert-butyl ester.
FIG. 11 shows a X-ray structure of (S)-4-Amino-5-biphenyl-4-yl-pentanoic acid ethyl ester hydrochloride.

Therefore, the subject-matter of the present invention is a pyrrolidin-2-one according to formula (1), or salt thereof, (1)

wherein R1 is hydrogen or a nitrogen protecting group, as defined hereinafter.

The compound according to formula (1), or salt thereof, is hereinafter referred to as "Key Lactam (1)".

The invention as a whole comprises the following sections:
Section A: The Key Lactam (1) as such
Section B: Use of the Key Lactam (1) in the preparation of NEP-inhibitors
Section C: Preparation methods for the Key Lactam (1)
Section D: Novel and inventive compounds occurring in one of the precedent sections
Section E: Examples The invention specially relates to the processes described in each section. The invention likewise relates, independently, to every single step described in a process sequence within the corresponding section. Therefore, each and every single step of any process, consisting of a sequence of steps, described herein is itself a preferred embodiment of the present invention. Thus, the invention also relates to those embodiments of the process, according to which a compound obtainable as an intermediate in any step of the process is used as a starting material.

The invention likewise relates to novel starting materials which have been specifically developed for the preparation of the compounds according to the invention, to their use and to processes for their preparation.

It is noted that in the present application usually explanations made in one section are also applicable for other sections, unless otherwise stated. For example, the explanations for the residue R1 in formula (1) given in section A also apply if formula (1) occurs in sections B, C, D and E, unless otherwise stated. When referring to compounds described in the present invention, it is understood that reference is also being made to salts thereof. Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms.

Section A: The Key Lactam (1) As Such

The subject-matter of the present invention is a lactam according to formula (1), or salt thereof,

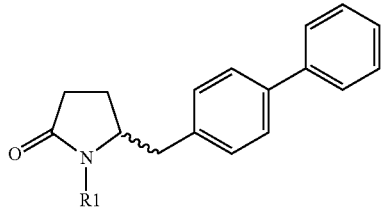

(1)

wherein R1 is hydrogen or a nitrogen protecting group, as defined hereinafter.

With regard to formula (1), two enantiomers according to formulae (1-a) and (1-b), or salts thereof, are possible.

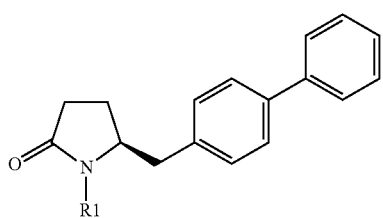

(1-a)

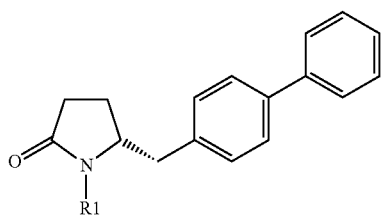

(1-b)

In the present invention compounds according to formula (1-a) (=S-enantiomer) are preferred. In formulae (1), (1-a) and (1-b), or salts thereof, the residue R1 is hydrogen or a nitrogen protecting group, as defined hereinafter, preferably the nitrogen protecting group is pivaloyl, pyrrolidinylmethyl, t-butoxycarbonyl, benzyl, silyl (such as TES), acetyl, benzyloxycarbonyl (Cbz) and trimethylsilylethoxymethyl (SEM); more preferably pivaloyl, pyrrolidinylmethyl, t-butoxycarbonyl, benzyl and silyl (such as TES).

Generally, in the present application all pyrrolidin-2-one compounds, or salts thereof, are usually shown in their keto form. However, in view of the possibly occurring keto-enol-tautomerism the present invention concerns also the described compounds, or salts thereof, in their corresponding enol form, as shown below, wherein the asterisk (*) denotes the point of binding to the rest of the molecule.

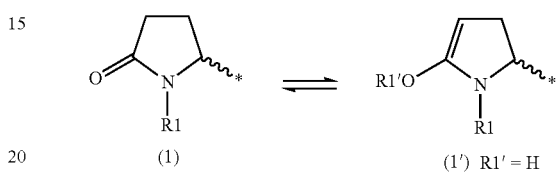

(1)  (1') R1' = H

In case of formula (1) a corresponding enol derivative is shown in formula (1'):

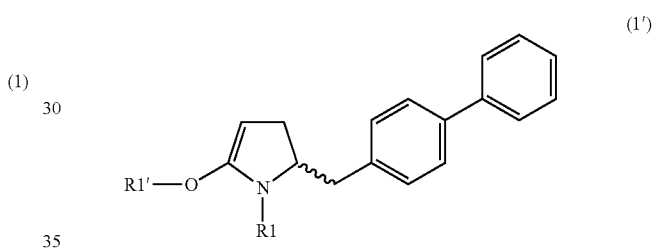

(1')

wherein R1 is hydrogen or a nitrogen protecting group, as defined hereinafter, and R1' is hydrogen or an oxygen protecting group, as defined hereinafter.

The above applies to all respective compounds of the present invention having a pyrrolidin-2-one structure, in particular for compounds according to formulae (1), (2), (4), (5), (12) and (13), or salts thereof, as well as for compounds having a preferred configuration as shown in formulae (1-a), (2-a), (4-a), (5-a), (12-a) and (13-a), or salts thereof.

In the present application the term "nitrogen protecting group" generally comprises any group which is capable of reversibly protecting a nitrogen functionality, preferably an amino and/or amide functionality. The term "oxygen protecting group" generally comprises any group which is capable of reversibly protecting the oxygen functionality.

Preferably the nitrogen protecting group is an amine protecting group and/or an amide protecting group. Suitable nitrogen protecting groups are conventionally used in peptide chemistry and are described e.g. in the relevant chapters of standard reference works such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, and in "*Methoden der organischen Chemie*" (Methods of Organic Chemistry), Houben Weyl, 4th edition, Volume 15/I, Georg Thieme Verlag, Stuttgart 1974.

Preferred nitrogen protecting groups generally comprise: $C_1$-$C_6$-alkyl, preferably $C_1$-$C_4$-alkyl, more preferably $C_1$-$C_2$-alkyl, most preferably $C_1$-alkyl which is mono-, di- or tri-substituted by trialkylsilylC$_1$-C$_7$-alkoxy (eg. trimethylsilyethoxy)aryl, preferably phenyl, or an heterocyclic group, preferably pyrrolidinyl, wherein the aryl ring or the heterocyclic group is unsubstituted or substituted by one or more, e.g. two or three, residues, e.g. selected from the group consisting of C$_1$-C$_7$-alkyl, hydroxy, C$_1$-C$_7$-alkoxy, C$_2$-C$_8$-alkanoyl-oxy, halogen, nitro, cyano, and CF$_3$; aryl-C1-C2-alkoxycarbonyl (preferably phenyl-C1-C2-alkoxycarbonyl eg. benzyloxycarbonyl); C$_{1-10}$alkenyloxycarbonyl; C$_{1-6}$alkylcarbonyl (eg. acetyl or pivaloyl); C$_{6-10}$arylcarbonyl; C$_{1-6}$alkoxycarbonyl (eg. t-butoxycarbonyl); C$_{6-10}$arylC$_{1-6}$alkoxycarbonyl; allyl or cinnamyl; sulfonyl or sulfenyl; succinimidyl group, silyl, e.g. triarylsilyl or trialkylsilyl (eg. triethylsilyl).

Examples of preferred nitrogen protecting groups are acetyl, benzyl, cumyl, benzhydryl, trityl, benzyloxycarbonyl (Cbz), 9-fluorenylmethyloxycarbony (Fmoc), benzyloxymethyl (BOM), pivaloyl-oxy-methyl (POM), trichloroethxoycarbonyl (Troc), 1-adamantyloxycarbonyl (Adoc), allyl, allyloxycarbonyl, trimethylsilyl, tert.-butyl-dimethylsilyl, triethylsilyl (TES), triisopropylsilyl, trimethylsilyethoxymethyl (SEM), t-butoxycarbonyl (BOC), t-butyl, 1-methyl-1,1-dimethylbenzyl, (phenyl)methyl benzene, pyrridinyl and pivaloyl. Most preferred nitrogen protecting groups are acetyl, benzyl, benzyloxycarbonyl (Cbz), triethylsilyl (TES), trimethylsilyethoxymethyl (SEM), t-butoxycarbonyl (BOC), pyrrolidinylmethyl and pivaloyl.

Examples of more preferred nitrogen protecting groups are pivaloyl, pyrrolidinylmethyl, t-butoxycarbonyl, benzyl and silyl groups, particularly silyl groups according to the formula SiR7R8R9, wherein R7, R8 and R9 are, independently of each other, alkyl or aryl. Preferred examples for R7, R8 and R9 are methyl, ethyl, isopropyl, t-butyl and phenyl.

Particularly preferred as nitrogen protecting groups are pivaloyl and t-butoxycarbonyl (BOC).

Preferred oxygen protecting groups are silyl groups according to the formula SiR7R8R9, wherein R7, R8 and R9 are, independently of each other, alkyl or aryl. Preferred examples for R7, R8 and R9 are methyl, ethyl, isopropyl, t-butyl and phenyl. In particular, R7, R8 and R9 are ethyl or methyl. Particular preferred oxygen protecting groups are SiMe$_3$ and SiEt$_3$.

Alkyl being a radical or part of a radical is a straight or branch (one or, if desired and possible, more times) carbon chain, and is especially C$_1$-C$_7$-alkyl, preferably C$_1$-C$_4$-alkyl.

The term "C$_1$-C$_7$-" defines a moiety with up to and including maximally 7, especially up to and including maximally 4, carbon atoms, said moiety being branched (one or more times) or straight-chained and bound via a terminal or a non-terminal carbon Cycloalkyl is, for example, C$_3$-C$_7$-cycloalkyl and is, for example, cyclopropyl, cyclobutyl, cyclopentyl, cyclohexyl and cycloheptyl. Cyclopentyl and cyclohexyl are preferred.

Alkoxy is, for example, C$_1$-C$_7$-alkoxy and is, for example, methoxy, ethoxy, n-propyloxy, isopropyloxy, n-butyloxy, isobutyloxy, sec-butyloxy, tert-butyloxy and also includes corresponding pentyloxy, hexyloxy and heptyloxy radicals. C$_1$-C$_4$alkoxy is preferred.

Alkanoyl is, for example, C$_2$-C$_8$-alkanoyl and is, for example, acetyl [—C(=O)Me], propionyl, butyryl, isobutyryl or pivaloyl. C$_2$-C$_5$-Alkanoyl is preferred, especially acetyl.

Halo or halogen is preferably fluoro, chloro, bromo or iodo, most preferably fluoro, chloro or bromo.

Halo-alkyl is, for example, halo-C$_1$-C$_7$alkyl and is in particular halo-C$_1$-C$_4$alkyl, such as trifluoromethyl, 1,1,2-trifluoro-2-chloroethyl or chloromethyl. Preferred halo-C$_1$-C$_7$alkyl is trifluoromethyl.

Alkenyl may be linear or branched alkyl containing a double bond and comprising preferably 2 to 12 C atoms, 2 to 10 C atoms being especially preferred. Particularly preferred is a linear C$_{2-4}$alkenyl. Some examples of alkyl groups are ethyl and the isomers of propyl, butyl, pentyl, hexyl, heptyl, octyl, nonyl, decyl, undecyl, dodecyl, tetradecyl, hexadecyl, octacyl and eicosyl, each of which containing a double bond. Especially preferred is allyl.

Alkylene is a bivalent radical derived from C$_{1-7}$alkyl and is especially C$_2$-C$_7$-alkylene or C$_2$-C$_7$-alkylene which is interrupted by, one or more, O, NR14 or S, wherein R14 is alkyl, each of which can be unsubstituted or substituted, by one or more substituents independently selected from for example, C$_1$-C$_7$-alkyl, C$_1$-C$_7$-alkoxy-C$_1$-C$_7$-alkyl or C$_1$-C$_7$-alkoxy.

Alkenylene is a bivalent radical derived from C$_{2-7}$alkenyl and can be interrupted by, one or more, O, NR14 or S, wherein R14 is alkyl, and is unsubstituted or substituted by one or more, e.g. up to three, substitutents preferably independently selected from the substitutents mentioned above for alkylene.

Aryl being a radical or part of a radical is, for example C$_{6-10}$aryl, and is, preferably a mono- or polycyclic, especially monocyclic, bicyclic or tricyclic aryl moiety with 6 to 10 carbon atoms, preferably phenyl, and which can be unsubstituted or substituted, by one or more substituents independently selected from for example, C$_1$-C$_7$-alkoxy-C$_1$-C$_7$-alkyl or C$_1$-C$_7$-alkoxy.

Aryloxy refers to a Aryl-O— wherein aryl is as defined above.

Unsubstituted or substituted heterocyclyl is a mono- or polycyclic, preferably a mono-, bi- or tricyclic-, most preferably mono-, unsaturated, partially saturated, saturated or aromatic ring system with preferably 3 to 14 (more preferably 5 to 14) ring atoms and with one or more, preferably one to four, heteroatoms independently selected from nitrogen, oxygen, sulfur, S(=O)— or S-(=O)$_2$, and is unsubstituted or substituted by one or more, e.g. up to three, substitutents preferably independently selected from the Preferred substituents are selected from the group consisting of halo, C$_1$-C$_7$-alkyl, C$_1$-C$_7$-alkoxy, halo-C$_1$-C$_7$-alkoxy, such as trifluoromethoxy and C$_1$-C$_7$-alkoxy-C$_1$-C$_7$-alkoxy. When the heterocyclyl is an aromatic ring system, it is also referred to as heteroaryl.

Acetyl is —C(=O)C$_1$-C$_7$alkyl, preferably —C(=O)Me.

Silyl is —SiRR'R", wherein R, R' and R" are independently of each other C$_{1-7}$alkyl, aryl or phenyl-C$_{1-4}$alkyl.

Sulfonyl is (unsubstituted or substituted) C$_1$-C$_7$-alkylsulfonyl, such as methylsulfonyl, (unsubstituted or substituted) phenyl- or naphthyl-C$_1$-C$_7$-alkyl-sulfonyl, such as phenylmethanesulfonyl, or (unsubstituted or substituted) phenyl- or naphthyl-sulfonyl; wherein if more than one substituent is present, e.g. one to three substituents, the substituents are selected independently from cyano, halo, halo-C$_1$-C$_7$alkyl, halo-C$_1$-C$_7$-alkyloxy- and C$_1$-C$_7$-alkyloxy. Especially preferred is C$_1$-C$_7$-alkylsulfonyl, such as methylsulfonyl, and (phenyl- or naphthyl)-C$_1$-C$_7$-alkyl-sulfonyl, such as phenylmethanesulfonyl.

Sulfenyl is (unsubstituted or substituted) C$_{6-10}$aryl-C$_1$-C$_7$-alkylsulfenyl or (unsubstituted or substituted) C$_{6-10}$arylsulfenyl, wherein if more than one substituent is present, e.g. one to four substituents, the substituents are selected independently from nitro, halo, halo-C$_1$-C$_7$alkyl and C$_1$-C$_7$-alkyloxy.

The term "saponification reagent" is to be understood as a base which is able to hydrolyze an ester to form an alcohol and the salt of a carboxylic acid, eg. an alkali metal hydroxide such as KOH or NaOH.

The term "group which can be saponified" is to be understood as an ester group —$CO_2R$ wherein R is alkyl, aryl or arylalkyl, which can be hydrolized, for example under basic conditions (e.g. alkalimetal base such as. NaOH, LiOH or KOH) or under acidic conditions (eg. by the use of mineral acids, such as HCl, $H_2SO_4$, HBr, $H_3PO_4$) to provide a carboxylic acid. As an extension, the term "group which can be saponified" can also include an ester group —$CO_2R$ wherein R is aryl or arylalkyl, which can be reacted by use of a hydrogenation catalyst (eg Pd/C, Pt/C, Rh/C, Pd/$Al_2O_3$, $PtO_2$), in the presence of an acid (eg. acetic acid) or a base (eg. triethylamine) or under neutral conditions, to provide a carboxylic acid.

The term "group which can be decarboxylated" is to be understood as a group —$CO_2R$, wherein R is hydrogen, alkyl, aryl or arylalkyl, which can be replaced by hydrogen under reaction conditions such as heating, optionally in the presence of a solvent, preferably initiated by boiling. An extension of this definition can include an ester group —$CO_2M$, wherein M is an alkali metal, for example Na or K, in the presence of a crown ether, for example, 18-crown-6. Suitable solvents are, for example, toluene, o-/m-/p-xylene, benzene, THF, 1,4-dioxane, DMF, water, tert-butyl methyl ether. Preferably a high boiling solvent is used, ideally a solvent with a boiling point at atmospheric pressure of more than 50° C. More preferably, a solvent with a boiling point of more than 100° C.

The term "tautomer" refers in particular to the enol tautomer of the pyrrolidin-2-one moiety of the compounds of the present invention.

The term "biphenyl" or "biphenylic" in expressions herein, such as, "biphenyl magnesium halide" or "biphenylic compound", are to be understood as meaning 4-biphenyl or 4-biphenylic, also called para-biphenyl or para-biphenylic, for example 4-biphenylmagnesium bromide or 4-bromobiphenyl.

The terms "PG", "PG1" and "PG2" refer, independently, to a nitrogen protecting group as defined herein.

In the formulae of the present application the term " $\sim$ " on a C-$sp^3$ represents a covalent bond, wherein the stereochemistry of the bond is not defined. This means that the term " $\sim$ " on a C-$sp^3$ comprises an (S) configuration as well as an (R) configuration of the respective chiral centre. Furthermore, mixtures are also encompassed.

In the formulae of the present application the term "∕" on a C-$sp^3$ indicates the absolute stereochemistry, either (R) or (S).

In the formulae of the present application the term "∕" on a C-$sp^3$ indicates the absolute stereochemistry, either (R) or (S).

Salts are especially pharmaceutically acceptable salts or generally salts of any of the intermediates mentioned herein, where salts are not excluded for chemical reasons the skilled person will readily understand. They can be formed where salt forming groups, such as basic or acidic groups, are present that can exist in dissociated form at least partially, e.g. in a pH range from 4 to 10 in aqueous solutions, or can be isolated especially in solid, especially crystalline, form.

Such salts are formed, for example, as acid addition salts, preferably with organic or inorganic acids, from compounds or any of the intermediates mentioned herein with a basic nitrogen atom (e.g. imino or amino), especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, lactic acid, fumaric acid, succinic acid, citric acid, amino acids, such as glutamic acid or aspartic acid, maleic acid, hydroxymaleic acid, methylmaleic acid, benzoic acid, methane- or ethane-sulfonic acid, ethane-1,2-di-sulfonic acid, benzenesulfonic acid, 2-naphthalenesulfonic acid, 1,5-naphthalene-disulfonic acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

When a basic group and an acid group are present in the same molecule, any of the intermediates mentioned herein may also form internal salts.

For isolation or purification purposes of any of the intermediates mentioned herein it is also possible to use pharmaceutically unacceptable salts, for example picrates or perchlorates.

In view of the close relationship between the compounds and intermediates in free form and in the form of their salts, including those salts that can be used as intermediates, for example in the purification or identification of the compounds or salts thereof, any reference to "compounds", "starting materials" and "intermediates" hereinbefore and hereinafter is to be understood as referring also to one or more salts thereof or a mixture of a corresponding free compound, intermediate or starting material and one or more salts thereof, each of which is intended to include also any solvate or salt of any one or more of these, as appropriate and expedient and if not explicitly mentioned otherwise. Different crystal forms may be obtainable and then are also included.

Where the plural form is used for compounds, starting materials, intermediates, salts, pharmaceutical preparations, diseases, disorders and the like, this is intended to mean one (preferred) or more single compound(s), salt(s), pharmaceutical preparation(s), disease(s), disorder(s) or the like, where the singular or the indefinite article ("a", "an") is used, this is not intended to exclude the plural, but only preferably means "one".

The compounds of the present invention can possess one or more asymmetric centers. The preferred absolute configurations are as indicated herein specifically. However, any possible pure enantiomer, pure diastereoisomer, or mixtures thereof, e.g., mixtures of enantiomers, such as racemates, are encompassed by the present invention.

The Key Lactam according to formula (1), or salt thereof, wherein R1 is hydrogen can be converted into a Key Lactam according to formula (1), or salt thereof, wherein R1 is a nitrogen protecting group, as defined above, according to standard methods of organic chemistry known in the art, in particular reference is made to conventional nitrogen protecting group methods described in J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999 and in Richard C. Larock, "Comprehensive Organic Transformations: A Guide to Functional Group Preparations", Second Edition, Wiley-VCH Verlag GmbH, 2000.

The same applies for the Key Lactam according to formula (1'), or salt thereof, wherein R1' is hydrogen. The conversion of R1' from hydrogen to an oxygen protecting group, as defined above, can be carried out by known methods; standard conditions for such methods are described, for example in reference books above-mentioned.

In a first preferred embodiment, R1' is hydrogen and R1 is a silyl protecting group, as defined below. In a second preferred embodiment, R1 and R1' are both a silyl protecting group, as defined below. The preparation of compounds of according to these two embodiments can be accomplished, for example, as described in U.S. Pat. No. 4,604,383. According to the second preferred embodiment, compounds according to formula (1"), or salts thereof, are provided

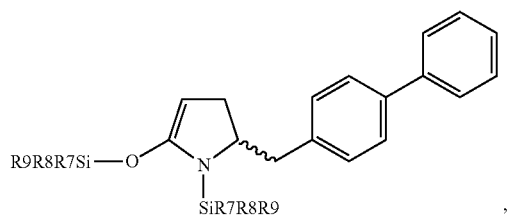

(1")

wherein R7, R8 and R9 are independently, of each other, aryl or alkyl, preferably methyl or ethyl. Preferred examples for R7, R8 and R9 are methyl, ethyl, isopropyl, t-butyl, phenyl. In particular, R7, R8 and R9 are ethyl or methyl. Particular preferred protecting groups are $SiMe_3$ and $SiEt_3$.

As mentioned above, the preferred stereochemical configuration is independent of whether the compounds are provided in the keto form or as enol derivatives.

Thus, in a preferred embodiment compounds according to formula (1"), or salts thereof, are provided as S-enantiomers according to formula (1"-a)

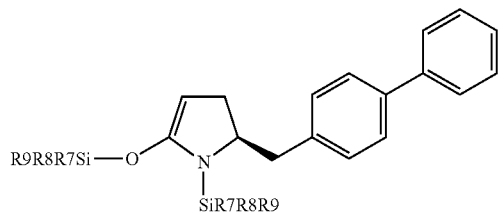

(1"-a)

wherein R7, R8 and R9 are defined as above.

In a preferred embodiment compounds according to formula (1"), or salts thereof, can be prepared by reacting a compound according to formula (1), or salt thereof, wherein R1 is hydrogen, with a compound R7R8R9SiX, wherein R7, R8 and R9 are defined as above and X is a leaving group, preferably, chlorine, bromine, triflate or tosylate. Preferably, the compound R7R8R9SiX is trimethylsilyl chloride or triethylsilyl chloride. Preferably, the reaction is carried out in the presence of a base. Preferred bases are triethylamine, diethylamine, lutidine and mixtures thereof. Examples for other suitable bases are LDA and KHMDS.

The formation of the silyl enol derivative according to formula (1"), or salt thereof, can be carried out under thermodynamic control. Therefore, the reaction can be driven to completion.

Section B: Use Of The Key Lactam In The Preparation Of Nep-Inhibitors

It is a subject of the present invention to use the key lactam according to formula (1), or salt thereof,

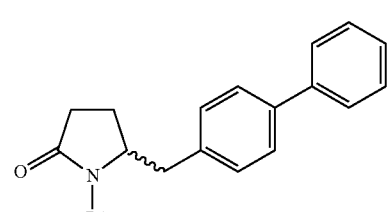

(1)

wherein R1 is hydrogen or a nitrogen protecting group, as defined above, in the synthesis of an NEP-inhibitor or a prodrug thereof. Preferably the key lactam used has an S-configuration according to formula (1-a).

In a preferred embodiment the NEP-inhibitor prodrug is N-(3-carboxyl-1-oxopropyl)-(4S)-(p-phenylphenylmethyl)-4-amino-(2R)-methyl butanoic acid ethyl ester, as shown in formula (18), or salt thereof:

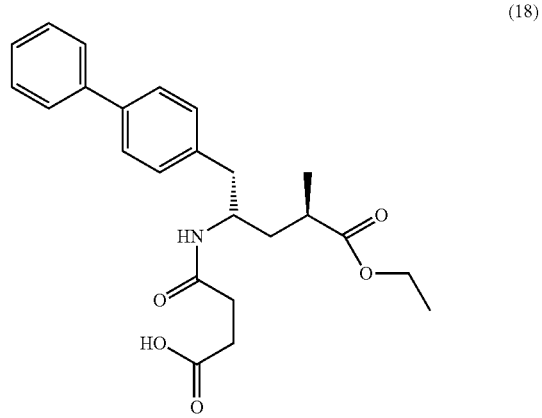

(18)

Section B of the present invention comprises 3 subsections:

Subsection B-1: Reacting a compound (1) to obtain a methylated lactam (2)

Subsection B-2: Reacting the methylated lactam (2) to obtain an intermediate (3)

Subsection B-3: Reacting the intermediate (3) to obtain a NEP-inhibitor or prodrug thereof, preferably a NEP-inhibitor prodrug according to formula (18) or salt thereof.

Subsection B-1: Reacting Compound (1) to Obtain a Methylated Lactam (2)

Another subject of the present invention is a process for producing a compound according to formula (2) or salt thereof

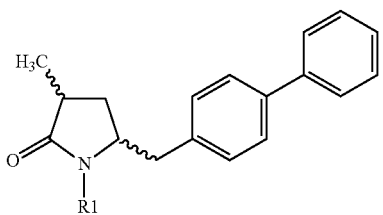

(2)

wherein R1 is hydrogen or a nitrogen protecting group, as defined above, comprising methylating a compound according to formula (1), or salt thereof, preferably methylating a compound of formula (1-a), or salt thereof. Generally, all explanations made above about preferred embodiments of the Key Lactam (1) also apply in the present section.

As stated above, the compound according to formula (2), or salt thereof, is shown in its keto form. However, also the corresponding enol forms according to formula (2') are also comprised by the present invention

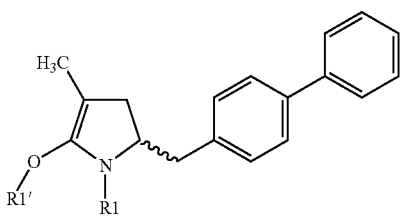

(2')

wherein R1 is hydrogen or a nitrogen protecting group, as defined above, and R1' is hydrogen or an oxygen protecting group, as defined above. In a preferred embodiment, the compound of formula (2'), or salt thereof, is according to formula (2'-a).

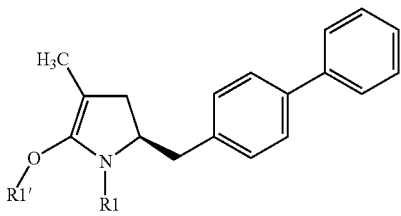

(2'-a)

Generally, the above-described methylation reaction is carried out in the presence of a methylating agent. Usually, any methylating agent known in the art is suitable. Examples for suitable methylating agents are methyl iodide, methyl bromide, methyl chloride, methyl fluoride, dimethylsulphate, methyl triflate (MeOTf), 4-methylsulfonyltoluene and mixtures thereof. Preferably, methyl iodide or dimethylsulphate or mixtures thereof are used.

The methylation reaction can be performed at a wide temperature range, e.g. between −100° C. and +50° C. Preferably, the reaction is carried out between −80° C. and +20° C., more preferably the reaction is carried out between −10° C. and +10° C., most preferably the reaction is carried out at 0° C. The reaction can be carried out in a variety of solvents e.g. tetrahydrofuran (THF), tert-butylmethylether (TBME), 1,2-dimethoxyethane, diethyl ether, toluene and mixtures thereof. Preferably, THF or toluene is used.

In a preferred embodiment the reaction is carried out in the presence of a base. The base is, for example, RcRdNM, wherein Rc and Rd are independently selected from alkyl, cycloalkyl, heterocyclyl or silyl and M is an alkali metal such as Na, Li or K. Examples for suitable bases are lithium bis (trimethylsilyl)amide (LHMDS), sodium bis(trimethylsilyl) amide (NaHMDS), potassium bis(trimethylsilyl)amide (KH-MDS), lithium diisopropylamide (LDA), n/sec/tert-butyllithium, isopropylmagnesium chloride, phenyllithium, and mixtures thereof. Alternative suitable bases are lithium dicyclohexylamine and lithium tetramethylpiperidine. Preferable, LDA, KHMDS or mixtures thereof are used. More preferably the base is lithium tetramethylpiperidine and potassium bis(trimethylsilyl)amide.

It can also be preferred that a "reaction enhancer" is added. Generally, as reaction enhancer compounds are suitable that improve the solubility of the formed products or help to deaggregate the base, thereby making it more reactive. Suitable reaction enhancers are described in relevant chapters in F A Carey, R J Sundberg, *Organische Chemie*, VCH, Weinheim, 1995 (German translation of English original). Examples of preferred reaction enhancers are hexamethylphosphoramide (HMPA), N,N'-dimethylpropyleneurea (DMPU), tetramethylethylenediamine (TMEDA), dimethylsulfoxide (DMSO) or mixtures thereof. Crown ethers or chiral crown ethers are also suitable for this purpose.

In a preferred embodiment the reaction can be carried out in two steps. Firstly a compound according to formula (1), or salt thereof, wherein R1 is hydrogen is reacted to obtain a compound according to formula (1), or salt thereof, wherein R1 is a nitrogen protecting group, as defined above. Secondly, a compound according to formula (1), or salt thereof, wherein R1 is a nitrogen protecting group, as defined above, is reacted to obtain a compound according to formula (2), or salt thereof, wherein R1 is a nitrogen protecting group, as defined above.

Alternatively, the compound according to formula (1), or salt thereof, wherein R1 is hydrogen can be reacted directly, e.g. in the presence of sec-BuLi as base and methyl iodide as methylating agent, to obtain a compound according to formula (2), or salt thereof, wherein R1 is hydrogen.

The compound according to formula (2), or salt thereof, wherein R1 is a nitrogen protecting group, as defined above, can either be deprotected (i.e. the protecting group is removed so that R1 is hydrogen) or directly converted into a compound according to formula (3), or salt thereof, wherein R1 and R2 are independently, of each other, hydrogen or a nitrogen protecting group, as defined above, and R3 is hydrogen or alkyl. (This reaction is explained in detail below in subsection B-2.) The deprotected compound according to formula (2) (i.e. wherein R1 is hydrogen), or salt thereof, can also be reacted to obtain a compound according to formula (3), or salt thereof, as detailed below, wherein R1 and R2 are independently, of each other, hydrogen or a nitrogen protecting group, as defined above, and R3 is hydrogen or alkyl.

The above-described reaction routes are shown in reaction Scheme 1, wherein "PG" means nitrogen protecting group, as defined above, preferably benzyl, benzyloxycarbonyl (Cbz), triethylsilyl (TES), trimethylsilyethoxymethyl (SEM), t-butoxycarbonyl (BOC), pyrrolidinylmethyl and pivaloyl, more preferably benzyl, trimethylsilyethoxymethyl, pyrrolidinylmethyl and pivaloyl, most preferably pivaloyl or t-butoxycarbonyl (BOC):

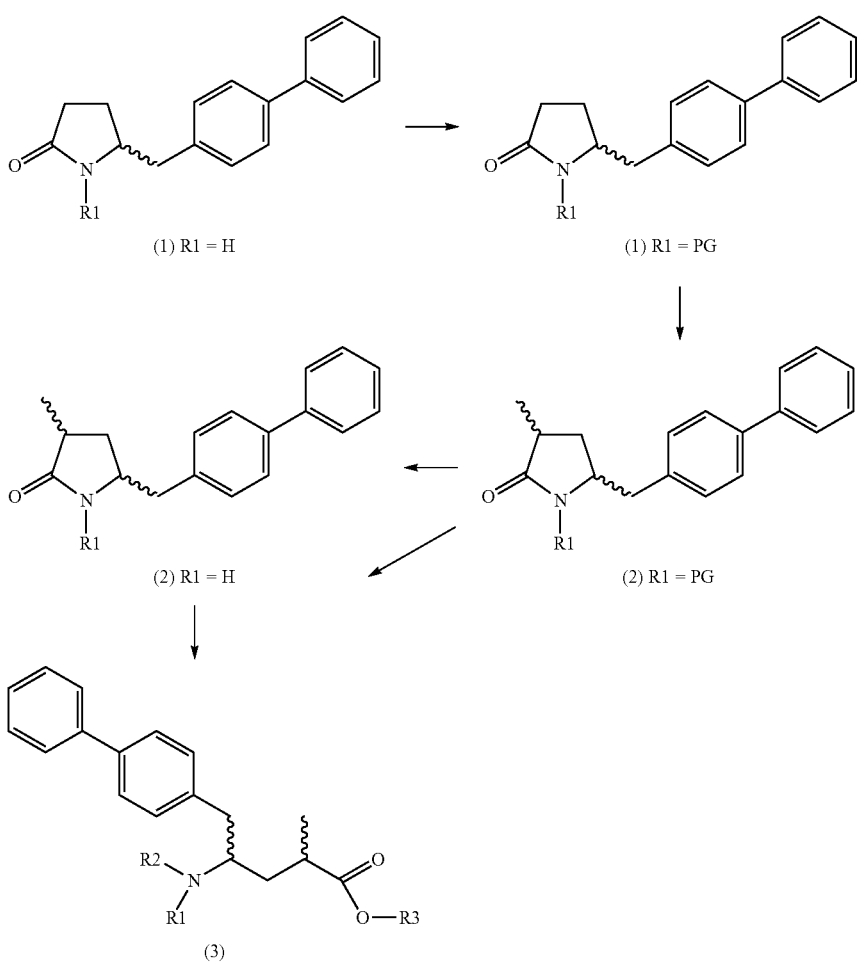

In another embodiment, the present invention relates to the complete reaction sequence described in Scheme 1, and it also relates to each of the reaction steps. In still another embodiment, the present invention relates to the product obtained according to the complete reaction sequence described in Scheme 1, and it also relates to the product obtained according to each of the reaction steps shown in Scheme 1.

If an embodiment requires the removal of the nitrogen protecting group, as defined above, the removal usually can be carried out by using known methods. Preferably, the nitrogen protecting group, as defined above, is removed by using acidic or basic conditions. Examples for acidic conditions are hydrochloric acid, trifluoroacetic acid, sulphuric acid. Examples of basic conditions are lithium hydroxide, sodium ethoxide. Nucleophiles such as sodium borohydride can be used.

In the case of N-benzyl as nitrogen protecting group it can be removed by hydrogenation or by the use of some suitable oxidising agents, e.g. ceric ammonium nitrate (CAN) or 2,3-dichloro-5,6-dicyano-p-benzoquinone (DDQ).

In another preferred embodiment, a compound according to formula (1″), or salt thereof, wherein R7, R8 and R9 are as defined above, is methylated to obtain a compound according to formula (2), or salt thereof, wherein R1 is hydrogen, as shown in Scheme 2. Compounds of formula (1″), or salts thereof, can be prepared from compounds of formula (1), or salts thereof, according to methods well known in the art, as described e.g. in relevant chapters of standard reference works such as J. F. W. McOmie, "Protective Groups in Organic Chemistry", Plenum Press, London and New York 1973 and in T. W. Greene and P. G. M. Wuts, "Protective Groups in Organic Synthesis", Third edition, Wiley, New York 1999.

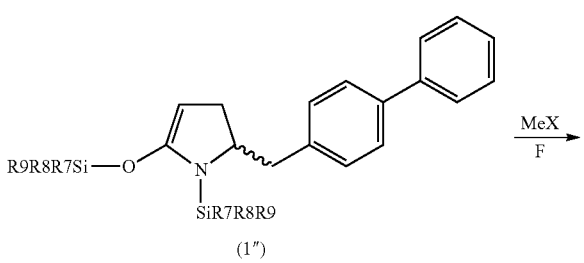

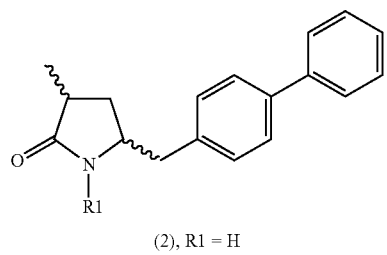

(2), R1 = H

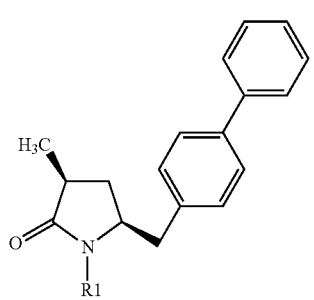

(2-b)

The methylation reaction is carried out in the presence of a methylating agent (eg. MeX). Preferred methylating agents are as described above. Furthermore, the reaction is preferably carried out in the presence of a fluoride source.

Preferred fluoride sources are alkali or earth alkali metal fluoride salts (e.g. LiF, $CaF_2$, CsF, KF) or other fluoride salts, e.g. tetrabutylammoniumfluoride (TBAF). The fluoride source can be used catalytically or stoichiometrically. Preferably, potassium fluoride or TBAF are used, in particular in catalytic amounts.

In a preferred embodiment the conversion of a compound of formula (1") into a compound of formula (2) can be achieved by a two step process, namely, reaction of (1") with a methylating agent followed by reaction of the resulting methylated product with a fluoride source (eg. alkali or earth alkali metal fluoride salt, such as LiF, $CaF_2$, CsF and KF, or other fluoride salts such as TBAF).

Using a compound according formula (1"), or salt thereof, as starting material may have the advantage that a separate protection of the N-group is avoided, since the N-silyl group can be removed in situ under the above described methylation reaction conditions.

The stereochemistry of the above reactions, shown in Schemes 1 and 2, might be of interest. In a preferred embodiment, the compound of formula (1), or salt thereof, in Scheme 1 is characterized in that the configuration is according to formula (1-a), (S-enantiomer). Analogously, in a preferred embodiment, the compound of formula (1"), or salt thereof, in Scheme 2 is characterized in that the configuration is according to formula (1"-a), (S-enantiomer).

If a compound according to formula (1-a), or salt thereof, is used as starting material, two compounds according to formula (2), or salts thereof, can be obtained, namely two diastereomers according to formulae (2-a) and (2-b), or salts thereof,

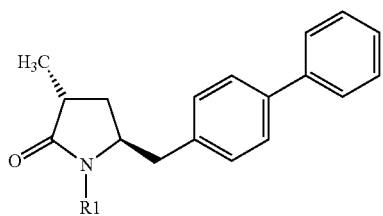

(2-a)

wherein R1 is hydrogen or an above-described nitrogen protecting group. Likewise, If a compound according to formula (1"-a), or salt thereof, is used as starting material, two compounds according to formula (2), or salts thereof, can be obtained, namely two diastereomers according to formulae (2-a) and (2-b), or salts thereof, wherein R1 is hydrogen. In a preferred embodiment, a compound of formula (2) or (3), or salts thereof, in Scheme 1 is of formula (2-a) or (3-a), respectively. In also a preferred embodiment, a compound of formula (1") or (2), or salts thereof, in Scheme 2 is of formula (1"-a) or (2-a), respectively.

The diastereomeric ratio achieved is dependent on the chosen reaction conditions, particularly on the nitrogen protecting group and on the base used. In a preferred embodiment a compound according to formula (2-a) is produced. In particular, a compound according to formula (1-a) is used as starting material and a compound according to formula (2-a) is produced in a diastereomeric ratio of more than 60:40, preferably more than 70:30, particularly preferred more than 80:20. More preferred the diastereomeric ratio is more than 90:10. The diastereomeric ratio can be up to 99:1, preferably 100:0.

It has been found that by employing a process according to the present invention, the alkylation of a compound of formula (1), or salt thereof, can be achieved in high diastereoselectivity. The process of the present invention provides means to obtain the compound of formula (2), or salt thereof, with high diastereoselectivity, by reacting a compound of formula (1) with a base, as described above, and a methylating agent, as described above. In particular, the methylation of a compound of formula (1-a), according to this embodiment, provides the compound of formula (2), wherein the ratio of diastereomers (2-a) to (2-b) is at least 80:20, more preferably at least 85:15, yet more preferably at least 91:9. In an embodiment of this preferred methylation reaction, the base is, for example, RcRdNM, wherein Rc and Rd are independently selected from alkyl, cycloalkyl, heterocyclyl or silyl and M is an alkali metal such as Na, Li or K. Preferred bases are lithium diisopropylamide, lithium dicyclohexylamine, lithium tetramethylpiperidine, lithium bis(trimethylsilyl)amide and potassium bis(trimethylsilyl)amide; more preferably lithium tetramethylpiperidine and potassium bis(trimethylsilyl)amide. The methylating agent is preferably dimethylsulfate, methyl iodide or methyl bromide, preferably methyl iodide or dimethylsulfate, more preferably dimethylsulfate. Preferably, the methylation is carried out at a temperature between a −78° C. and 20° C., preferably between −10° C. and 20° C., more preferably between −10° C. and 0° C. It has been surprisingly found, the methylation reaction proceeds in high diastereoselectivity and with high yield at 0° C. The methylation is usually carried out in a solvent, as described above, preferably tetrahydrofuran, toluene or mixtures thereof.

In a further embodiment, the methylation of the compound of formula (1) or (1"), preferably of formula (1-a) or (1'-a), or salts thereof, with a base, as described above, and a methylating agent, as described above, can lead to a compound of formula (2"), preferably of formula (2"-a), or salts thereof,

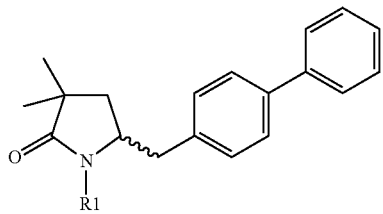

(2")

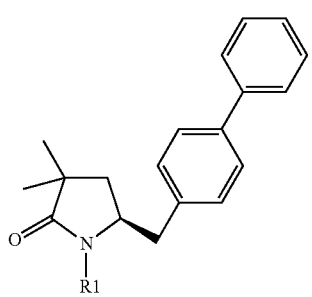

(2"-a)

wherein R1 is hydrogen or a nitrogen protecting group, as defined above.

In a still further embodiment, a compound of formula (2"), preferably of formula (2"-a), or salts thereof, wherein R1 is hydrogen or a nitrogen protecting group, as defined above, can also be prepared by treating the compound of formula (2), preferably of formula (2-a), or salts thereof, wherein R1 is hydrogen or a nitrogen protecting group, with a base, as described above, and a methylating agent, as described above.

Compounds according to formula (2-a), or salts thereof, can be obtained as crystalline solids. Preferably, R1 is pivaloyl or t-butoxycarbonyl, more preferably R1 is pivaloyl. Optionally, compounds according to formula (2-a), or salts thereof, can be purified by crystallisation.

In a preferred embodiment the yield of the desired isomer can be enhanced. In this embodiment reaction steps according to Scheme 3 are carried out. In one embodiment according to Scheme 3, when R1 is PG it is preferably pivaloyl or t-butoxycarbonyl.

Scheme 3

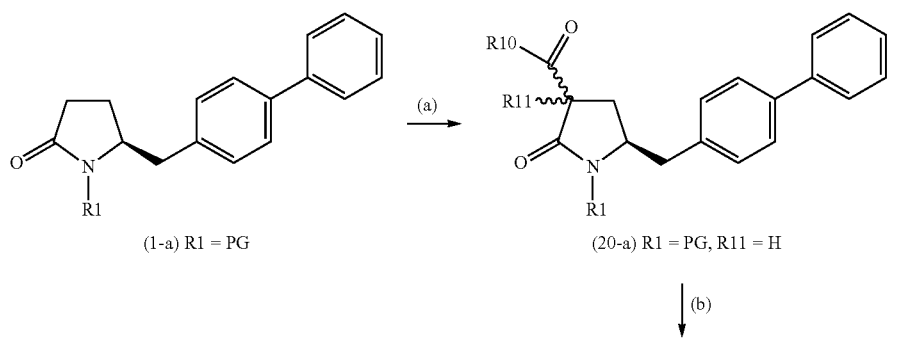

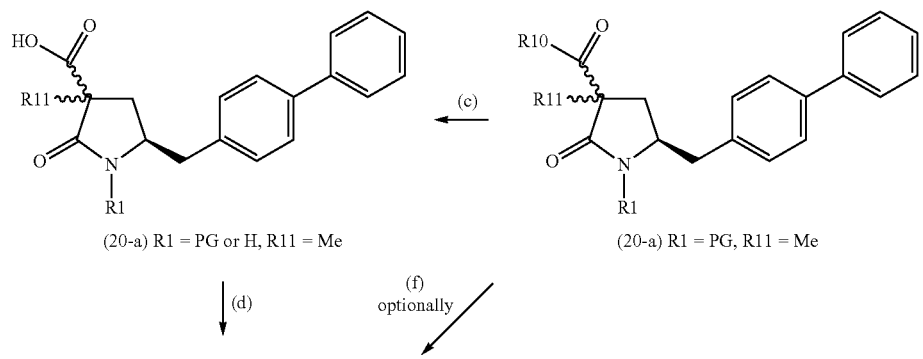

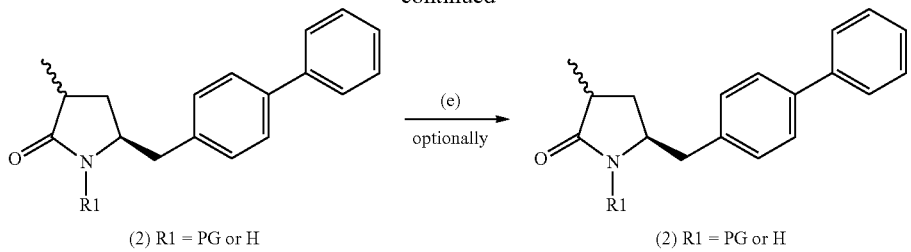

(2) R1 = PG or H                  (2) R1 = PG or H

In another embodiment, the present invention relates to the complete reaction sequence described in Scheme 3, and it also relates to each of the reaction steps. In still another embodiment, the present invention relates to the product obtained according to the complete reaction sequence described in Scheme 3, and it also relates to the product obtained according to each of the reaction steps shown in Scheme 3.

In Scheme 3 "PG" means an above defined nitrogen protecting group. R10 is any group which can be suitably saponified and/or decarboxylated. Preferably, R10 is —O-alkyl, or —O-aryl in particular —O-Et, —O-phenyl or is —O-alkylaryl such as —O-benzyl; preferably R10 is —O-Et or —O-phenyl. For each one of the reactions of Scheme 3 preferably the following reaction conditions are used:

(a): Treatment with a base (e.g. NaH, NaHMDS or KHMDS, preferably NaH or NaHMDS) and then with a further reagent that, after eliminating a leaving group, provides a —C(=O)— group, for example a —C(=O)OR group wherein R is alkyl or aryl or alkylaryl; preferably alkyl or aryl. Such further reagents are preferably carbonates of the formula (RO)(R'O)CO or compounds of the formula XCOOR, wherein R and R' independently, of each other, are alkyl, aryl or arylalkyl, preferably alkyl or aryl and wherein X is halogen in particular chloride; preferred further reagents of the formulae (RO)(R'O)CO or XCOOR are $(MeO)_2CO$, $(EtO)_2CO$, $(BnO)_2CO$, $ClCO_2Me$, $ClCO_2Et$, $ClCO_2Bn$; most preferably the further reagent is $(MeO)_2CO$, $(EtO)_2CO$, $ClCO_2Me$ or $ClCO_2Et$;

(b): Treatment with a base, preferably as described in step (a) and a methylating agent as described above;

(c): Treatment with a saponification reagent (such as base), e.g. sodium hydroxide, or treatment under hydrogenation conditions, e.g. Pd/C and hydrogen; preferably treatment with a saponification reagent. If under such saponification reaction conditions there is simultaneous deprotection of nitrogen, compounds according to the formula (20-a) wherein R1=H are formed. If desired, before step (d), re-protection of the nitrogen such that R1=PG can be performed. Re-protection can be done on treatment with a suitable nitrogen protecting agent, as defined above, whereby PG can be the same or different from the original PG used;

(d): Treatment under decarboxylation reaction conditions, e.g. heating, preferably in the presence of a solvent, more preferably initiated by boiling;

(e): Treatment with a suitable nitrogen de-protecting agent, preferably amine de-protecting agent, for example treatment with an acid or a base, preferably treatment with p-toluene sulfonic acid; or treatment with a suitable nitrogen protecting agent, preferably amine protecting agent, as defined above, to protect the N with a protecting group PG, which can be the same or different from the original PG used. Step (e) is optional.

(f): Treatment under decarboxylation reaction conditions, e.g. heating, preferably in the presence of a solvent, more preferably initiated by boiling, optionally in the presence of a base, for example as described for compound 3c in Scheme 3 in Org. Lett., 2004, 6(25), 4727

The decarboxylation step (d) provides means to obtain the compound of formula (2), or salt thereof, in a diastereoselective manner. In one embodiment, the decarboxylation of the compound of formula (20-a), wherein R1 is hydrogen or a nitrogen protecting group, preferably pivaloyl, and R11 is methyl, provides the compound of formula (2), wherein R1 is hydrogen or a nitrogen protecting group, preferably pivaloyl, in a ratio of diasteromers (2-a) to (2-b) of at least 55:45. In another embodiment, the decarboxylation of the compound of formula (20-a), wherein R1 is hydrogen or a nitrogen protecting group, preferably hydrogen, and R11 is methyl, provides the compound of formula (2), wherein R1 is hydrogen or a nitrogen protecting group, preferably hydrogen, in a ratio of diasteromers (2-a) to (2-b) of at least 29:79.

The decarboxylation step (f) can also provide means to obtain the compound of formula (2), wherein R1 is hydrogen or a nitrogen protecting group, or salt thereof, with diastereoselectivity.

In a preferred embodiment compounds of formula (2) obtained upon steps (d), (e) or (f), in Scheme 3, are according to formula (2-a). In another preferred embodiment for step (d) R is pivaloyl or hydrogen. In yet another preferred embodiment R1 is a nitrogen protecting group for compounds of formula (20-a) and/or (2).

Steps (c) or (d) can be performed, for example, as described in Org. Biomol. Chem 2007, 5, 143 and in Org. Lett. 2003, 5, 353.

Subsection B-2: Reacting the Methylated Lactam According to Formula (2) to Obtain an Intermediate According to Formula (3)

Another subject of the present invention is a process for producing a compound according to formula (3) or a salt thereof (3)

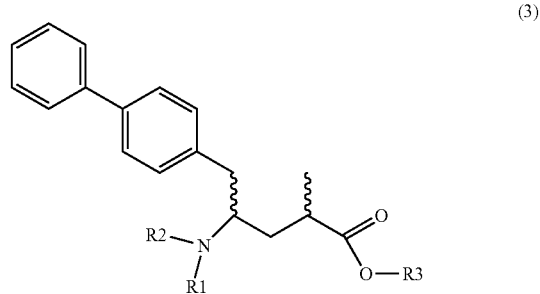

wherein R1 and R2 are independently, of each other, hydrogen or a nitrogen protecting group, as defined above, and R3 is hydrogen or alkyl, comprising reacting a compound according to formula (2), or salt thereof,

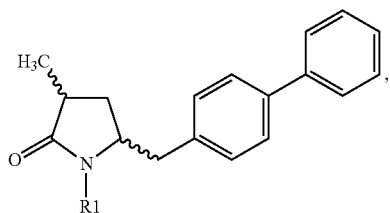
(2)

wherein R1 is hydrogen or a nitrogen protecting group, as defined above, with a ring opening agent, as defined below. In a preferred embodiment, R1 and R2 are hydrogen and R3 is an ethyl group.

Alternatively, in formula (3), or salt thereof, R1 and R2 along with the N atom to which they are attached to can together form a cyclic ring structure, preferably a five-membered ring (and thus form a bifunctional cyclic nitrogen protecting group, which together with said N atom results, for example, in a five-membered ring succinimide- or maleimide structure). The compound according to formula (2), or salt thereof, is preferably obtained by a reaction as described above in subsection B-1.

In formula (3), or salt thereof, preferably R1 is hydrogen or a nitrogen protecting group as defined above and R2 is hydrogen. Furthermore, R3 is preferably hydrogen or ethyl.

Generally, following the above-described methylation reaction, a compound of formula (2) or salt thereof, preferably a compound of formula (2-a) or salt thereof, can be reacted with a ring opening agent to yield a compound of formula (3) or salt thereof. The lactam ring opening reaction can occur under basic, neutral or acidic conditions. Examples for ring opening agents are nucleophilic bases such as alkali metal hydroxides (for example sodium hydroxide or lithium hydroxide) or neutral compounds such as hydrogenperoxides (such as lithium hydrogenperoxide). Further examples are Lewis or BrØnsted acids, preferably in the presence of water. Preferred acids are mineral acids such as sulphuric, perchloric and hydrochloric acid. Sulphonic acids such as para-toluenesulphonic acid are also suitable as are polymer-bound acids such as Amberlyst®. Especially hydrochloric acid is used as a ring opening agent.

The ring opening agent can be used catalytically or stoichiometrically. Preferably, the ring opening agent is used in an amount from 1 to 10 equivalents.

Compounds according to formula (3) can exist as salts, for example as carboxylate salts or as acid addition salts. Acid addition salts are preferred. Generally, various acids are suitable to produce an acid addition salt. Preferred are mineral acids, in particular sulfuric acid, hydrochloric acid, hydrobromic acid or perchloric acid. Sulphonic acids such as para-toluenesulphonic acid are also suitable. Especially hydrochloric acid is used. Alternatively, compounds according to formula (3) can also exist as the free base (zwitterions).

The ring opening reaction can be performed at a wide temperature range, e.g. between −10° C. and +150° C. Preferably, the reaction is carried out between +20° C. and +125° C. The reaction can be carried out in a variety of solvents e.g. water, or ethanol or mixtures of these. Additional solvents such as toluene, isopropyl acetate, tetrahydrofuran or tert-butylmethylether can be used, Preferably, ethanol and/or water is used.

In a preferred embodiment the ring opening reaction is carried out such that a compound having a configuration according to formula (3-a) or a salt thereof is obtained

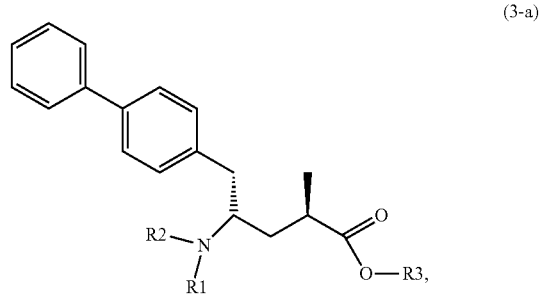
(3-a)

wherein R1 and R2 are independently, of each other, hydrogen or a nitrogen protecting group, as defined above, and R3 is hydrogen or alkyl. In a preferred embodiment, R1 and R2 are hydrogen and R3 is ethyl. The compound according to formula (3-a), or salt thereof, can be obtained if a compound according to formula (2-a), or salt thereof, is used as starting material.

The compound according to formula (3-a), or salt thereof, is the so-called 2R,4S-diastereoisomer. Alternatively, also the 2R,4R-diastereoisomer, 2S,4S-diastereoisomer and 2S,4R-diastereoisomer can be produced.

The reaction from compound (2), or salt thereof, to compound (3), or salt thereof, can be carried out in various embodiments. For example, a compound according to formula (2), or salt thereof, wherein R1 is hydrogen can be used as starting material. Also a compound according to formula (2), or salt thereof, wherein R1 is a nitrogen protecting group, as defined above, preferably a pivaloyl group or a BOC group. If a compound according to formula (2), or salt thereof, wherein R1 is a nitrogen protecting group, as defined above, is used as starting material, preferably the nitrogen protecting group is removed during the ring opening reaction. This means that preferably a compound according to formula (3), or salt thereof, wherein R1 and R2 are hydrogen, is obtained.

If desired, a compound of formula (3), or salt thereof, wherein R1 and R2 are hydrogen can be converted again into a compound of formula (3), or salt thereof, wherein either R1 and/or R2 are, independently of each other, a nitrogen protecting group, as defined above. This might be the case if R3 of formula (3) should be changed from a hydrogen atom into an alkyl residue. In Scheme 4 below preferred embodiments are exemplified.

Scheme 4
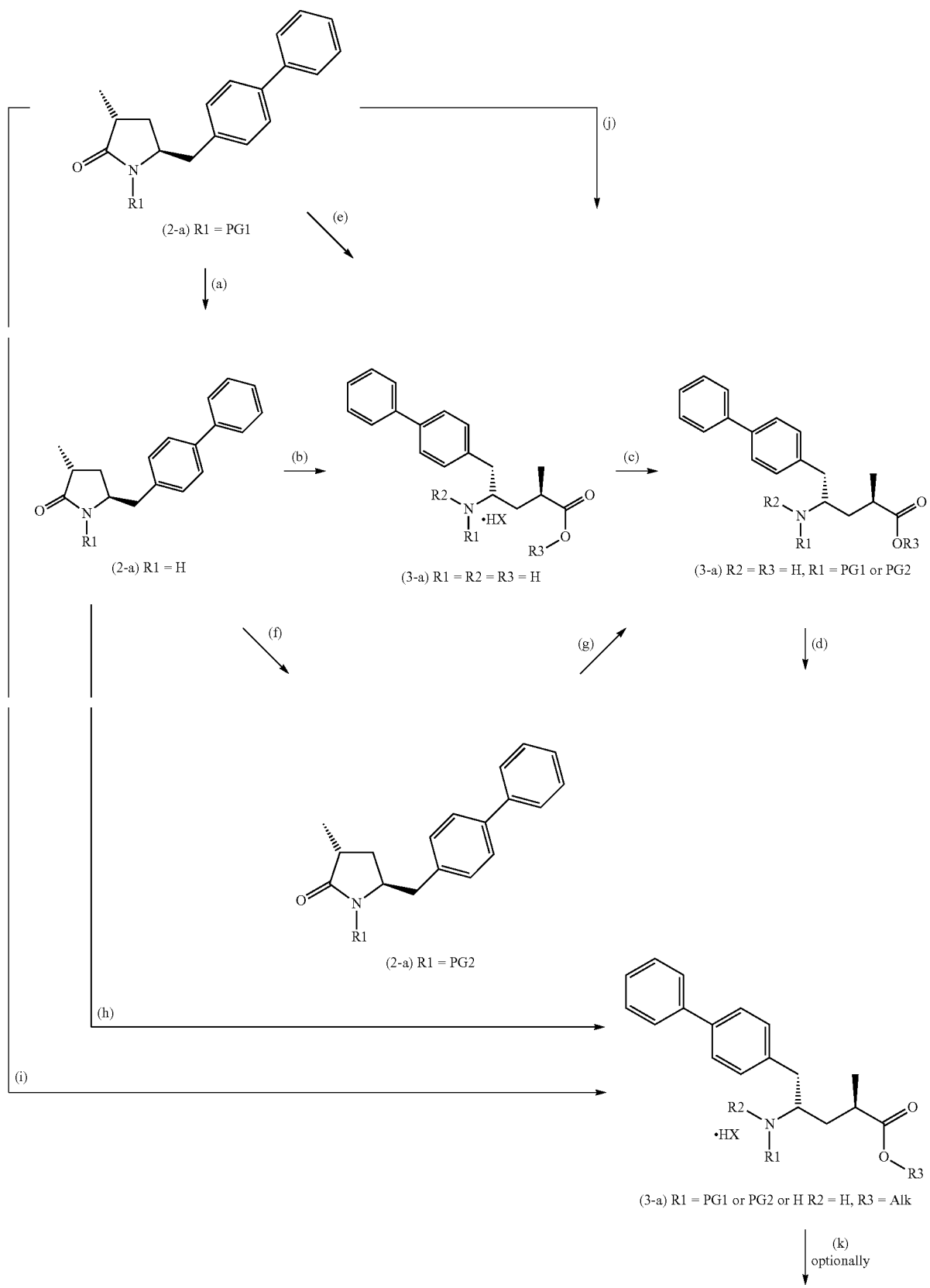

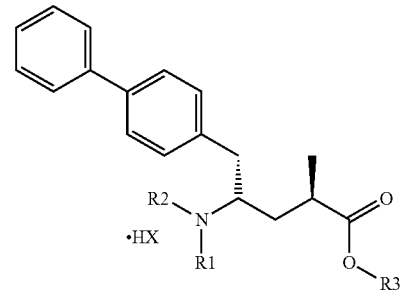

(3-a) R1 = PG1 or PG2 or H, R2 = H, R3 = Alk

In another embodiment, the present invention relates to the complete reaction sequences described in Scheme 4 converting the compound of formula (2-a), as defined herein, into the compound of formula (3-a), as define herein, and it also relates to each of the reaction steps. In still another embodiment, the present invention relates to the product obtained according to the complete reaction sequence described in Scheme 4, and it also relates to the product obtained according to each of the reaction steps shown in Scheme 4.

In Scheme 4 "PG1" is a nitrogen protecting group, as defined above, preferably pivaloyl. "PG2" is also a nitrogen protecting group, as defined above, preferably different from PG1, in particular BOC. "Alk" is an alkyl group, preferably ethyl. The term ".HX" indicates that the compound is preferably present as an acid addition salt, especially in form of HCl.

The reactions shown in Scheme 4 are not limited to the specific stereochemistry disclosed. Contrary, they can also be carried out with compounds having any other possible configuration.

Generally, the reactions (a) to (j) can be carried out under various conditions. Preferred conditions for each one of the reactions (a) to (j) of Scheme 4 are given below.

(a): Treatment with a suitable nitrogen de-protecting agent, preferably amine de-protecting agent, for example treatment with an acid or a base, preferably treatment with p-toluene sulfonic acid;

(b): Treatment with the above-described ring opening agents, preferably with hydrochloric acid or a mixture of acetic acid and hydrochloric acid;

(c): Treatment with a suitable nitrogen protecting agent, preferably amine protecting agent, more preferably with di-tert-butyl-dicarbonate;

(d): Treatment with an aliphatic alcohol, preferably ethanol. Optionally in the presence of thionyl chloride or an acid, such as a mineral acid, for example HCl, $H_2SO_4$, $H_3PO_4$ or HBr; preferably optionally in the presence of thionyl chloride. Optionally, when PG1 or PG2 are acid labile, this step can include treatment with a suitable alkylating reagent, for example, an alkyl halide (such as ethyl chloride, ethyl bromide or ethyl iodide, preferably ethyl iodide) in the presence of a base (eg NaH, $Cs_2CO_3$).

(e): Treatment with acid or base in the presence of water, preferably hydrochloric acid in water. This step can include further treatment with a suitable nitrogen de-protecting agent, for example Pd/C and hydrogen, when PG1 is neither acid not base labile N-protecting group. Treatment with acid or base in the presence of water is preferred;

(f): Treatment with suitable nitrogen protecting agent, preferably amine protecting agent, more preferably with BOC;

(g): Treatment with a ring opening agent, as described above, preferably lithium hydroxide;

(h): Treatment with acid or base in alcoholic solution, preferably hydrochloric acid in ethanol;

(i): Treatment with acid or base in alcoholic solution, preferably hydrochloric acid in ethanol;

(j): Treatment with a ring opening agent, as described above, preferably lithium hydroxide; optionally, when PG1 is a base labile N-protecting group, this step can further include further treatment with a suitable nitrogen protecting agent, which can be the same or different from the original PG1 used;

(k): Treatment with a suitable nitrogen protecting agent, as defined above, preferably amine protecting agent, preferably in the presence of a base, such as triethylamine; or treatment with a suitable nitrogen de-protecting agent, preferably amine de-protecting agent, for example treatment with Pd/C and hydrogen or treatment with a base. Step (k) is optional.

The protecting group preferably changes in the reaction routes (a)/(f) and (e)/(c), e.g. from PG1 to PG2. The protecting group preferably does not change in the reaction route (j).

In a preferred embodiment, R1 and R2 are H for the compound of formula (3-a) shown in Scheme 4.

It is preferred that reactions (d), (h) and (i) of Scheme 4 lead to a compound, wherein "Alk" is ethyl. Said compound is preferably used in the production of an NEP-inhibitor as described below in subsection B-3.

In a further aspect, the present invention relates to step (d), preferably wherein a compound of formula (3-a), wherein R1 and R3 are H and R2 is a nitrogen protecting group, preferably an acid labile nitrogen protecting group such as BOC, is converted into the compound of formula (3-a), or salt thereof, wherein R1 and R2 are H and R3 is alkyl, preferably ethyl, by treatment with thionyl chloride and an aliphatic alcohol, preferably ethanol. In a preferred embodiment, the compound of formula (3-a), obtained according to this process, wherein R1 and R2 are H and R3 is alkyl, is (2R,4S)-4-amino-5-biphenyl-4-yl-2-methylpentanoic acid ethyl ester, or salt thereof.

Scheme 4 encompasses the preferred absolute configuration of compounds of formulae (2) and (3). However, the present invention also relates to the complete reaction sequences and to each of the reaction steps, wherein any of the compounds (product or starting material) is a pure diastereomer, or mixture thereof, or enantiomer, or mixtures thereof, e.g., mixtures of enantiomers, such as racemates. In a preferred embodiment, step (d) provides a method to prepare a compound of formula (3), preferably wherein R1 and R2 are H and R3 is ethyl, or salt thereof, in a diastereomeric ratio of (3-a) to (3-b) of at least 60:40, preferably of at least 70:30, more preferably of at least 80:20, yet more preferably of at least 90:10, most preferably of at least 99:1.

Subsection B-3: Reacting the Intermediate (3) to Obtain a NEP-Inhibitor or Prodrug Thereof, Preferably an NEP-Inhibitor Prodrug According to Formula (18)

The compound according to formula (3), or salt thereof, especially the compound according to formula (3-a), or salt thereof, can be used in the production of an NEP-inhibitor or prodrug thereof.

The term "NEP inhibitor" describes a compound which inhibits the activity of the enzyme neutral endopeptidase (NEP, EC 3.4.24.11) and it is understood to include salts thereof.

The term "prodrug" describes a pharmacological substance which is administered in an inactive (or less active) form. Once administered, the prodrug is metabolised in the body in vivo into the active compound.

Therefore, an embodiment of the process of the present invention comprises one or more additional steps wherein the compound according to formula (1) is further reacted to obtain an NEP-inhibitor or a prodrug thereof.

In the present invention the terms "NEP-inhibitor" or "NEP-inhibitor prodrug" relates to the substances as such or to salts thereof, preferably pharmaceutically acceptable salts thereof. Examples are sodium, potassium, magnesium, calcium or ammonium salts. Calcium salts are preferred.

Preferably compounds according to formula (1-a), or salts thereof, are further reacted to obtain a NEP-inhibitor or a prodrug thereof. Particularly preferred is a compound according to formula (3-a), or salt thereof, wherein R1 and R2 are hydrogen and R3 is ethyl.

In a preferred embodiment a compound according to formula (3-a) is further reacted to obtain the NEP inhibitor prodrug N-(3-carboxy-1-oxopropyl)-(4S)-p-phenylphenylmethyl)-4-amino-(2R)-methylbutanoic acid ethyl ester, or salt thereof, according to formula (18) (known in the art as AHU 377) or a salt thereof.

Hence, another object of the present invention is a process for producing a compound according to formula (18) or a salt thereof.

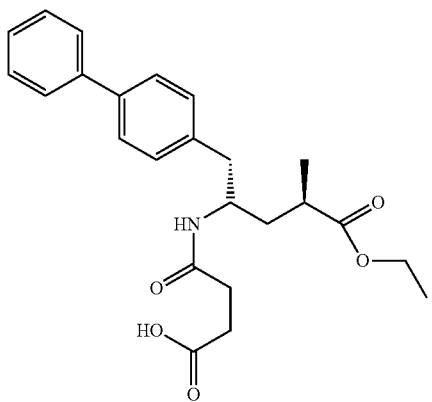

(18)

comprising the steps a) providing a compound according to formula (1-a), or salt thereof,

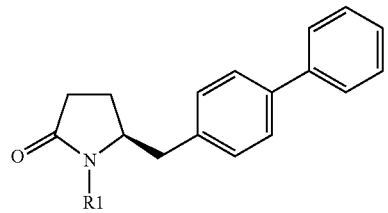

(1-a)

b) methylating the compound according to formula (1-a), or salt thereof, to obtain a compound according to formula (2-a), or salt thereof,

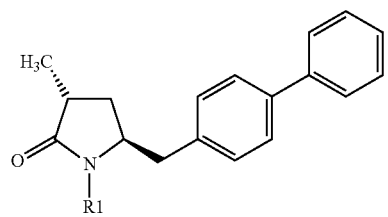

(2-a)

c) reacting the compound according to formula (2-a), or salt thereof, with a ring opening agent to obtain a compound according to formula (3-a) or a salt thereof

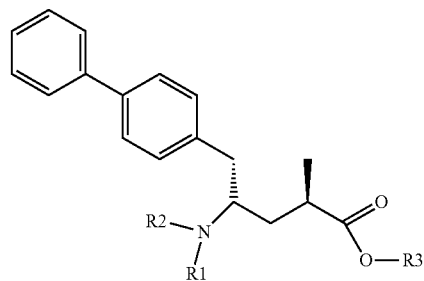

(3-a)

d) reacting a compound according to formula (3-a) or a salt thereof to obtain a compound according to formula (18) or a salt thereof,
wherein in the above formulae R1 and R2 are independently, of each other, hydrogen or a nitrogen protecting group, as defined above, and R3 is hydrogen or alkyl.

In another embodiment, the present invention relates to the above process comprising the steps (a) to (d) and it also relates to each of the reaction steps (a) to (d). In still another embodiment, the present invention also relates to the product obtained according to each of the reaction steps (a) to (d) and to the product obtained according to the complete reaction sequence (a) to (d).

The reactions from compound (1-a), or salt thereof, to (2-a), or salt thereof, and from compound (2-a), or salt thereof, to (3-a), or salt thereof, are described above in the previous subsections B-1 and B-2, respectively.

Generally, the present invention comprises any pharmaceutically acceptable salt of N-(3-carboxy-1-oxopropyl)-(4S)-p-phenylphenylmethyl)-4-amino-(2R)-methyl-butanoic acid ethyl ester, wherein the calcium salt is preferred.

The NEP inhibitor prodrug N-(3-carboxy-1-oxopropyl)-(4S)-p-phenylphenylmethyl)-4-amino-(2R)-methylbutanoic acid ethyl ester, or salt thereof, optionally is further reacted to obtain the active NEP inhibitor N-(3-carboxy-1-oxopropyl)-(4S)-p-phenylphenylmethyl)-4-amino-(2R)-methylbutanoic acid, or salt thereof.

In a preferred embodiment of the present invention the synthesis of N-(3-carboxy-1-oxopropyl)-(4S)-p-phenylphenylmethyl)-4-amino-(2R)-methylbutanoic acid ethyl ester, or salt thereof, is carried out according to Scheme 5:

Section C: Preparation Methods For The Key Lactam (1)

The present invention comprises seven methods for preparing the Key Lactam (1), or salt thereof, which are described below in subsections C-1 to C-7.

Subsection C-1: Method 1

In one embodiment, the subject of the present invention is a process for preparing a compound according to formula (1), or salt thereof, Scheme 5

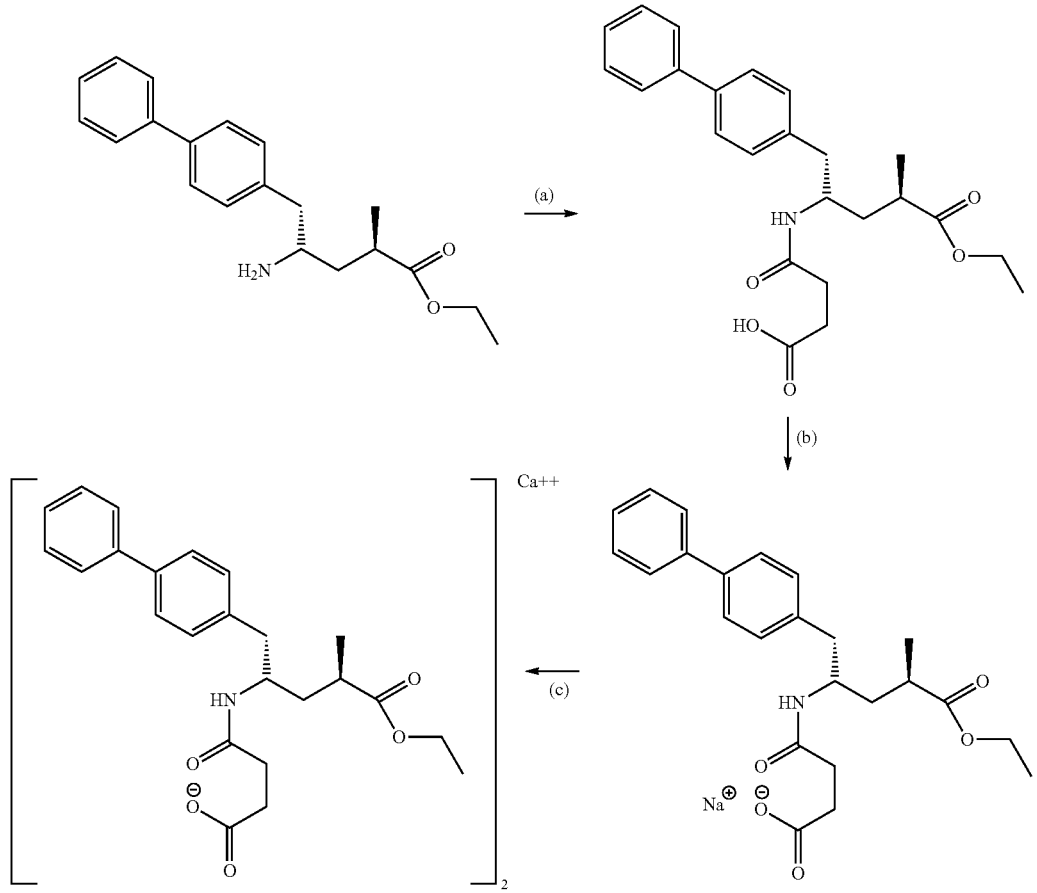

Generally, reactions (a) to (c) can be carried out under various conditions. Steps (b) and (c), which provide, respectively, the corresponding sodium and calcium salts thereof, are optional steps. Preferred conditions for each of the reactions (a) to (c) of Scheme 5 are given below.

(a): Treatment with succinic anhydride, preferably in the presence of a base. Preferred bases are triethylamine, pyridine, sodium carbonate, sodium hydrogen carbonate and potassium carbonate; more preferably the base is triethylamine;
(b): Treatment with a sodium base, preferably NaOH
(c): Treatment with a calcium salt, preferably CaCl$_2$.

In a preferred embodiment, the starting material for the synthesis of N-(3-carboxy-1-oxopropyl)-(4S)-p-phenylphenylmethyl)-4-amino-(2R)-methylbutanoic acid ethyl ester, or salt thereof, according to Scheme 5, is in the form of an acid addition salt HX, preferably HCl. In this preferred embodiment, step (a) according to Scheme 5 requires a base, such as triethylamine, pyridine, sodium carbonate, sodium hydrogen carbonate or potassium carbonate, preferably the base is triethylamine.

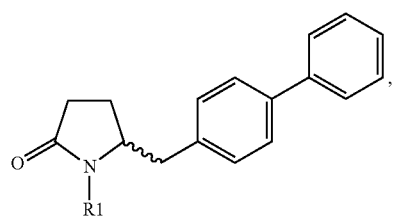

(1)

wherein R1 is as defined above, comprising the following steps:

a) providing a compound according to formula (4), or salt thereof,

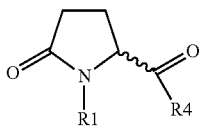

(4)

wherein R1 is hydrogen or a nitrogen protecting group, as defined above, and R4 is an CO-activating group, as defined below, b) reacting the compound according to formula (4), or salt thereof, with a biphenylic compound to obtain a compound according to formula (5)

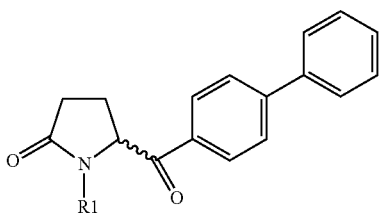

(5)

wherein R1 is hydrogen or a nitrogen protecting group, as defined above, and c) reduction, for example by hydrogenation or by using a reducing agent known in the art (e.g. a hydride reagent such as sodium borohydride), preferably by hydrogenation, of a compound according to formula (5), or salt thereof, to obtain a compound according to formula (1), or salt thereof.

In another embodiment, the present invention relates to the above process comprising the steps (a) to (c) and it also relates to each of the reaction steps (a) to (c). In still another embodiment, the present invention also relates to the product obtained according to each of the reaction steps (a) to (c) and to the product obtained according to the complete reaction sequence (a) to (c).

Explanations Regarding Step (4)→(5):

Compounds according to formula (4), or salts thereof, are readily available from glutamic acid and/or pyroglutamic acid or derivatives thereof, i.e. from the chiral pool.

In formula (4) R4 is a CO-activating group. A suitable CO-activating group generally is any group which can act as a leaving group. Examples of groups which can act as a CO-activating group are —$NR_2$, —OR, —SR or halogen, wherein R is hydrogen or (optionally substituted) alkyl or (optionally substituted) aryl.

Preferably, the following groups are suitable as CO-activating group R4 in formula (4):

a) R4 can be an amino group, in particular, —NR12R13, wherein R12 and R13 are independently selected from the group consisting of alkyl, alkoxy, aryl, aryloxy, arylalkyl and arylalkoxy; preferably R12 is alkyl (eg methyl) and R13 is selected from the group consisting of alkoxy (eg. methoxy or ethoxy), aryloxy (eg. phenyloxy) and arylalkoxy (eg, benzyloxy); or together are unsubstituted or substituted alkylene or unsubstituted or substituted alkenylene; for example piperidinyl, morpholinyl, 1-alkylpiperazinyl (for example 1-methylpiperazinyl), 2-, 3-, 4-alkylpiperidinyl, 1,2,3,6-tetrahydropyridinyl, pyrrolidinyl or imidazolyl; or R12 is alkyl (eg. methyl) and R13 is —X—R14, wherein X is S and R14 is alkyl (eg. methyl or ethyl), aryl (eg. phenyl) or arylalkyl (eg. benzyl); or R12 is alkyl (eg. methyl) and R13 is —NRaRb, wherein Ra and Rb are independently selected from alkyl (eg. methyl or ethyl), aryl (eg. phenyl) or arylalkyl (eg. benzyl).

Preferred R4 is a dialkylated amino group, which can be cyclic (e.g. morpholinyl or imidazolyl) or acyclic (eg. dimethylamino). Cyclic amino groups preferably comprise a 5-member or 6-member ring, with or without additional substitution, in particular substitution refers to one or more substituents selected from the group consisting of halo, alkyl, alkoxy, aryl, aryloxy, arylalkyl and arylalkoxy. Also suitable are alkylaryl amino groups (e.g. phenylmethylamino) or diaryl amino groups (e.g. diphenylamino). Further suitable are so-called Weinreb derivatives (i.e. derivatives of methylmethoxyamine), in particular —NR12R13, wherein R12 is methyl or methoxy and R13 is independently selected from alkyl, alkoxy, aryl, aryloxy, arylalkyl or arylalkoxy. Further suitable are amino groups possessing an alkyl/aryl group and a coordinating group, e.g. alkoxy, alkylthio.

b) R4 can be a group having the formula —X—R, wherein X is O or S and R is alkyl or aryl. Furthermore, R4 can be a group having the formula —O—CO—R, wherein R is alkyl or aryl.

c) R4 can be a halo, preferably chloro.

d) R4 can be —O—R15 wherein R15 is —NR12R13, as defined above, or R15 is unsubstituted or substituted heterocyclyl.

Preferably, the CO-activating group is selected from dimethylamino, morpholinyl, imidazolyl, methylmethoxyamino, —O-methyl, —O-ethyl, chloro, bromo, pivaloyl and acetyl. In particular the CO-activating group is morpholine.

If the CO-activating group is chosen from the above groups a) or b) in formula (4), the residue R1 is preferably a nitrogen protecting group, as defined above, or alternatively hydrogen. If the CO-activating group is chosen from the above group c) in formula (4), the residue R1 is preferably hydrogen.

The compound according to formula (4), or salt thereof, is reacted with a biphenylic compound.

In a preferred embodiment the biphenylic compound can be activated. A suitable method for the activation is the preparation of an organometallic complex comprising a biphenyl ligand.

Preferred Activated Biphenylic Compounds are:

Biphenylmagnesium halide or di(biphenyl)magnesium (Grignard reagents). Suitable halides generally are chloride, bromide and iodide, wherein bromide is especially preferred.

Further examples for activated biphenylic compounds are biphenyllithium, biphenylcuprate (low and higher-order cuprates) and biphenylzinc. Those compounds can be used individually or in the presence of another metal, e.g. copper, zinc, palladium, platinum, iron, iridium or ruthenium.

Generally, 2.0 to 2.5 equivalents of biphenylmagnesium halide or di(biphenyl)magnesium are used. In an embodiment initial deprotonation of the N—H group with, for example, another Grignard reagent (e.g. isopropylmagnesium chloride) or a base (e.g. sodium hydride) may be performed before addition of the activated biphenylic compound to reduce the required amount of biphenylmagnesium halide or di(biphenyl)magnesium. In this embodiment, 0.7 to 1.5 equivalents, preferably 1.0 to 1.25 equivalents are used.

Generally, there are two preferred embodiments to carry out the above-mentioned reaction:

1) Reacting a compound according to formula (4), or salt thereof, wherein R4 (the CO-activating group) is chosen from the above groups a) or b). In this case, an activated (e.g. metallated) biphenylic compound is preferably used, in particular a biphenylmagnesium halide is used.

2) Reacting a compound according to formula (4), or salt thereof, wherein R4 (the CO-activating group) is chosen from the above group c). In this case, biphenyl is preferably used as biphenylic compound. The reaction is preferably carried out in the presence of a suitable Lewis acid, e.g. aluminium trichloride. Alternatively, the biphenylic compound may be activated with a suitable functional group (for example para-silyl) to allow for milder conditions to be used during the Friedel-Crafts acylation. Furthermore, reference is made to the Friedel Crafts' method described in J. Am. Chem. Soc., Vol 103, No. 20, 1981, 6157.

Hence, it is preferred that R4 of formula (4) is morpholinyl and the biphenylic compound used in step b) is a biphenylmagnesium halide, or R4 of formula (4) is chloride and the biphenlyic compound used in step b) is biphenyl.

The embodiments 1) and 2) are exemplified in Scheme 6 below.

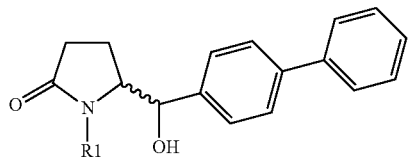

(13)

wherein R1 is hydrogen or a nitrogen protecting group, as defined above.

Complete reduction of the carbonyl group (i.e. reaction (5)→(1)) can be achieved using a hydrogenation catalyst, such as palladium on carbon (hereinafter referred to as Pd/C). This can be done in the presence or absence of an acid. Preferred is Pd/C selected from the group consisting of 10% Pd/C type K-0218 (commercially available from Heraeus GmbH), 10% type PD CP 4505 D/R (commercially available from BASF), 5% Pd/C type 39, 10% Pd/C type 39, 10% Pd/C type 39 (7200), 20% Pd/C type 91, 10% Pd/C type 338, 10% Pd/C type 394, 10% Pd/C type 394 (6065), 10% Pd/C type 394 (6249), 10% Pd/C type 395, 10% Pd/C type 395 (6002),

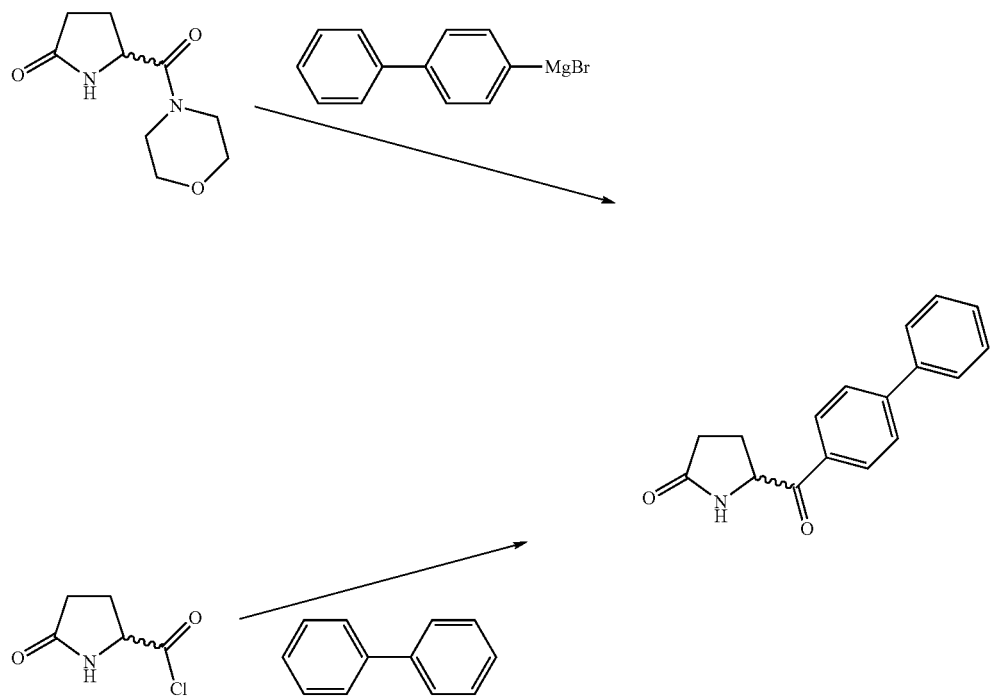

Scheme 6

Explanations Regarding Step (5)→(1):

The reduction of the carbonyl group of a compound according to formula (5), or salt thereof, for example by hydrogenation or by using a reducing agent known in the art (e.g. a hydride reagent such as sodium borohydride) forms a compound according to formula (1) or salt thereof. Preferably the reduction of a compound according to formula (5), or salt thereof, is accomplished by hydrogenation. Depending on reaction conditions, the reaction can be carried out directly, or via the corresponding alcohol according to formula (13), or salt thereof, as intermediate 10% Pd/C type mod (72595), 15% Pd/C type A101023 and 15% Pd/C type A502085 (which are commercially available from Johnson Matthey); more preferably 10% Pd/C type 338, 10% Pd/C Mod (72595), 10% Pd/C type 39, 10% Pd/C type 394 (6065) and 10% Pd/C type 395; most preferably 10% Pd/C type 39 and 10% Pd/C type 394 (6065).

In one embodiment, the hydrogenation usually is carried out at a temperature between 0° C. and 60° C., preferably between 20° C. and 50° C. The applied hydrogen pressure usually ranges between 1 bar and 30 bar, preferably between 2 bar to 25 bar. The reaction time usually ranges between 1 hour and 30 hours, preferably between 5 hours and 20 hours.

In another embodiment, the hydrogenation usually is carried out at a temperature of from of 0° C. to 100° C., preferably of from 20° C. to 80° C., more preferably of from 40° C. to 80° C., most preferably of from 50° C. to 80° C.

Solvents generally known in the art can be used. Preferred solvents are, for example, isopropyl acetate, methyltetrahydrofuran, toluene or a monovalent alcohol., such as methanol or ethanol. More preferably, toluene is used. The amount of solvent employed may be such that the concentration of substrate is in a the range of from 0.1 to 1.5 M, preferably of from 0.2 to 0.8 M.

The amount of hydrogenation catalyst to substrate, typically employed in the process, may be in the range of from 1 to 30 wet wt %, preferably of from 2 to 25 wet wt %, more preferably of from 5 to 20 wet wt %.

Depending on reaction conditions, the hydrogenation can be stopped at the corresponding secondary alcohol (13) (as a mixture of diastereoisomers), which can then be isolated. Reduction of the carbonyl to the alcohol generally can be achieved using reducing agents known in the art (e.g. sodium borohydride). Conversion of the OH into a leaving group, such as halogen, by methods well-known to person skilled in the art, and subsequent treatment with a hydride reagent (for example with sodium borohydride or diisobutylaluminium hydride) would yield a compound according to formula (1). If required, the alcohol intermediate according to formula (13), or salt thereof, can also be obtained as a single diastereoisomer (either R or S) by use of, for example, an enantioselective/diastereoselective hydrogenation catalyst, for example as described in Angew. Chem. Int. Ed 2001, 40, 40-73, in particular as described in Scheme 36 therein.

In the reactions (4)→(5) and (5)→(1) the stereochemistry might be important. In a preferred embodiment the configuration of the compounds of formulae (4), (5) and (1), or salts thereof, is according to formulae (4-a), (5-a) and (1-a)

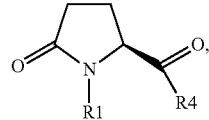
(4-a)

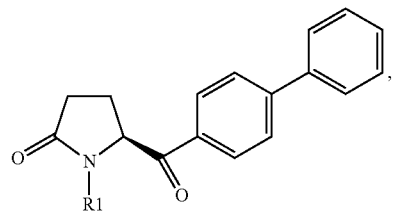
(5-a)

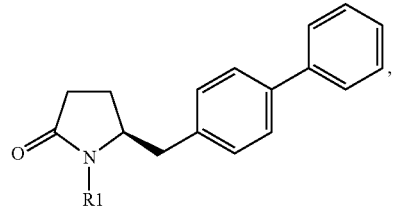
(1-a)

wherein R1 is hydrogen or a nitrogen protecting group, as defined above, and R4 is an CO-activating group, as defined above.

If a secondary alcohol according to formula (13), or salt thereof, as intermediate is produced, it preferably has a configuration as shown in formula (13-a)

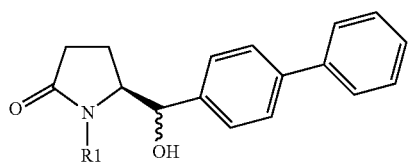

wherein R1 is hydrogen or a nitrogen protecting group, as defined above.

Subsection C-2: Method 2

In another embodiment, the subject of the present invention is a process for preparing a compound according to formula (1), or salt thereof,

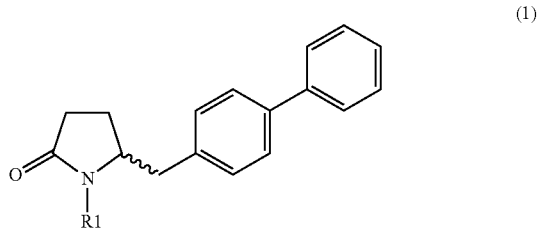
(1)

wherein R1 is hydrogen or a nitrogen protecting group, as defined above, comprising the following steps:

a) providing a compound according to formula (7), or salt thereof,

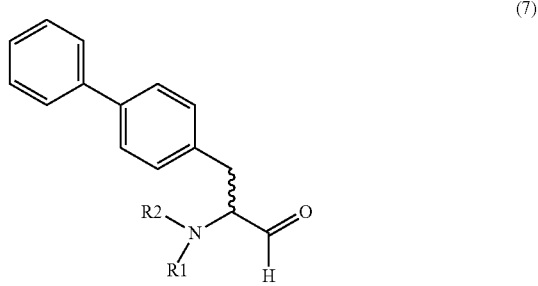
(7)

wherein R1 and R2 are independently, of each other, hydrogen or a nitrogen protecting group, as defined above, b) reacting a compound according to formula (7), or salt thereof, in a Wittig reaction to obtain a compound according to formula (8), or salt thereof,

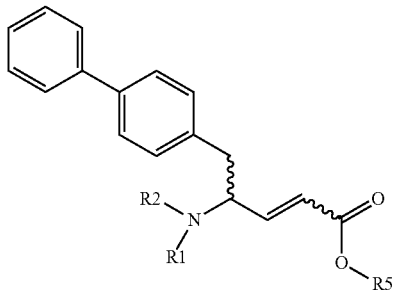

(8)

wherein R1 and R2 are independently, of each other, hydrogen or a nitrogen protecting group, as defined above, and R5 is hydrogen or alkyl, c) reduction of a compound according to formula (8), or salt thereof, to obtain a compound according to formula (9), or salt thereof,

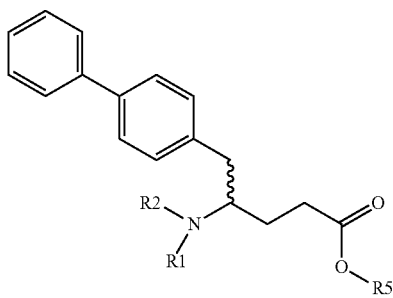

(9)

wherein R1 and R2 are independently, of each other, hydrogen or a nitrogen protecting group, as defined above, and R5 is hydrogen or alkyl, d) optionally removing the nitrogen protecting groups, thereby yielding a compound according to formula (10) or a salt thereof

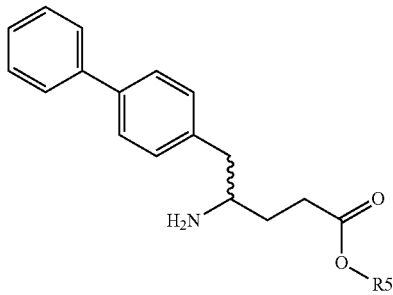

(10)

wherein R5 is hydrogen or alkyl, and e) reacting the compound according to formula (10) or (9), or salt thereof, preferably reacting a compound of formula (10), under ring-closing conditions to obtain a compound according to formula (1), or salt thereof, wherein R1 is hydrogen or a nitrogen protecting group, preferably R1 is hydrogen.

The present invention relates to the above process comprising the steps (a) to (e) and it also relates to each of the reaction steps (a) to (e). Moreover, the present invention also relates to the product obtained according to each of the reaction steps (a) to (e) and to the product obtained according to the complete reaction sequence (a) to (e).

Optionally, upon reacting a compound according to formula (10), or salt thereof, under ring-closing conditions to obtain a compound according to formula (1), or salt thereof, wherein R1 is hydrogen, treatment with a suitable nitrogen protecting agent, as defined above, can follow to provide a compound of formula (1) wherein R1 is a nitrogen protecting group.

In a preferred embodiment in formula (7) R1 is a nitrogen protecting group (as defined above in section A) and R2 is hydrogen. The same applies to formulae (8) and (9).

The compound according to formula (7), or salt thereof, is reacted in a Wittig reaction to obtain a compound according to formula (8), or salt thereof. In the Wittig reaction usually the aldehyde according to formula (7), or salt thereof, is treated with a phosphorus ylide (also called a phosphorane) to obtain the olefin of formula (8), or salt thereof. Phosphorus ylides are usually prepared by treatment of a phosphonium salt with a base and phosphonium salts are usually prepared from a phosphine and an alkyl halide, by methods well-known to the person skill in the art.

In the present application preferably a compound according to formula $(Ar)_3P=CH-CO_2-R$ is used in the Wittig reaction, wherein Ar is aryl and R is alkyl. In particular, $Ph_3P=CH-CO_2-C_2H_5$ is used in the Wittig reaction.

The term "⌇" on olefins of the present application represents a covalent bond, which comprises an (E) stereoisomer as well as a (Z) stereoisomer of the respective olefin. Furthermore, mixtures of (E) and (Z) stereoisomers are also encompassed.

Furthermore, in formula (8) the residue R5 is hydrogen or alkyl. Preferably, R5 is C1-C6 alkyl, more preferably ethyl. The same applies to formulae (9) and (10).

The double bond of the compound according to formula (8), or salt thereof, is hydrogenated to obtain a compound according to formula (9), or salt thereof.

Generally, the hydrogenation can be carried out by known methods. Preferably, the hydrogenation is carried out in the presence of Pd/C as catalyst.

The hydrogenation usually is carried out at a temperature between 0° C. and 60° C., preferably between 20° C. and 50° C. The applied hydrogen pressure usually ranges between 1 bar and 30 bar, preferably between 2 bar to 25 bar. The reaction time usually ranges between 1 hour and 30 hours, preferably between 5 hours and 20 hours.

If at least one residue R1 or R2 of formula (9) is a nitrogen protecting group, as defined above, it can be removed in an optional reaction step, by methods well-known in the art, in particular as described in reference books above mentioned, in the relevant chapters thereof, to obtain a compound according to formula (10). If an embodiment requires the removal of the nitrogen protecting group, the removal usually can be carried out by using known methods. Preferably, the nitrogen protecting group is removed by using $SOCl_2$, hydrochloric acid, sulphuric acid or trifluoroacetic acid. In the case of N-benzyl, as nitrogen protecting group, it can be removed by hydrogenation or some suitable oxidising agents, e.g. ceric ammonium nitrate (CAN) or 2,3-dichloro-5,6-dicyano-p-benzoquinone (DDQ).

The compound according to formula (10), or salt thereof, is subjected to ring-closing conditions to obtain a compound according to formula (1) or salt thereof. Suitable ring closing conditions are those that employ a base. Preferred bases used are alkylamines or alkali metal alkoxides. Particularly preferred are triethylamine or sodium methoxide.

In the above reactions the stereochemistry might be of importance. In a preferred embodiment compounds, or salts thereof, are used having a configuration as shown in formula (7-a), (8-a), (9-a) and (10-a)

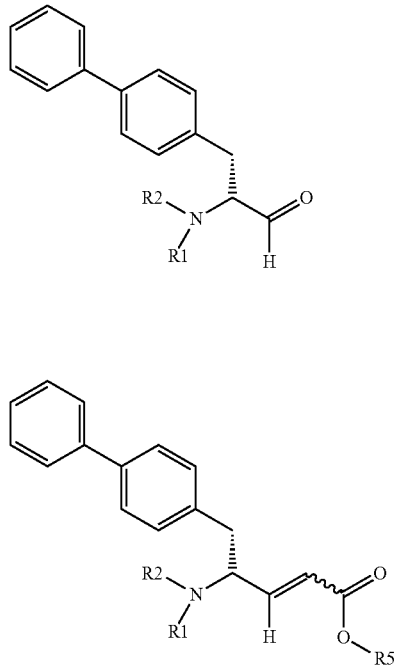

(7-a)

(8-a)

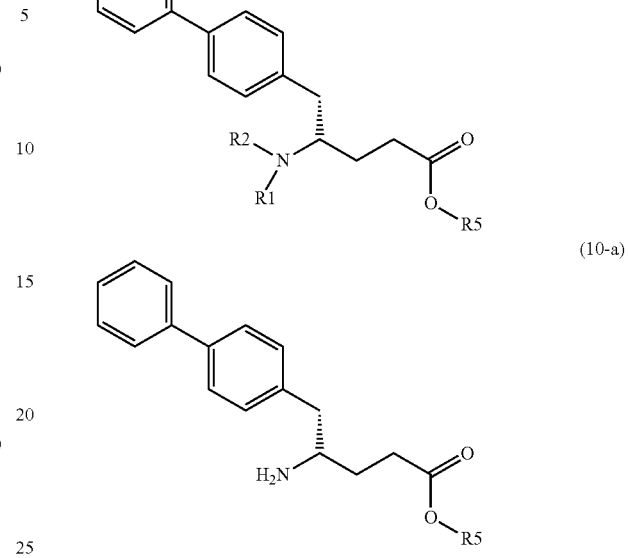

(9-a)

(10-a)

wherein in the above formulae R1, R2 and R5 are as defined above for formulae (7) to (10). Furthermore, preferably a compound according to formula (1-a), or salt thereof, as defined above, is obtained.

A preferred embodiment for the preparation of the Key Lactam (1), or salt thereof, starting from the compound according to formula (7), or salt thereof, is shown in Scheme 7 below.

Scheme 7

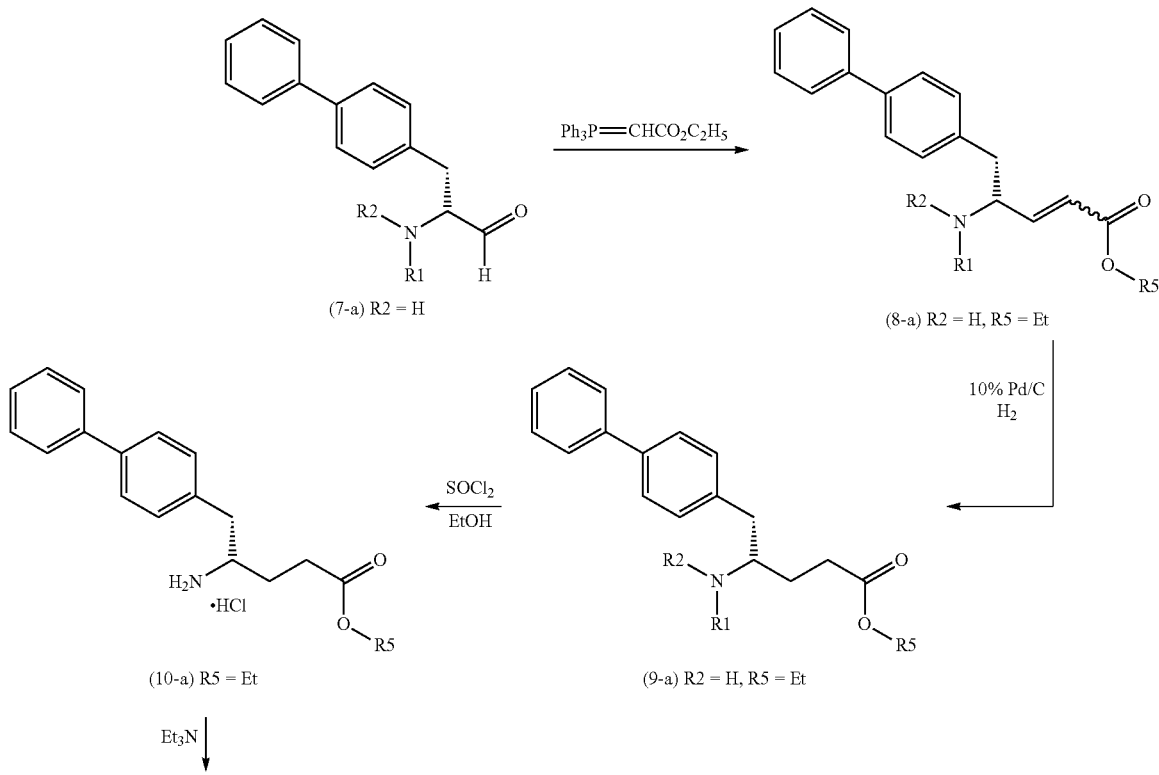

(7-a) R2 = H (8-a) R2 = H, R5 = Et (9-a) R2 = H, R5 = Et (10-a) R5 = Et

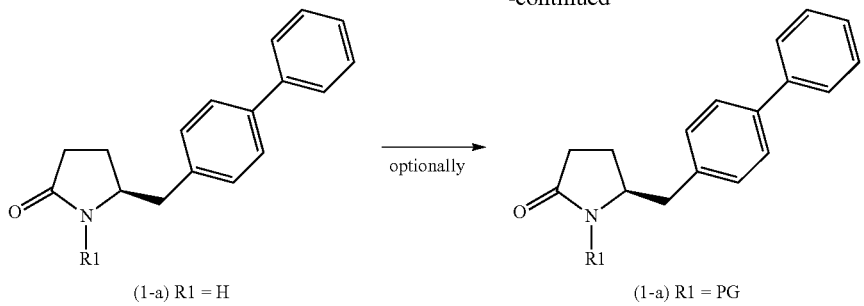

(1-a) R1 = H    optionally    (1-a) R1 = PG

In Scheme 7 "R1" is a nitrogen protecting group, preferably BOC.

In another embodiment, the present invention relates to the complete reaction sequences described in Scheme 7 converting the compound of formula (7-a), as defined herein, into the compound of formula (1-a), as define herein, but it also relates to each of the reaction steps. In still another embodiment, the present invention relates to the product obtained according to the complete reaction sequence described in Scheme 7, but it also relates to the product obtained according to each of the reaction steps shown in Scheme 7.

Subsection C-3: Method 3

As an alternative to the reduction of the aryl ketone according to formula (5) that is formed in method 1, addition of a biphenyl anion to a $sp^a$ hybridised leaving group, can be performed.

Hence, a further object of the present invention is a process for preparing a compound according to formula (1), or salt thereof,

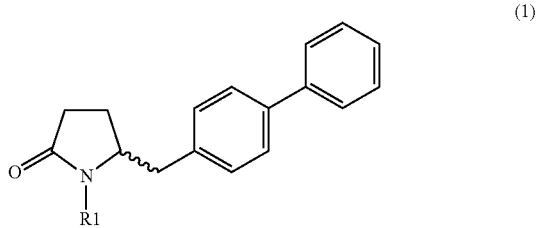

(1)

wherein R1 is hydrogen or a nitrogen protecting group, as defined above,
comprising reacting a compound according to formula (11), or salt thereof,

(11)

wherein R1 is hydrogen or a nitrogen protecting group, as defined above, and R6 is a leaving group, as defined below, with an activated (e.g. metallated) biphenylic compound, preferably with a biphenylmagensium halide.

R1 can be a nitrogen protecting group as described above in section A: The Key Lactam (1), or salt thereof, as such. Preferably, R1 is hydrogen.

Generally, R6 is a suitable leaving group. Examples of suitable leaving groups are amino, alkoxy (e.g. methoxy, ethoxy), carboxylate, halogen (e.g. fluoride, chloride, bromide, iodide), azide, thiocyanate, nitro, cyanide, tosylate, triflate and mesylate. Preferably, R6 is iodide, tosylate or mesylate.

Regarding the term "activated biphenylic compound" it is referred to the explanations above for method 1 in subsection C-1. Preferably the activated biphenylic compound is a biphenylmagnesium halide, especially biphenylmagnesium bromide.

The reaction can be carried out according to the following preferred embodiment, wherein R1 is hydrogen:

Starting from known pyroglutaminol (CAS#17342-08-4), the replacement of the alcohol with a leaving group (e.g. iodide [CAS#29266-73-7], tosylate [CAS#51693-17-5] or mesylate), according to well-known methods, for example as described in Richard C. Larock, "Comprehensive Organic Transformations: A Guide to Functional Group Preparations", Second Edition, Wiley-VCH Verlag GmbH, 2000, in particular as described in the relevant chapters thereof, yields a compound according to formula (11). The following addition of biphenylmagnesium halide, in particular biphenylmagnesium bromide, (or an alternative metallated biphenyl, e.g. Li, Zn), optionally in the presence of another metal (e.g. copper, zinc, palladium) in either catalytic or stoichiometric amounts, yields the compound according to formula (1).

In another embodiment, the coupling of the compound of formula (11), or salt thereof, wherein R6 is a leaving group, preferably halo (such as bromo or iodo) or a tosylate or a mesylate group, with a biphenylmagnesium halide takes place under Fe- or Mn-catalyzed cross coupling reaction conditions, for example by the use of $FeCl_3$, $Fe(acac)_3$ or $MnCl_2$, as described, for example, in Angew. Chem. Int. Ed., 2004, 43 3955-3957, in Org. Lett., 2004, 6, 1297-1299, in Chem. Commun., 2004, 2822-2823, in J. Am. Chem. Soc., 2004, 126, 3686-3687, in Synlett, 2001, 1901-1903 or in Synthesis, 1998, 1199-1205. The Fe-catalyzed cross coupling reaction conditions preferably takes place by the use of $FeCl_3$.

In still another embodiment, the coupling of the compound of formula (11), or salt thereof, wherein R6 is a leaving group, preferably halo (such as bromo or iodo) or a tosylate or a mesylate group, with a biphenylmagnesium halide takes place in the presence of a metal salt additive, which is used in catalytic or stoichiometric amounts. A useful metal salt additive is, for example, a copper(I), copper(II), zinc(II), silver(I), cadmium(II), mercury(II), aluminum(III), gallium(III), indium(III), tin(IV), titanium(IV) or zirconium(IV) salt. Examples of such salts are the corresponding chloride, bromide, iodide, carbonate, hydroxide, oxide, $C_1$-$C_7$-alkanoates such as the acetate and propionate, $C_1$-$C_7$-alkoxides such as the methoxide and ethoxide, trifluoroacetate, acetylacetonate, nitrate, cyanide, sulfate, trifluoromethanesulfonate, methanesulfonate, benzenesulfonate or para-toluenesulfonate. Preferred metal salt additives are copper salts, such as copper cyanide, which is preferably used in a stoichiometric amount.

Generally, the use of more than one equivalent of a Grignard reagent (or other metallated species) can be prevented by adding an additional base (eg isopropylmagnesium chloride or NaH) to remove the NH proton if R1 is hydrogen.

The stereochemistry of the reaction might be of interest. Preferably, a compound, or salt thereof, having a configuration according to formula (11-a) is used

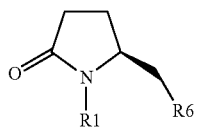
(11-a)

wherein R1 and R6 are defined as above for compounds according to formula (11), or salts thereof. Furthermore, preferably a compound according to formula (1-a), or salt thereof, is obtained.

In addition to the compound of formula (1), preferably of formula (1-a), the corresponding aziridine according to formula (19), preferably of formula (19-a), or salt thereof, may form when R1, for the compound of formula (11), preferably of formula (11-a) is hydrogen.

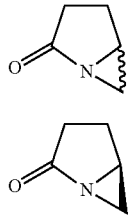
(19)

(19-a)

The compound according to formula (19), which is described in J. Org. Chem., 1988, 53, 4006, or salt thereof, may be isolated, allowing the conversion of the compound of formula (11) to the compound of formula (1) to proceed in a step-wise manner. Alternatively, the compound of formula (19) may be generated in situ.

Subsection C-4: Method 4

An alternative preparation method of the Key Lactam (1), or salt thereof, is oxidation of the primary alcohol of pyroglutaminol to the aldehyde followed by the addition of activated (e.g. metallated) biphenyl and the removal of the secondary alcohol (e.g. by hydrogenation or reduction). The addition of activated (e.g. metallated) biphenyl to an aldehyde of formula (12), or salt thereof, may be achieved by methods well known in the art, for example, as described in J. Org. Chem., 1987, 52, 4352. Moreover, methods to prepare compounds of the formula (12), or salts thereof, are described in the literature, for example, in Biochemistry, 1985, 24, 3907.

Hence, a further subject of the present invention is a process for preparing a compound according to formula (1), or salt thereof,

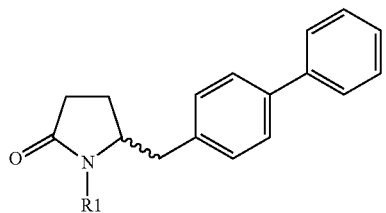
(1)

wherein R1 is hydrogen or a nitrogen protecting group, as defined above, comprising the following steps:

a) providing a compound according to formula (12), or salt thereof,

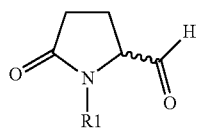
(12)

wherein R1 is hydrogen or a nitrogen protecting group, as defined above, b) reacting compound (12), or salt thereof, with an activated (e.g. metallated) biphenylic compound to obtain a compound according to formula (13), or salt thereof,

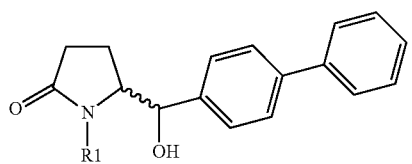
(13)

wherein R1 is hydrogen or a nitrogen protecting group, as defined above, and c) reducing the compound according to formula (13), or salt thereof, to obtain the compound according formula (1), or salt thereof.

In another embodiment, the present invention relates to the above process comprising the steps (a) to (c) and it also relates to each of reaction steps (a) to (c). In still another embodiment, the present invention also relates to the product obtained according to each of the reaction steps (a) to (c) and to the product obtained according to the complete reaction sequence (a) to (c).

R1 can be a nitrogen protecting group as described above in section A: The Key Lactam (1), or salt thereof, as such. Preferably, R1 is hydrogen.

Regarding the term "activated biphenylic compound" it is referred to the explanations above for method 1 in section C-1. Preferably the activated biphenylic compound is a metallated biphenyl, eg. biphenylmagnesium halide, especially biphenylmagnesium bromide.

The secondary alcohol according to formula (13), or salt thereof, generally can be reduced according to known methods. In a preferred embodiment the OH group is converted into a leaving group. Preferred leaving groups are described above in subsection C-4. Subsequent treatment with a reducing agent would lead to a compound according to formula (1), or salt thereof. Suitable reducing agents are described, for example, above in subsection C-1.

In a preferred embodiment the compounds (12) and (13), or salts thereof, have a configuration according to formulae (12-a) and (13-a)

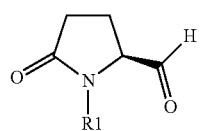
(12-a)

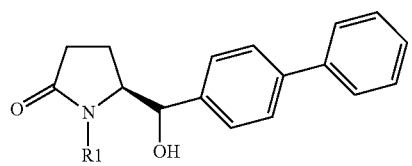
(13-a)

wherein R1 is defined as above for compounds (12) and (13). Furthermore, preferably a compound according to formula (1-a), or salt thereof, is obtained.

The preparation of compounds of formula (12) is described in the literature, for example in Biochemistry, 1985, 24, 3907.

In a preferred embodiment, the reaction of a compound of formula (12) to provide a compound of formula (13) is analogous to the Grignard addition described in JOC 1987, 52, 4352.

Subsection C-5: Method 5

An alternative preparation method of the Key Lactam (1) is a reaction starting from 1,5-dihydropyrrol-2-one, or salt thereof, employing a chemo- and enantio-selective hydrogenation as the key step.

Hence, a further subject of the present invention is a process for preparing a compound according to formula (1), or salt thereof,

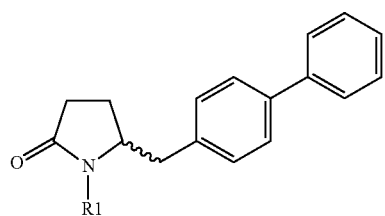
(1)

wherein R1 is hydrogen or a nitrogen protecting group, as defined above,
comprising the following steps:
a) providing a compound according to formula (14), or salt thereof,

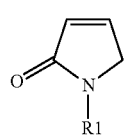
(14)

b) reacting the compound according to formula (14), or salt thereof, with 4-formyl biphenyl to obtain a compound according to formula (15), or salt thereof,

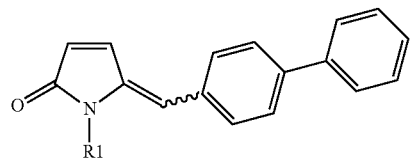
(15)

c) hydrogenating compound (15), or salt thereof, to obtain a compound according to formula (16), or salt thereof,

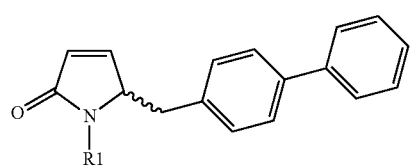
(16)

and
d) reducing the compound according to formula (16), or salt thereof, to obtain a compound according to formula (1), or salt thereof, wherein in formulae (14) to (16) R1 is hydrogen or a nitrogen protecting group, as defined above.

In another embodiment, the present invention relates to the above process comprising the steps (a) to (d) and it also relates to each of the reaction steps (a) to (d). In still another embodiment, the present invention also relates to the product obtained according to each of the reaction steps (a) to (d) and to the product obtained according to the complete reaction sequence.

R1 can be a nitrogen protecting group as described above in section A: The Key Lactam (1), or salt thereof, as such. Preferably, R1 is hydrogen.

The reaction of the compound according to formula (14), or salt thereof, with 4-formyl biphenyl preferably is carried out in the presence of a base, particularly sodium hydroxide.

The hydrogenation of compound (15), or salt thereof, to obtain compound (16), or salt thereof, is preferably carried out by an enantioselective hydrogenation, preferably as described below.

The hydrogenation of compound (16), or salt thereof, to obtain compound (1), or salt thereof, is preferably carried out with palladium on carbon as catalyst.

Alternatively, a compound of formula (16), or salt thereof, can be converted into a compound of formula (1), or salt thereof, under reduction conditions, for example, by the use a hydride reducing agent, such as $NaBH_4$—$NiCl_2$, $NaBH_4$—$BiCl_3$, or $NaBH_4$—$InCl_3$.

In a preferred embodiment the configuration of compound (16), or salt thereof, is according to formula (16-a)

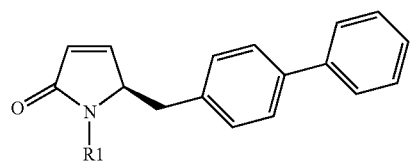
(16-a)

wherein R1 is as defined above in formula (16). Furthermore, preferably a compound according to formula (1-a), or salt thereof, is obtained.

A preferred embodiment of method 5 is exemplified in Scheme 8 below.

Scheme 8

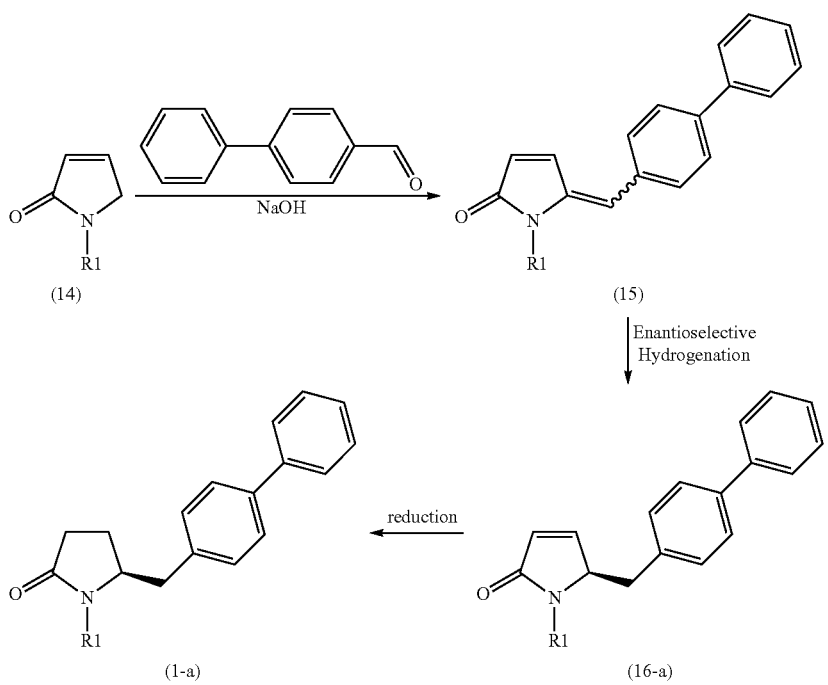

In another embodiment, the present invention relates to the complete reaction sequences described in Scheme 8 converting the compound of formula (14), as defined herein, into the compound of formula (1-a), as define herein, and it also relates to each of the reaction steps shown in Scheme 8. In still another embodiment, the present invention relates to the product obtained according to the complete reaction sequence described in Scheme 8, and it also relates to the product obtained according to each of the reaction steps shown in Scheme 8.

The compound of formula (14), or salt thereof, wherein R1 is hydrogen is commercially available, for example from suppliers such as J & W PharmaLab LLC. Treatment of a compound of formula (14), wherein R1 is H, with a suitable nitrogen protecting agent, as defined above, to protect the N with a protecting group PG can be accomplished, according to the methods described above.

Conversion of a compound of formula (14), or salt thereof, wherein R1 is hydrogen or a nitrogen protecting group, into a compound of formula (15), or salt thereof, wherein R1 is hydrogen or a nitrogen protecting group, can be achieved upon reaction with biphenyl-4-carbaldehyde in the presence of a base, such as an alkalimetal base (e.g. NaOH or KOH), for example, as described in J. Org. Chem., 2002, 67 (14), 4702, in Synthesis, 2004, (10), 1560 and in Synth. Commun., 2002, 32 (7), 1031.

Chemoselective and enantioselective hydrogenation of a compound of formula (15), or salt thereof, wherein R1 is hydrogen or a nitrogen protecting group, into a compound of formula (16-a), or salt thereof, wherein R1 is hydrogen or a nitrogen protecting group, can be achieved, by the use of, for example, asymmetric hydrogenation conditions employed for enamide substrates, such as conditions described in Tetrahedron Asymm., 1991, 2(1), 51, in particular for compounds of formula 8a and 8b therein, or as described in J Org Chem 1994, 59(2), 297.

Reduction of the compound of formula (16-a), or salt thereof, wherein R1 is hydrogen or a nitrogen protecting group, into the compound of formula (1-a), or salt thereof, wherein R1 is hydrogen or a nitrogen protecting group, can be effected, for example, under hydrogenation conditions, for example, by the use of Pd/C as described, for example, in Synthesis, 1993, 216, or by the use of a reducing agent, for example by the use of a hydride reagent, such as NaBH$_4$, as described, for example, in J. Org. Chem, 2006, 71(5), 2173, in particular, as described in the conversion of the compound 8 into the compound 15, therein.

A preferred embodiment of the method described in Scheme 8 relates to compounds wherein R1 is hydrogen. A further preferred embodiment of the method described in Scheme 8 relates to compounds wherein R1 is hydrogen and wherein the reduction of the compound (16-a) to (1-a) takes place with Pd/C and hydrogen.

Alternatively, a compound of formula (14), or salt thereof, can be converted into a compound of formula (1), preferably of formula (1-a), or salts thereof, as detailed in Schemes 9 to 12 below. In a preferred embodiment of the methods described in Schemes 9 to 12, R1 for compounds therein is hydrogen.

Scheme 9

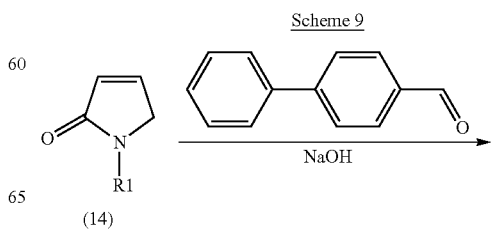

51
-continued

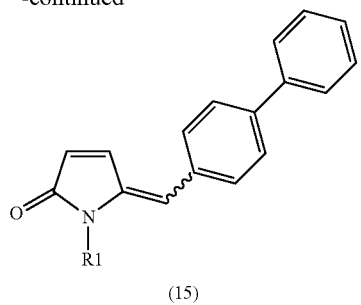
(15)

|Enantioselective
Hydrogenation
↓

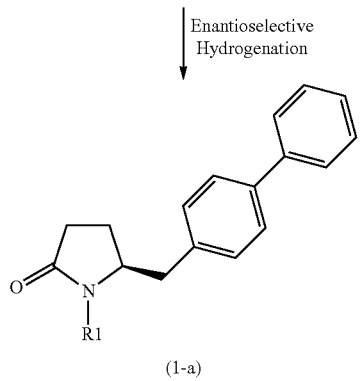
(1-a)

52

In another embodiment, the present invention relates to the complete reaction sequences described in Scheme 9 converting the compound of formula (14), as defined herein, into the compound of formula (1-a), as define herein, and it also relates to each of the reaction steps shown in Scheme 9. In still another embodiment, the present invention relates to the product obtained according to the complete reaction sequence described in Scheme 9, and it also relates to the product obtained according to each of the reaction steps shown in Scheme 9.

Scheme 9 encompasses a particular embodiment of Scheme 8, wherein the enantioselective hydrogenation of the compound of formula (15), as above detailed, leads directly to the compound of formula (1-a). Namely, this embodiment refers to the enantioselective hydrogenation of the compound of formula (15), or salt thereof, wherein there is no chemoselectivity and thus both the endo and exo C=C bonds of the pyrrolidinone moiety are reduced under the enantioselective hydrogenation conditions.

Scheme 10

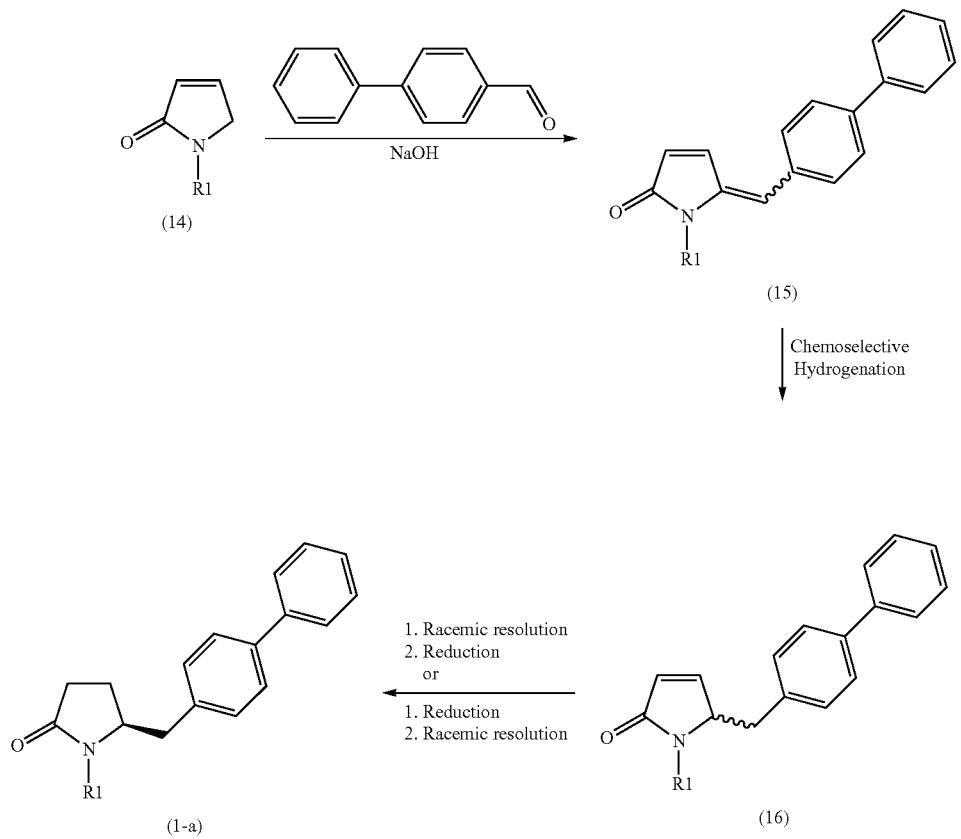

In another embodiment, the present invention relates to the complete reaction sequences described in Scheme 10 converting the compound of formula (14), as defined herein, into the compound of formula (1-a), as define herein, and it also relates to each of the reaction steps shown in Scheme 10. In still another embodiment, the present invention relates to the product obtained according to the complete reaction sequence described in Scheme 10, and it also relates to the product obtained according to each of the reaction steps shown in Scheme 10.

Scheme 10 describes an alternative route, wherein the reduction of a compound of formula 15, or salt thereof, wherein R1 is hydrogen or a nitrogen protecting group, is chemoselective and provides the compound of formula (16), or salt thereof, wherein R1 is hydrogen or a nitrogen protecting group. This chemoselective hydrogenation can be accomplished, for example, under conditions which employ $Na_2(S_2O_4)$ and $NaHCO_3$ in DMF, as described in Monatshefte fuer Chemie 1995, 126(3), 355, in Monatshefte fuer Chemie 1986, 117(2), 185 and in Liebigs Annalen der Chemie, 1986, 1241. Alternatively, it can be achieved by the use of Pd/C, for example, as described in Helv. Chim. Acta, 1987, 70(8), 2098. Racemic resolution of the compound of formula (16), or salt thereof, for example, as described for compound of formula 5 in Helv Chim Acta 1987, 70, 2098 and subsequent reduction of the resulting compound of formula (16-a), for example, under the same reactions conditions described in Scheme 8, can lead to the compound of formula (1-a), or salt thereof. These two last steps, racemic resolution and reduction can be performed in reverse order, namely, reduction of the compound of formula (16), or salt thereof, for example under the same reactions conditions described above for the compound of formula (16-a) in Scheme 8, followed by racemic resolution of the compound of formula (1), or salt thereof, for example, under the same reactions conditions described above for the compound of formula (16).

Scheme 11

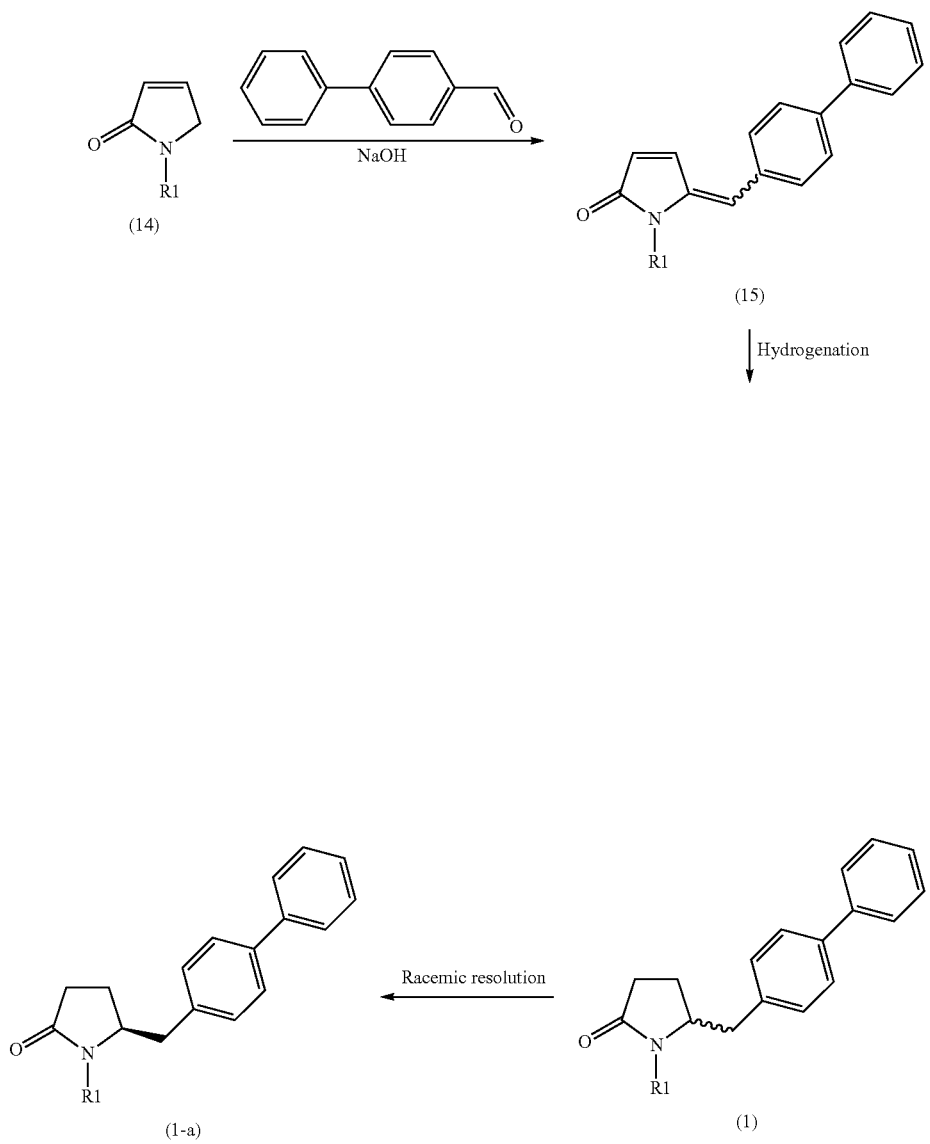

In another embodiment, the present invention relates to the complete reaction sequences described in Scheme 11 converting the compound of formula (14), as defined herein, into the compound of formula (1-a), as define herein, and it also relates to each of the reaction steps shown in Scheme 11. In still another embodiment, the present invention relates to the product obtained according to the complete reaction sequence described in Scheme 11, and it also relates to the product obtained according to each of the reaction steps shown in Scheme 11.

Another alternative route to convert the compound of formula (14), or salt thereof, into the compound of formula (1-a), or salt thereof, is detailed in Scheme 11. According to this route the reduction of the compound of formula (15), as defined above, or salt thereof leads directly to the compound of formula (1), as defined herein, or salt thereof. This reduction can be achieved, for example, under standard hydrogenation conditions, such as Pd/C and hydrogen. Subsequently, racemic resolution, as described above, can lead to the compound of formula (1-a), as defined herein, or salt thereof.

Scheme 12

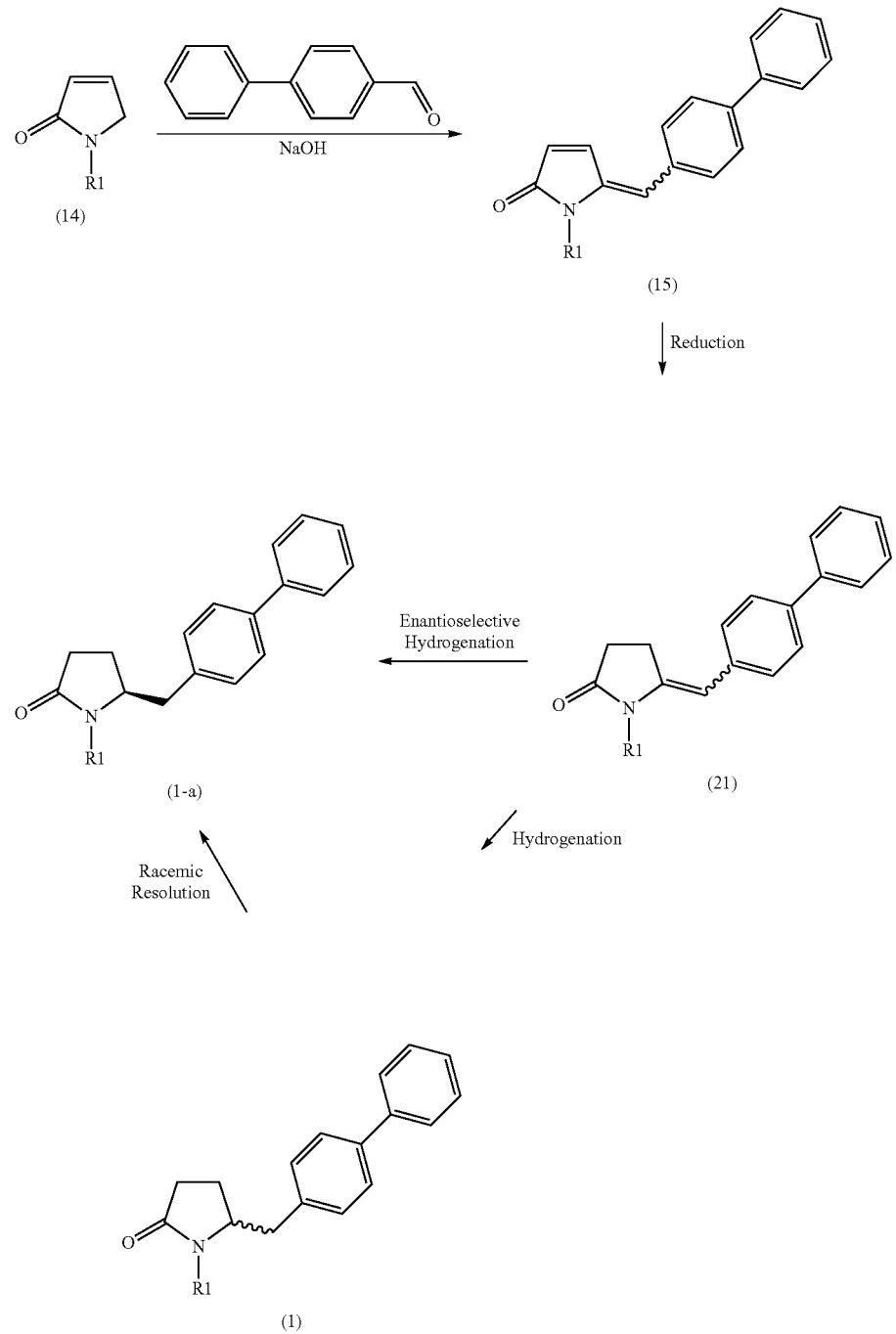

In another embodiment, the present invention relates to the complete reaction sequences described in Scheme 12 converting the compound of formula (14), as defined herein, into the compound of formula (1-a), as define herein, and it also relates to each of the reaction steps shown in Scheme 12. In still another embodiment, the present invention relates to the product obtained according to the complete reaction sequence described in Scheme 12, and it also relates to the product obtained according to each of the reaction steps shown in Scheme 12.

According to Scheme 12, the compound of formula (15), as defined herein, or salt thereof, alternatively, can be reduced chemoselectively to the compound of formula (21), or salt thereof, wherein R1 is hydrogen or a nitrogen protecting group. This reduction can be effected, for example, as described for the compound of formula (16-a) in Scheme 8. Subsequently, the compound of formula (21), as described herein, or salt thereof, can be converted into the compound of formula (1-a), or salt thereof, under enantioselective hydrogenation reaction conditions, for example, as described in J. Chem. Soc., Perkin Trans 1, 1998, 1403, in particular as described for compounds 7a-d therein. Alternatively, standard hydrogenation, for example by the use of Pd/C and hydrogen, of said compound of formula (21), or salt thereof, can afford the compound of (1) or salt thereof. Racemic resolution, as described above, can lead to the compound of formula (1-a), as defined herein, or salt thereof.

Subsection C-6: Method 6

Method 6 for preparing the Key Lactam (1), or salt thereof, also comprises the reaction step of reducing a compound according to formula (16), or salt thereof. However, the method for preparing compound (16), or salt thereof, differs from method 5.

Method 6 comprises a synthesis from 1,5-dihydropyrrol-2-one, or salt thereof, optionally using a chiral phase transfer catalyst to establish the desired configuration at the chiral centre of the compound of formula (16). Subsequent reduction, for example by hydrogenation, for example, as described above for a compound of formula (16-a) in Scheme 8, yields the Key Lactam (1), or salt thereof.

Hence, a further subject of the present invention is a process for preparing a compound according to formula (16), or salt thereof,

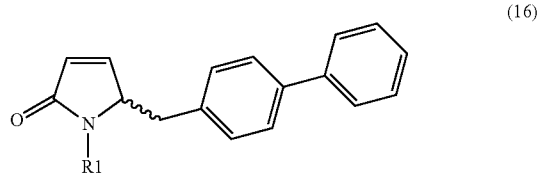

(16)

comprising reacting a compound according to formula (14), or salt thereof,

(14)

with an activated 4-methyl biphenyl to obtain a compound according to formula (16), or salt thereof, in the presence of a base, preferably in the presence of a base and a chiral phase transfer catalyst, wherein in formulae (14) and (16) R1 is hydrogen or a nitrogen protecting group, as defined above.

R1 can be a nitrogen protecting group as described above in section A: The Key Lactam (1), or salt thereof, as such. Preferably, R1 is hydrogen.

Preferably, a chiral phase transfer catalyst is used to produce compound (16), or salt thereof, having a configuration as shown in formula (16-a). Preferably the Key Lactam, or salt thereof, having a configuration according to formula (1-a) is produced.

Generally, known phase transfer catalysts are suitable. Examples of chiral phase transfer catalysts include chiral crown ethers or, more preferably, cinchona alkaloids. Specific examples of suitable chiral phase transfer catalysts are given in issue 17, pages 1 to 15 of "Industrial Phase-Transfer Catalysis", published by PTC Communications, Inc., 900 Briggs Road, Suite 145, Mt. Laurel, N.J. 08054 USA.

The activated 4-methyl biphenyl is a compound of the formula Ph-Ph-CH$_2$—X, wherein X is a leaving group. Generally, the explanations given above in subsection C-3 for leaving groups apply. Preferably, X is halogen, especially bromide.

In a preferred embodiment, the base used in this step is an alkyllithium base, such as BuLi, or an alkali metal hydroxide, such as KOH, or is LDA; for example, as described in Synlett, 2003, (2), 271, in Synlett, 2004, (2), 247 and in Perkin Transactions 1, 1990, (8), 2350.

In a particular embodiment of this route, compounds of formula (16) or (1), or salts thereof, can be resolved, as detailed in subsection C-5, to provide compounds of formula (16-a) or (1-a), or salts thereof, respectively.

A preferred embodiment of method 6 is exemplified in Scheme 13 below.

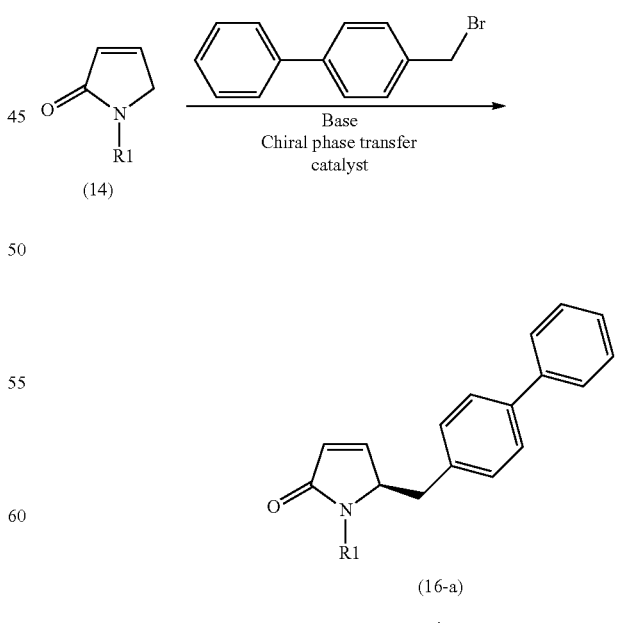

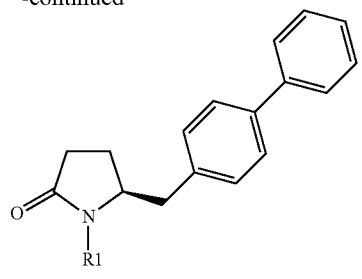

(1-a)

In another embodiment, the present invention relates to the complete reaction sequences described in Scheme 13 converting the compound of formula (14), as defined herein, into the compound of formula (1-a), as define herein, and it also relates to each of the reaction steps shown in Scheme 13. In still another embodiment, the present invention relates to the product obtained according to the complete reaction sequence described in Scheme 13, and it also relates to the product obtained according to each of the reaction steps shown in Scheme 13.

A preferred embodiment of the method described in Scheme 13 relates to compounds wherein R1 is hydrogen. A further preferred embodiment of the method described in Scheme 13 relates to compounds wherein R1 is hydrogen and wherein the reduction of the compound (16-a) to (1-a) takes place with Pd/C and hydrogen.

Particularly preferred bases and chiral transfer catalysts of the first step (conversion of a compound of formula (14), or salt thereof, into a compound of formula (16-a), or salt thereof) in this embodiment are selected, for example, from the group of bases and chiral catalysts above mentioned. Subsequent reduction of the compound of formula (16-a), or salt thereof, to yield the compound of formula (1-a), or salt thereof, can be accomplished, for example, under hydrogenation conditions by the use of Pd/C or as described in previous subsection C-5.

Subsection C-7: Method 7

Method 7 for preparing the Key Lactam (1), or salt thereof, also comprises the reaction steps of hydrogenating a compound according to formula (15), or salt thereof, to obtain compound (16), or salt thereof, and reducing a compound according to formula (16), or salt thereof, to obtain the Key Lactam (1), or salt thereof. However, the method for preparing compound (15), or salt thereof, differs from method 5.

Method 7 starts from an N-protected succinimide, or salt thereof, followed by a chemo- and enantio-selective hydrogenation as the key step.

Hence, a further subject of the present invention is a process for preparing a compound according to formula (15), or salt thereof,

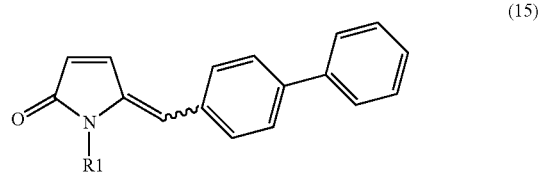

(15)

wherein R1 is hydrogen or a nitrogen protecting group, as defined above, comprising reacting a compound according to formula (17), or salt thereof,

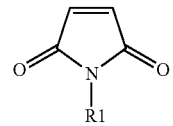

(17)

with an organometallic reagent derived from 4-methyl biphenyl to obtain a compound according to formula (15), or salt thereof. In a preferred embodiment according to this process, the compound of formula (15) has the following stereochemistry

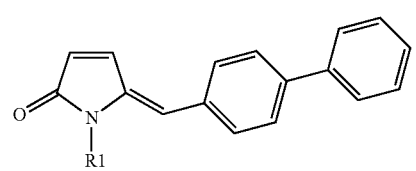

(15-a)

wherein R1 is hydrogen or a nitrogen protecting group, as defined above.

Preferably R1 is hydrogen or a nitrogen protecting group as described above in section A: The Key Lactam (1), or salt thereof, as such. In particular, R1 is pivaloyl or BOC.

The organometallic reagent derived from 4-methyl biphenyl preferably is a compound of the formula Ph-Ph-CH$_2$—Y, preferably 4-biphenyl-CH$_2$—Y, wherein Y is a nucleophilic group. Preferred compounds of formula Ph-Ph-CH$_2$—Y, preferably 4-biphenyl-CH$_2$—Y, are, for example, 4-biphenylmethylmagnesium halides (Grignard reagents). The nucleophilic group Y is preferably a group MX, wherein X is a halogen and M is Mg or Zn. Suitable halides generally are chloride, bromide and iodide, wherein bromide is especially preferred.

Further examples for organometallic reagents derived from 4-methyl biphenyl are 4-biphenylmethyllithium, 4-biphenylmethylcuprate (low- and higher-order cuprates), 4-biphenylmethylzinc. These compounds can be used individually or in the presence of another metal, e.g. copper, zinc, palladium, platinum, iron, iridium or ruthenium.

Preferably, in the above formula Y is MgBr (4-biphenylmethylmagnesium bromide).

A preferred embodiment of method 7 is exemplified in Scheme 14 below.

Scheme 14

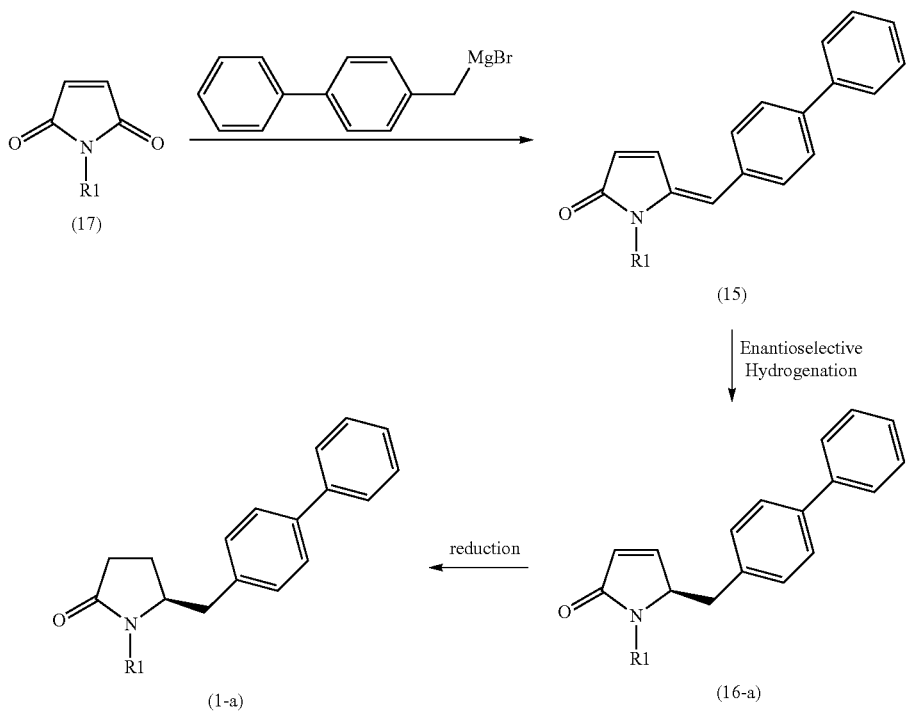

In another embodiment, the present invention relates to the complete reaction sequences described in Scheme 14 converting the compound of formula (17), as defined herein, into the compound of formula (1-a), as define herein, and it also relates to each of the reaction steps shown in Scheme 14. In still another embodiment, the present invention relates to the product obtained according to the complete reaction sequence described in Scheme 14, and it also relates to the product obtained according to each of the reaction steps shown in Scheme 14.

In this embodiment, a compound of formula (15), or salt thereof, is prepared from a compound of formula (17), or salt thereof, under Grignard conditions, for example, analogous to those described in Perkin Transactions 1, 1993, (21), 2567. Next, the compound of formula (15), or salt thereof, can be converted into the compound of formula (16-a), or salt thereof, via enantioselective hydrogenation, for example, as described above. Further reduction of the compound of formula (16-a), or salt thereof, to yield the compound of formula (1-a), or salt thereof, can be accomplished, for example, under hydrogenation conditions. In a preferred embodiment, the reduction of the compound of formula (16-a), or salt thereof, is achieved by the use of Pd/C. Alternatively, the compound of formula (15), which is prepared from a compound of formula (17) as described above, can be converted into the compound of formula (1), preferably of formula (1-a), as described in Schemes 9 to 12.

Subsection C-8: Method 8

In still another embodiment of the present invention, the compound of formula (21), or salt thereof, wherein R1 is hydrogen or a nitrogen protecting group, as described above, can be prepared from a compound of formula (6), or salt thereof, wherein R1 is hydrogen or a nitrogen protecting group, for example, as described in Scheme 14.

Scheme 14

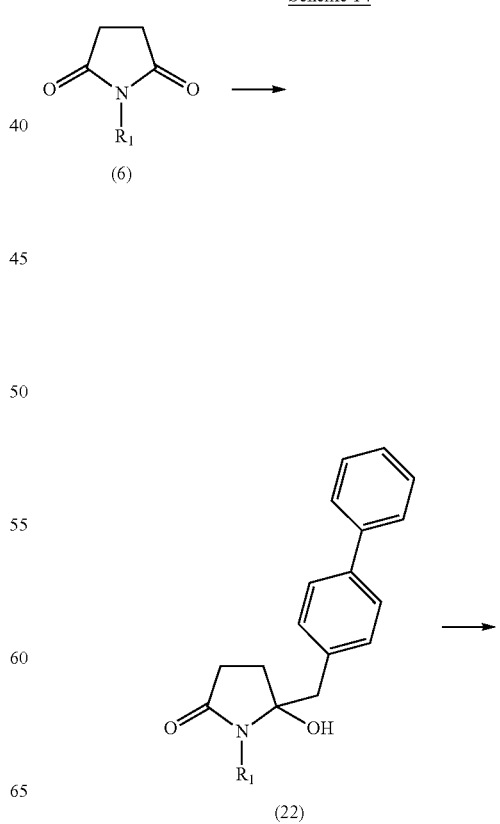

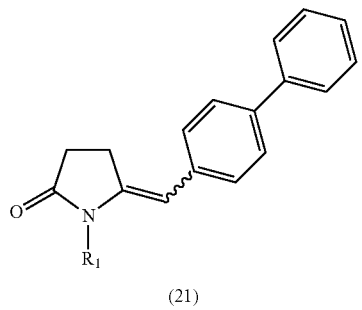

(21)

In another embodiment, the present invention relates to the complete reaction sequences described in Scheme 14 converting the compound of formula (6), as defined herein, into the compound of formula (21), as define herein, and it also relates to each of the reaction steps shown in Scheme 14. In still another embodiment, the present invention relates to the product obtained according to the complete reaction sequence described in Scheme 14, and it also relates to the product obtained according to each of the reaction steps shown in Scheme 14.

In this embodiment, a compound of formula (22), or salt thereof, wherein R1 is hydrogen or a nitrogen protecting group, is prepared from a compound of formula (6), or salt thereof, wherein R1 is hydrogen or a nitrogen protecting group, for example, by the use of an organometallic reagent derived from 4-methyl biphenyl, as described above. Next, the compound of formula (22), or salt thereof, is converted into the compound of formula (21), wherein R1 is as above described, or salt thereof, under dehydration conditions, for example by the use of the Burgess reagent. Alternatively, the tertiary alcohol maybe activated, for example by being mesylated, and subsequent treatment with a base, for example, NaOH, may provide the compound of formula (21) or salt thereof.

In a preferred embodiment according to the process outlined in Scheme 14, the compound of formula (21) has the following stereochemistry

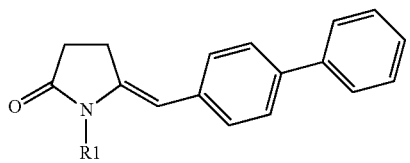

(21-a)

wherein R1 is hydrogen or a nitrogen protecting group, as defined above.

The compound of formula (21), or salt thereof, preferably of formula (21-a), can be converted into the compound of formula (1), or salt thereof, preferably of formula (1-a), or salt thereof, for example, as above described.

Section D: Novel And Inventive Compounds Occurring In One Of The Precedent Sections In the processes shown above several novel and inventive compounds are involved. Consequently, further subjects of the present invention are the compounds shown below.

A compound according to formula (2), or salt thereof,

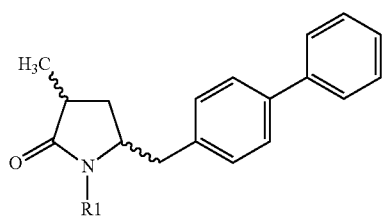

(2)

wherein R1 is hydrogen or a nitrogen protecting group, as defined above, preferably having a configuration according to formula (2-a)

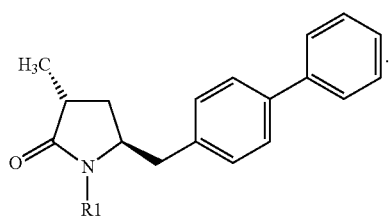

(2-a)

In a preferred embodiment of formula (2-a) R1 is hydrogen or a nitrogen protecting group selected from pivaloyl and t-butyloxycarbonyl (BOC).

A compound according to formula (4), or salt thereof,

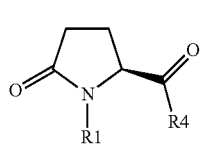

(4)

wherein R1 is hydrogen or a nitrogen protecting group, as defined above, and R4 is morpholine, preferably having a configuration according to formula (4-a)

(4-a)

wherein R1 and R4 are defined as above in formula (4).

A compound according to formula (8), or salt thereof, (8)

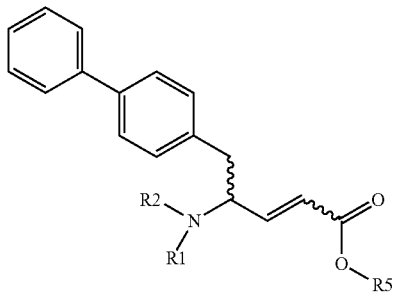

wherein R1 and R2 are independently, of each other, hydrogen or a nitrogen protecting group, as defined above, and R5 is hydrogen or alkyl, preferably having a configuration according to formula (8-a)

(8-a)

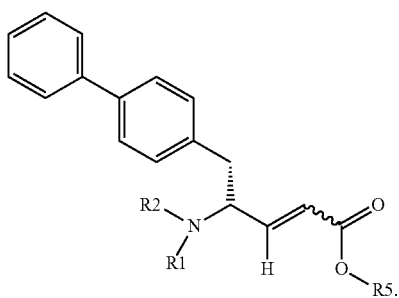

A compound according to formula (9), or salt thereof, (9)

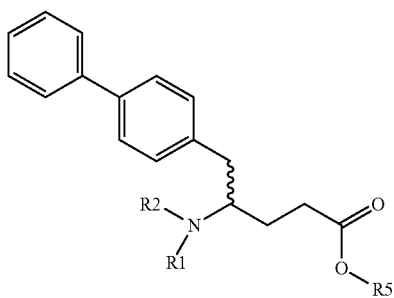

wherein R1 and R2 are independently, of each other, hydrogen or a nitrogen protecting group, as defined above, and R5 is hydrogen or alkyl, preferably having a configuration according to formula (9-a)

(9-a)

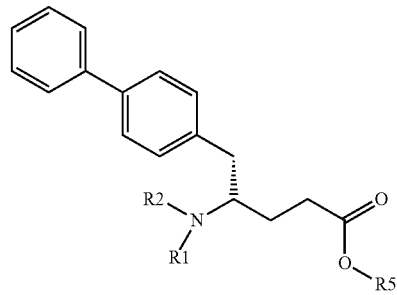

A compound according to formula (10), or salt thereof, (10)

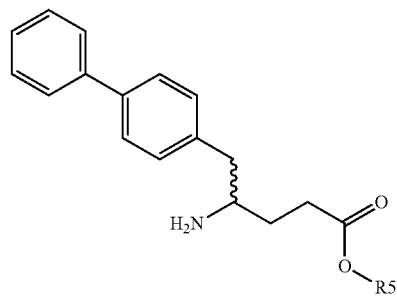

wherein R5 is hydrogen or alkyl, preferably having a configuration according to formula (10-a)

(10-a)

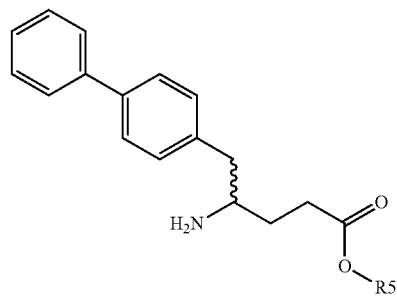

A compound according to formula (13), or salt thereof, (13)

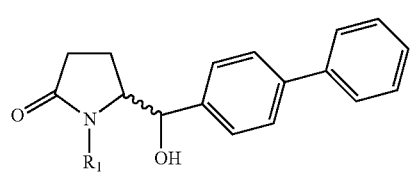

wherein R1 is hydrogen or a nitrogen protecting group, as defined above, preferably having a configuration according to formula (13-a)

A compound according to formula (15), or salt thereof,

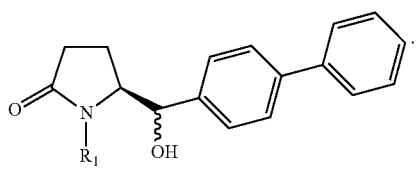
(13-a)

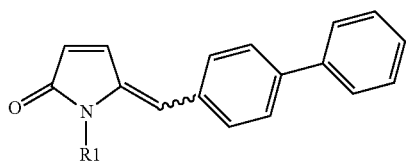
(15)

wherein R1 is hydrogen or a nitrogen protecting group, as defined above.

A compound according to formula (16), or salt thereof,

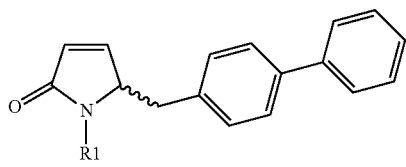
(16)

wherein R1 is hydrogen or a nitrogen protecting group, as defined above, preferably having a configuration according to formula (16-a)

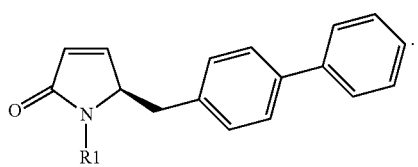
(16-a)

A compound according to formula (20), or salt thereof,

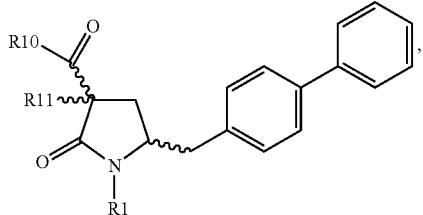
(20)

preferably having a configuration according to formula (20-a)

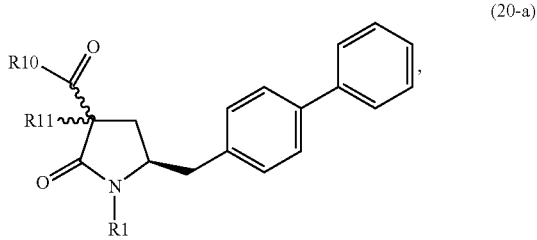
(20-a)

wherein in the above formulae R1 is hydrogen or a nitrogen protecting group, as defined above, R10 is a group which can be saponified and/or decarboxylated, as defined herein, and R11 is hydrogen or methyl. Preferably, R10 is —O-alkyl, in particular —O-Et or —O-Me, preferably —O-Et, or is —O-aryl, in particular aryl is phenyl. In another preferred embodiment R10 is —O-alkylaryl, for example, —O-benzyl.

A compound according to formula (21), or salt thereof,

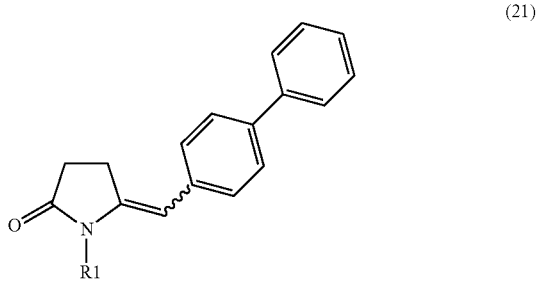
(21)

wherein R1 is hydrogen or a nitrogen protecting group, as defined above.

A compound according to formula (22), or salt thereof,

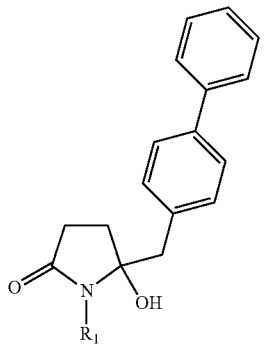
(22)

wherein R1 is hydrogen or a nitrogen protecting group, as defined above.

A compound according to formula (5), or salt thereof, in crystalline form,

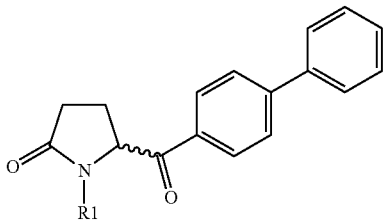

wherein R1 is hydrogen or a nitrogen protecting group, as defined above, preferably having a configuration according to formula (5-a)

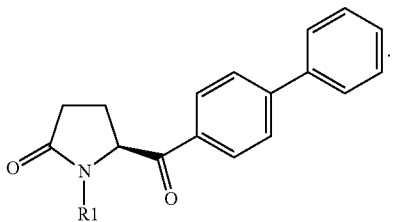

In a preferred embodiment the crystalline compounds according to formula (5-a), or salts thereof, comprise a monoclinic crystal system. Further preferred, the crystalline products of the invention comprise the space group P21.

In further embodiment, the invention relates to a compound of the formula (1), (1-a), (1-b), (1'), (1"), (1'-a), (1"-a), (2), (2-a), (2-b), (2'), (2'-a), (2"), (2"-a), (3), (3-a), (3-b), (4), (4-a), (5), (5-a), (7), (7-a), (8), (8-a), (9), (9-a), (10), (10-a), (11), (11-a), (12), (12-a), (13), (13-a), (14), (15), (15-a), (16), (16-a), (17), (18), (19), (20), (20-a), (21), (21-a) or (22), or salts thereof, as defined hereinbefore or hereinafter; more preferably a compound of the formula (1), (1-a), (1-b), (1'), (1"), (1'-a), (2), (2-a), (2-b), (2'), (2' a), (3), (3-a), (4), (4-a), (5), (5-a), (7), (7-a), (8), (8-a), (9), (9-a), (10), (10-a), (13), (13-a), (15), (16), (16-a), (20), (20-a), (21) or (22), or salts thereof, as defined hereinbefore or hereinafter; in particular wherein R1 is selected from the preferred definitions described hereinbefore.

In still further embodiment, the invention relates to a compound of the formula (1), (2), (3) or (10), preferably (1-a), (2-a) or (10-a), or salts thereof, in crystalline form, as defined hereinbefore or hereinafter.

Particular embodiments of the invention are provided in the Examples—the invention thus, in a very preferred embodiment, relates to a compound of the formula above mentioned or a salt thereof, selected from the compounds given in the Examples, as well as the use thereof according to the invention.

Section E: Examples

The following Examples serve to illustrate the invention without limiting the scope thereof, while they on the other hand represent preferred embodiments of the reaction steps, intermediates and/or the process of the present invention.

Abbreviations
δ chemical shift
μl microlitre
Ac acetyl
Bn benzyl
Boc tert-butoxycarbonyl
BOC$_2$O di-tert-butyl carbonate
Cbz benzyl carbamate
Cbz-Cl benzyl chloroformate
de diastereomeric excess
DMAP 4-(dimethylamino)pyridine
DMF N,N-dimethylformamide
DMPU 1,3-dimethyl-3,4,5,6-tetrahydro-2(1H)-pyrimidinone
DMSO dimethylsulfoxide
ee enantiomeric excess
ES electrospray
ESI electrospray ionisation
Et ethyl
EtOAc ethyl acetate
h hour(s)
HNMR proton nuclear magnetic resonance
HOBt 1-hydroxybenzotriazole
HPLC high performance liquid chromatography
i-Pr isopropyl
iPrOAc isopropyl acetate
IR infra red
KHMDS potassium bis(trimethylsilyl)amide
L litre
LC-MS liquid chromatography-mass spectrometry
LDA lithium diisopropylamide
LHMDS lithium bis(trimethylsilyl)amide
M molarity
m/e mass-to-charge ratio
Me methyl
mg milligram
min minute(s)
mL millilitre
mmol(s) millimole(s)
mol(s) mole(s)
MS mass spectrometry
NaHMDS sodium bis(trimethylsilyl)amide
nm nanometre
NMR nuclear magnetic resonance
Pd/C palladium on carbon
Ph phenyl
Piv pivaloyl
Piv-Cl pivaloyl chloride
ppm parts per million
psi pounds per square inch
RT room temperature
SEM 2-(Trimethylsilyl)ethoxymethyl
SEM-Cl (2-chloromethoxyethyl)-trimethylsilane
TES triethylsilyl
TFA trifluoroacetic acid
THF tetrahydrofuran
TLC thin layer chromatography
TMEDA N,N,N,N-tetramethylethylenediamine
$t_R$ retention time
Ts tosylate/tosyl

Example 1-1

(S)-5-(morpholine-4-carbonyl)pyrrolidin-2-one

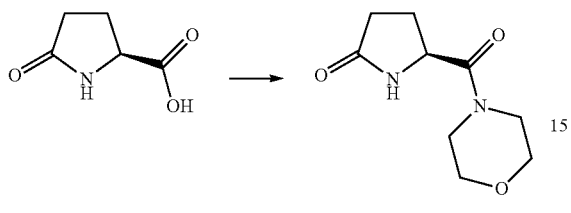

Method 1

To a mixture of 48 g dicyclohexylcarbodiimide, 30 g commercially available L-pyroglutamic acid and 3.1 g hydroxybenzotriazole 20.2 g of morpholine were added in 170 ml dichloromethane at about −15° C. The mixture was allowed to warm to room temperature. The suspension was filtered and diluted with 290 ml THF. The mixture was concentrated to obtain a suspension, which was filtered yielding 41 g of (S)-5-(morpholine-4-carbonyl)pyrrolidin-2-one.

Melting point (hereinafter referred to as "mpt"): 130-132° C. $^1$H-NMR (DMSO): 1.87 (1H); 2.19 (1H); 2.28 (1H); 3.35-3.65 (8H); 4.51 (1H); 7.70 (1H). MS (ESI, m/e) 199 [M+H]$^+$; 397 [2M+H]$^+$.

Enantiomeric excess (ee): 98.0% (4-a, R1=H; R4=morpholine) as determined by GC.

Method 2

A suspension of 5 g S-pyroglutamic acid (38.737 mmol) in 50 ml THF and 250l DMF is cooled to 0° C. and 3.09 ml (5.07 g, 42.611 mmol) thionylchloride is added within 5 min. The reaction mixture is allowed to warm up to room temperature within 2 h. The resulting clear solution is again cooled to 0° C. and is then treated with 7.25 ml (7.25 g, 170.1 mmol) morpholine. After warming up the reaction mixture to ambient temperature within 2 h, the suspension is filtered.

The filtrate is concentrated under reduced pressure to give a crude residue. Enantiomeric excess (ee): 98.0% (4-a, R1=H; R4=morpholine) as determined by GC

Method 3

The reaction vessel is charged with 30 g L-pyroglutamic acid and 4.71 g 1-hydroxybenzotriazole hydrate. The solids are then suspended in 190 ml anhydrous acetonitrile and the mixture is then heated to 45° C. Subsequently, 20.24 ml morpholine is added via a dropping funnel within 20 min, and the dropping funnel is then washed with 5 ml anhydrous acetonitrile. The resulting mixture is then heated to 65° C. and 29.32 g N—N'-diisopropylcarbodiimide added within 1 h via a dropping funnel. After complete addition, the dropping funnel is washed with 5 ml anhydrous acetonitrile and the reaction mixture is stirred at 65° C. for an additional 30 min. The resulting suspension is then cooled to ambient temperature, filtered and the filter cake washed with 3×30 ml acetonitrile. The filtrate is concentrated under heating and reduced pressure to approx. ½ of its original volume and the residue is then seeded with 16 mg (S)-5-(morpholine-4-carbonyl)pyrrolidine-2-one. Concentration under reduced pressure is continued until approx ⅓ of the original volume of the filtrate is reached. While further concentrating the filtrate under reduced pressure and removing approx. 95 ml of distillate, simultaneously 210 ml 2-methyltetrahydrofuran is added. The suspension is then cooled to 0° C. and the solids are isolated by filtration. The filter cake is washed with 3×20 ml icooled 2-methyltetrahydrofuran and dried at 55° C. under vacuum to give 42.54 g of (S)-5-(morpholine-4-carbonyl) pyrrolidine-2-one as fine white crystals (98.0% purity by HPLC, ee (HPLC)>99.6% [4-a, R1=H; R4=morpholine]).

Example 1-2

(R)-5-(morpholine-4-carbonyl)pyrrolidin-2-one

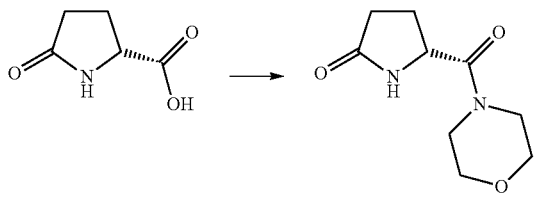

To a mixture of 30 g R-pyroglutamic acid and 4.71 g hydroxybenzotriazole in 200 ml acetonitrile is added 20.24 g of morpholine at 50° C. The mixture is heated to 60° C. and 29.32 g N,N'-diisopropylcarbodiimide are added. After 1 h, the suspension is cooled to room temperature and the precipitate removed by filtration. The mother liquor is distilled under reduced pressure. During the distillation methyltetrahydrofuran is added. The resulting suspension is cooled to 0° C. and then filtered. The filter cake is washed with methyltetrahydrofuran and dried under reduced pressure to yield (R)-5-(morpholine-4-carbonyl)pyrrolidin-2-one. $^1$H-NMR (DMSO): 1.88 (1H); 2.11 (1H); 2.32 (1H); 3.46 (4H); 3.59 (4H); 4.54 (1H, dd, J=3.3, 8.8); 7.72 (1H). MS (ESI, m/e) 199 [M+H]$^+$; 397 [2M+H]$^+$. IR (solution in CH$_2$Cl$_2$, /cm$^{-1}$): 3341; 2860; 1709; 1694; 1639; 1462; 1270; 1255; 1116; 655. Enantiomeric excess (ee): 99.6% (4-b, R1=H; R4=morpholine) as determined by GC

Example 1-3

(R/S)-5-(morpholine-4-carbonyl)pyrrolidin-2-one

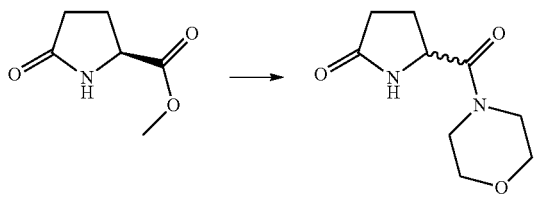

A mixture of 143 g of pyroglutamic acid methyl ester (1 mol) and 139 g morpholine (1.60 mol) in 900 ml of xylene is heated to 140° C. for 20 h. The xylene is evaporated to a volume of 500 ml. From the suspension obtained, the precipitate is filtered off, washed with THF to yield the desired compound after drying in vacuo. From the filtrate the solvent is evaporated completely. This crude product [(R/S)-5-(morpholine-4-carbonyl)pyrrolidin-2-one] is filtered over 800 g silica gel with THF as the solvent and evaporated to dryness to yield a second crop of the desired compound. This compound is used directly in the next step. HPLC analysis shows the material to be in an enantiomeric ratio: 55.8:44.2 [(4-a, R1=H; R4=morpholine): (4-b, R1=H; R4=morpholine), respectively].

Example 1-4

(S)-5-(morpholine-4-carbonyl)pyrrolidin-2-one

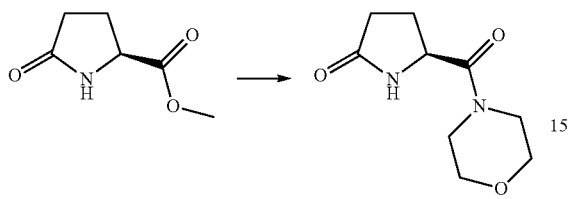

L-pyroglutamic acid methyl ester (23.91 g, 177 mmol), morpholine (21.8 g, 250 mmol) and 4-dimethylaminopyridine (0.2 g, 1.64 mmol) are heated under reflux in toluene (130 ml) for 12 hours. The product precipitates as an oil. The oil is separated from the toluene, diluted with dichloromethane (100 ml) and washed successively with 0.1 M HCl, 0.1 M NaOH and water (50 ml each). The dichloromethane phase is concentrated to obtain a suspension, which is filtered yielding the crude product. The crude product is dissolved in THF (200 ml) at 45° C. and, upon cooling in an ice bath, (S)-5-morpholine-4-carbonyl)pyrrolidin-2-one precipitates as white crystals. Enantiopurity (GC) 88.7% (S)-Enantiomer.

Example 1-5

(R/S)-5-(morpholine-4-carbonyl)pyrrolidin-2-one

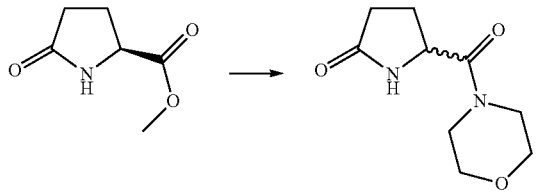

A mixture of 14.5 g of pyroglutamic acid methylester (100 mmol) and 13.1 g morpholine (150 mmol) in 80 ml of toluene is heated to reflux (110° C.) for 48 h. During this reaction time, methanol formed is distilled from the reaction mixture. Finally two phases are formed. The upper, toluene phase, was decanted and the lower product phase is filtered over silica gel (180 g) with ethyl acetate:methanol=70:30. the solvent is evaporated to yield the product as an oil. The enantiomeric ratio is 93:7 [(4-a, R1=H; R4=morpholine) to (4-b, R1=H; R4=morpholine), respectively] and the GC purity is 96.4% area %.

HPLC Method (Example 1):
Column: Chirobiotic-T; 100×4.6 mm; 5 µm. Mobile Phase A (0.01 M NH$_4$OAc in MeOH+0.1% TFA). Isocratic: 0 min (100%); 10 min (100% A). Flow rate: 1.0 ml min$^{-1}$. Wavelength: 210 nm. Column temperature: 10° C.
Retention Times:
4-a (R1=H; R4=morpholine): 2.3 min
4-b (R1=H; R4=morpholine): 2.8 min GC Method (Example 1):
Column: Fused-Silica-Capillary, CHIRALDEX G-BP; 20 m×0.25 mm. Pre-column: Deactivated fused silica, 1 m×0.53 mm. Injection block temperature: 250° C. Detector temperature: 300° C. Carrier gas: helium, 3.0 ml min$^{-1}$, constant flow. Injection volume: 2.0 µl. Split ratio: 20:1. Oven temperature: 200° C. (initial) isocratic for 50 min.
Retention Times:
4-a (R1=H; R4=morpholine): 27.5 min
4-b (R1=H; R4=morpholine): 30.1 min Example 2-1

(S)-5-(biphenyl-4-carbonyl)pyrrolidin-2-one

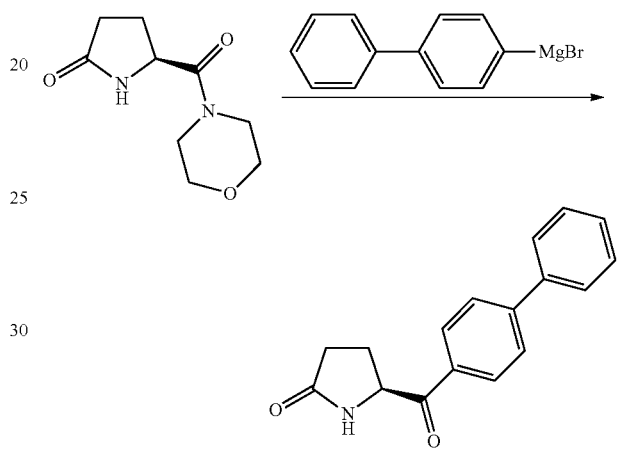

Method 1

39 g of (S)-5-(morpholine-4-carbonyl)pyrrolidin-2-one of example 1 were suspended in 300 ml of dry, degassed THF. The solution was cooled to about −15° C. 200 ml of a 2.2 M solution of 4-biphenylmagnesiumbromide in THF were added over about 20 min. The mixture was allowed to warm to room temperature over about 19 hours. The mixture was quenched by the addition of ice-cold 2 M hydrochloric acid and the organic layer was separated. A partial concentration yielded a precipitate, which was collected by filtration, washed with water and toluene to obtain 44 g of (S)-5-(biphenyl-4-carbonyl)pyrrolidin-2-one. mpt 163-203° C. (decomp.). $^1$H-NMR (DMSO): 1.88 (1H); 2.15 (2H); 2.53 (1H); 5.30 (1H); 7.34-7.60 (3H); 7.77 (2H); 7.90 (3H); 8.11 (2H). Enantiomeric excess (ee): 98.08% (5-a, R1=H) as determined by hplc.

The X-ray Structure of the obtained crystals is shown in FIG. 4. Respective crystal data is as follows:

Empirical formula $C_{17}H_{15}NO_2$; formula weight 265.30; temperature 100(2) K; wavelength 1.54178 Å; crystal system monoclinic; space group P21 unit cell dimensions a=10.362 (3) Å, α=90°, b=8.236(2) Å, b=90.872(15)°, c=15.583(4) Å, g=90°; volume 1329.7(6) Å3; Z 4; density (calculated) 1.325 mg/m$^3$; absorption coefficient 0.698 mm$^{-1}$; F(000) 560.

Reflections in the X-ray diffraction pattern show the following interlattice plane intervals (average 2θ in [°] are indicated with error limit of ±0.2): 2θ in [°]: 3.8, 5.6, 8.3, 10.1, 13.4, 14.2, 14.6, 17.6, 18.9, 19.8, 20.4, 20.7, 21.1, 22.7. Data taken using a Bruker D8 Advance diffractometer using Cu-Kα radiation.

Method 2

50 g of (S)-5-(morpholine-4-carbonyl)pyrrolidin-2-one are suspended in 450 ml of THF. The solution is then cooled to about −5° C. Next, 127 ml of isopropylmagnesium chloride solution in THF (1.90 M) is added over 30 min. The mixture is stirred for a further 30 min and then 300 ml of 4-biphenyl-magnesium bromide solution in THF (1.01 M) is added. The mixture is warmed to room temperature. Stirring is continued for 10 h. The mixture is then added to 585 ml hydrochloric acid (2 M) at 0° C. The mixture is then warmed to room temperature. Subsequently, 162 ml sodium hydroxide (2 M) is added. The mixture is heated to 60° C. and the volatile solvents removed under vacuum. To the residue is added 250 ml toluene and the mixture is stirred for 30 min. The mixture is cooled to room temperature. A solid is collected by filtration and washed with 150 ml toluene and 150 ml water to provide, after drying, (S)-5-(biphenyl-4-carbonyl)pyrrolidin-2-one. Enantiomeric excess (ee): 99.8% (5-a, R1=H) as determined by hplc.

Example 2-2

(R)-5-(biphenyl-4-carbonyl)pyrrolidin-2-one

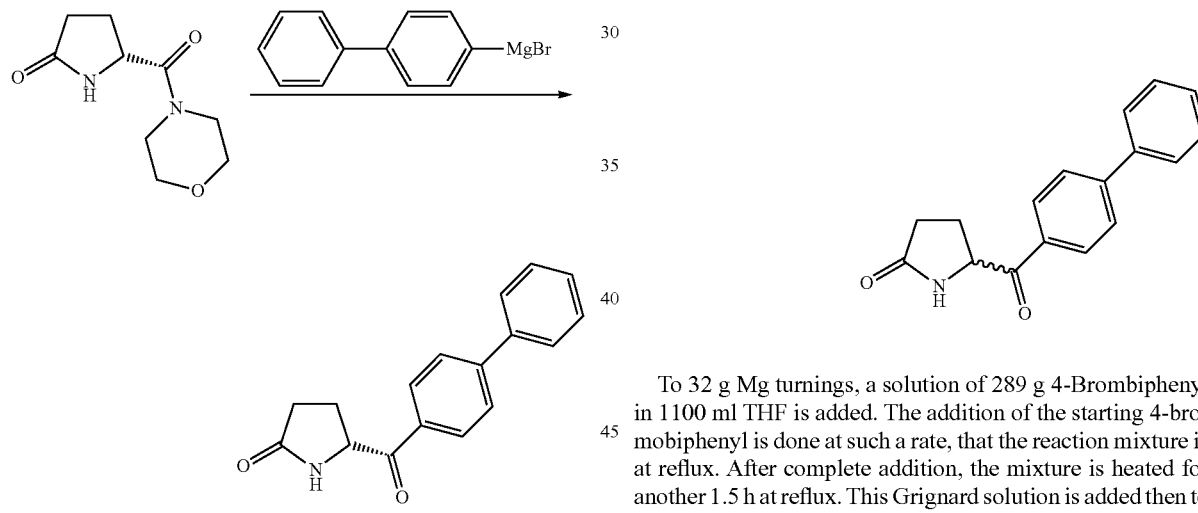

35.48 g of (R)-5-(morpholine-4-carbonyl)pyrrolidin-2-one are suspended in 302 ml of dry, degassed THF. The solution is cooled to −5° C. 92.3 ml of a solution of isopropylmagnesiumchloride in tetrahydrofuran (1.9M) is added over 30 min. Subsequently 210 ml of a solution of 4-biphenylmagnesiumbromide in THF (1.0M) is added over 20 min. The mixture is allowed to warm to room temperature over 19 hours. The mixture is quenched by the addition of ice-cold 2 M hydrochloric acid and the organic solvent removed under reduced pressure. To the resulting suspension, 133 ml toluene is added and the precipitate, which is collected by filtration, is washed with water and toluene. The filter cake is dried under reduced pressure to provide (R)-5-(biphenyl-4-carbonyl)pyrrolidin-2-one. $^1$H-NMR (DMSO): 1.93 (1H); 2.17 (2H); 2.55 (1H); 5.33 (1H, dd, J=4.5, 9.6); 7.45 (1H); 7.53 (2H, t, J=7.6); 7.77 (2H, d, J=7.1); 7.89 (3H, t, J=8.5); 8.11 (2H, d, J=8.5). MS (ESI, m/e) 266 [M+H]$^+$. IR (solution in CH$_2$Cl$_2$, /cm$^{-1}$): 3203; 3103; 2880; 1699; 1684; 1604; 1407; 1238; 980; 769; 733; 698. Enantiomeric excess (ee): 99.0% (5-b, R1=H) as determined by hplc.

Example 2-3

(R)-5-(biphenyl-4-carbonyl)pyrrolidin-2-one and (S)-5-(biphenyl-4-carbonyl)pyrrolidin-2-one

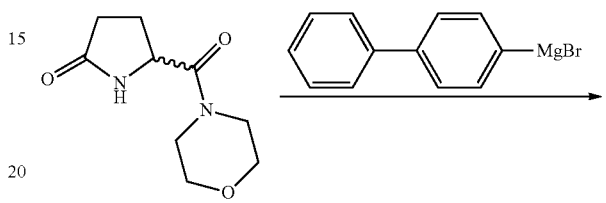

To 32 g Mg turnings, a solution of 289 g 4-Brombiphenyl in 1100 ml THF is added. The addition of the starting 4-bromobiphenyl is done at such a rate, that the reaction mixture is at reflux. After complete addition, the mixture is heated for another 1.5 h at reflux. This Grignard solution is added then to a solution of 100 g of (R/S)-5-(morpholine-4-carbonyl)pyrrolidin-2-one in 1000 l THF at <−50° C. The cooling bath is removed and the reaction mixture is stirred over night. The reaction mixture is then quenched with H$_2$O/NH$_4$Cl and 2M HCl. The pH of the reaction mixture is pH 8. The reaction mixture is concentrated to a volume of 360 ml and the precipitate removed by filtration. The precipitate is then stirred in 400 ml toluene at 70° C. and is then filtered, to yield after drying, (S)-5-(biphenyl-4-carbonyl)pyrrolidin-2-one and (R)-5-(biphenyl-4-carbonyl)pyrrolidin-2-one in a ratio of 64:38, respectively, as determined by hplc. 1H-NMR: (400 MHz; CDCl$_3$): 2.04-2.16 (m, 1H), 2.26-2.45 (m, 2H), 2.54-2.67 (m, 1H), 5.08-5.13 (m, 1H), 7.32-7.94 (m, 9H).

HPLC Method (Example 2):

Column: Chiralpak AS-RH (DAICEL); 150×4.6 mm; 5 μm. Mobile Phase A (water); Mobile Phase B (Acetonitrile). Isocratic: 0 min (50% B); 15 min (50% B). Flow rate: 0.8 ml min$^{-1}$. Wavelength: 285 nm. Temperature 25° C.

Retention Times:
5-a (R1=H): 7.1 min
5-b (R1=H): 6.5 min

Example 3-1

(S)-5-biphenyl-4-ylmethylpyrrolidin-2-one [Key Lactam (1-a, R1=H)]

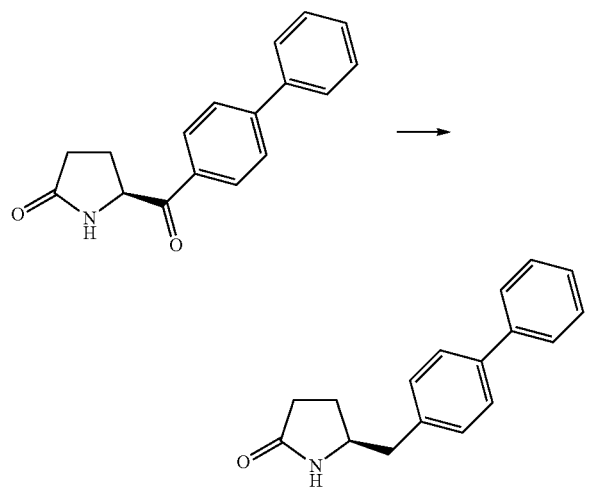

Method 1

200 mg of (S)-5-(biphenyl-4-carbonyl)pyrrolidin-2-one of example 2 were suspended in 3 ml THF. 20 mg of sulphuric acid and 5 mg of palladium on carbon 10% m/m (W. C. Heraeus GmbH, Type K-0218) were added and the mixture was stirred under 3 bar hydrogen for about 20 hours. The mixture was neutralised with 50 mg sodium carbonate and the precipitate removed by filtration. The filtrate was concentrated to dryness to obtain (S)-5-biphenyl-4-ylmethylpyrrolidin-2-one. $^1$H-NMR (DMSO): 1.66 (1H, m, 4-CHH); 1.94 (1H, m, 4-CHH); 2.01 (2H, m, 3-CH$_2$); 2.65 (1H, dd, 1-CHH); 2.84 (1H, dd, 1-CHH); 3.78 (1H, m, 5-CH); 7.30 (2H, d, aromatic); 7.33 (1H, m, aromatic); 7.43 (2H, t, aromatic); 7.57 (2H, d, aromatic); 7.63 (2H, m, aromatic); 7.81 (1H, s, NH). m/z: 252 (MH$^+$, 100%).

The X-ray Structure of the obtained crystals is shown in FIG. 1.

| Crystal data [recorded at 100(2)K] | |
|---|---|
| Empirical formula | C$_{17}$H$_{17}$NO |
| Formula weight | 251.32 |
| Crystal system | Monoclinic |
| Space group | P21 |
| Cell parameters | a = 5.725(2) Å |
| | b = 26.815(9) Å |
| | c = 25.932(8) Å |
| | α = 90° |
| | β = 94.280(18)° |
| | γ = 90° |
| Volume of unit cell | 3970(2) Å$^3$ |
| Z* | 12 |
| Calculated density | 1.261 mg m$^{-3}$ |

*(number of asymmetric units in the unit cell)

Method 2

100 g of (S)-5-(biphenyl-4-carbonyl)pyrrolidin-2-one are suspended in 860 ml THF. 2.4 g of sulphuric acid and 10 g of palladium on carbon 10% m/m (W. C. Heraeus GmbH, Type K-0218) are then added. The mixture is then warmed to 40° C. and a pressure of 3 bar hydrogen gas applied. After 10 h, the mixture is cooled to room temperature, filtered and the filter cake is washed with 300 ml THF. 100 ml water is added to the combined filtrates and 21.9 g sodium hydroxide solution (2 M) is added. The mixture is then warmed to 60° C. and the volatile solvents are removed under vacuum. The resulting suspension is filtered and the cake is washed with 200 ml water. The solid is then added to 820 ml isopropyl acetate at 65° C. and is partially concentrated. The mixture is then cooled to 3° C. and the solid collected by filtration to provide, after drying, (S)-5-biphenyl-4-ylmethylpyrrolidin-2-one.

Method 3

(S)-5-biphenyl-4-ylmethylpyrrolidin-2-one (106 mg) is added to toluene (2 ml) and 10% Pd/C (10.6 mg, 10 wet wt % loading, type 394 (6249) catalyst, Johnson Matthey) is added. Hydrogen pressure is applied to 30 psi and the mixture is heated to 70° C. After 16 h, the mixture is cooled to room temperature. Analysis by hplc showed 94% purity.

Method 4

(S)-5-biphenyl-4-ylmethylpyrrolidin-2-one (106 mg) is added to toluene (2 ml) and 10% Pd/C (10.6 mg, 10 wet wt % loading, type 338 catalyst, Johnson Matthey) is added. Hydrogen pressure is applied to 30 psi and the mixture is heated to 70° C. After 16 h, the mixture is cooled to room temperature. Analysis by hplc showed 98% purity.

Method 5

(S)-5-biphenyl-4-ylmethylpyrrolidin-2-one (106 mg) is added to toluene (2 ml) and 10% Pd/C (10.6 mg, 10 wet wt % loading, type Mod (72595) catalyst, Johnson Matthey) is added. Hydrogen pressure is applied to 30 psi and the mixture is heated to 70° C. After 16 h, the mixture is cooled to room temperature. Analysis by hplc showed 96% purity.

Method 6

(S)-5-biphenyl-4-ylmethylpyrrolidin-2-one (848 mg) is added to toluene (4 ml) and 10% Pd/C (85 mg, 10 wet wt % loading, type 39 catalyst, Johnson Matthey) is added. Hydrogen pressure is applied to 30 psi and the mixture is heated to 70° C. After 16 h, the mixture is cooled to room temperature. Analysis by hplc showed 97% purity.

Method 7

(S)-5-biphenyl-4-ylmethylpyrrolidin-2-one (5.07 g) is added to toluene (24 ml) and 10% Pd/C (0.25 g, 5 wet wt % loading, type 39 catalyst, Johnson Matthey) is added. Hydrogen pressure is applied to 30 psi and the mixture is heated to 70° C. After 16 h, the mixture is cooled to room temperature. The catalyst is filtered. Product is obtained by precipitation with heptane. Analysis by hplc showed 97% purity.

Method 8

(S)-5-biphenyl-4-ylmethylpyrrolidin-2-one (848 mg) is added to toluene (4 ml) and 10% Pd/C (85 mg, 5 wet wt % loading, type 394 (6065) catalyst, Johnson Matthey) is added. Hydrogen pressure is applied to 30 psi and the mixture is heated to 70° C. After 16 h, the mixture is cooled to room temperature. Analysis by hplc showed 97% purity.

Method 9

(S)-5-biphenyl-4-ylmethylpyrrolidin-2-one (848 mg) is added to toluene (4 ml) and 10% Pd/C (42 mg, 5 wet wt % loading, type 394 (6065) catalyst, Johnson Matthey) is added. Hydrogen pressure is applied to 30 psi and the mixture is heated to 70° C. After 16 h, the mixture is cooled to room temperature. Analysis by hplc showed 97% purity.

Example 3-2

(R)-5-biphenyl-4-ylmethylpyrrolidin-2-one [Key Lactam (1-b, R1=H)]

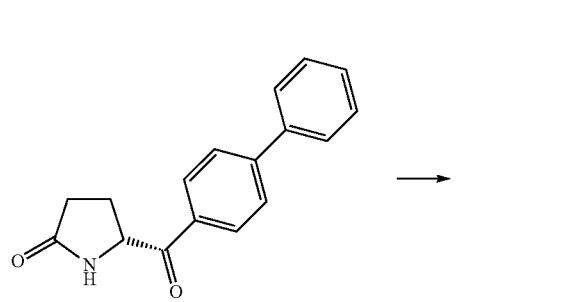

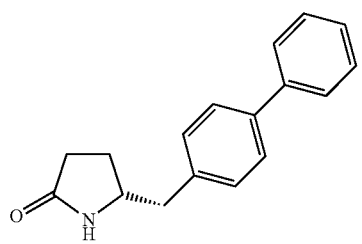

14 g of (R)-5-(biphenyl-4-carbonyl)pyrrolidin-2-one are suspended in 80 ml tetrahydrofuran. Subsequently 331 mg of concentrated sulphuric acid are added and the reaction vessel is purged with argon. 1.4 g of palladium on carbon 10% m/m (W. C. Heraeus GmbH, Type K-0218) is added and the mixture is stirred under an atmosphere of hydrogen (3 bar) at 30° C. for 20 h. The black suspension is filtered and the filter cake is washed with tetrahydrofuran. After the addition of 50 ml water, the pH of the emulsion is adjusted to pH 5.5 using sodium hydroxide solution (2M). Under reduced pressure, the organic solvent is removed and 100 ml of isopropyl acetate are added. The aqueous layer is then separated and the remaining organic layer is concentrated to approx. half of its original volume. The suspension is cooled to −5° C. and filtered. The filter cake is washed with cooled isopropyl acetate and is dried under reduced pressure to give (R)-5-biphenyl-4-ylmethylpyrrolidin-2-one as colourless crystals. $^1$H-NMR (CDCl$_3$): 1.93 (1H); 2.37 (3H); 2.80 (1H, dd, J=8.5, 13.5); 2.92 (1H, dd, J=5.4, 13.5); 3.95 (1H); 5.70 (1H); 7.29 (1H, d, J=7.5); 7.38 (1H); 7.47 (2H); 7.59 (4H). MS (ESI, m/e) 252 [M+H]$^+$; 503 [2M+H]$^+$. IR (solution in CH$_2$Cl$_2$, /cm$^{-1}$): 3191; 3055; 2930; 1692; 1489; 1272; 762; 692.

Example 3-3

(R/S)-5-biphenyl-4-ylmethylpyrrolidin-2-one [Key Lactam (1, R1=H)]

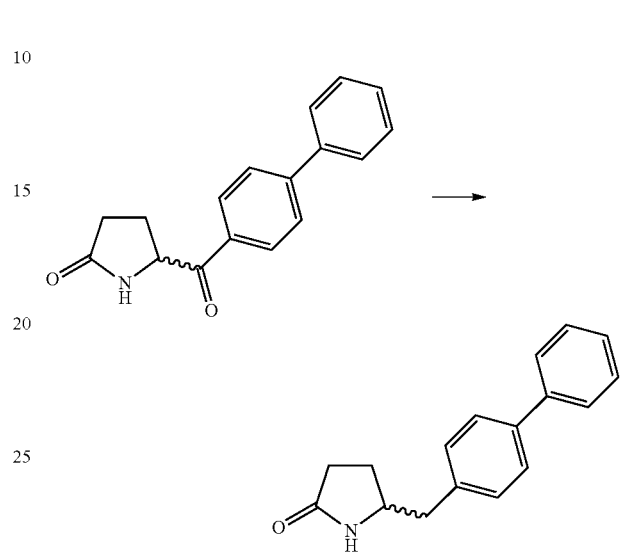

A mixture of 26.5 g (100 mmol) (R/S)-5-(biphenyl-4-carbonyl)pyrrolidin-2-one, 3.0 g Pd/C (10% PD CP 4505 D/R Catalyst, BASF), 5 g conc. H$_2$SO$_4$ in 300 ml THF and 300 ml MeOH are hydrogenated at 1 atm pressure and heated at 50° C. After 10 h the hydrogen uptake stops. The catalyst is filtered off, washed with methanol and the resulting filtrate is concentrated in vacuo. The evaporation residue is dissolved in toluene and is washed with aqueous Na$_2$CO$_3$ solution. A part of the product precipitates and is filtered and dried in vacuo (96.5% HPLC area %). The toluene phase is washed twice with H$_2$O and evaporated completely, to yield further crude product. This further crude product is purified over silica gel chromatography with toluene/methanol=4:1, to yield the product. This product is stirred in 70 ml toluene at 60° C. for 2 h. Then 70 ml heptanes fraction are added and the precipitate is filtered. The precipitate is dried in vacuo to yield (R/S)-5-biphenyl-4-ylmethylpyrrolidin-2-one (96.5% HPLC area %). $^1$H NMR (DMSO): 1.69 (1H), 1.96-2.05 (2H), 2.67 (1H), 2.84 (1H), 3.80 (1H), 7.31 (2H), 7.44 (2H), 7.57 (2H), 7.63 (2H), 7.74 (1H).

HPLC Method 1 (Example 3):
Column: YMC-Pack ODS-AQ HP; 150×3.0 mm; 3 μm. Mobile Phase A (10 mM KH$_2$PO$_4$ in water); Mobile Phase B (Acetonitrile). Gradient: 0 min (25% B); 7 min (40% B); 10 min (40% B); 12 min (80% B); 20 min (80% B); 20.1 min (25% B). Flow rate: 1.0 ml min$^{-1}$. Wavelength: 210 nm. Temperature 45° C.

Retention Times:
  13 (R1=H): 7.3 min and 7.4 min
  5 (R1=H): 8.9 min
  1 (R1=H): 10.9 min HPLC Method 2 (Example 3):
Column: Chiralpak AS-RH (DAICEL); 150×4.6 mm; 5 μm. Mobile Phase A (water); Mobile Phase B (Acetonitrile). Isocratic: 0 min (60% B); 15 min (60% B).

Flow rate: 0.8 ml min$^{-1}$. Wavelength: 254 nm. Temperature 25° C.

1-a (R1=H): 9.9 min 1-b (R1=H): 8.3 min

Example 4

(S)-5-biphenyl-4-ylmethyl-1-(2,2-dimethylpropionyl)pyrrolidin-2-one (1-a, R1=pivaloyl)

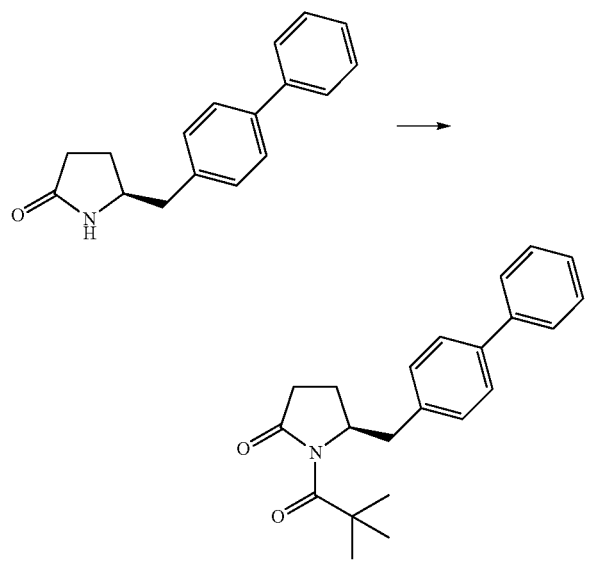

Method 1

20 g of (S)-5-biphenyl-4-ylmethylpyrrolidin-2-one (1-a, R1=H) of example 3 were dissolved in 200 ml tetrahydrofuran. The mixture was cooled to about −78° C. and 55 ml n-butyllithium (1.6 M) were added. After about 0.5 hours, 11.8 ml of pivaloyl chloride were added. After 1 hour, the mixture was quenched with 210 ml ammonium chloride solution and extracted with 70 ml ethyl acetate. The mixture was concentrated to dryness to obtain 26.7 g of (S)-5-biphenyl-4-ylmethyl-1-(2,2-dimethylpropionyl)pyrrolidin-2-one (1, R1=pivaloyl). $^1$H-NMR (CDCl$_3$): 1.40 (9H, s, C(CH$_3$)$_3$); 1.91 (1H, m, 4-CHH); 2.03 (1H, m, 4-CHH); 2.47 (1H, m, 3-CHH); 2.55 (1H, m, 3-CHH); 2.74 (1H, dd, 1-CHH); 3.18 (1H, dd, 1-CHH); 4.67 (1H, m, 5-CH); 7.34 (2H, m, aromatic); 7.36 (1H, m, aromatic); 7.46 (2H, m, aromatic); 7.58 (4H, m, aromatic). m/z: 336 (MH$^+$, 100%).

The X-ray Structure of the obtained crystals is shown in FIG. 9. Single crystal for this determination is obtained from diisopropylether as solvent.

| Crystal data [recorded at 100(2)K] | |
|---|---|
| Empirical formula | C$_{22}$H$_{25}$NO$_2$ |
| Formula weight | 335.43 |
| Crystal system | Monoclinic |
| Space group | P21 |
| Cell parameters | a = 11.633(4) Å |
| | b = 8.486(3) Å |
| | c = 18.894(6) Å |
| | α = 90° |
| | β = 94.429(15)° |
| | γ = 90° |
| Volume of unit cell | 1859.6(11) Å$^3$ |
| Z* | 4 |
| Calculated density | 1.198 mg m$^{-3}$ |

*(number of asymmetric units in the unit cell)

Method 2

(S)-5-biphenyl-4-ylmethylpyrrolidin-2-one (1-a, R1=H) (100 g, 398 mmol) and triethylamine (166 ml, 1.2 mol) are added to toluene (1 L) at room temperature. The mixture is heated to 60° C. Pivaloyl chloride (73.5 ml, 597 mmol) is added over 2 h. After a further 1 h, citric acid solution (237 g in 1 L) is added and the phases are separated. The water phase is washed with toluene (0.5 L). The organic portions are combined, washed with water (0.5 L) and then dried (MgSO$_4$). The mixture is concentrated in vacuo. The residue is suspended in heptane (550 ml) and is heated to reflux. The mixture is then cooled to room temperature. After 1 h, the mixture is cooled to 0° C., and then filtered to give (S)-5-biphenyl-4-ylmethyl-1-(2,2-dimethylpropionyl)pyrrolidin-2-one (1, R1=pivaloyl)

Example 5-1

(3R,5S)-5-biphenyl-4-ylmethyl-1-(2,2-dimethylpropionyl)-3-methylpyrrolidin-2-one (2-a, R1=pivaloyl)

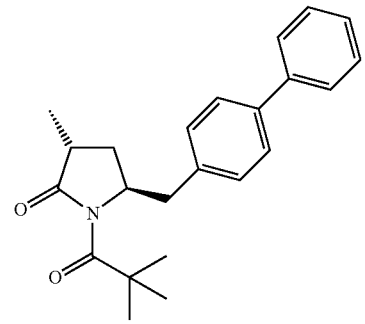

Method 1

0.37 ml of n-butyllithium (1.6 M) was added to a solution of 88 μl diisopropylamine in 1 ml tetrahydrofuran at about 0° C. After about 15 min, 200 mg (S)-5-biphenyl-4-ylmethyl-1-(2,2-dimethylpropionyl)pyrrolidin-2-one (1-a, R1=pivaloyl) of example 4 dissolved in 2 ml tetrahydrofuran were added. After about 15 min, 59 μl dimethylsulphate were added. After about 2 hours at about 0° C., the mixture was diluted with ammonium chloride solution, extracted with ethyl acetate and concentrated to dryness (196 mg). According to HNMR analysis, the ratio of diastereoisomers is 83:17 [(3R,5S):(3S,5S)]. The material was purified by chromatography to afford 43 mg (3R,5S)-5-biphenyl-4-ylmethyl-1-(2,2-dimethylpropionyl)-3-methylpyrrolidin-2-one—$^1$H-NMR (DMSO): (2-a, R1=pivaloyl) 1.07 (3H, d, 1-CH$_3$); 1.29 (9H, s, C(CH$_3$)$_3$); 1.63 (1H, m, 4-CHH); 2.03 (1H, m, 4-CHH); 2.81 (2H, m, 3-CH, 1-CHH); 2.94 (1H, dd, 1-CHH); 4.45 (1H, m, 5-CH); 7.34 (3H, m, aromatic); 7.44 (2H, m, aromatic); 7.61 (4H, m, aromatic). m/z: 350 (MH$^+$, 100%). Spectroscopic data for (2-b, R1=pivaloyl) as Example 5-2.

An X-ray structure of the preferred diastereoisomer (compound according to formula (2-a)) is shown in FIG. 2.

| Crystal data [recorded at 100(2)K] | |
|---|---|
| Empirical formula | C$_{23}$H$_{27}$NO$_2$ |
| Formula weight | 349.46 |
| Crystal system | Monoclinic |
| Space group | P21 |
| Cell parameters | a = 5.645(3) Å |
| | b = 9.949(5) Å |
| | c = 17.443(9) Å |
| | α = 90° |
| | β = 91.47(3)° |
| | γ = 90° |
| Volume of unit cell | 979.3(9) Å$^3$ |
| Z* | 2 |
| Calculated density | 1.185 mg m$^{-3}$ |

*(number of asymmetric units in the unit cell)

Method 2

10 g of (S)-5-biphenyl-4-ylmethyl-1-(2,2-dimethylpropionyl)pyrrolidin-2-one (1-a, R1=pivaloyl) were dissolved in 150 ml toluene. The mixture was cooled to about 0° C. and 71.5 ml potassium bis(trimethylsilyl)amide solution (0.5 M in toluene) were added. After 15 min, 11 ml dimethyl sulphate were added and the mixture was stirred for a further hour. The reaction was quenched with ammonium chloride solution and extracted with ethyl acetate. The combined organic phases were concentrated to dryness to obtain 15.3 g of crude (3R,5S)-5-biphenyl-4-ylmethyl-1-(2,2-dimethylpropionyl)-3-methylpyrrolidin-2-one. According to HNMR analysis, on the crude, the ratio of diastereoisomers is 83:17 [(3R,5S):(3S,5S)]. Spectroscopic data for (2-a, R1=Pivaloyl) is reported in Example 5-1, Method 1. Spectroscopic data for (2-b, R1=Pivaloyl) is reported in Example 5-2.

Method 3

65 μl (60 mg, 0.323 mmol) dicyclohexylamine is dissolved in 1 ml dry THF, and the solution is then cooled to 0° C. After adding 197 μl butyl lithium in hexane (1.59 M), the solution is stirred at 0° C. for 15 min. A solution of 100 mg (2.84 mmol) (S)-5-biphenyl-4-ylmethyl-1-(2,2-dimethylpropionyl)pyrrolidin-2-one (1-a, R1=pivaloyl) in 1 ml THF is then added drop wise and stirred at 0° C. for a further 15 min. 20 μl (47 mg, 0.328 mmol) methyl iodide is then added within 20 min. The resulting mixture is stirred at 0° C. for 2 h. The mixture is quenched through the addition of 2 ml saturated NH$_4$Cl solution, 2 ml water and 20 ml isopropyl acetate. The organic layer is separated, dried over MgSO$_4$, filtered and evaporated. HPLC of the residue reveals two methylated diastereomeric compounds 2-a (R1=Piv) and 2-b (R1=Piv). Ratio (3R,5S) to (3S,5S) 85:15 as determined by hplc.

Method 4

65 μl (60 mg, 0.323 mmol) 2,2,6,6-tetramethylpiperidine is dissolved in 1 ml dry THF, and the solution is then cooled to 0° C. After the addition of 197 μl butyl lithium in hexane (1.59 M) the solution is stirred at 0° C. for 15 min. A solution of 100 mg (2.84 mmol) (S)-5-biphenyl-4-ylmethyl-1-(2,2-dimeth-ylpropionyl)pyrrolidin-2-one (1-a, R1=pivaloyl) in 1 ml THF is then added drop wise and the mixture is stirred at 0° C. for a further 15 min. 20 μl (47 mg, 0.328 mmol) methyl iodide is then added within 20 min. The resulting mixture is stirred at 0° C. for 2.5 h. The mixture is quenched through the addition of 2 ml saturated NH$_4$Cl solution, 2 ml water and 20 ml isopropyl acetate. The organic layer is separated, dried over MgSO$_4$, filtered and evaporated. HPLC of the residue reveals two methylated diastereomeric compounds 2-a (R1=Piv) and 2-b (R1=Piv); ratio (3R,5S) to (3S,5S) 88:12.

Method 5

(S)-5-biphenyl-4-ylmethyl-1-(2,2-dimethylpropionyl)pyrrolidin-2-one (1-a, R1=pivaloyl) (10 g, 29.8 mmol) is dissolved in toluene (50 ml) and is cooled to 0° C. 0.5 M Potassium bis(trimethylsilyl)amide solution in toluene (77.5 ml, 38.7 mmol) is added over a period of 30 min. Dimethylsulfate (4.2 ml, 44.7 mmol) is then added over 0.5 h. After 15 min, 1 M HCl (50 ml) is added and the mixture allowed to warm to room temperature. The phases are separated and the organic phase is washed with 1 M NaOH (50 ml) and then with water (50 ml). Solvent is then removed from the organic phase in vacuo to yield a residue containing the product. Residue contains (3R,5S)-5-biphenyl-4-ylmethyl-1-(2,2-dimethylpropionyl)-3-methylpyrrolidin-2-one (2-a, R1=pivaloyl). Ratio (3R,5S) to (3S,5S) 86:14 as determined by hplc.

The residue is heated at reflux in methanol (50 ml). Water (5 ml) is then added and the mixture is cooled to room temperature. After 1 h the mixture is cooled to 0° C. and is stirred for a further 1 h. A solid is collected by filtration, washed with MeOH/H$_2$O (5 ml, 9:1), then dried in vacuo to give further purified product. Ratio (3R,5S) to (3S,5S) 84:16 as determined by hplc.

Method 6

(S)-5-biphenyl-4-ylmethyl-1-(2,2-dimethylpropionyl)pyrrolidin-2-one (1-a, R1=pivaloyl) (5 g, 14.9 mmol) is dissolved in toluene (25 ml) and is cooled to −10° C. 0.5 M Potassium bis(trimethylsilyl)amide solution in toluene (38.8 ml, 19.4 mmol) is added over a period of about 30 min. Dimethylsulfate (2.1 ml, 22.4 mmol) is then added over 40 min. After 30 min, saturated NH$_4$Cl solution (25 ml) and water (25 ml) are added. Phases are separated and the aqueous phase is washed with toluene (25 ml). The combined organic phases are dried (MgSO$_4$). Solvent is then removed from the organic phase in vacuo to yield a residue containing the product: Ratio (3R,5S) to (3S,5S) 92:8 as determined by hplc.

Method 7

(S)-5-biphenyl-4-ylmethyl-1-(2,2-dimethylpropionyl)pyrrolidin-2-one (1, R1=pivaloyl) (10 g, 29.8 mmol) is dissolved in toluene (50 ml) and is cooled to 0° C. 0.5 M Potassium bis(trimethylsilyl)amide solution in toluene (77.5 ml, 38.7 mmol) is added over a period of 30 min. Dimethylsulfate (4.2 ml, 44.7 mmol) is then added over 0.5 h. After 15 min, morpholine (2.6 ml, 29.8 mmol) is added. After 0.5 h, 1 M HCl (50 ml) is added and the mixture allowed to warm to room temperature. The phases are separated and the organic phase is washed with 1 M NaOH (50 ml) and then with water (50 ml). Solvent is then removed in vacuo from the organic phase to yield a residue containing the product: Ratio (3R,5S) to (3S,5S) is 86:14 as determined by hplc.

The residue is heated at reflux in methanol (50 ml). Water (5 ml) is then added and the mixture is cooled to room temperature. After 1 h the mixture is cooled to 0° C. and is stirred for a further 1 h. A solid is collected by filtration, washed with MeOH/H$_2$O (5 ml, 9:1) and then dried in vacuo to give a further purified solid containing the product: ratio (3R,5S) to (3S,5S) 86:14 as determined by hplc.

Method 8

(S)-5-biphenyl-4-ylmethyl-1-(2,2-dimethylpropionyl)pyrrolidin-2-one (1, R1=pivaloyl) (5 g, 14.9 mmol) is dissolved in toluene (25 ml) and cooled to −10° C. 0.5 M Potassium bis(trimethylsilyl)amide solution in toluene (19.4 ml, 38.8 mmol) is added over a period of 30 min. Dimethylsulfate (2.1 ml, 22.4 mmol) dissolved in THF (6 ml) is then added over 20 min. After 30 min, morpholine (2.0 ml, 22.4 mmol) is added. After 1 h, 1 M HCl (50 ml) is added and the mixture allowed to warm to room temperature. The phases are separated and the organic phase is washed with water (3×50 ml). Phases separated. Solvent is then removed from the organic phase in vacuo to yield a residue containing the product: Ratio (3R,5S) to (3S,5S) 85:15 as determined by hplc.

Method 9

(S)-5-biphenyl-4-ylmethyl-1-(2,2-dimethylpropionyl)pyrrolidin-2-one (1, R1=pivaloyl) (5 g, 14.9 mmol) is dissolved in toluene (15 ml) and is cooled to ca 0° C. 0.5 M Potassium bis(trimethylsilyl)amide solution in toluene (19.4 ml, 38.8 mmol) is added over a period of 30 min. This mixture is then transferred over 30 min to a solution of dimethyl sulfate (2.1 ml, 22.4 mmol) in toluene (2 ml) at 0° C. After 30 min, morpholine (2.0 ml, 22.4 mmol) is added. After 1 h, 1 M HCl (50 ml) is added and the mixture allowed to warm to room temperature. The phases are separated and the organic phase is washed with water (3×50 ml). Phases separated and the solvent is then removed from the organic phase in vacuo to yield a residue containing the product: ratio (3R,5S) to (3S,5S) 91:9 as determined by hplc.

Method 10

(S)-5-biphenyl-4-ylmethyl-1-(2,2-dimethylpropionyl)pyrrolidin-2-one (1, R1=pivaloyl) (5 g, 14.9 mmol) is dissolved in toluene (10 ml) and is cooled to 0° C. This solution is transferred to a vessel containing 0.5 M Potassium bis(trimethylsilyl)amide solution in toluene (19.4 ml, 38.8 mmol) maintained at 0° C. The mixture is then transferred over 30 min to a solution of dimethyl sulfate (2.1 ml, 22.4 mmol) in toluene (2 ml) at 0° C. After 30 min, morpholine (2.0 ml, 22.4 mmol) is added. After 1 h, 1 M HCl (50 ml) is added and the mixture is allowed to warm to room temperature. The phases are separated and the organic phase is washed with water (3×50 ml). Phases are separated and the solvent is then removed from the organic phase in vacuo to yield a residue containing the product: ratio (3R,5S) to (3S,5S) 91:9 as determined by hplc.

Method 11

(S)-5-biphenyl-4-ylmethyl-1-(2,2-dimethylpropionyl)pyrrolidin-2-one (1, R1=pivaloyl) (10 g, 29.8 mmol) is dissolved in toluene (50 ml) and is cooled to 0° C. 0.66 M Potassium bis(trimethylsilyl)amide solution in toluene (58.6 ml, 38.7 mmol) is added over a period of about 30 min. Dimethylsulfate (4.2 ml, 44.7 mmol) is then added over 0.5 h. After about 15 min, morpholine (3.9 ml, 44.7 mmol) is added. After 0.5 h, 1 M HCl (50 ml) is added and the mixture allowed to warm to room temperature. The phases are separated and the organic phase is washed with 1 M NaOH (50 ml) and then with water (50 ml). Solvent is then removed from the organic phase in vacuo to yield a residue containing the product: ratio (3R,5S) to (3S,5S) 87:13 as determined by hplc.

Example 5-2

(3S,5S)-5-biphenyl-4-ylmethyl-1-(2,2-dimethylpropionyl)-3-methylpyrrolidin-2-one (2-b, R1=pivaloyl)

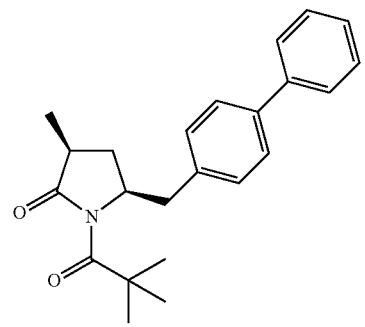 [SMILES: C[C@H]1C[C@@H](Cc2ccc(-c3ccccc3)cc2)N(C(=O)C(C)(C)C)C1=O]

Prepared during the reaction (1) to (2) as given in Example 5-1, Method 1. Separated by chromatography eluting with 7:1 Heptane/Ethyl acetate [$R_f$(2-a=0.33); (2-b=0.26)]. $^1$H-NMR (DMSO): 1.10 (3H, d, CH$_3$); 1.29 (9H, s, C(CH$_3$)$_3$); 1.46 (1H, m, 4-CHH); 2.15 (1H, m, 4-CHH); 2.57 (2H, m, 3-CH, 1-CHH); 3.19 (1H, m, 1-CHH); 4.31 (1H, m, 5-CH); 7.29-7.63 (9H, 4×m, aromatic). m/z: 350 (MH$^+$, 100%); 320 (11); 266 (10).

An X-ray structure of the other diastereoisomer (compound according to formula (2-b)) is shown in FIG. 3. The X-ray also shows some of compound (2-a) which co-crystallised since the sample was a mixture of diastereoisomers. The pure compound can, however, be obtained via column chromatography.

| Crystal data [recorded at 100(2)K] | |
|---|---|
| Empirical formula | C$_{23}$H$_{27}$NO$_2$ |
| Formula weight | 349.46 |
| Crystal system | Monoclinic |
| Space group | P21 |
| Cell parameters | a = 5.969(2) Å |
| | b = 7.678(2) Å |
| | c = 21.212(4) Å |
| | α = 90° |
| | β = 97.788(9)° |
| | γ = 90° |
| Volume of unit cell | 963.2(4) Å$^3$ |
| Z* | 2 |
| Calculated density | 1.205 mg m$^{-3}$ |

*(number of asymmetric units in the unit cell)

Example 5-3

(R)-5-Biphenyl-4-ylmethyl-1-(2,2-dimethylpropionyl)-3,3-dimethyl-pyrrolidin-2-one

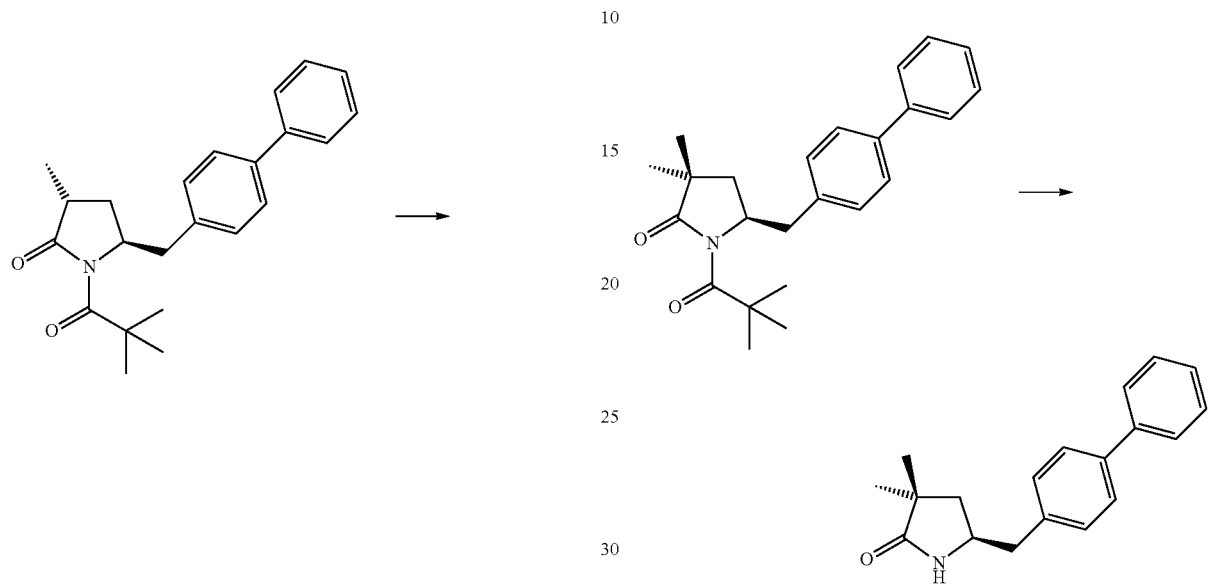

10 g (3R,5S)-5-biphenyl-4-ylmethyl-1-(2,2-dimethylpropionyl)-3-methylpyrrolidin-2-one (2-a, R1=Piv) is added to THF (100 ml). The mixture is cooled to −30° C. Lithium diisopropylamide (17.16 ml, 2 M) is added and the mixture is stirred for 1 h. Methyl iodide (5.4 ml) is added and the mixture is stirred for 3 h. Aminoethylethanolamine (6.1 ml) is added and the mixture is warmed to 40° C. and stirred for 15 min. Sulphuric acid (12 g) is then added. The mixture is concentrated in vacuo and the residue taken up in toluene. The phases are separated. The organic phase is concentrated in vacuo and taken up in methanol (300 ml) at reflux. On cooling, the precipitate is collected by filtration to give (R)-5-Biphenyl-4-ylmethyl-1-(2,2-dimethylpropionyl)-3,3-dimethyl-pyrrolidin-2-one. $^1$H NMR (DMSO): 1.04 (3H), 1.15 (3H), 1.28 (9H), 1.72 (1H), 1.38 (1H), 2.59 (1H), 3.14 (1H), 4.37 (1H), 7.31 (3H), 7.45 (2H), 7.62 (4H).

Example 5-4

(R)-5-Biphenyl-4-ylmethyl-3,3-dimethylpyrrolidin-2-one

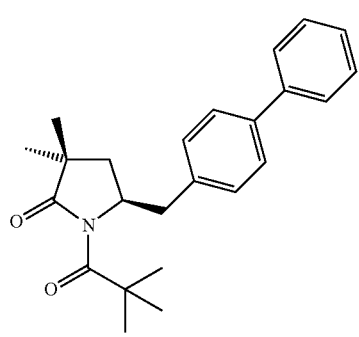

6 g (R)-5-Biphenyl-4-ylmethyl-1-(2,2-dimethylpropionyl)-3,3-dimethyl-pyrrolidin-2-one is added to THF (6 ml). Lithium hydroxide (15.6 ml, 3 mol L$^{-1}$) is added followed by tetra-butylammonium bromide (0.15 g). This mixture is then added to a mixture of hydrogen peroxide (4.54 g) and THF (12 ml) at 0° C. After 2.5 h, sodium bisulfite solution (12 g, 38-40%) is added. THF is removed in vacuo. Toluene (70 ml) is added and the phases separated. The organic phase is washed with water (15 ml). The phases are separated. The organic phase is concentrated in vacuo and then heptane (60 ml) is added and the mixture cooled to 0° C.). The precipitate is collected by filtration and dried in vacuo to give (R)-5-Biphenyl-4-ylmethyl-3,3-dimethylpyrrolidin-2-one $^1$H NMR (DMSO): 0.96 (3H), 0.97 (3H), 1.52 (1H), 1.78 (1H), 2.61 (1H), 2.93 (1H), 3.75 (1H), 7.32 (3H), 7.45 (2H), 7.58 (2H), 7.63 (2H), 7.70 (1H).

HPLC Method (Examples 5-1 to 5-4):
Column: Gemini C6 Phenyl (Phenomenex); 150×3.0 mm; 3 μm. Mobile Phase A (0.01 M (NH$_4$)H$_2$PO$_4$ pH 6.6); Mobile Phase B (Acetonitrile). Gradient: 0 min (40% A; 60% B); 15 min (40% A; 60% B); 20 min (20% A; 80% B); 23 min (20% A; 80% B); 23.1 min (40% A; 60% B); 26 min (40% A; 60% B). Flow rate: 0.8 ml min$^{-1}$. Wavelength: 254 nm.

Retention Times:
  1-a (R1=H): 1.7 min
  2-a (R1=H): 2.0 min
  Example 5-4: 2.3 min
  1-a (R1=Piv): 6.4 min
  2-b (R1=Piv)=(3S,5S): 8.2 min
  2-a (R1=Piv)=(3R,5S): 8.6 min
  Example 5-3: 10.4 min Ratio of diastereoisomers (3R,5S):(3S,5S)[-5-biphenyl-4-ylmethyl-1-(2,2-dimethylpropionyl)-3-methylpyrrolidin-2- one (2-a)] is determined from the peak areas of peaks for 2-a (R1=Piv) [8.6 min] and 2-b (R1=Piv) [8.2 min].

Example 6

(3R,5S)-5-biphenyl-4-ylmethyl-3-methylpyrrolidin-2-one (2-a, R1=H)

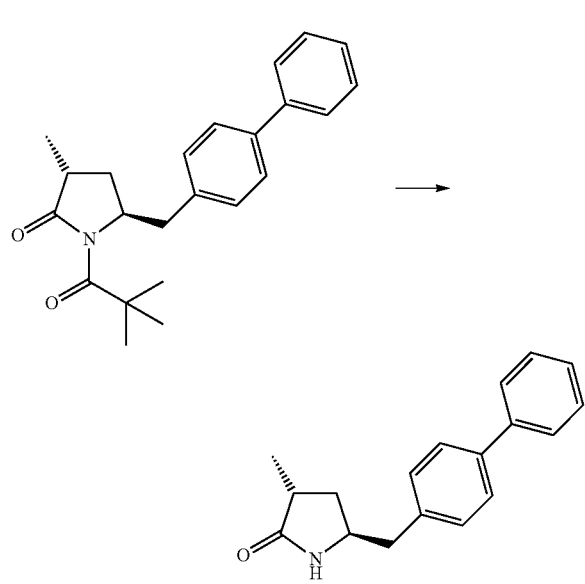

2 g (3R,5S)-5-biphenyl-4-ylmethyl-1-(2,2-dimethylpropionyl)-3-methylpyrrolidin-2-one of example 5 and 2 g paratoluene sulfonic acid in 40 ml toluene were heated under reflux for about 1 hour. Afterwards, the solution was cooled to room temperature and neutralized with 10 ml diluted aqueous sodium carbonate solution. The organic phase was separated, washed with water and concentrated to dryness. The residue was crystallized from iso-propyl acetate/heptane to yield 1.2 g of (3R,5S)-5-biphenyl-4-ylmethyl-3-methylpyrrolidin-2-one (2-a, R1=H). $^1$H-NMR (CDCl$_3$): 1.90 (3H, s, CH$_3$); 1.83 (1H, m, 4-CHH); 2.12 (1H, m, 4-CHH); 2.42 (1H, m, 3-H); 2.82 (2H, m, 1-CH$_2$); 3.87 (1H, m, 5-CH); 7.10 (1H, s, NH); 7.26 (2H, d, aromatic); 7.34 (1H, t, aromatic); 7.43 (2H, m, aromatic); 7.54 (2H, m, aromatic); 7.58 (2H, m, aromatic). m/z: 266 (MH$^+$, 100%).

The X-ray Structure of the obtained crystals is shown in FIG. 7. Single crystal for this determination is obtained from isopropylacetate as solvent.

| Crystal data [recorded at 100(2)K] | |
|---|---|
| Empirical formula | C$_{18}$H$_{19}$NO |
| Formula weight | 265.34 |
| Crystal system | Monoclinic |
| Space group | P21 |
| Cell parameters | a = 10.591(3) Å |
| | b = 8.832(2) Å |
| | c = 15.319(4) Å |
| | α = 90° |
| | β = 92.986(12)° |
| | γ = 90° |
| Volume of unit cell | 1431.0(6) Å$^3$ |
| Z* | 4 |
| Calculated density | 1.232 mg m$^{-3}$ |

*(number of asymmetric units in the unit cell)

Example 7

(2R,4S)-4-amino-5-biphenyl-4-yl-2-methylpentanoic acid hydrochloride (3-a, R1=R2=R3=H)

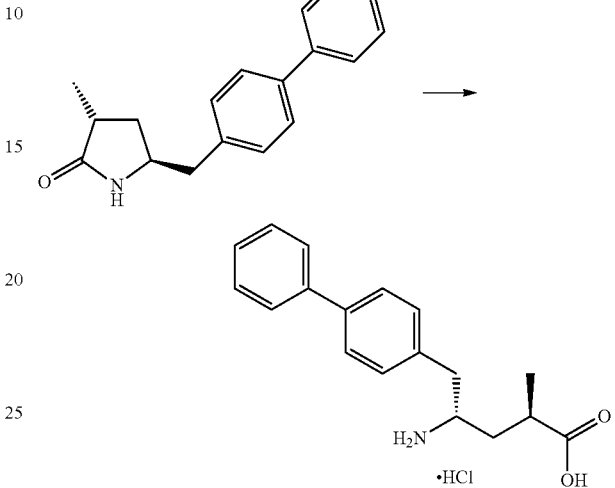

5 g (3R,5S)-5-biphenyl-4-ylmethyl-3-methylpyrrolidin-2-one of example 6 were mixed with a mixture of acetic acid and concentrated hydrochloric acid (50 ml ratio 1:1) and stirred under reflux for about 20 hours. The solution was then concentrated under vacuum and the residue crystallised from acetic acid/ethyl acetate to yield 4.7 g of (2R,4S)-4-amino-5-biphenyl-4-yl-2-methylpentanoic acid hydrochloride (3-a, R1=R2=R3=H). $^1$H-NMR (DMSO): 1.10 (3H, s, CH$_3$); 1.58 (1H, m, 3-CHH); 1.88 (1H, m, CHH); 2.64 (1H, m, 4-CH); 2.88 (1H, dd, 5-CHH); 3.01 (1H, dd, 5-CHH); 3.45 (1H, m, 2-CH); 7.38 (3H, m, aromatic); 7.47 (2H, m, aromatic); 7.66 (4H, m, aromatic); 8.07 (2H, s, NH); 12.25 (1H, s, CO$_2$H). m/z: 284 (MH$^+$, 100%); 267 (25); 249 (47); 221 (13); 193 (24).

The X-ray Structure of the obtained crystals is shown in FIG. 5. Single crystal for this determination is obtained from acetonitrile/methanol as solvent.

| Crystal data [recorded at 100(2)K] | |
|---|---|
| Empirical formula | C$_{18}$H$_{22}$ClNO$_2$ |
| Formula weight | 319.82 |
| Crystal system | Monoclinic |
| Space group | C2 |
| Cell parameters | a = 37.419(8) Å |
| | b = 5.587(2) Å |
| | c = 7.807(2) Å |
| | α = 90° |
| | β = 94.431(8)° |
| | γ = 90° |
| Volume of unit cell | 1627.3(8) Å$^3$ |
| Z* | 4 |
| Calculated density | 1.305 mg m$^{-3}$ |

*(number of asymmetric units in the unit cell)

Example 8

(2R,4S)-5-biphenyl-4-yl-4-tert-butoxycarbonylamino-2-methylpentanoic acid (3-a, R1=BOC, R2=R3=H)

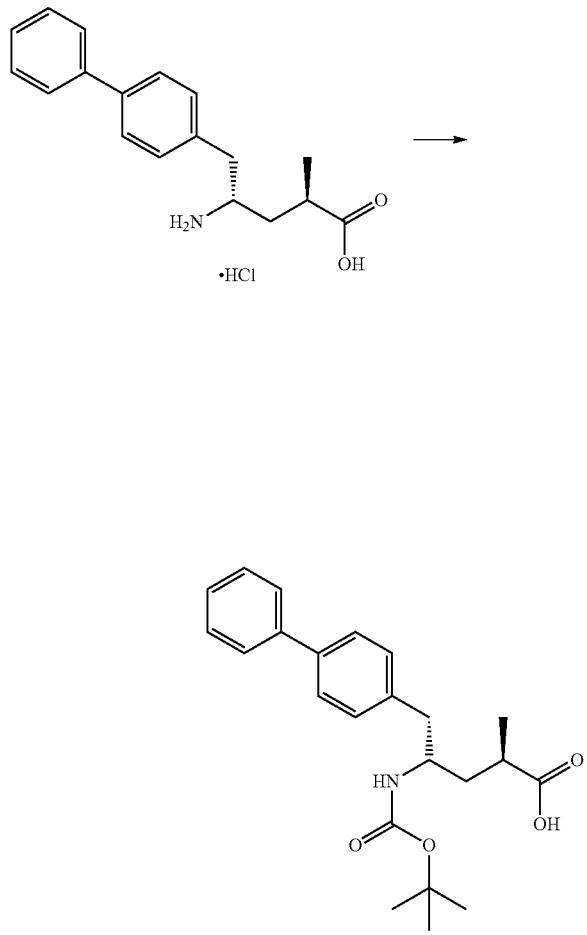

3.2 g of (2R,4S)-4-amino-5-biphenyl-4-yl-2-methylpentanoic acid hydrochloride (3-a, R1=R2=R3=H) were mixed with 3.2 g di-tert-butyl-dicarbonate, 5 g potassium carbonate and 50 ml water/iso-propanol mixture 1:1 and stirred at room temperature for 1 hour. Afterwards, the mixture was acidified with diluted phosphoric acid, extracted with iso-propyl acetate, washed with water, concentrated and crystallised from iso-propyl acetate/heptane to yield 2.8 g of (2R,4S)-5-biphenyl-4-yl-4-tert-butoxycarbonylamino-2-methylpentanoic acid (3-a, R1=BOC, R2=R3=H). Mpt 146-147° C.; $\delta_H$ (500 MHz; DMSO) 1.07 (3H, d, J 7.0, 1-$CH_3$), 1.34 (9H, s, $(CH_3)_3$), 1.38 (1H, m, 3-$H_A$), 1.77 (1H, m, 3-$H_B$), 2.43 (1H, m, 2-H), 2.70 (2H, d, J 7.0, 5-H), 3.69 (1H, m, 4-H), 6.74 (1H, d, J 9.0, NH), 7.27 (2H, d, J 8.0, Ar-ortho-H(Ph)), 7.36 (1H, t, J 7.0, Ar-(Ph)-para-H), 7.46 (2H, t, J 7.5, Ar-(Ph)-meta-H), 7.57 (2H, d, J 8.0, Ar-meta-H(Ph)), 7.64 (2H, d, J 7.5, Ar-(Ph)-ortho-H), 12.01 (1H, s, $CO_2H$); $\delta_C$ (500 MHz, DMSO) 18.1 (1-$CH_3$), 28.3 [$(CH_3)_3$], 35.9 (2-C), 37.9 (3-C), 40.7 (5-C), 50.0 (4-C), 77.4 [$C(CH_3)_3$], 126.3, 126.5, 127.2, 128.9, 129.8 (Ar—CH), 137.7 (Ar-ipso-C(Ph)), 138.3 (Ar-para-C(Ph)), 140.1 (Ar-(Ph)-ipso-C), 155.2 (NCO), 177.2 ($CO_2H$); m/z (+ESI) 406 ([MNa]$^+$, 6%), 384 ([MH]$^+$, 31), 328 (100), 284 (19); Found: [MH]$^+$, 384.21691. $C_{23}H_{30}NO_4$ requires MH 384.21693.

Example 9-1

(2R,4S)-4-amino-5-biphenyl-4-yl-2-methylpentanoic acid ethyl ester hydrochloride (3-a, R1=R2=H, R3=Et)

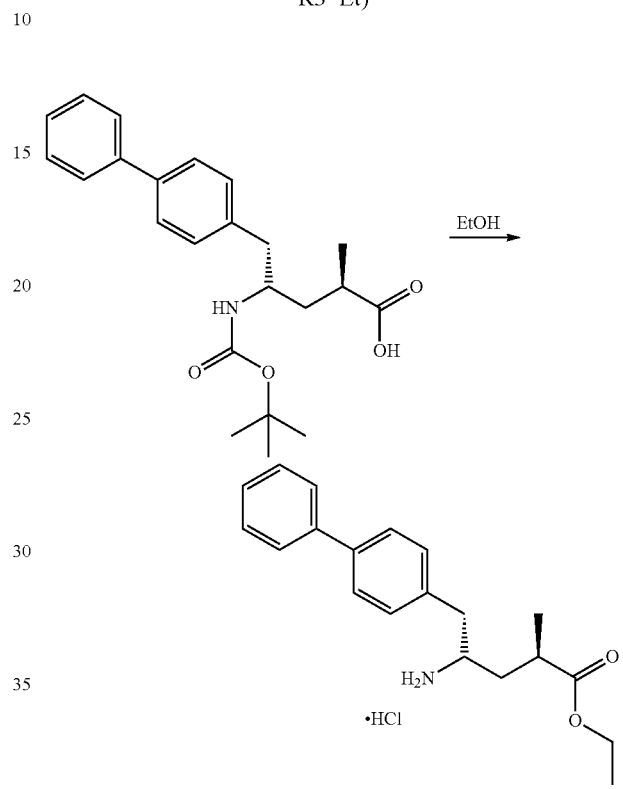

Method 1

150 g (2R,4S)-5-biphenyl-4-yl-4-tert-butoxycarbonylamino-2-methylpentanoic acid (3-a, R1=BOC, R2=R3=H) were dissolved in 1500 ml ethanol at 70° C. 43 ml of thionyl chloride were then added over about 1 hour. The mixture was then stirred for a further 2 hours. The mixture was concentrated to dryness and then suspended in 3400 ml heptane. The precipitate was collected by filtration, yielding 133 g of (2R,4S)-4-amino-5-biphenyl-4-yl-2-methylpentanoic acid ethyl ester hydrochloride (3-a, R1=R2=H, R3=Et). $^1$H-NMR (DMSO): 1.05 (3H, t, 1-$CH_3$); 1.08 (3H, t, $CH_2CH_3$); 1.61 (1H, m, 3-CHH); 1.85 (1H, m, 3-CHH); 2.74 (1H, m, 2-CH); 2.81 (1H, dd, 5-CHH); 3.08 (1H, dd, 5-CHH); 3.36 (1H, m, 4-CH); 3.95 (2H, q, $CH_2CH_3$); 7.31 (1H, m, aromatic); 7.35 (2H, m, aromatic); 7.43 (2H, m, aromatic); 7.62 (4H, m, aromatic); 8.30 (3H, s, $NH_3^+$). m/z 312 (MH$^+$, 100%)

Method 2

150 g (2R,4S)-5-biphenyl-4-yl-4-tert-butoxycarbonylamino-2-methylpentanoic acid (3-a, R1=BOC, R2=R3=H) are added to 1500 ml ethanol at room temperature. The mixture is then warmed to an internal temperature of 60-70° C. 42.8 ml Thionyl chloride is then added over a period of 1 h to the reaction mixture. The mixture is then stirred for a further 2 h. 810 ml of the solvent is removed by distillation under reduced pressure. 1460 ml Heptane fraction is then added. 1310 ml of solvent is then removed by distillation under reduced pressure. 1460 ml Heptane fraction is then added.

520 ml of solvent is then removed by distillation under reduced pressure. 1460 ml Heptane fraction is then added. The mixture is then cooled to room temperature over a period of 1 h. The mixture is then stirred at room temperature for 2 h. The solid is then collected by filtration. The solid is then washed with heptane fraction (600 ml) and dried to give (2R,4S)-4-amino-5-biphenyl-4-yl-2-methylpentanoic acid ethyl ester hydrochloride (3-a, R1=R2=H, R3=Et). Spectroscopic data as given in Example 9-1 Method 1.

Significant reflections in the X-ray diffraction pattern show the following interlattice plane intervals (average 2θ in [°] are indicated with error limit of ±0.2): 2θ in [°]: 5.7, 6.2, 7.7, 11.3, 12.5, 17.1, 22.4, 22.9. Data taken using a Bruker D8 Advance diffractometer using Cu-Kα radiation.

The X-ray Structure of the obtained crystals is shown in FIG. 6a and FIG. 6b. Single crystal for this determination is obtained from acetonitrile as solvent.

| Crystal data [recorded at 293(2)K] | |
| --- | --- |
| Empirical formula | $C_{20}H_{26}ClNO_2$ |
| Formula weight | 347.87 |
| Crystal system | Monoclinic |
| Space group | C2 |
| Cell parameters | a = 40.672(12) Å |
| | b = 6.543(2) Å |
| | c = 14.757(4) Å |
| | α = 90° |
| | β = 99.167(13)° |
| | γ = 90° |
| Volume of unit cell | 3877(2) Å$^3$ |
| Z* | 8 |
| Calculated density | 1.192 mg m$^{-3}$ |

*(number of asymmetric units in the unit cell)

Example 9-2

(2R,4S)-4-amino-5-biphenyl-4-yl-2-methylpentanoic acid ethyl ester hydrochloride (3-a, R1=R2=H, R3=Et)

(3-a, R1=R2=H, R3=Et) prepared in accordance Example 9-1 and is crystallised according to the following Methods:

Method 1

500 mg (2R,4S)-4-amino-5-biphenyl-4-yl-2-methylpentanoic acid ethyl ester hydrochloride (3-a, R1=R2=H, R3=Et) is added to 3 ml toluene at room temperature. The mixture is then heated to 75° C. and is stirred at this temperature until the material has dissolved. The mixture is then cooled to room temperature and stirred for 16 h. The precipitate is collected by filtration.

Significant reflections in the X-ray diffraction pattern show the following interlattice plane intervals (average 2θ in [°] are indicated with error limit of ±0.2): 2θ in [°]: 16.9, 18.2, 22.2, 22.7, 24.0. Data taken using a Bruker D8 Advance diffractometer using Cu-Kα radiation.

Method 2

500 mg (2R,4S)-4-amino-5-biphenyl-4-yl-2-methylpentanoic acid ethyl ester hydrochloride (3-a, R1=R2=H, R3=Et) is added to 3 ml xylene at room temperature. The mixture is then heated to 80° C. and is stirred at this temperature until the material is dissolved. The mixture is then cooled to room temperature and stirred for 16 h. The precipitate is collected by filtration.

Significant reflections in the X-ray diffraction pattern show the following interlattice plane intervals (average 2θ in [°] are indicated with error limit of ±0.2): 2θ in [°]: 16.9, 18.2, 22.2, 22.7, 23.9. Data taken using a Bruker D8 Advance diffractometer using Cu-Kα radiation.

Method 3

500 mg (2R,4S)-4-amino-5-biphenyl-4-yl-2-methylpentanoic acid ethyl ester hydrochloride (3-a, R1=R2=H, R3=Et) is added to 5 ml ethyl acetoacetate at room temperature. The mixture is then heated to 80° C. and is stirred at this temperature until the material is dissolved. The mixture is then cooled to room temperature and stirred for 16 h. The precipitate is collected by filtration.

Significant reflections in the X-ray diffraction pattern show the following interlattice plane intervals (average 2θ in [°] are indicated with error limit of ±0.2): 2θ in [°]: 7.7, 17.2, 18.5, 22.4, 22.9, 24.0. Data taken using a Bruker D8 Advance diffractometer using Cu-Kα radiation.

Method 4

500 mg (2R,4S)-4-amino-5-biphenyl-4-yl-2-methylpentanoic acid ethyl ester hydrochloride (3-a, R1=R2=H, R3=Et) is added to 5 ml ethyl acetate at room temperature. The mixture is then heated to reflux. The mixture is then cooled to room temperature and stirred for 16 h. The precipitate is collected by filtration. Significant reflections in the X-ray diffraction pattern show the following interlattice plane intervals (average 2θ in [°] are indicated with error limit of ±0.2): 2θ in [°]: 7.5, 17.0, 18.3, 22.2, 22.8, 24.0. Data taken using a Bruker D8 Advance diffractometer using Cu-Kα radiation.

Method 5

500 mg (2R,4S)-4-amino-5-biphenyl-4-yl-2-methylpentanoic acid ethyl ester hydrochloride (3-a, R1=R2=H, R3=Et) is added to 5 ml xylene at room temperature. The mixture is then heated to an external oil bath temperature of 120° C. and is stirred at this temperature until the material is dissolved. The mixture is then cooled to room temperature and stirred for 4 h The mixture is then cooled to 0° C. and stirred for 1 h. The mixture is then stirred at room temperature for ca 72 h. The precipitate is collected by filtration.

Significant reflections in the X-ray diffraction pattern show the following interlattice plane intervals (average 2θ in [°] are indicated with error limit of ±0.2): 2θ in [°]: 7.6, 17.1, 18.3, 19.7, 22.4, 22.8, 24.0. Data taken using a Bruker D8 Advance diffractometer using Cu-Kα radiation.

Method 6

500 mg (2R,4S)-4-amino-5-biphenyl-4-yl-2-methylpentanoic acid ethyl ester hydrochloride (3-a, R1=R2=H, R3=Et) is added to 5 ml xylene at room temperature. The mixture is then heated to an external oil bath temperature of 120° C. and is stirred at this temperature until the material is dissolved. The mixture is then cooled slowly to room temperature over a period of several hours The mixture is then stirred at room temperature for 16 h. The precipitate is collected by filtration.

Significant reflections in the X-ray diffraction pattern show the following interlattice plane intervals (average 2θ in [°] are indicated with error limit of ±0.2): 2θ in [°]: 7.5, 17.0, 18.3, 22.3, 22.7, 24.0. Data taken using a Bruker D8 Advance diffractometer using Cu-Kα radiation.

Method 7

500 mg (2R,4S)-4-amino-5-biphenyl-4-yl-2-methylpentanoic acid ethyl ester hydrochloride (3-a, R1=R2=H, R3=Et) is added to 5 ml ethyl acetoacetate at room temperature. The mixture is then heated to an external oil bath temperature of 120° C. and is stirred at this temperature until the material is dissolved. The mixture is then cooled to room temperature and stirred for 16 h. The precipitate is collected by filtration.

Significant reflections in the X-ray diffraction pattern show the following interlattice plane intervals (average 2θ in [°] are indicated with error limit of ±0.2): 2θ in [°]: 7.5, 16.1, 16.9, 18.2, 20.2, 22.2, 22.7, 23.9. Data taken using a Bruker D8 Advance diffractometer using Cu-Kα radiation.

Example 10

(S)-5-((S,R)-biphenyl-4-yl-hydroxymethyl)pyrrolidin-2-one (13, R1=H)

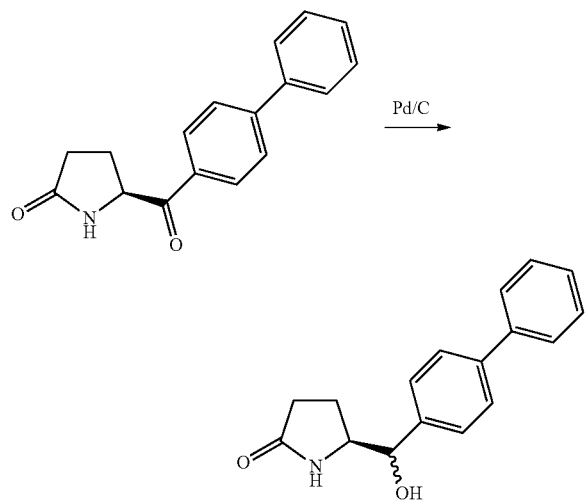

2 g of (S)-5-(biphenyl-4-carbonyl)pyrrolidin-2-one were dissolved in 40 ml THF. 200 mg Palladium on carbon were added and the mixture was stirred under a hydrogen atmosphere for 14 hours. The removal of the catalyst by filtration and concentration of the filtrate to dryness yielded the desired product (13) as a mixture of alcohol diastereoisomers. $^1$H NMR (CDCl$_3$): 1.71-2.35 (4H); 3.66-3.87 (1H); 4.45 (about 0.7H) and 4.60 (about 0.3H); 5.70 (about 0.3H) and 6.24 (about 0.7H); 6.85-7.66 (9H). The resulting alcohol can then be converted into (S)-5-biphenyl-4-ylmethylpyrrolidin-2-one by using for example the same conditions as used above in example 3. Ratio of diastereoisomers is calculated to be 70:30 (1H NMR), based on the integrations of the signals at 4.45 ppm (0.7H) and 4.60 (0.3H).

Example 11

(2-a, R1=pivaloyl) to (3-a, R1=R2=R3=H)

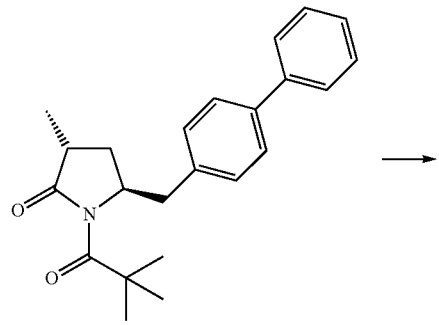

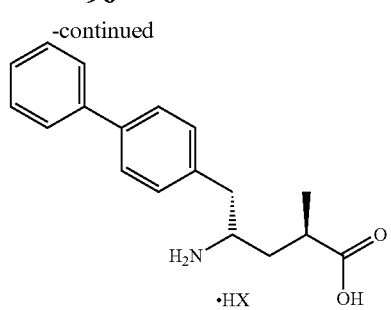

Method 1

0.5 g (3R,5S)-5-biphenyl-4-ylmethyl-1-(2,2-dimethylpropionyl)-3-methylpyrrolidin-2-one in 2.5 ml water, 2.5 ml concentrated hydrochloric acid and 2 ml ethyl acetate were heated at about 80° C. for about 15 hours. The mixture was evaporated to dryness to obtain (2R,4S)-4-amino-5-biphenyl-4-yl-2-methylpentanoic acid hydrochloride (3-a, R1=R2=R3=H, hydrochloride salt). Spectroscopic data as reported in Example 7.

Method 2

0.5 g (3R,5S)-5-biphenyl-4-ylmethyl-1-(2,2-dimethylpropionyl)-3-methylpyrrolidin-2-one in 5 ml hydrobromic acid (48%) and 4 ml ethyl acetate were heated at about 80° C. for about 15 hours. The mixture was evaporated to dryness to obtain (2R,4S)-4-amino-5-biphenyl-4-yl-2-methylpentanoic acid hydrobromide (3-a, R1=R2=R3=H, hydrobromide salt). MS (ES+): 284 ([MH]$^+$, 100%), 267 (17), 249 (18), 221 (3), 194 (3), 193 (25), 167 (4).

Example 12

(2-a, R1=pivaloyl) to (3-a, R1=R2=H, R3=Et)

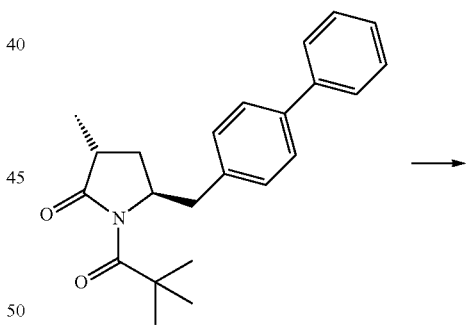

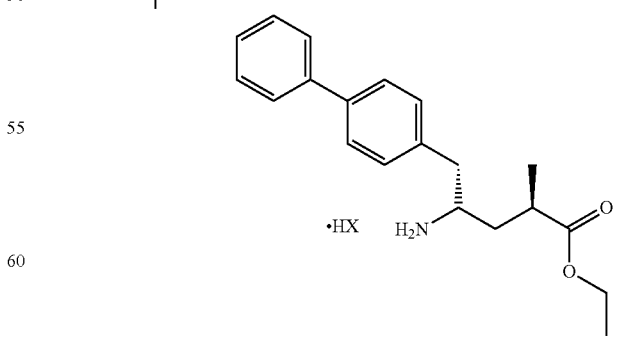

Method 1

0.5 g (3R,5S)-5-biphenyl-4-ylmethyl-1-(2,2-dimethylpropionyl)-3-methylpyrrolidin-2-one, 5 ml ethanol and 0.5 ml concentrated hydrochloric acid were heated at about 80-120° C. for about 24 hours. The mixture was evaporated to dryness to obtain (2R,4S)-4-amino-5-biphenyl-4-yl-2-methylpentanoic acid ethyl ester (hydrochloride salt). Spectroscopic data as reported in Example 9.

Method 2

0.5 g (3R,5S)-5-biphenyl-4-ylmethyl-1-(2,2-dimethylpropionyl)-3-methylpyrrolidin-2-one, 5 ml ethanol and 0.3 ml concentrated sulphuric acid were heated at about 80-120° C. for about 24 hours. The mixture was evaporated to dryness to obtain (2R,4S)-4-amino-5-biphenyl-4-yl-2-methylpentanoic acid ethyl ester (hydrogen sulphate salt). Spectroscopic data as in Example 44.

Method 3

0.5 g (3R,5S)-5-biphenyl-4-ylmethyl-1-(2,2-dimethylpropionyl)-3-methylpyrrolidin-2-one, 5 ml ethanol and 0.3 ml perchloric acid were heated at about 80-120° C. for about 24 hours. The mixture was evaporated to dryness to obtain (2R,4S)-4-amino-5-biphenyl-4-yl-2-methylpentanoic acid ethyl ester (perchlorate salt). $^1$H NMR (CDCl$_3$): 1.17 (3H), 1.20 (3H), 1.98 (2H), 2.76 (1H), 2.96 (1H), 3.29 (1H), 3.82 (1H), 3.96 (2H), 7.32-7.59 (13H), 8.21 (3H).

Method 4

0.5 g (3R,5S)-5-biphenyl-4-ylmethyl-1-(2,2-dimethylpropionyl)-3-methylpyrrolidin-2-one, 5 ml ethanol and 1.1 g para-toluenesulphonic acid were heated at about 80-120° C. for about 24 hours. The mixture was evaporated to dryness to obtain (2R,4S)-4-amino-5-biphenyl-4-yl-2-methylpentanoic acid ethyl ester (p-toluenesulphonate salt). $^1$H NMR (CDCl$_3$): 1.08 (3H), 1.16 (3H), 1.87 (1H), 1.95 (1H), 2.38 (3H), 2.77 (1H), 2.92 (1H), 3.15 (1H), 3.69 (1H), 4.07 (2H), 7.16-7.77 (13H), 9.89 (3H).

Example 13

(2-a, R1=H) to (3-a, R1=R2=H, R3=Et)

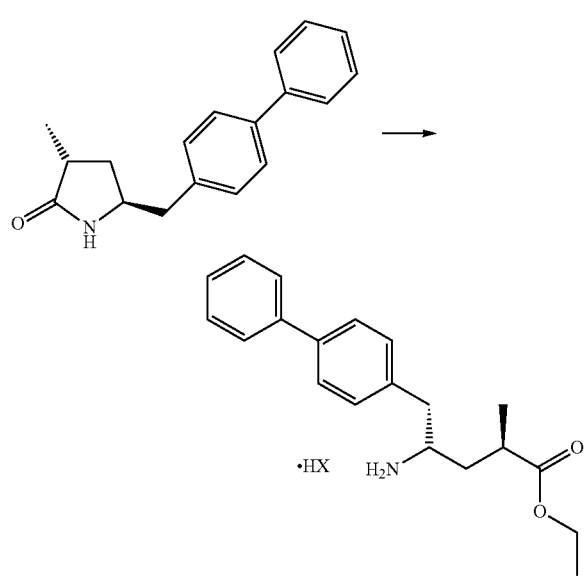

Method 1

1 g (3R,5S)-5-biphenyl-4-ylmethyl-3-methylpyrrolidin-2-one (2-a, R1=H), 10 ml ethanol and 1.4 ml concentrated hydrochloric acid were heated at about 80-120° C. for about 24 hours. The mixture was evaporated to dryness to obtain (2R,4S)-4-amino-5-biphenyl-4-yl-2-methylpentanoic acid ethyl ester (hydrochloride salt). Spectroscopic data as reported in Example 9.

Method 2

1 g (3R,5S)-5-biphenyl-4-ylmethyl-3-methylpyrrolidin-2-one (2-a, R1=H), 10 ml ethanol and 0.4 ml concentrated sulphuric acid were heated at about 80-120° C. for about 24 hours. The mixture was evaporated to dryness to obtain (2R,4S)-4-amino-5-biphenyl-4-yl-2-methylpentanoic acid ethyl ester (hydrogen sulphate salt). Spectroscopic data as in Example 44.

Method 3

1 g (3R,5S)-5-biphenyl-4-ylmethyl-3-methylpyrrolidin-2-one (2-a, R1=H), 10 ml ethanol and 1.4 g para-toluenesulphonic acid were heated at about 80-120° C. for about 24 hours. The mixture was evaporated to dryness to obtain (2R,4S)-4-amino-5-biphenyl-4-yl-2-methylpentanoic acid ethyl ester (p-toluenesulfonate salt). Spectroscopic data as in Example 12.

Example 14

(2-a, R1=H) to (3R,5S)-5-biphenyl-4-ylmethyl-3-methyl-2-oxo-pyrrolidine-1-carboxylic acid tert-butyl ester (2-a, R1=BOC)

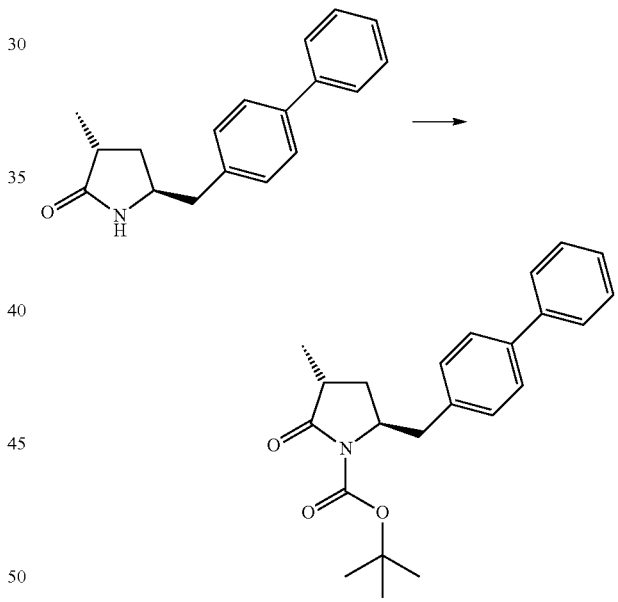

5 g (3R,5S)-5-biphenyl-4-ylmethyl-3-methylpyrrolidin-2-one (2-a, R1=H) in solution in 50 ml ethyl acetate were mixed with 6.6 g di-tert-butyl-dicarbonate, 3.5 g triethylamine and 1 g dimethyl-aminopyridine. After 1 hour at 50° C. the solution was mixed with water. After separation of the layers the organic phase was concentrated under vacuum and diluted with heptane. The crystalline solid obtained was collected and dried under vacuum to yield about 5.5 g of (3R,5S)-5-biphenyl-4-ylmethyl-3-methyl-2-oxo-pyrrolidine-1-carboxylic acid tert-butyl ester (2-a, R1=BOC).

Material may be purified by column chromatography, eluting ethylacetate/heptane (6:1).

$^1$H-NMR (DMSO): 0.95 (3H, d, 1-CH$_3$); 1.42 (9H, s, C(CH$_3$)$_3$); 1.56 (1H, m, 4-CHH); 1.90 (1H, m, 4-CHH); 2.50-2.57 (2H, m, 3-CH$_2$); 2.78 (1H, dd, 1-CHH); 2.99 (1H, dd,

1-CHH); 4.14 (1H, m, 5-CH); 7.25-7.31 (3H, m, aromatic); 7.39 (2H, m, aromatic); 7.58 (4H, m, aromatic).

Example 15

(2-a, R1=BOC) to [(2R,4S)-5-biphenyl-4-yl-4-tert-butoxycarbonylamino-2-methylpentanoic acid] (3-a, R1=BOC, R2=R3=H)

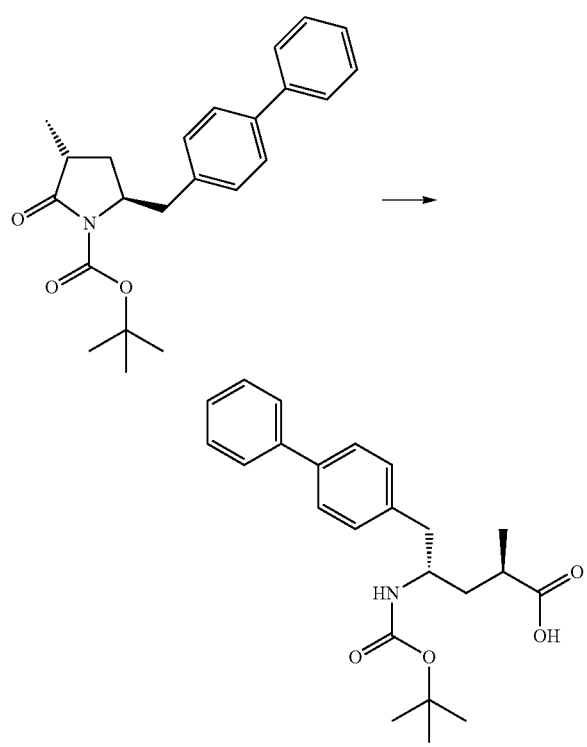

5 g (3R,5S)-5-biphenyl-4-ylmethyl-3-methyl-2-oxo-pyrrolidine-1-carboxylic acid tert-butyl ester (2-a, R1=BOC) was dissolved in 50 ml of a mixture of THF and a 2 M lithium hydroxide solution (ratio 1:1). After 1 hour at room temperature, phosphoric acid was added to neutralise the excess of lithium hydroxide. The slurry was concentrated under vacuum to remove most of the solvent and extracted with iso-propyl acetate. The organic phase was then washed with water, partially concentrated under vacuum and brought to crystallisation upon addition of heptane. The crystalline solid obtained was collected and dried under vacuum to yield about 3.6 g of [(2R,4S)-5-biphenyl-4-yl-4-tert-butoxycarbonylamino-2-methylpentanoic acid] (3-a, R1=BOC, R2=R3=H). Mpt 146-147° C.; $\delta_H$ (500 MHz; DMSO) 1.07 (3H, d, J 7.0, 1-CH$_3$), 1.34 (9H, s, (CH$_3$)$_3$), 1.38 (1H, m, 3-H$_A$), 1.77 (1H, m, 3-H$_B$), 2.43 (1H, m, 2-H), 2.70 (2H, d, J 7.0, 5-H), 3.69 (1H, m, 4-H), 6.74 (1H, d, J 9.0, NH), 7.27 (2H, d, J 8.0, Ar-ortho-H(Ph)), 7.36 (1H, t, J 7.0, Ar-(Ph)-para-H), 7.46 (2H, t, J 7.5, Ar-(Ph)-meta-H), 7.57 (2H, d, J 8.0, Ar-meta-H (Ph), 7.64 (2H, d, J 7.5, Ar-(Ph)-ortho-H), 12.01 (1H, s, CO$_2$H); $\delta_C$ (500 MHz, DMSO) 18.1 (1-CH$_3$), 28.3 [(CH$_3$)$_3$], 35.9 (2-C), 37.9 (3-C), 40.7 (5-C), 50.0 (4-C), 77.4 [(C(CH$_3$)$_3$], 126.3, 126.5, 127.2, 128.9, 129.8 (Ar—CH), 137.7 (Ar-ipso-C(Ph)), 138.3 (Ar-para-C(Ph)), 140.1 (Ar-(Ph)-ipso-C), 155.2 (NCO), 177.2 (CO$_2$H); m/z (+ESI) 406 ([MNa]$^+$, 6%), 384 ([MH]$^+$, 31), 328 (100), 284 (19); Found: [MH]$^+$, 384.21691. C$_{23}$H$_{30}$NO$_4$ requires MH 384.21693.

Example 16

(S)-5-biphenyl-4-ylmethyl-2-oxo-pyrrolidine-1-carboxylic acid tert-butyl ester (1-a, R1=BOC)

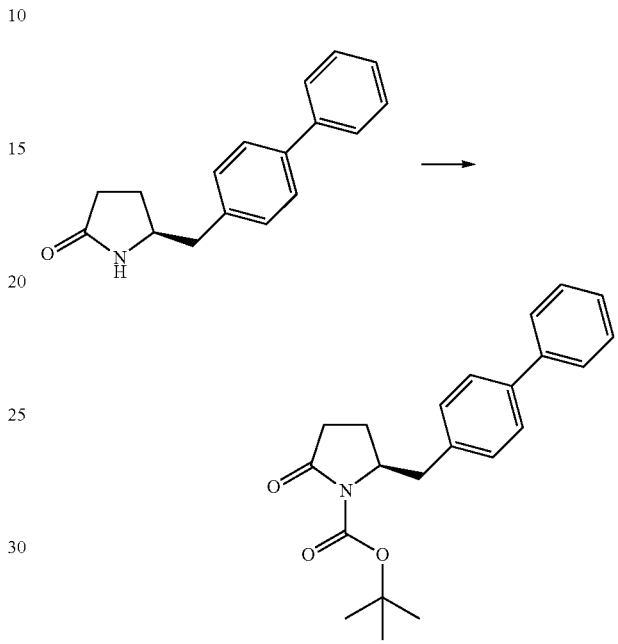

Method 1

520 mg di-tert-butyldicarbonate and 12 mg 4-(dimethylamino)pyridine were added to a suspension of 500 mg (S)-5-biphenyl-4-ylmethylpyrrolidin-2-one (1-a, R1=H) in 3 ml acetonitrile. After about 20 hours, the mixture was concentrated to dryness. The mixture was partitioned between ethyl acetate and aqueous potassium hydrogen sulphate and the organic layer separated and evaporated to dryness to yield 630 mg of (S)-5-biphenyl-4-ylmethyl-2-oxo-pyrrolidine-1-carboxylic acid tert-butyl ester (1-a, R1=BOC). $^1$H-NMR (CDCl$_3$): 1.62 (9H, s, C(CH$_3$)$_3$); 1.88 (1H, m, 4-CHH); 2.03 (1H, m, 4-CHH); 2.34-2.43 (2H, m, 3-CH$_2$); 2.80 (1H, dd, 1-CHH); 3.21 (1H, dd, 1-CHH); 4.42 (1H, m, 5-CH); 7.28 (2H, m, aromatic); 7.76 (1H, m, aromatic); 7.46 (2H, m, aromatic); 7.59 (4H, m, aromatic). m/z: 352 (MH$^+$, 14%); 337 (16); 296 (100); 293 (13); 252 (25).

The X-ray Structure of the obtained crystals is shown in FIG. 10. Single crystal for this determination is obtained from diethylether as solvent.

| Crystal data [recorded at 100(2)K] | |
|---|---|
| Empirical formula | C$_{22}$H$_{25}$NO$_3$ |
| Formula weight | 351.43 |
| Crystal system | Monoclinic |
| Space group | P21 |
| Cell parameters | a = 5.801(2) Å |
| | b = 8.180(2) Å |
| | c = 19.891(4) Å |
| | α = 90° |
| | β = 96.278(9)° |
| | γ = 90° |

-continued

| Crystal data [recorded at 100(2)K] | |
|---|---|
| Volume of unit cell | 938.2(4) Å$^3$ |
| Z* | 2 |
| Calculated density | 1.244 mg m$^{-3}$ |

*(number of asymmetric units in the unit cell)

Method 2

8.6 g (S)-5-Biphenyl-4-ylmethylpyrrolidin-2-one (1-a, R1=H) (34.22 mmol) is dissolved in 135 ml methylene chloride. 4.2 g DMAP (34.22 mmol) is added. The mixture is further diluted with 10 ml methylene chloride. Then 14.9 g BOC$_2$O (68.44 mmol) is added and further 10 ml methylene chloride is added. This reaction mixture is then stirred at reflux for 7.5 h. Then a further 3.7 g BOC$_2$O is added. After a total reaction time of 24 h at reflux the solvent is evaporated completely. The evaporation residue is then filtered over 460 g of silica gel with an eluent of toluene:ethyl acetate 4:1. The product fractions are concentrated in vacuo to yield the crude product, which is recrystallised from methylene chloride/heptane fraction 1:6, to yield (S)-5-biphenyl-4-ylmethyl-2-oxo-pyrrolidine-1-carboxylic acid tert-butyl ester (1-a, R1=BOC).

Method 3

(S)-5-Biphenyl-4-ylmethylpyrrolidin-2-one (1-a, R1=H) (100 g, 398 mmol) is added to toluene (1 L) at room temperature. N,N-Dimethylaminopyridine (4.9 g, 29.8 mmol) is then added followed by triethylamine (72 ml, 517 mmol). The mixture is then heated to 65° C. Di-tert-butyl dicarbonate (104 g, 478 mmol) is then added over 0.5 h. After 0.5 h, the mixture is concentrated in vacuo. The residue is then dissolved in methanol (1 L) and warmed to 60° C. 400 ml of solvent is removed. Water (100 ml) is then added and the mixture is cooled to room temperature. After 2 h, the mixture is further cooled to 0° C. After 1 h, the mixture is filtered and the solid washed with methanol-water (5:1, 30 ml×3) mixture. The solid is dried in vacuo to yield (S)-5-biphenyl-4-ylmethyl-2-oxo-pyrrolidine-1-carboxylic acid tert-butyl ester (1-a, R1=BOC).

Example 17

(S)-5-biphenyl-4-ylmethyl-1-pyrrolidin-1-ylmethylpyrrolidin-2-one (1-a, R1=methylpyrrolidin)

-continued

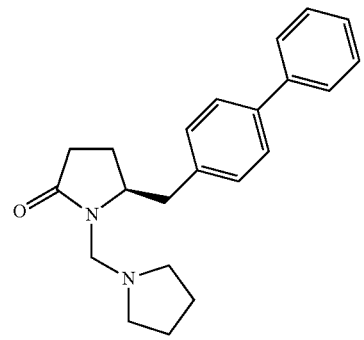

A mixture of 500 mg (S)-5-biphenyl-4-ylmethylpyrrolidin-2-one (1-a, R1=H), 329 µl pyrrolidine and 415 µl formaldehyde in 3.5 ml ethanol were heated at reflux for 3 h. A further quantity of 164 µl pyrrolidine and 148 µl formaldehyde were added and the mixture refluxed for about 24 h. The mixture was concentrated to dryness and purified by chromatography to obtain 533 mg of (S)-5-biphenyl-4-ylmethyl-1-pyrrolidin-1-ylmethylpyrrolidin-2-one (1-a, R1=methylpyrrolidin). $^1$H NMR (DMSO): 1.69 (4H, m, 2×NCH$_2$CH$_2$); 1.68-2.15 (4H, m, 3-CH$_2$, 4-CH$_2$); 2.50 (4H, 2×NCH$_2$); 2.66 (1H, dd, 1-CHH); 3.12 (1H, dd, 1-CHH); 3.94 (1H, d, NCHHN); 4.21 (1H, d, NCHHN); 7.29 (2H, d, aromatic); 7.33 (1H, t, aromatic); 7.44 (2H, t, aromatic); 7.59 (2H, d, aromatic); 7.64 (2H, d, aromatic). m/z: 335 (MH$^+$, 100%)

Example 18

(3R,5S)-5-biphenyl-4-ylmethyl-3-methyl-2-oxo-pyrrolidine-1-carboxylic acid tert-butyl ester (2-a, R1=BOC)

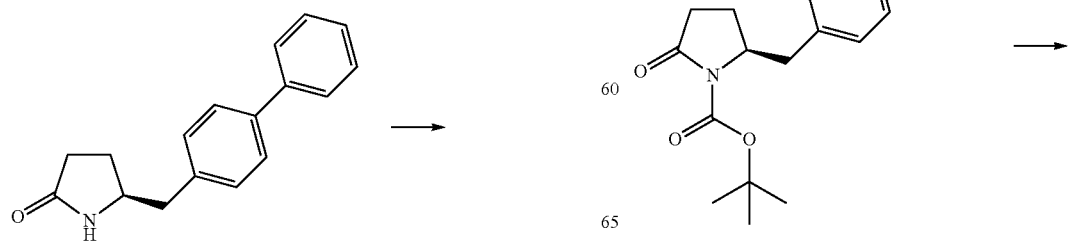

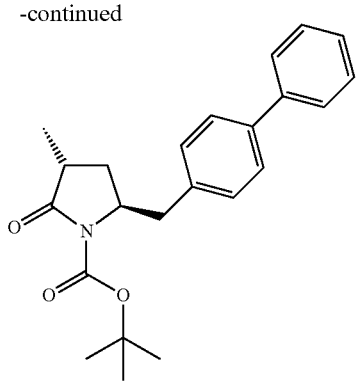

Method 1

46 µl diisopropylamine were dissolved in 2 ml tetrahydrofuran at 0° C. 0.2 ml of n-butyllithium (1.6 M in hexanes) were added and the mixture stirred for about 15 min. The mixture was then cooled to −78° C. 100 mg of starting material (1-a, R1=BOC) dissolved in 1 ml tetrahydrofuran were added. After 15 min, 71 µl methyl iodide were added and the mixture was stirred at −78° C. for a further 5 hours. The reaction was quenched by adding ammonium chloride solution and extracted with ethyl acetate. The organic phase was separated and concentrated to dryness to give a mixture of (3R,5S):(3S,5S) diastereoisomers of 57:43, respectively. Ratio as determined by HPLC analysis. Spectroscopic data for major diastereomer (2-a, R1=Boc) is in agreement with the data provided in Example 14 (2-a, R1=Boc).

Method 2

459 1 (331 mg, 3.27 mmol) diisopropylamine is dissolved in 5 ml dry THF and is cooled to 0° C. After the addition of 1.97 ml butyl lithium in hexane (1.59 M), the solution is stirred at 0° C. for 15 min. Subsequently the reaction mixture is cooled to −78° C. and a solution of 1 g (2.84 mmol) (S)-5-biphenyl-4-ylmethyl-2-oxo-pyrrolidine-1-carboxylic acid tert-butyl ester (1-a, R1=BOC), and 1.03 ml (1.09 g, 8.52 mmol) 1,3-dimethyl-3,4,5,6-tetrahydro-2(1H)-pyrimidinone (DMPU) in 5 ml THF are added over 15 min. After stirring for 15 min, 708 1 (1.61 g, 11.38 mmol) methyl iodide is added over 10 min. The resulting mixture is stirred at −78° C. for 3 h. The reaction is quenched through the addition of 1 ml morpholine followed by 1 ml saturated $NH_4Cl$ solution and 15 ml isopropyl acetate. The organic phase is separated and washed with water (3×10 ml). The organic layer is separated, dried over $MgSO_4$, filtered and evaporated. HPLC of the residue reveals two methylated diastereomeric compounds [(3R,5S)-5-biphenyl-4-ylmethyl-3-methyl-2-oxo-pyrrolidine-1-carboxylic acid tert-butyl ester (2-a, R1=BOC) and (3S,5S)-5-biphenyl-4-ylmethyl-3-methyl-2-oxo-pyrrolidine-1-carboxylic acid tert-butyl ester (2-b, R1=BOC)].
$^1$HNMR indicates a 50:50 ratio of the two diastereoisomers. (Spectroscopic data for diastereomer mixture). NMR (300 MHz, DMSO-$d_6$, /ppm): 7.50 (m, 4H); 7.37 (m, 2H); 7.27 (m, 1H); 7.18 (m, 2H); 4.29-4.12 (m, 1H); 3.45 (m, 1H); 3.10 (m, 1H); 2.73-2.34 (m, 2H); 2.17-1.97 (m, 1H); 1.54, 1.51 (2×s, 9H); 1.13, 1.09 (2×d with ratio approx. 1:1, J=7.2, 7.0, 3 H). MS (ESI, m/e) 366 [M+H]$^+$ Method 3

100 mg (0.284 mmol) (S)-5-biphenyl-4-ylmethyl-2-oxo-pyrrolidine-1-carboxylic acid tert-butyl ester (1-a, R1=BOC) is dissolved in 2 ml THF and the solution is cooled to −78° C. Subsequently, 312 µl Lithium bis(trimethylsilyl)-amide in THF (1 M) is added over 5 min. After stirring for 15 min, 71 µl (161 mg, 1.136 mmol) methyl iodide is added. The resulting mixture is stirred for 5 h and then quenched with morpholine and water. According to HPLC analysis the ratio of diastereoisomers is determined to be 67:32.

HPLC Method (1):

Column: CC 125/3 Nucleosil 10-3. Mobile Phase A (Water); Mobile Phase B (Acetonitrile). Gradient: 0 min (90% A; 10% B); 20 min (10% A; 90% B); 25 min (0% A; 100% B); 25.1 min (90% A; 10% B). Flow rate: 1.0 ml min$^{-1}$.

Wavelength: 254 nm.

Retention Times:
1-a, R1=Boc: 14.9 min
2-a, R1=Boc and 2-b, R1=Boc:
Under these hplc conditions, no separation of 2-a, R1=Boc and 2-b, R1=Boc is observed. Consequently, the residues from the reactions are treated with trifluoroacetic acid prior to HPLC analysis in order to remove the Boc protecting group.

Retention Times:
1-a, R1=H, 12.1 min
1-b, R1=H, 12.3 min

HPLC Method (2):

Column: Chiralpak AD-RH, 150×2.6 mm, 5.0 µm. Mobile Phase A (Water); Mobile Phase B (Acetonitrile). Isocratic: 0 min (80% B); 15 min (80% B). Flow rate: 0.5 ml min$^{-1}$. Wavelength: 210 nm.

Retention Times:
2-a, R1=Boc: 6.3 min
2-b, R1=Boc: 6.9 min

Example 19

(3R,5S)-5-biphenyl-4-ylmethyl-3-methyl-1-pyrrolidin-1-ylmethylpyrrolidin-2-one (2-a, R1=methylpyrrolidin)

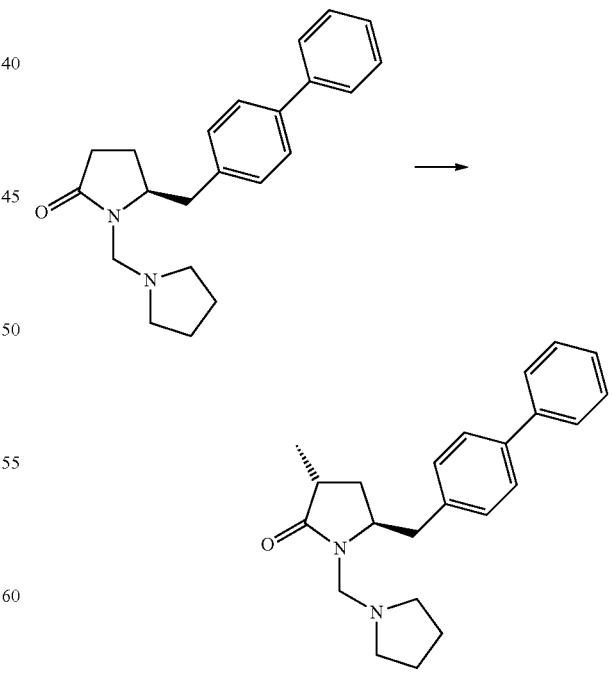

Method 1

93 µl Diisopropylamine were dissolved in 2 ml tetrahydrofuran at 0° C. 0.4 ml of n-butyllithium (1.6 M in hexanes) was added and the mixture stirred for about 30 min. 200 mg of starting material (1-a, R1=methylpyrrolidin) dissolved in 1 ml tetrahydrofuran were added. After 30 min, 41 μl methyl iodide were added and the mixture was stirred at 0° C. for a further 2 hours. The reaction was quenched by adding ammonium chloride solution and extracted with ethyl acetate. The organic phase was separated and concentrated to dryness to obtain 188 mg of crude product.

According to NMR analysis the diastereomeric ratio 2-a R1=methylpyrrolidin: 2-b, R1=methylpyrrolidin is 85:15 (integrations of signals at 3.06 and 3.40 ppm).

$^1$H-NMR (DMSO, Major stereoisomer): 0.99 (3H, d, 1-CH$_3$); 1.55 (1H, m, 4-CHH); 1.69 (4H, m, 2×NCH$_2$CH$_2$); 2.00 (1H, m, 4-CHH); 2.20 (1H, m, 3-CH); 2.50 (4H, 2×NCH$_2$); 2.69 (1H, dd, 1-CHH); 3.06 (1H, dd, 1-CHH); 3.90 (1H, m, 5-CH); 3.93 (1H, m, NCHHN); 4.22 (1H, m, NCHHN); 7.30 (2H, d, aromatic); 7.34 (1H, t, aromatic); 7.44 (2H, t, aromatic); 7.60 (2H, d, aromatic); 7.65 (2H, d, aromatic). m/z: 349 (MH$^+$, 100%).

Method 2

(1-a, R1=methylpyrrolidin) (200 mg, 0.6 mmol) is dissolved in THF (3.4 ml). The mixture is cooled to 0° C. Lithium bis(trimethylsilyl)amide (0.66 ml, 1M in THF) is added and the mixture is stirred for 1 h. Methyl iodide (40.9 μl, 0.65 mmol) is added and the resulting mixture is stirred for 4 h at 0° C. The reaction is quenched by the addition of saturated ammonium chloride solution (2 ml), water (1 ml) and ethyl acetate (1 ml). Phases are separated. The organic phase is washed with brine, dried (MgSO$_4$) and concentrated in vacuo (222 mg crude). According to NMR analysis, ratio 2-a R1=methylpyrrolidin:2-b, R1=methylpyrrolidin is 66:34.

Example 20

(3R,5S)-5-biphenyl-4-ylmethyl-3-methyl-1-pyrrolidin-1-ylmethylpyrrolidin-2-one (2-a, R1=methylpyrrolidin)

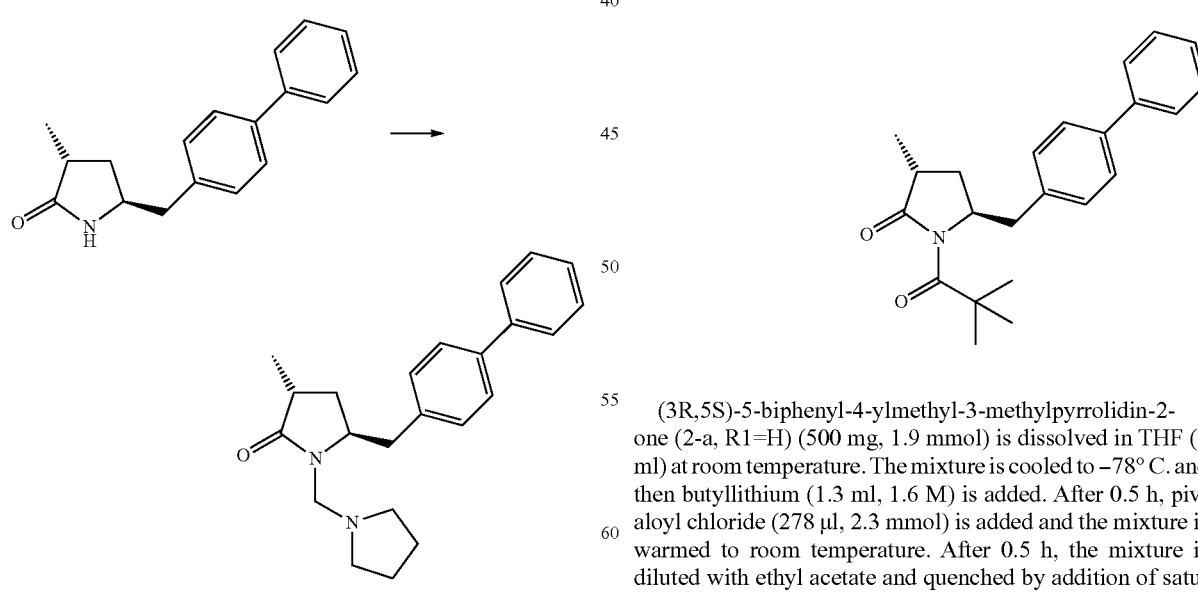

(3R,5S)-5-biphenyl-4-ylmethyl-3-methylpyrrolidin-2-one (2-a, R1=H) (1 g, 3.8 mmol) is added to ethanol (7 ml). Pyrrolidine (312 μl, 3.8 mmol) and aqueous formaldehyde (393 μl, 5.3 mmol) are added. The mixture is heated at reflux for 3 h. The mixture is next cooled to room temperature and concentrated in vacuo to afford (3R,5S)-5-biphenyl-4-ylmethyl-3-methyl-1-pyrrolidin-1-ylmethylpyrrolidin-2-one (2-a, R1=methylpyrrolidin). Spectroscopic data as reported in Example 19.

Example 21

(3R,5S)-5-biphenyl-4-ylmethyl-1-(2,2-dimethylpropionyl)-3 methylpyrrolidin-2-one (2-a, R1=Piv)

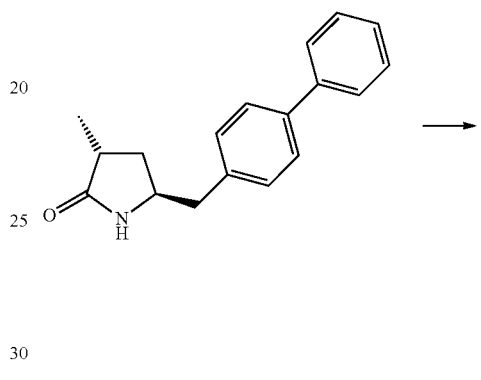

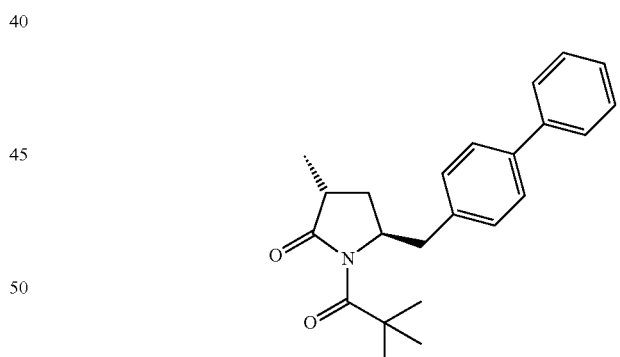

(3R,5S)-5-biphenyl-4-ylmethyl-3-methylpyrrolidin-2-one (2-a, R1=H) (500 mg, 1.9 mmol) is dissolved in THF (5 ml) at room temperature. The mixture is cooled to −78° C. and then butyllithium (1.3 ml, 1.6 M) is added. After 0.5 h, pivaloyl chloride (278 μl, 2.3 mmol) is added and the mixture is warmed to room temperature. After 0.5 h, the mixture is diluted with ethyl acetate and quenched by addition of saturated ammonium chloride solution followed by water. The phases are separated. The organic phase is washed with brine, dried (MgSO$_4$) and concentrated in vacuo The crude material is purified by column chromatography, by eluting with ethyl acetate/heptane (1:6) to give (3R,5S)-5-biphenyl-4-ylmethyl-1-(2,2-dimethylpropionyl)-3-methylpyrrolidin-2-one (2-a, R1=Piv). Spectroscopic data as reported in Example 5-1, Method 1.

Example 22

((S)-2-Biphenyl-4-ylmethyl-5-oxo-pyrrolidin-1-yl)acetonitrile (1-a, R1=cyanomethyl)

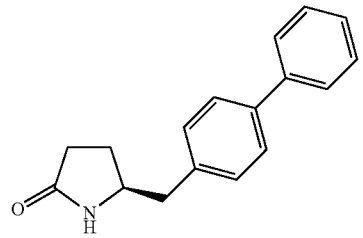

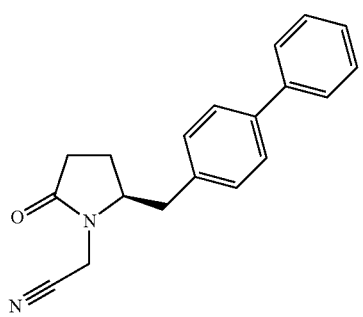

1.5 g (5.97 mmol) (S)-5-biphenyl-4-ylmethylpyrrolidin-2-one (1, $R_1$=H) is dissolved in 15 ml dry THF and cooled to −78° C. After the addition of 4.13 ml butyl lithium in hexane (1.59 M) the yellow solution is stirred at −78° C. for 30 min. Subsequently, 475 l (855 mg, 7.16 mmol) bromoacetonitrile is added and the mixture is warmed up to room temperature overnight. The reaction is then quenched on addition of 10 ml saturated NH$_4$Cl solution followed by the addition of 6 ml water and the mixture is extracted with 2×40 ml ethyl acetate. The combined organic layers are separated, dried over MgSO$_4$, filtered and evaporated. The resulting residue is purified by column chromatography (dichloromethane:methanol=99:1) to give ((S)-2-Biphenyl-4-ylmethyl-5-oxo-pyrrolidin-1-yl)acetonitrile (1-a, R1=cyanomethyl) as off-white solid. NMR (400 MHz, DMSO-d$_6$, /ppm): 7.65 (m, 4H); 7.47 (t, J=7.4, 2 H); 7.40 (m, 3H); 4.57 (d, J=17.7, 1H); 4.44 (d, J=17.7, 1H); 3.91 (m, 1H); 3.19 (dd, J=3.9, 13.8, 1H); 2.70 (dd, J=9.2, 13.8, 1H); 2.18 (m, 2H); 1.95 (m, 1H); 1.77 (m, 1H). MS (ESI, m/e) 291 [M+H]$^+$. IR (solution in CH$_2$Cl$_2$, /cm$^{-1}$): 3025; 2985; 2257; 1697; 1688; 1486; 1421; 1323; 1271; 1182; 760; 699.

Example 23

(S)-1-Acetyl-5-biphenyl-4-ylmethyl-pyrrolidin-2-one (1-a, R1=Ac)

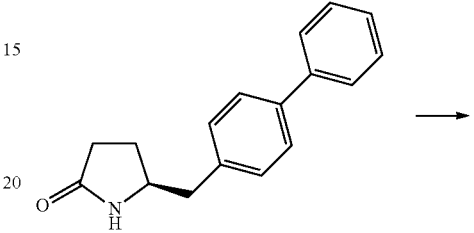

(S)-5-biphenyl-4-ylmethylpyrrolidin-2-one (1-a, R1=H) (5 g, 19.9 mmol) is dissolved in THF (50 ml). The mixture is cooled to −78° C. and n-butyllithium (14 ml, 1.6 M) added. After 0.5 h, acetyl chloride (1.7 ml, 24 mmol) is added and the mixture is allowed to warm to room temperature. After 1 h, the mixture is quenched with saturated ammonium chloride (40 ml) and water (10 ml) and ethyl acetate (20 ml) are added. The organic phase is washed with brine, dried (MgSO$_4$) and concentrated in vacuo to give (S)-1-Acetyl-5-biphenyl-4-ylmethyl-pyrrolidin-2-one (1-a, R1=Ac). $^1$H NMR (CDCl$_3$): 1.84 (1H), 1.93 (1H), 2.30 (1H), 2.32 (1H), 2.50 (3H), 2.72 (1H), 3.09 (1H), 4.56 (1H), 7.20 (2H), 7.28 (1H), 7.37 (2H), 7.49 (4H).

Example 24

(S)-5-Biphenyl-4-ylmethyl-1-triethylsilanyl-pyrrolidin-2-one (1-a, R1=TES)

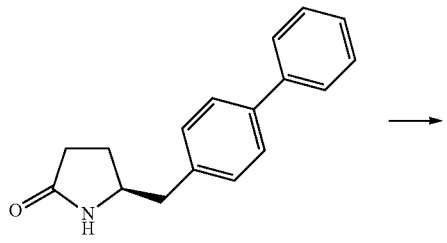

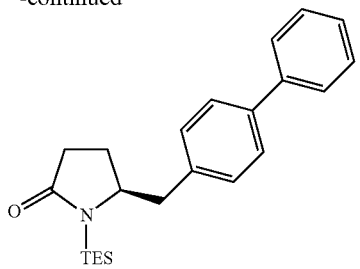

A dry flask is charged with 1.256 g (5 mmol) (S)-5-biphenyl-4-ylmethylpyrrolidin-2-one (1-a, R1=H) and 15 ml dry THF. To the resulting clear solution, 2.02 g (20 mmol) triethylamine is added followed by 904 mg (6 mmol) triethylchlorosilane (TES-Cl). The reaction mixture is stirred at room temperature for 4 h and then quenched on addition of 5 ml saturated NaHCO$_3$ solution, 10 ml water and 10 ml isopropyl acetate. The layers are separated and the aqueous layer extracted with 10 ml isopropyl acetate. The combined organic layers are dried over MgSO$_4$, filtered and evaporated. The resulting residue is purified by column chromatography (dichloromethane+1% v/v triethylamine) to give (S)-5-Biphenyl-4-ylmethyl-1-triethylsilanyl-pyrrolidin-2-one (1-a, R1=TES) as a yellow oil. NMR (300 MHz, DMSO-d$_6$, /ppm): 7.63 (m, 4H); 7.55 (m, 2H); 7.32 (m, 3H); 3.80 (m, 1H); 2.85 (m, 1H), 2.70 (m, 1H), 2.10-1.70 (m, 4H), 1.02-0.80 (m, 15H). MS (ESI, m/e) 366 [M+H]$^+$; 731 [2M+H]$^+$. IR (solution in CH$_2$Cl$_2$, /cm$^{-1}$): 3426; 3047; 2957; 1698; 1672; 1487; 1378; 1242; 1114; 1008.

Example 25

(3R,5S)-5-Biphenyl-4-ylmethyl-3-methyl-1-triethylsilanyl-pyrrolidin-2-one (2-a, R1=TES) and (3S,5S)-5-Biphenyl-4-ylmethyl-3-methyl-1-triethylsilanyl-pyrrolidin-2-one (2-b, R1=TES)

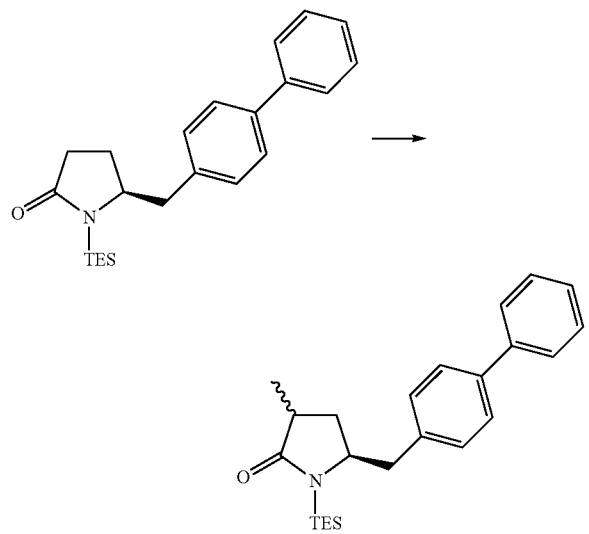

109 mg (0.2981 mmol) (S)-5-Biphenyl-4-ylmethyl-1-triethylsilanyl-pyrrolidin-2-one (1-a, R1=TES) is dissolved in 1.5 ml toluene and the solution is cooled to 0° C. After slow addition of 628 l potassium-bis-(trimethylsilyl)-amide in toluene (0.57 M), the solution is stirred at 0° C. for 15 min. Subsequently, 113 l (150 mg, 1.19 mmol) dimethylsulfate is added to the suspension over 5 min. The mixture is then stirred at 0° C. for 1 h. The reaction is quenched by addition of 2 ml saturated NH$_4$Cl solution, 2 ml water followed by 20 ml isopropyl acetate. The organic phase is washed with water (3×10 ml), separated, dried over MgSO$_4$, filtered and evaporated. HPLC of the residue reveals conversion to the two methylated diastereomeric compounds [(3R,5S)-5-Biphenyl-4-ylmethyl-3-methyl-1-triethylsilanyl-pyrrolidin-2-one (2-a, R1=TES) and (3S,5S)-5-Biphenyl-4-ylmethyl-3-methyl-1-triethylsilanyl-pyrrolidin-2-one (2-b, R1=TES)].

Example 26

(S)-2-Biphenyl-4-ylmethyl-5-oxo-pyrrolidine-1-carboxylic acid benzyl ester (1-a, R1=Cbz)

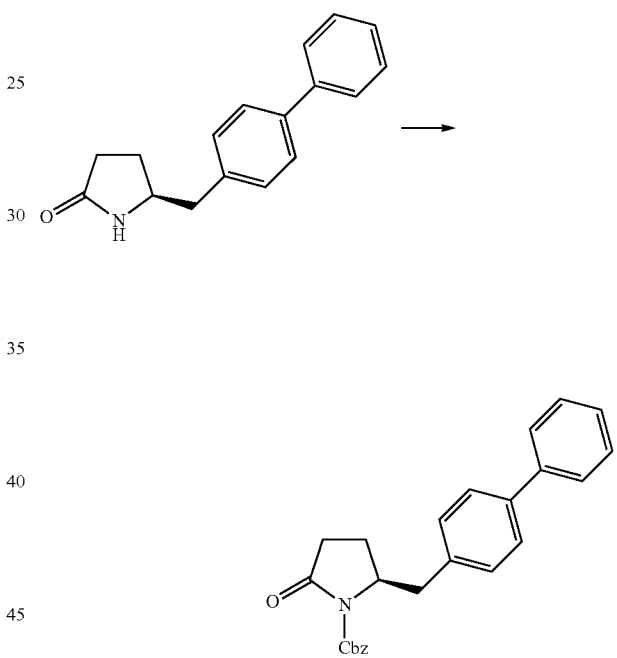

1 g (4 mmol) (S)-5-biphenyl-4-ylmethylpyrrolidin-2-one (1-a, R1=H) is dissolved in 10 ml dry THF and cooled to −78° C. After the addition of 2.76 ml butyl lithium in hexane (1.59 M), the yellow solution is stirred at −78° C. for 30 min. Subsequently, 676 l (820 mg, 4.8 mmol) benzyl chloroformate (Cbz-Cl) is added and stirring is continued at −78° C. for 2 h. The reaction is then quenched by addition of 12 ml saturated NH$_4$Cl solution followed by 10 ml water and then extracted with 2×40 ml isopropyl acetate. The layers are separated and the organic layer is dried over MgSO$_4$, filtered and evaporated. The resulting residue (1.73 g) is purified on column chromatography (dichloromethane:methanol=99.5:0.5) to give (S)-2-Biphenyl-4-ylmethyl-5-oxo-pyrrolidine-1-carboxylic acid benzyl ester (1-a, R1=Cbz) as off-white solid. NMR (400 MHz, DMSO-d$_6$, /ppm): 7.66 (m, 2H); 7.60 (m, 2H); 7.51-7.34 (m, 8H); 7.26 (d, J=8.2, 2 H); 5.28 (s, 2H); 4.37 (m, 1H); 3.05 (dd, J=3.3, 13.1, 1H); 2.88 (dd, J=9.0, 13.1, 1H); 2.45 (m, 1H); 2.28 (m, 1H); 2.01 (m, 1H); 1.77 (m, 1H). MS (ESI, m/e) 386 [M+H]$^+$, 788 [2M+NH$_4$$^+$]. IR (solution in CH$_2$Cl$_2$, /cm$^{-1}$): 3092; 2957; 1756; 1705; 1488; 1396; 1304; 1287; 1231; 1139; 1043; 952; 750.

Example 27

(3R,5S)-5-Biphenyl-4-ylmethyl-3-methyl-2-oxo-pyrrolidine-1-carboxylic acid benzyl ester (2-a, R1=Cbz) and (3S,5S)-5-Biphenyl-4-ylmethyl-3-methyl-2-oxo-pyrrolidine-1-carboxylic acid benzyl ester (2-b, R1=Cbz)

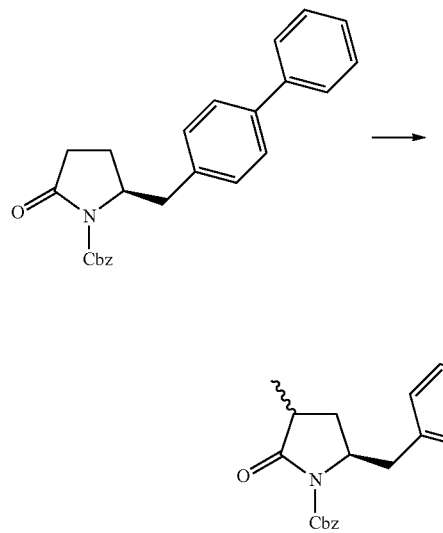

Method 1

119 mg (0.309 mmol) (S)-2-Biphenyl-4-ylmethyl-5-oxo-pyrrolidine-1-carboxylic acid benzyl ester (1a, R1=Cbz) is dissolved in 1.5 ml toluene and the solution is cooled to −78° C. After the addition of 665 l potassium-bis-(trimethylsilyl)-amide in toluene (0.57 M) the solution is stirred at −75° C. for 20 min. Subsequently, 117 l (155 mg, 1.23 mmol) dimethylsulfate is added to the orange solution over 5 min. The resulting mixture is stirred at −78° C. for 3 h and then warmed to 0° C. over 1 h. The reaction is then quenched by addition of 2 ml saturated NH$_4$Cl solution, 2 ml water followed by the addition of 20 ml isopropyl acetate. The organic phase is washed with water (3×10 ml), dried over MgSO$_4$, filtered and evaporated. HPLC and LC-MS of the residue reveals the two methylated diastereomeric compounds [(3R,5S)-5-Biphenyl-4-ylmethyl-3-methyl-2-oxo-pyrrolidine-1-carboxylic acid benzyl ester (2-a, R1=Cbz) and (3S,5S)-5-Biphenyl-4-ylmethyl-3-methyl-2-oxo-pyrrolidine-1-carboxylic acid benzyl ester (2-b, R1=Cbz)], which were inseparable from one another MS (ESI): 399 [MH]$^+$, 816 [2M+NH$_4$]$^+$.

Method 2

53 l (38 mg, 0.379 mmol) diisopropylamine is dissolved in 1 ml dry THF and is cooled to 0° C. After the addition of 226 l butyl lithium in hexane (1.59 M), the solution is stirred at 0° C. for 10 min. Subsequently, a solution of (S)-2-Biphenyl-4-ylmethyl-5-oxo-pyrrolidine-1-carboxylic acid benzyl ester (1-a, R1=Cbz) in 1 ml THF is added over 10 min followed by the addition of 24 l (54 mg, 0.379 mmol) methyl iodide over 5 min. The resulting mixture is stirred at 0° C. for 2 h. Then, the reaction is quenched by addition of 2 ml saturated NH$_4$Cl solution, 1 ml water and 5 ml ethyl acetate. The organic phase is separated and then washed with water (3×5 ml). The organic layer is then dried over MgSO4, filtered and evaporated. HPLC and LC-MS of the residue reveals the two methylated diastereomeric compounds [(3R,5S)-5-Biphenyl-4-ylmethyl-3-methyl-2-oxo-pyrrolidine-1-carboxylic acid benzyl ester (2-a, R1=Cbz) and (3S,5S)-5-Biphenyl-4-ylmethyl-3-methyl-2-oxo-pyrrolidine-1-carboxylic acid benzyl ester (2-b, R1=Cbz)], which were inseparable from one another.

Example 28

(S)-5-Biphenyl-4-ylmethyl-1-(2-trimethylsilanylethoxymethyl)pyrrolidin-2-one (1-a, R1=SEM)

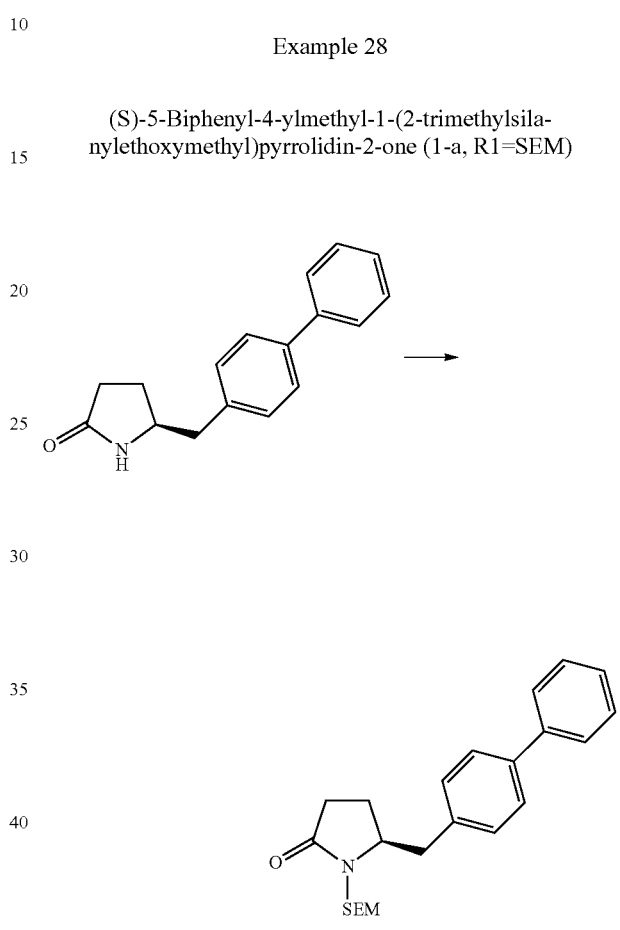

804 mg (3.2 mmol) (S)-5-biphenyl-4-ylmethylpyrrolidin-2-one (1-a, R1=H) is dissolved in 16 ml dry THF and cooled to −78° C. After the addition of 2.21 ml butyl lithium in hexane (1.59 M), the yellow solution is stirred at −78° C. for 30 min. Subsequently, 680 l (640 mg=3.84 mmol) (2-chloromethoxyethyl)-trimethylsilane (SEM-Cl) is added and stirring is continued at −20° C. for 5 h. The mixture is then allowed to warm up to room temperature overnight. The reaction is then quenched by addition of 10 ml saturated NH$_4$Cl solution followed by 10 ml water and extracted with 2×40 ml isopropyl acetate. The layers are separated and the organic layer dried over MgSO$_4$, filtered and evaporated. The resulting residue (1.33 g) is purified using column chromatography (dichloromethane:triethylamine=99.5:0.5→dichloromethane:methanol:triethylamine=98.5:1:0.5) to give (S)-5-Biphenyl-4-ylmethyl-1-(2-trimethylsilanylethoxymethyl)pyrrolidin-2-one (1-a, R1=SEM) as a yellow oil. NMR (400 MHz, CDCl$_3$, /ppm): 7.58 (m, 4H); 7.47 (m, 2H); 7.37 (m, 1H); 7.30 (m, 2H); 5.04 (d, J=10.6, 1H); 4.70 (d, J=10.6, 1 H); 4.03 (m, 1H); 3.59 (m, 2H); 3.24 (dd, J=4.2, 13.4, 1H); 2.67 (dd, J=9.1, 13.4, 1H); 2.33 (t, J=8.2, 2 H); 2.10 (m, 1H); 1.81 (m, 1H); 1.00 (m, 2H); 0.06 (s, 9H).

MS (ESI, m/e) 382 [M+H]$^+$; 763 [2M+H]$^+$. IR (solution in CH$_2$Cl$_2$, /cm$^{-1}$): 3057; 2951; 1702; 1487; 1414; 1249; 1073; 859; 836; 759; 697.

Example 29

(3R,5S)-5-Biphenyl-4-ylmethyl-3-methyl-1-(2-trimethylsilanylethoxymethyl)pyrrolidin-2-one (2-a, R1=SEM) and (3S,5S)-5-Biphenyl-4-ylmethyl-3-methyl-1-(2-trimethylsilanylethoxymethyl)pyrrolidin-2-one (2-b, R1=SEM)

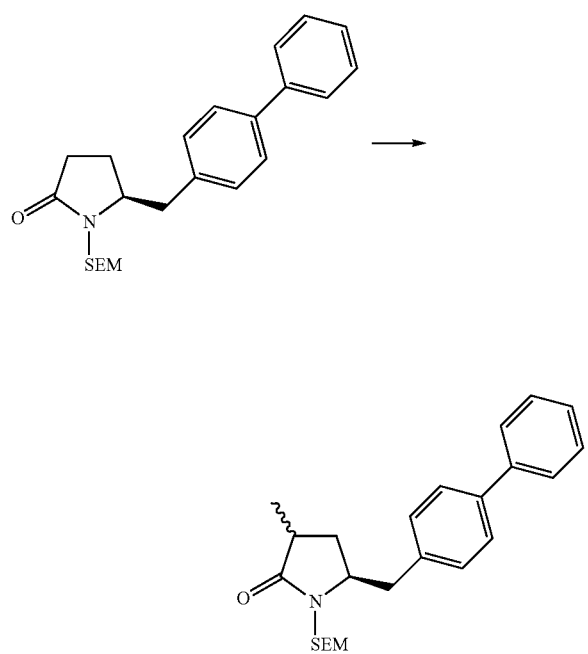

118 mg (0.309 mmol) (S)-5-Biphenyl-4-ylmethyl-1-(2-trimethylsilanylethoxymethyl)pyrrolidin-2-one (1-a, R1=SEM) is dissolved in 1.5 ml toluene and the solution is cooled to 0° C. with an ice bath. After the slow addition of 664 l potassium-bis-(trimethylsilyl)-amide in toluene (0.57 M), the solution is stirred at 0° C. for 15 min. Subsequently, 114 l (151 mg, 1.2 mmol) dimethylsulfate is added to the orange solution over 5 min. The resulting mixture is stirred at 0° C. for 2 h. Then, the reaction is quenched by addition of 2 ml saturated NH$_4$Cl solution, 2 ml water, and 20 ml isopropyl acetate. The organic phase is separated, washed with water (3×10 ml), dried over MgSO$_4$, filtered and evaporated. HPLC of the residue (100 mg) reveals the two methylated diastereomeric compounds R3R,5S)-5-Biphenyl-4-ylmethyl-3-methyl-1-(2-trimethylsilanylethoxymethyl)pyrrolidin-2-one (2-a, R1=SEM) and (3S,5S)-5-Biphenyl-4-ylmethyl-3-methyl-1-(2-trimethylsilanylethoxymethyl)pyrrolidin-2-one (2-b, R1=SEM)] and 25% unchanged starting material (S)-5-Biphenyl-4-ylmethyl-1-(2-trimethylsilanylethoxymethyl)pyrrolidin-2-one (1-a, R1=SEM). NMR analysis indicates an 80:20 ratio of diastereoisomers. (Spectroscopic data for the mixture) NMR (300 MHz, CDCl$_3$, /ppm): 7.58 (m, 4H); 7.47 (m, 2H); 7.35 (m, 1H); 7.25 (m, 2H); 5.00 (m, 1H); 4.63 (m, 1H); 3.96 (m, 1H); 3.55 (m, 2H); 3.15 (m, 1H); 2.60 (m, 1H); 2.30 (m, 1H); 2.05 (m, 1H); 1.65 (m, 1H); 1.16, 1.13 (2×d with ratio 2:8, J=7.2, 7.0, 3 H); 0.90 (m, 2H); 0.06 (s, 9H). MS (ESI, m/e) 395 [M+H]$^+$, 791 [2M+H]$^+$.

Example 30

(S)-5-biphenyl-4-ylmethylpyrrolidin-2-one [Key Lactam (1-a, R1=H)]

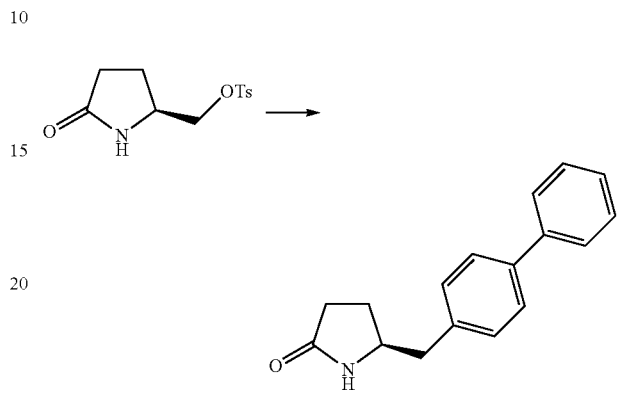

11 g of Mg turnings (452 mmol) are placed into a reactor. A solution of 93.2 g 4-bromobiphenyl (400 mmol), dissolved in 380 ml THF is added. Formation of the corresponding Grignard reagent starts after the addition of 5% of the total volume of the above solution and after the addition of a 10 mg I$_2$. The THF solution of the 4-bromobiphenyl is added at such a rate, that the IT can be kept at 50-55° C. (duration of the addition: 1 h). After the addition is complete, the reaction mixture is heated to reflux for 1.5 h. Then the mixture is cooled to rt, and next 800 ml THF are added, followed by 22 g 1,4-dioxane. Then the mixture is cooled in an ice bath and 18.0 g CuCN (200 mmol) are added. The reaction mixture is then cooled to −40° C. and then over 40 minutes a solution of 27 g (100 mmol) toluene-4-sulphonic acid-(S)-5-oxo-pyrrolidin-2-ylmethyl ester in 270 ml THF is added. After complete addition of the tosylate solution, the mixture is heated for 0.5 h to IT 35° C. The reaction mixture is stirred at that temperature overnight. Then, the reaction mixture is cooled to 20° C. and 200 ml 25% NH$_3$ (aq), followed by 900 ml NH$_4$Cl 29% (aq) are added. The phases are separated and the aqueous phase is re-extracted with 250 ml THF. The combined organic phases are washed twice with 200 ml 15% NaCl solution and are concentrated in vacuo to give 74.5 g of crude product. This crude product is purified twice over silica gel (eluent: toluene:methanol 93:7), to yield (S)-5-biphenyl-4-ylmethylpyrrolidin-2-one [Key Lactam (1-a, R1=H)] Spectroscopic data as in Example 3.

Example 31

(S)-5-biphenyl-4-ylmethylpyrrolidin-2-one [Key Lactam (1-a, R1=H)]

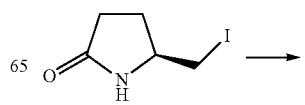

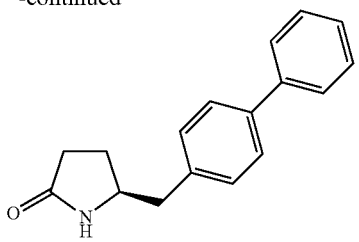

(S)-5-Iodomethylpyrrolidin-2-one (225 mg) is added to a solution of anhydrous iron(III) chloride (9.5 ml, 0.1 M in THF). The mixture is then cooled to 0° C. Biphenylmagnesium bromide (5 ml, 0.5 M in THF) and TMEDA (180 μl) are added dropwise over 0.5 h. The mixture is stirred for a further 10 min. Water (2 ml) is added. The mixture is extracted using dichloromethane (3×5 ml). The combined organic extracts are washed with 2 M HCl (2×5 ml), dried ($Na_2SO_4$), and then concentrated in vacuo. Purification by column chromatography provides (S)-5-biphenyl-4-ylmethylpyrrolidin-2-one [Key Lactam (1-a, R1=H)]. Spectroscopic data as in Example 3.

Example 32

(S)-5-biphenyl-4-ylmethylpyrrolidin-2-one [Key Lactam (1-a, R1=H)]

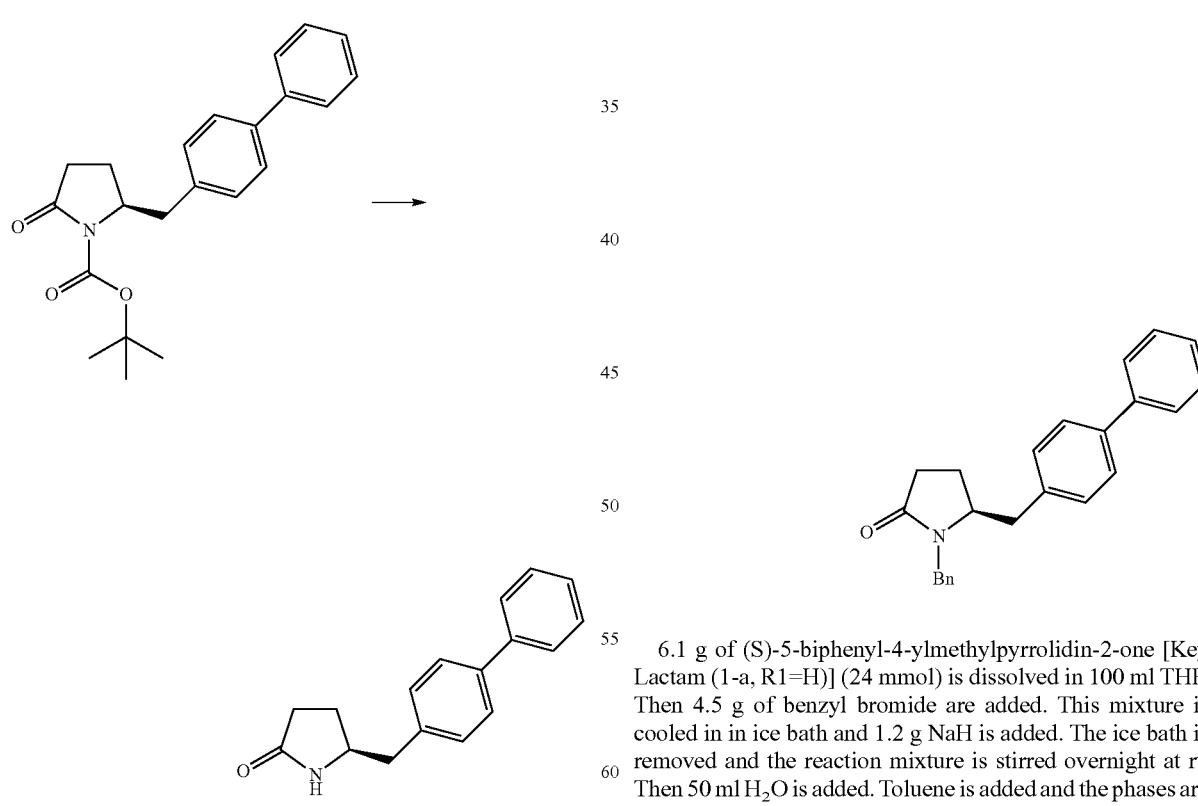

8.9 g of (S)-5-biphenyl-4-ylmethyl-2-oxo-pyrrolidine-1-carboxylic acid tert-butyl ester (1-a, R1=BOC) (25.3 mmol) is dissolved in 90 ml methylene chloride. Then 5 ml $CF_3COOH$ are added. This mixture is stirred at rt for 1.5 h. The reaction mixture is concentrated. Heptane fraction is then added to the residue. The product is crystallized. The obtained product is dissolved in toluene and then it is washed with $NaHCO_3$ (aq) solution. The organic layer is evaporated to yield (S)-5-biphenyl-4-ylmethylpyrrolidin-2-one [Key Lactam (1-a, R1=H)]. Spectroscopic data as in Example 3.

Example 33

(S)-1-Benzyl-5-biphenyl-4-ylmethyl-pyrrolidin-2-one (1-a, R1=Bn)

6.1 g of (S)-5-biphenyl-4-ylmethylpyrrolidin-2-one [Key Lactam (1-a, R1=H)] (24 mmol) is dissolved in 100 ml THF. Then 4.5 g of benzyl bromide are added. This mixture is cooled in in ice bath and 1.2 g NaH is added. The ice bath is removed and the reaction mixture is stirred overnight at rt. Then 50 ml $H_2O$ is added. Toluene is added and the phases are separated. The combined organic phases are washed with $H_2O$ and the solvent is evaporated under reduce pressure. The crude product is purified by column chromatography on 150 g silica gel, to yield (S)-1-Benzyl-5-biphenyl-4-ylmethyl-pyrrolidin-2-one (1-a, R1=Bn). $^1H$ NMR (400 MHz, DMSO): 1.79 (1H), 1.93 (1H), 2.31 (2H), 2.61 (1H), 3.03

(1H), 3.69 (1H), 4.02 (1H), 5.10 (1H), 7.12 (2H), 7.26 (2H), 7.33 (4H), 7.42 (2H), 7.49 (2H), 7.56 (2H).

Example 34

(3R,5S)-1-Benzyl-5-biphenyl-4-ylmethyl-3-methyl-pyrrolidin-2-one (2-a, R1=Bn)

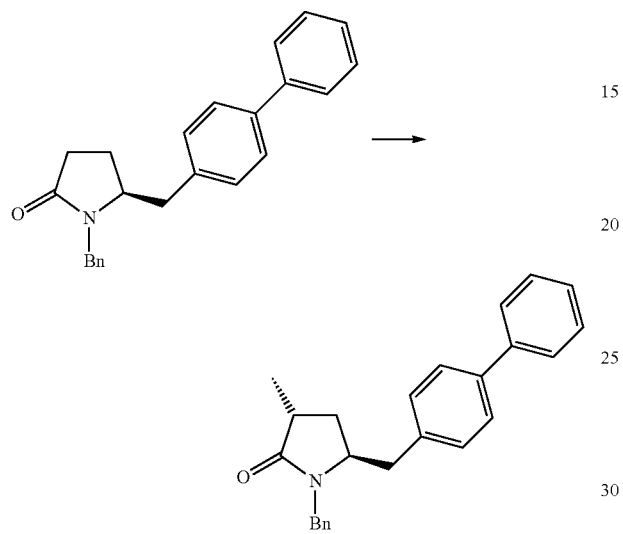

Method 1

Under Ar, 15 ml 1 M LiN(TMS)$_2$ are added to 20 ml THF. This solution is cooled to −78° C. Then over 10 minutes a solution of 3.6 g (S)-1-Benzyl-5-biphenyl-4-ylmethyl-pyrrolidin-2-one (1-a, R1=Bn) in 20 ml THF is added at −78° C. The addition funnel is rinsed with 3 ml THF. The mixture is heated to 0° C. and stirred for 10 minutes at that temperature. Then the reaction mixture is cooled down to −78° C. and over 5 minutes a solution of 1.87 g methyl iodide in 0.5 ml THF is added. The addition funnel is rinsed with 0.5 ml THF. This reaction mixture is stirred for 18 h at −78° C. Then it is quenched by the addition of 18 ml saturated NH$_4$Cl (aq) solution. Then 36 ml toluene is added, followed by 9 ml H$_2$O. The phases are separated. The aqueous phase is re-extracted with 10 ml toluene and the combined organic phases are washed twice with 25 ml of H$_2$O. The solvent is evaporated under reduced pressure, to yield the crude product. NMR analysis reveals a mixture of diasteromers 77:33 (2-a, R1=Bn/2-b, R1=Bn). Purification by column chromatography on silica gel with ethyl acetate:heptane fraction (4:6) provides (3R,5S)-1-Benzyl-5-biphenyl-4-ylmethyl-3-methyl-pyrrolidin-2-one (2-a, R1=Bn). $^1$H NMR (400 MHz, CDCl$_3$): 1.20 (3H), 1.59 (1H), 2.07 (1H), 2.40 (1H), 2.66 (1H), 2.99 (1H), 3.63 (1H), 4.02 (1H), 5.11 (1H), 7.14 (2H), 7.24 (2H), 7.33 (4H), 7.43 (2H), 7.50 (2H), 7.56 (2H).

Method 2

Reaction is performed in accordance with the procedure given in Method 1 with the following change: after addition of methyl iodide and rinsing of the funnel with THF, the mixture is stirred for 4 h at −78° C. as appose to the 18 h indicated in Method 1. The reaction is quenched and worked up using the same conditions employed in Method 1. Under such conditions, on the basis of NMR analysis, the ratio of diastereoisomers is 88:12 (2-a, R1=Bn/2-b, R1=Bn).

Example 35

(E/Z)—(R)-5-Biphenyl-4-yl-4-tert-butoxycarbonylaminopent-2-enoic acid ethyl ester (8-a, R1=Boc, R2=H, R5=Et)

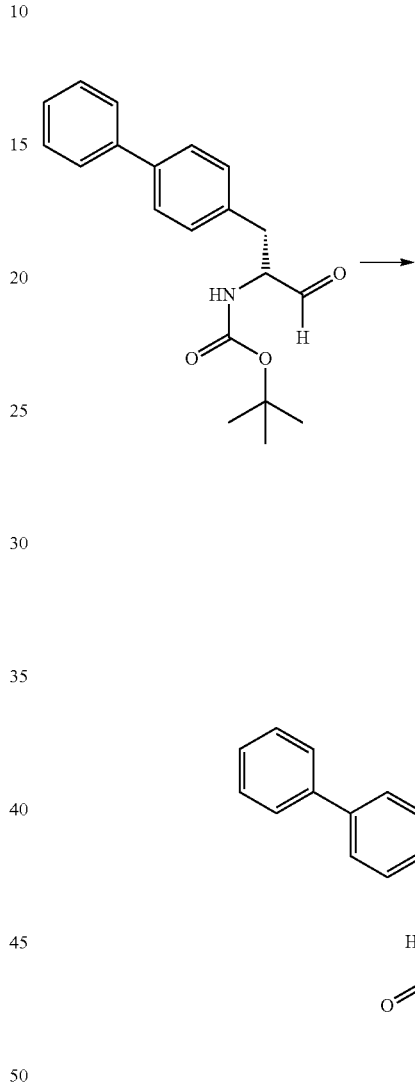

To a solution of 159 g of (2-biphenyl-4-yl-1-formyl-ethyl)carbamic acid tert-butyl ester (7-a, R1=Boc, R1=H) in isopropyl acetate (3.2 L) is added ethyl(triphenylphosphoranylidene)acetate (199 g). The mixture is stirred for 2 hours. To the mixture is added a solution of citric acid (79 g) in water (400 ml). After 1 hour, the phases are separated and the organic phase concentrated to dryness. The crude mixture is purified by chromatography (heptane/ethyl acetate) to give (E/Z)—(R)-5-biphenyl-4-yl-4-tert-butoxycarbonylaminopent-2-enoic acid ethyl ester (8-a, R1=Boc, R2=H, R5=Et) as a mixture of cis and trans isomers. $^1$H NMR (DMSO) major (trans double bond isomer): 1.19 (3H, t, CH$_3$); 1.30 (9H, s, C(CH$_3$)$_3$); 2.74 (1H, m, 5-CHH); 2.90 (1H, dd, 5-CHH); 4.11 (2H, m, CH$_2$CH$_3$); 4.41 (1H, m, 4-CH); 5.85 (1H, d, 2-CH); 6.89 (1H, dd, 3-CH); 7.32 (3H, m, aromatic); 7.43 (2H, m, aromatic); 7.57 (2H, m, aromatic); 7.62 (2H, m, aromatic). m/z: 413 (MNH$_4^+$, 100%), 396 (MH$^+$, 17); 340 (60); 296 (96); 250 (11).

Example 36

(S)-5-Biphenyl-4-yl-4-tert-butoxycarbonylaminopentanoic acid ethyl ester [9-a, R1=Boc, R2=H, R5=Et]

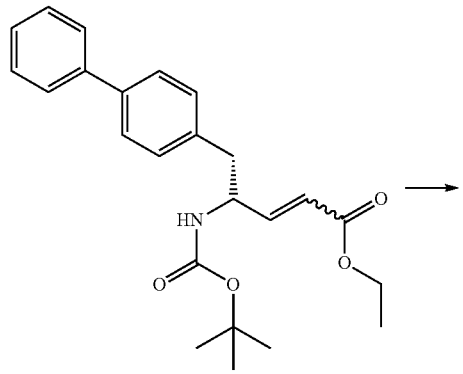

115 g of (E/Z)—(R)-5-Biphenyl-4-yl-4-tert-butoxycarbonylaminopent-2-enoic acid ethyl ester (8-a, R1=Boc, R2=H, R5=Et) is dissolved in isopropyl acetate (1.2 L). Palladium on carbon (10% loading; 11.5 g) is added and hydrogen gas is applied to the vessel. After about 1 h, the vessel is purged with argon and the catalyst is removed by filtration. The solution is concentrated to dryness, affording (S)-5-Biphenyl-4-yl-4-tert-butoxycarbonylaminopentanoic acid ethyl ester [9-a, R1=Boc, R2=H, R5=Et]. $^1$H-NMR (DMSO): 1.14 (3H, t, CH$_3$); 1.31 (9H, s, C(CH$_3$)$_3$); 1.56 (1H, m, 3-CHH); 1.71 (1H, m, 3-CHH); 2.28 (2H, m, 2-CH$_2$); 2.69 (2H, m, 5-CH$_2$); 3.62 (1H, m, 4-CH); 4.01 (2H, q, CH$_2$CH$_3$); 6.75 (1H, d, NH); 7.25 (2H, d, aromatic); 7.33 (1H, t, aromatic); 7.43 (2H, t, aromatic); 7.55 (2H, t, aromatic); 7.62 (2H, t, aromatic). m/z: 398 (MH$^+$, 100%); 342 (52); 298 (59).

Example 37

(S)-4-Amino-5-biphenyl-4-yl-pentanoic acid ethyl ester hydrochloride [10-a, R5=Et]

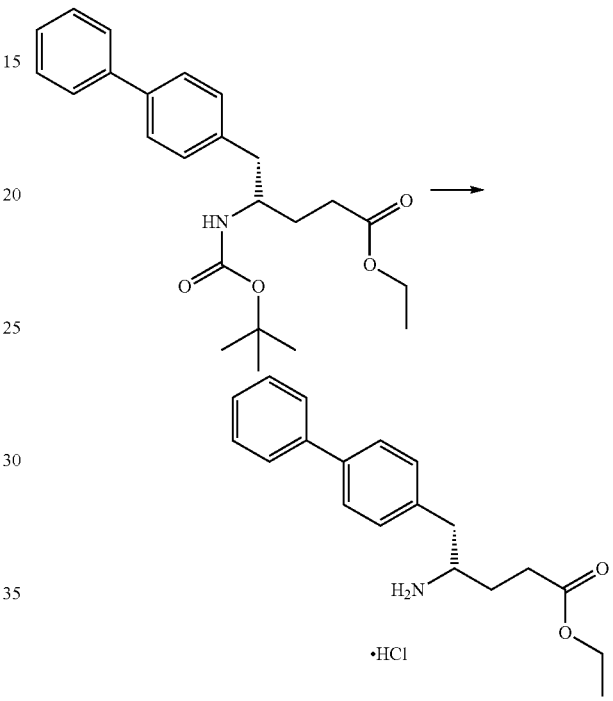

To a solution of (S)-5-Biphenyl-4-yl-4-tert-butoxycarbonylaminopentanoic acid ethyl ester [9-a, R1=Boc, R2=H, R5=Et] (115 g) in ethanol (1.1 L) at 70° C. is added thionyl chloride (32 ml) over 45 min. After a further 1.5 hours, the mixture is concentrated to dryness. The crude material is suspended in ethyl acetate and filtered to give (S)-4-Amino-5-biphenyl-4-yl-pentanoic acid ethyl ester hydrochloride [10-a, R5=Et]. $^1$H NMR (DMSO): 1.08 (3H, d, CH$_3$); 1.73 (2H, m, 3-CH$_2$); 2.35-2.52 (2H, m, 2-CH$_2$); 2.79 (1H, dd, 5-CHH); 2.97 (1H, dd, CHH); 3.38 (1H, m, 4-CH); 3.97 (2H, q, CH$_2$CH$_3$); 7.30 (3H, m, aromatic); 7.40 (2H, m, aromatic); 7.58 (4H, m, aromatic); 8.15 (3H, s, NH$_3^+$). m/z: 298 (MH$^+$, 100%); 281 (4); 235 (3).

The X-ray Structure of the obtained crystals is shown in FIG. 11. Single crystal for this determination is obtained from methanol as solvent.

| Crystal data [recorded at 100(2)K] | |
|---|---|
| Empirical formula | C$_{19}$H$_{24}$ClNO$_2$ |
| Formula weight | 333.84 |
| Crystal system | Orthorhombic |
| Space group | P2$_1$2$_1$2$_1$ |
| Cell parameters | a = 5.307(2) Å |
| | b = 16.570(4) Å |
| | c = 39.778(10) Å |

121

-continued

| Crystal data [recorded at 100(2)K] | |
|---|---|
| | α = 90° |
| | β = 90° |
| | γ = 90° |
| Volume of unit cell | 3498.0(18) Å$^3$ |
| Z* | 8 |
| Calculated density | 1.268 mg m$^{-3}$ |

*(number of asymmetric units in the unit cell)

Example 38

(S)-5-biphenyl-4-ylmethylpyrrolidin-2-one [Key Lactam (1-a, R1=H)]

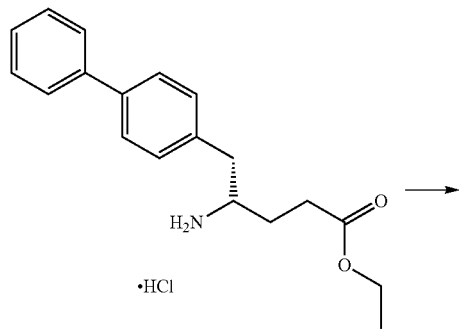

To a mixture of (S)-4-Amino-5-biphenyl-4-yl-pentanoic acid ethyl ester hydrochloride [10-a, R5=Et] (86 g) in isopropyl acetate (1 L) is added triethylamine (43 g). The mixture is then stirred at about 55° C. for 1 h and then filtered. The filtrate is heated at reflux for 24 hours. To the mixture is added saturated ammonium chloride solution and the phases are separated. The organic layer is concentrated to dryness and crystallized from isopropyl acetate to yield (S)-5-biphenyl-

122

4-ylmethylpyrrolidin-2-one [Key Lactam (1-a, R1=H)]. Spectroscopic data agree with data provided above.

Example 39

(2R,4S)-5-Biphenyl-4-yl-4-[3-(2-bromoethoxycarbonyl)-propionylamino]-2-methylpentanoic acid (3-a, R1=4-oxo-pentanoic acid 2-bromoethyl ester, R2=H, R3=Et)

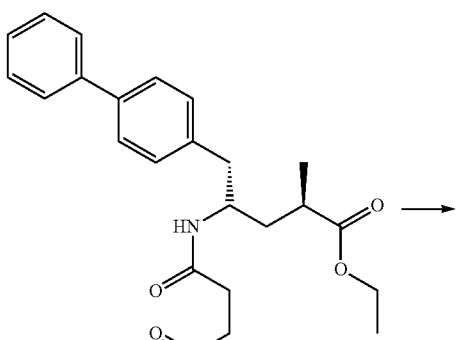

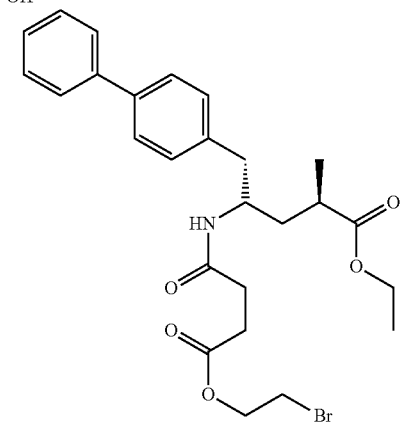

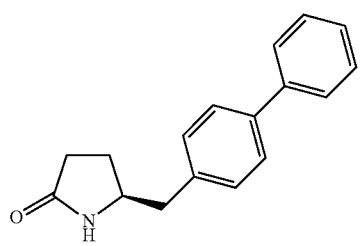

(2R,4S)-5-Biphenyl-4-yl-4-(3-carboxypropionylamino)-2-methylpentanoic acid ethyl ester (3-a, R1=4-oxo-pentanoic acid, R2=H, R3=Et) (5.5 g) is dissolved in toluene (33 ml) at room temperature. Dimethylformamide (0.1 ml) is added. Thionyl chloride (2.4 ml) is then added. The solution is cooled to 0° C. and 2-bromoethanol (0.94 ml) is added. The mixture is stirred at 0° C. for 2 h and then at room temperature for a further 1 h. A further portion of 2-bromoethanol (0.94 ml) is added and the mixture stirred for 0.5 h at room temperature. A further portion of 2-bromoethanol (0.94 ml) is then added and the resulting mixture stirred for 16 h at room temperature. The mixture is concentrated in vacuo to give the crude product. Purification by chromatography Heptane/EtOAc (2:1) gives (2R,4S)-5-Biphenyl-4-yl-4-[3-(2-bromoethoxycarbonyl)propionylamino]-2-methylpentanoic acid (3-a, R1=4-oxo-pentanoic acid 2-bromoethyl ester, R2=H, R3=Et). $^1$H NMR (DMSO): 1.07 (3H), 1.14 (3H), 1.41 (1H), 1.79 (1H), 2.37 (2H), 2.48 (1H), 2.50 (2H), 2.71 (2H), 3.66

(2H), 3.94 (1H), 3.99 (2H), 4.33 (2H), 7.25 (2H), 7.35 (1H), 7.46 (2H), 7.57 (2H), 7.64 (2H), 7.78 (1H).

Example 40

(2R,4S)-5-Biphenyl-4-yl-4-(2,5-dioxopyrrolidin-1-yl)-2-methylpentanoic acid ethyl ester

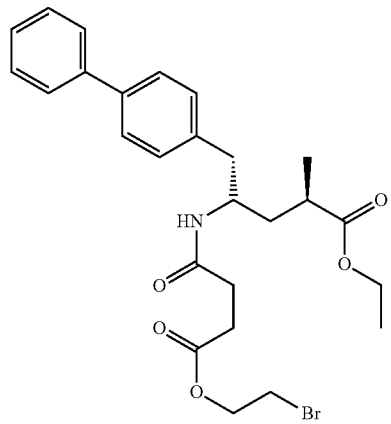

(2R,4S)-5-Biphenyl-4-yl-4-[3-(2-bromoethoxycarbonyl)propionylamino]-2-methylpentanoic acid (3-a, R1=4-oxo-pentanoic acid 2-bromoethyl ester, R2=H, R3=Et) (6 g, 11.6 mmol) is dissolved in DMF (30 ml). Cesium carbonate (8.2 g, 23.2 mmol) is added and mixture is stirred at 50° C. for 2 h. Water (150 ml) is then added followed by addition of ethyl acetate (150 ml). Next, the phases are separated. The organic phase is washed with brine, dried (Na$_2$SO$_4$) and concentrated in vacuo. The mixture is purified by chromatography: Heptane/EtOAc (2:1) to afford (2R,4S)-5-Biphenyl-4-yl-4-(2,5-dioxopyrrolidin-1-yl)-2-methylpentanoic acid ethyl ester. $^1$H NMR (DMSO): 1.05 (3H), 1.14 (3H), 1.94 (1H), 2.20 (1H), 2.39 (1H). 2.51 (4H), 2.98 (1H), 3.12 (1H), 4.01 (2H), 4.29 (1H), 7.18 (2H), 7.32 (1H), 7.43 (2H), 7.56 (2H), 7.62 (2H).

Example 41

(2R,4S)-5-Biphenyl-4-yl-4-(3-carboxypropionylamino)-2-methyl-pentanoic acid (3-a, R1=4-oxo-pentanoic acid, R2=H, R3=H)

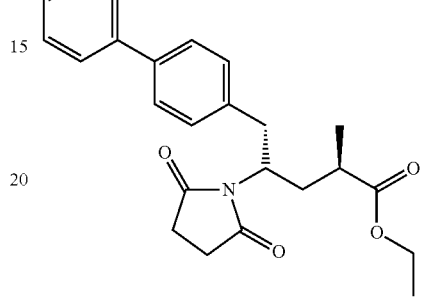

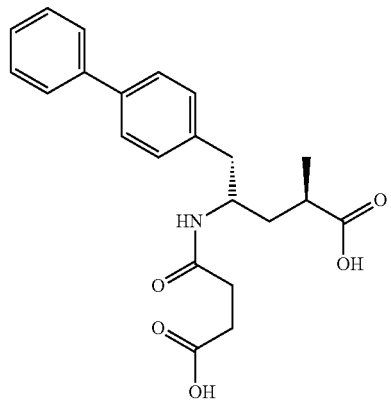

(2R,4S)-5-Biphenyl-4-yl-4-(2,5-dioxopyrrolidin-1-yl)-2-methylpentanoic acid ethyl ester (590 mg) is added to a mixture of 1 M NaOH (2.75 ml), THF (9 ml) and ethanol (9 ml). The mixture is stirred for 16 h. The mixture is diluted with water (20 ml) and extracted with isopropyl acetate. The water phase is acidified with 1 M HCl (5 ml) and extracted with isopropyl acetate. The combined organic phases are dried (MgSO$_4$) and concentrated in vacuo to give (2R,4S)-5-Biphenyl-4-yl-4-(3-carboxypropionylamino)-2-methyl-pentanoic acid (3-a, R1=4-oxo-pentanoic acid, R2=H, R3=H). $^1$H NMR (DMSO): 1.05 (2H), 1.35 (1H), 1.79 (1H), 2.29 (2H), 2.39

(3H), 2.70 (2H), 3.97 (1H), 7.25 (2H), 7.34 (1H), 7.44 (2H), 7.56 (2H), 7.63 (2H), 7.74 (1H), 12.01 (2H).

Example 42

(2R,4S)-5-biphenyl-4-yl-4-tert-butoxycarbonylamino-2-methylpentanoic acid ethyl ester (3-a, R1=BOC, R2=H, R3=Et)

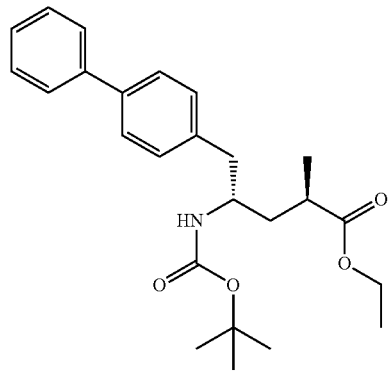

→

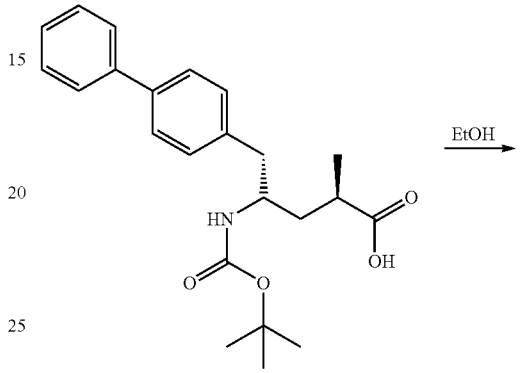

50 g of (2R,4S)-5-biphenyl-4-yl-4-tert-butoxycarbonylamino-2-methylpentanoic acid (3-a, R1=BOC, R2=R3=H) is added to dimethylformamide (80 ml). Cesium carbonate (69 g) is then added. Ethyl iodide (13.6 g) is then added and the mixture is stirred overnight at room temperature. Water (200 ml) is added to the mixture and the mixture is then extracted with isopropyl acetate (2×200 ml). The combined organic phases are washed with brine, dried (MgSO$_4$) and concentrated in vacuo to give (2R,4S)-5-biphenyl-4-yl-4-tert-butoxycarbonylamino-2-methylpentanoic acid ethyl ester (3-a, R1=BOC, R2=H, R3=Et) (56 g). $^1$H NMR (DMSO): 1.12 (3H), 1.19 (3H), 1.36 (9H), 1.53 (1H), 1.84 (1H), 2.55 (1H), 2.75 (2H), 3.74 (1H), 4.05 (2H), 6.04 (1H), 7.23 (2H), 7.30 (1H), 7.41 (2H), 7.50 (2H), 7.57 (2H). m/z (ES+): 412 ([MH]$^+$, 100%), 356 (63), 312 (73).

Example 43

(2R,4S)-4-amino-5-biphenyl-4-yl-2-methylpentanoic acid ethyl ester hydrobromide (3-a, R1=R2=H, R3=Et)

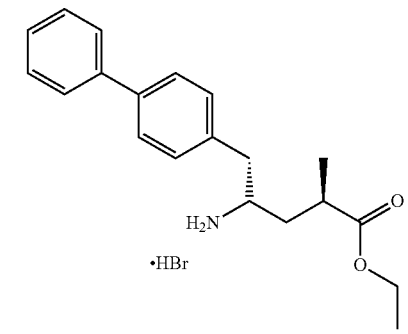

10 g (2R,4S)-5-biphenyl-4-yl-4-tert-butoxycarbonylamino-2-methylpentanoic acid (3-a, R1=BOC, R2=R3=H) are added to ethanol (100 ml). The mixture is heated to 65° C. 3 ml of thionyl bromide is then added over 0.5 hour. The mixture is then stirred for a further 1 hour. The ethanol is removed and heptane added. Further azeotropic distillations are performed using heptane to remove any residual ethanol. The solvent is removed in vacuo to afford (2R,4S)-4-amino-5-biphenyl-4-yl-2-methylpentanoic acid ethyl ester hydrobromide (3-a, R1=R2=H, R3=Et). $^1$H NMR (DMSO): 1.11 (6H), 1.61 (1H), 1.87 (1H), 2.73 (1H), 2.84 (1H), 3.04 (1H), 3.42 (1H), 4.01 (2H), 7.36 (3H), 7.47 (2H), 7.65 (4H), 8.03 (3H). m/z (ES+) 312 ([MH]+, 100%).

Example 44

(2R,4S)-4-amino-5-biphenyl-4-yl-2-methylpentanoic acid ethyl ester hydrogen sulphate (3-a, R1=R2=H, R3=Et)

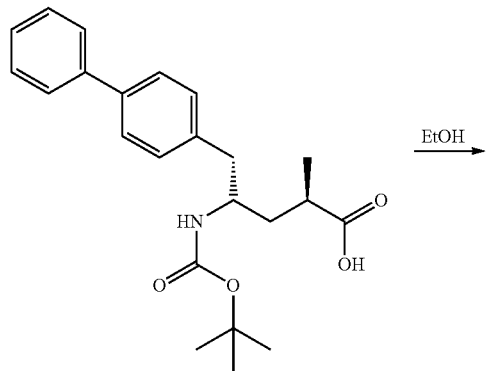

10 g (2R,4S)-5-biphenyl-4-yl-4-tert-butoxycarbonylamino-2-methylpentanoic acid (3-a, R1=BOC, R2=R3=H) are added to ethanol (100 ml). The mixture is heated to 65° C. 2 ml of concentrated sulphuric acid is then added over 0.5 h. The mixture is then stirred overnight. The ethanol is removed and heptane added. Further azeotropic distillations are performed using heptane to remove any residual ethanol. The solvent is removed in vacuo to afford (2R,4S)-4-amino-5-biphenyl-4-yl-2-methylpentanoic acid ethyl ester hydrogen sulphate (3-a, R1=R2=H, R3=Et). $^{1}$H NMR (DMSO): 1.12 (6H), 1.56 (1H), 1.87 (1H), 2.67 (1H), 2.78 (1H), 2.98 (1H), 3.76 (2H), 7.34 (3H), 7.47 (2H), 7.64 (4H), 8.57 (3H). m/z (ES+) 312 ([MH]+, 100.

Example 45

(2R,4S)-4-amino-5-biphenyl-4-yl-2-methylpentanoic acid hydrochloride (3-a, R1=R2=R3=H)

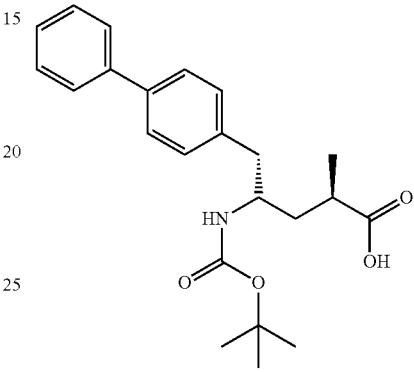

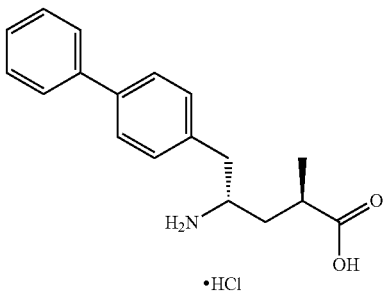

A mixture of 37% hydrochloric acid (85 ml), ethyl acetate (100 ml) and water (100 ml) is heated to an external oil bath temperature of 130° C. 50 g (2R,4S)-5-biphenyl-4-yl-4-tert-butoxycarbonylamino-2-methylpentanoic acid (3-a, R1=BOC, R2=R3=H) in ethyl acetate (100 ml) is then added to the mixture over 45 min. The mixture is stirred for a further 1 h. The mixture is then cooled to 0° C. and the solid collected by filtration to give (2R,4S)-4-amino-5-biphenyl-4-yl-2-me-

Example 46

(2R,4S)-5-Biphenyl-4-yl-4-(2,2-dimethylpropionylamino)-2-methylpentanoic acid ethyl ester (3-a, R1=Piv, R2=H, R3=Et)

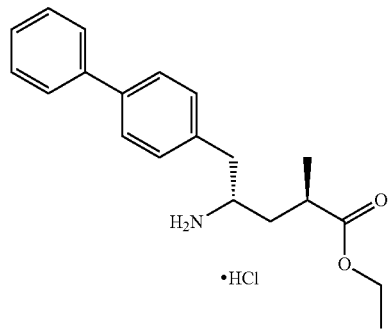

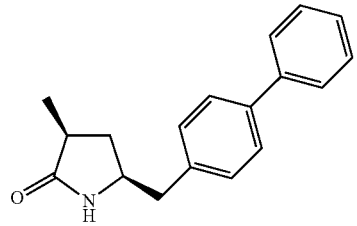

10 g (2S,4S)-4-amino-5-biphenyl-4-yl-2-methylpentanoic acid ethyl ester hydrochloride (3-a, R1=R2=H, R3=Et) in isopropyl acetate (50 ml) is added to a mixture of pivaloyl chloride (4.1 ml) in isopropyl acetate (50 ml). The mixture is then stirred for 40 min at room temperature. Triethylamine (10.3 ml) in isopropyl acetate (30 ml) is then added over a period of 1 h. The resulting mixture is stirred for 16 h. Citric acid (7.5 g) dissolved in water (30 ml) is added and the phases are separated. The organic phase is washed twice with water (30 ml) and concentrated in vacuo to give (2R,4S)-5-Biphenyl-4-yl-4-(2,2-dimethylpropionylamino)-2-methylpentanoic acid ethyl ester (3-a, R1=Piv, R2=H, R3=Et). $^1$H NMR (DMSO): 1.05 (9H), 1.09 (3H), 1.15 (3H), 1.54 (1H), 1.78 (1H), 2.48 (1H), 2.72 (2H), 3.97 (1H), 4.00 (2H), 7.15 (1H), 7.25 (2H), 7.34 (1H), 7.45 (2H), 7.55 (2H), 7.62 (2H).

Example 47

(3S,5S)-5-biphenyl-4-ylmethyl-3-methylpyrrolidin-2-one (2-b, R1=H)

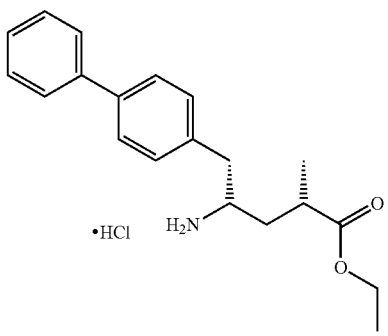

To a mixture of (2S,4S)-4-amino-5-biphenyl-4-yl-2-methylpentanoic acid ethyl ester hydrochloride (3-b, R1=R2=H, R3=Et) [9:1 diastereoisomer mixture [(2S,4S):(2R,4S)]] (840 mg) in isopropyl acetate (10 ml) triethylamine (418 mg) is added. The mixture is then stirred at 55° C. for 1 h and then filtered. The filtrate is heated at reflux for 24 hours. To the mixture is added saturated ammonium chloride solution and the phases are separated. The organic layer is concentrated to dryness. The residue is purified by chromatography, eluting first with IPA/Heptane 2:1 then with a mixture 1:1 to afford (3S,5S)-5-biphenyl-4-ylmethyl-3-methylpyrrolidin-2-one (2-b, R1=H) and (3R,5S)-5-biphenyl-4-ylmethyl-3-methylpyrrolidin-2-one (2-a, R1=H). Ratio of diastereoisomers determined by $^1$H NMR to be 9:1 [(3S,5S):(3R,5S)]. $^1$H NMR (CDCl$_3$) for (2-b, R1=H): 1.15 (3H), 1.38 (1H), 2.42 (2H), 2.63 (1H), 2.82 (1H), 3.75 (1H), 5.51 (1H), 7.17 (2H), 7.28 (1H), 7.37 (2H), 7.49 (4H). Spectroscopic data for (2-a, R1=H) as in Example 6.

Example 48

(3S,5S)-5-biphenyl-4-ylmethyl-1-(2,2-dimethylpropionyl)-3-methylpyrrolidin-2-one (2-b, R1=pivaloyl)

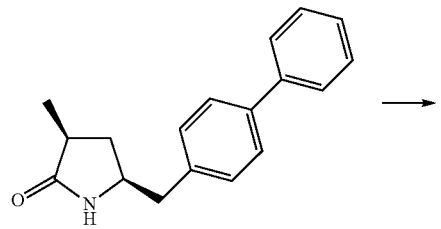

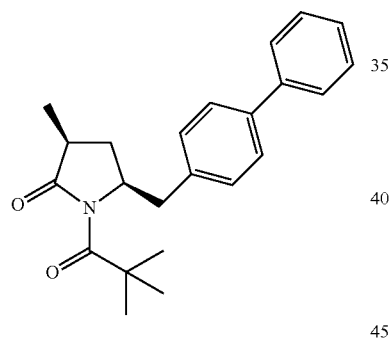

146 mg (3S,5S)-5-biphenyl-4-ylmethyl-3-methylpyrrolidin-2-one (2-b, R1=H) [9:1 diastereoisomer mixture [(2S,4S):(2R,4S)]] is added to 10 ml THF. The mixture is cooled to −78° C. and 381 μl butyllithium (1.59 M in hexane) are added. 81 μl Pivaloyl chloride is then added. After 4 h, the mixture is warmed to room temperature. The mixture is then quenched by the addition of saturated ammonium chloride solution and isopropyl acetate. The phases are separated and the organic phase dried (MgSO4) and then concentrated in vacuo. The residue is purified by column chromatography, by eluting with isopropyl acetate/hexane 3:1 to 1:0 to afford (3S,5S)-5-biphenyl-4-ylmethyl-1-(2,2-dimethylpropionyl)-3-methylpyrrolidin-2-one (2-b, R1=pivaloyl) and (3R,5S)-5-biphenyl-4-ylmethyl-1-(2,2-dimethylpropionyl)-3-methylpyrrolidin-2-one (2-a, R1=pivaloyl). Ratio of diastereoisomers determined by $^1$H NMR to be 4:1 [(3S,5S): (3R,5S)]. $^1$H NMR (CDCl3) for (2-b, R1=Piv): 1.09, 1.14 (3H), 1.30 (9H), 1.34 (1H), 2.01-2.66 (3H), 3.03, 3.27 (1H), 4.31, 4.50 (1H), 7.21-7.53 (9H). Diastereomeric ratio is determined by integration of the pairs of signals at [3.03 ppm (2-a, R1=Piv) and 3.27 ppm (2-b, R1=Piv)] or those at [4.31 ppm (2-b, R1=Piv) and 4.50 ppm (2-a, R1=Piv)] from the $^1$H NMR spectrum. Spectroscopic data for (2-a, R1=Piv) as in Example 5.

Example 49

1-Benzyl-5-biphenyl-4-ylmethyl-5-hydroxy-pyrrolidin-2-one

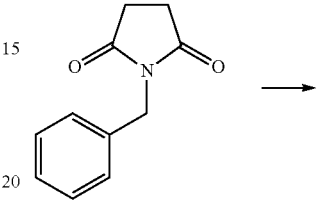

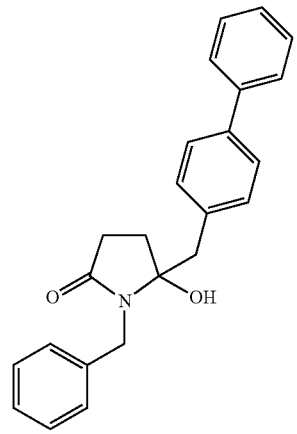

9.5 g N-Benzylsuccinimide is added to 120 ml THF and the mixture is then cooled to −78° C. A solution of 4-methylbiphenylmagnesium chloride in THF (1.3 eq) is then added. The subsequent mixture is then stirred for 2 h at −78° C. The mixture is then warmed to 10° C. and 100 ml saturated ammonium chloride solution is added. The phases are separated and the aqueous phase is extracted with toluene. The combined organic phases are washed with water then brine and then concentrated in vacuo. The crude material is crystallized from toluene to give 1-Benzyl-5-biphenyl-4-ylmethyl-5-hydroxypyrrolidin-2-one. $^1$H NMR (DMSO): 1.72 (1H), 1.91 (1H), 2.27 (2H), 2.72 (1H), 2.97 (2H), 4.40 (1H), 4.55 (1H), 7.21-7.66 (14H).

Example 50

1-Benzyl-5-[1-biphenyl-4-yl-meth-(E/Z)-ylidene]-pyrrolidin-2-one

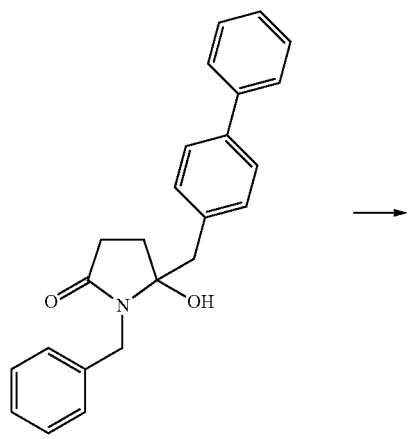

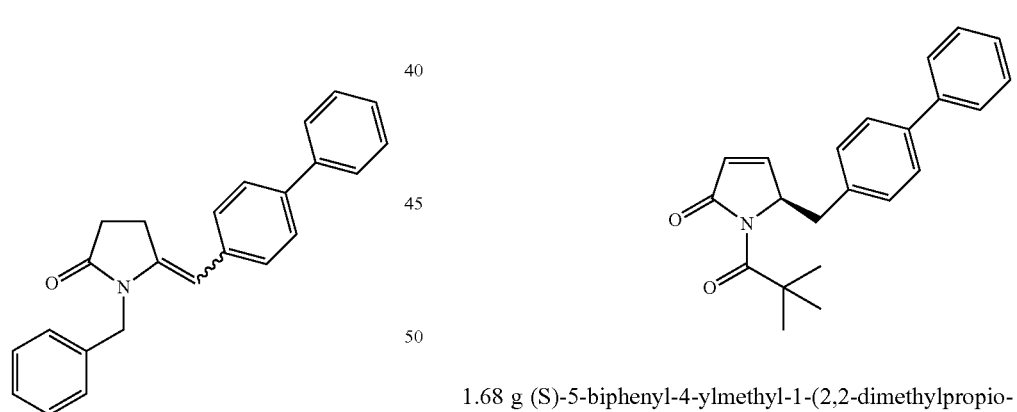

5.5 g 1-Benzyl-5-biphenyl-4-ylmethyl-5-hydroxy-pyrrolidin-2-one is added to dichloromethane (55 ml) at room temperature. 22 ml Trifluoroacetic acid is then added and the resulting mixture is allowed to stir overnight. The mixture is then filtered and concentrated in vacuo. Toluene (100 ml) and saturated sodium hydrogen carbonate (50 ml) are added to the residue. The phases are separated and the organic phase is concentrated in vacuo. The residue is added to 30 ml methanol and heated to reflux. The mixture is then cooled to room temperature, filtered and dried in vacuo to afford 1-Benzyl-5-[1-biphenyl-4yl-meth-(E/Z)-ylidene]-pyrrolidin-2-one. $^1$H NMR (DMSO): (E-Isomer): 2.67 (2H), 3.07 (2H), 4.80 (2H), 5.83 (1H), 7.26-7.36 (8H), 7.44 (2H), 7.59 (2H), 7.63 (2H). m/e (ES+): 340 ([MH]$^+$, 100%), 262 (28), 249 (63).

Example 51

(R)-5-Biphenyl-4-ylmethyl-1-(2,2-dimethylpropionyl)-1,5-dihydropyrrol-2-one 1.68 g (S)-5-biphenyl-4-ylmethyl-1-(2,2-dimethylpropionyl)pyrrolidin-2-one (1, R1=pivaloyl) is added to 10 ml toluene. The mixture is then cooled to −15° C. 5.5 ml Lithium bis(trimethylsilyl)amide (1 M in THF) is then added. After 1 h, a mixture of 1.3 g phenyl selenyl bromide in 10 ml toluene is added. After a further 30 min, 100 ml water is added. The phases are separated and the organic phase concentrated in vacuo. The residue is taken up in 25 ml ethyl acetate and then 5.1 ml hydrogen peroxide (37%) is added at room temperature. After 1 h, the phases are separated and the organic phase washed with a saturated sodium hydrogen carbonate solution and then dried (MgSO$_4$). The mixture is concentrated in vacuo and purified by column chromatography, eluting with heptane/ethyl acetate 5:1 to afford (R)-5-Biphenyl-4-ylmethyl-1-(2,2-dimethylpropionyl)-1,5-dihydropyrrol-2-one.

¹H NMR (CDCl₃): 1.28 (9H), 2.70 (1H), 3.30 (1H), 4.97 (1H), 5.89 (1H), 7.06 (2H), 7.19 (2H), 7.31 (2H), 7.41 (4H).

Example 52

(3R,5R)-5-Biphenyl-4-ylmethyl-1-(2,2-dimethylpropionyl)-3-methyl-2-oxo-pyrrolidine-3-carboxylic acid ethyl ester (R1=Piv; R10=OEt; R11=Me) and (3S,5R)-5-Biphenyl-4-ylmethyl-1-(2,2-dimethylpropionyl)-3-methyl-2-oxo-pyrrolidine-3-carboxylic acid ethyl ester (R1=Piv; R10=OEt; R11=Me)

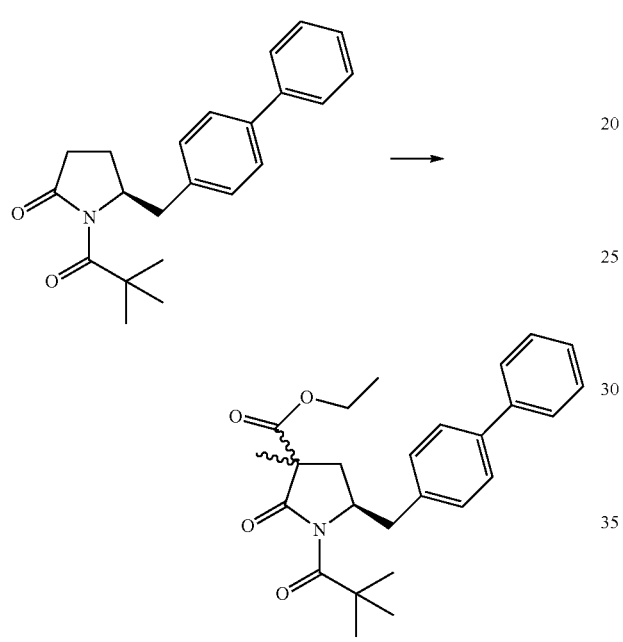

2.0 g (S)-5-biphenyl-4-ylmethyl-1-(2,2-dimethylpropionyl)pyrrolidin-2-one (1-a, R1=pivaloyl) in 7.5 ml toluene is added to 26.2 ml potassium bis(trimethylsilyl)amide (0.5 M in toluene) at −10° C. After 1 h, 568 μl ethyl chloroformate is added and the mixture is stirred for 1.5 h at −5 to 0° C. 733 μl Dimethylsulfate are then added and the mixture is stirred at room temperature for 1.5 h. 8 ml saturated ammonium chloride solution are then added, along with 10 ml water and 20 ml ethyl acetate. The aqueous phase is extracted with ethyl acetate and the combined organic phases are then washed with brine, dried (MgSO₄) and concentrated in vacuo. According to HNMR analysis the ratio of diastereoisomers is 62:38. The residue is purified by column chromatography, eluting with ethyl acetate/heptane (1:12) to afford (3R,5R)-5-Biphenyl-4-ylmethyl-1-(2,2-dimethylpropionyl)-3-methyl-2-oxo-pyrrolidine-3-carboxylic acid ethyl ester (R1=Piv; R10=OEt; R11=Me) and (3S,5R)-5-Biphenyl-4-ylmethyl-1-(2,2-dimethylpropionyl)-3-methyl-2-oxo-pyrrolidine-3-carboxylic acid ethyl ester (R1=Piv; R10=OEt; R11=Me). Fractions containing both diastereoisomers are combined. According to HNMR analysis the ratio of diastereoisomers is 62:38. ¹H NMR (CDCl₃) Major diastereomer: 1.11 (3H), 1.17 (9H), 1.23 (3H), 1.62 (1H), 2.26 (2H), 2.95 (1H), 4.07 (2H), 4.30 (1H), 7.03-7.37 (9H). ¹H NMR (CDCl₃) Minor diastereomer: 0.99 (3H), 1.16 (9H), 1.25 (3H), 1.51 (1H), 2.20 (2H), 3.13 (1H), 3.91 (2H), 4.34 (1H), 7.03-7.37 (9H). Data for mixture of diastereoisomers.

Example 53

(3R,5R)-5-Biphenyl-4-ylmethyl-3-methyl-2-oxopyrrolidine-1,3-dicarboxylic acid-1-tert-butyl ester-3-ethyl ester (R1=Boc; R10=OEt; R11=Me) and (3S,5R)-5-Biphenyl-4-ylmethyl-3-methyl-2-oxopyrrolidine-1,3-dicarboxylic acid-1-tert-butyl ester-3-ethyl ester (R1=Boc; R10=OEt; R11=Me)

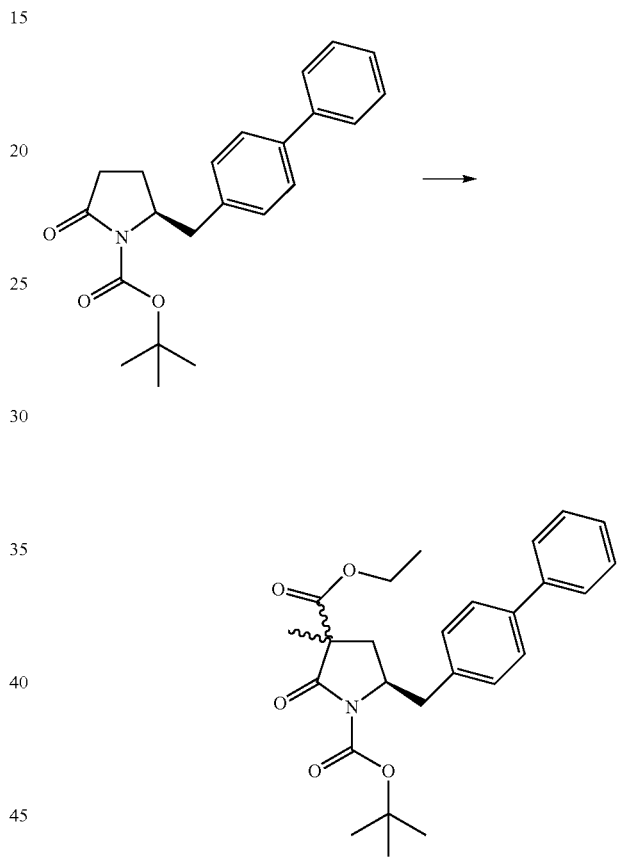

2.0 g (S)-5-biphenyl-4-ylmethyl-1-(2,2-dimethylpropionyl)pyrrolidin-2-one (1-a, R1=pivaloyl) in 7.5 ml toluene is added to 25 ml potassium bis(trimethylsilyl)amide (0.5 M in toluene) at −10° C. After 1 h, 542 μl ethyl chloroformate is added and the mixture is stirred for 1.5 h at −5 to 0° C. 733 μl Dimethylsulfate are then added and the mixture stirred at room temperature for 1.5 h. 8 ml saturated ammonium chloride solution are then added, along with 10 ml water and 20 ml ethyl acetate. The aqueous phase is extracted with ethyl acetate and the combined organic phases are then washed with brine, dried (MgSO₄) and concentrated in vacuo. According to HNMR analysis the ratio of diastereoisomers is 55:45. The residue is purified by column chromatography, eluting with ethyl acetate/heptane (1:6). Pure samples of each diastereoisomer are obtained for analysis. ¹H NMR (CDCl₃) Major diastereomer (R_f 0.13): 1.28 (3H), 1.41 (2H), 1.54 (9H), 1.72 (1H), 2.43 (1H), 2.59 (1H), 3.28 (1H), 4.16 (1H), 4.19 (2H), 7.22 (3H), 7.37 (2H), 7.47 (4H). ¹H NMR (CDCl₃) Minor diastereomer (R_f 0.17): 1.15 (3H), 1.36 (3H), 1.54

(9H), 1.58 (1H), 2.36 (1H), 2.59 (1H), 3.41 (1H), 4.04 (2H), 4.31 (1H), 7.16 (2H), 7.25 (1H), 7.34 (2H), 7.46 (4H).

Example 54

(3R,5R)-5-Biphenyl-4-ylmethyl-3-methyl-2-oxo-pyrrolidine-3-carboxylic acid (R1=H; R10=OH; R11=Me) and (3S,5R)-5-Biphenyl-4-ylmethyl-3-methyl-2-oxo-pyrrolidine-3-carboxylic acid (R1=H; R10=OH; R11=Me)

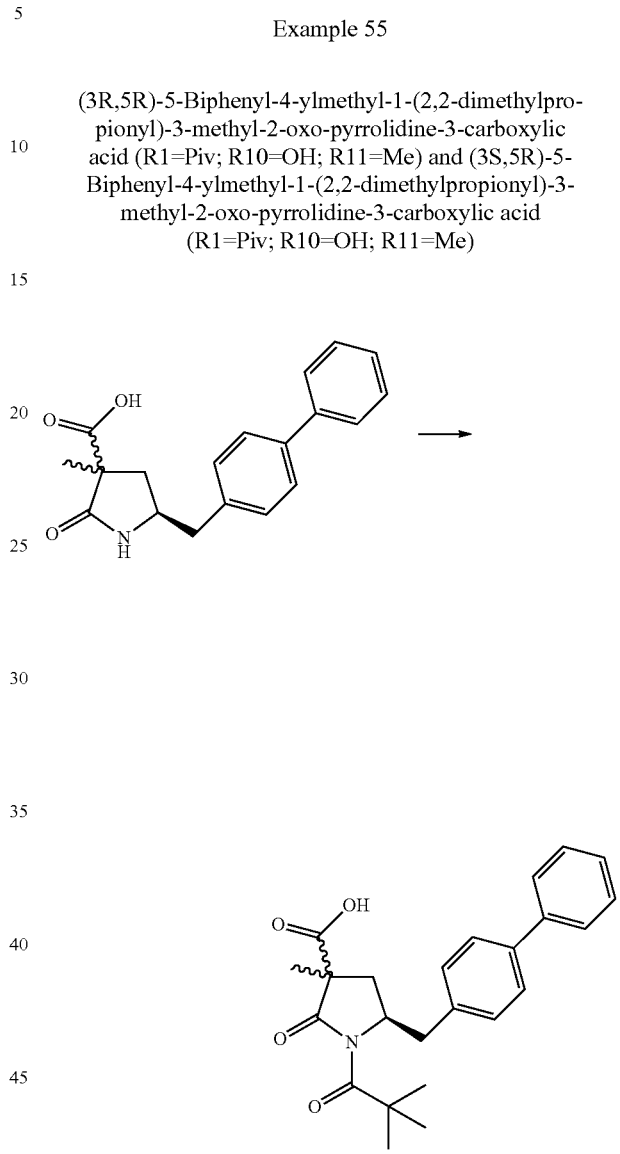

252 mg (3R,5R)-5-Biphenyl-4-ylmethyl-1-(2,2-dimethyl-propionyl)-3-methyl-2-oxo-pyrrolidine-3-carboxylic acid ethyl ester (R1=Piv; R10=OEt; R11=Me) [62:38 mixture of C3-isomers] is added to 1 ml acetonitrile at 0° C. 0.3 ml 3 M Sodium hydroxide solution is added and the mixture stirred at room temperature for 20 h. Two further 50 μl portions of 3 M sodium hydroxide are added. Stirring is continued for another 2 h. The mixture is concentrated in vacuo. 2.5 ml of water is added to the residue and it is then extracted twice with 1 ml toluene. 5 ml Ethyl acetate is added to the aqueous phase, which is then cooled to 0° C. 500 μl 2 M Hydrochloric acid is added and the phases are separated. The aqueous phase is then extracted with ethyl acetate. The combined organic phases are combined, dried (MgSO$_4$) and concentrated in vacuo to afford (3R,5R)-5-Biphenyl-4-ylmethyl-3-methyl-2-oxo-pyrrolidine-3-carboxylic acid (R1=H; R10=OH; R11=Me) and (3S,5R)-5-Biphenyl-4-ylmethyl-3-methyl-2-oxo-pyrrolidine-3-carboxylic acid (R1=H; R10=OH; R11=Me). According to HNMR analysis there is a 66:34 mixture of C3-stereoisomers. Identity of major isomer not determined. $^1$H NMR (DMSO) [mixture of stereoisomers]: 1.21 (3H), 1.59, 1.84, 2.20, 2.29 (total 2H), 2.66 (1H), 2.93 (1H), 3.81 (1H), 7.31 (3H), 7.44 (2H), 7.60 (4H), 8.10, 8.15 (total 1H), 12.58 (1H).

Example 55

(3R,5R)-5-Biphenyl-4-ylmethyl-1-(2,2-dimethylpropionyl)-3-methyl-2-oxo-pyrrolidine-3-carboxylic acid (R1=Piv; R10=OH; R11=Me) and (3S,5R)-5-Biphenyl-4-ylmethyl-1-(2,2-dimethylpropionyl)-3-methyl-2-oxo-pyrrolidine-3-carboxylic acid (R1=Piv; R10=OH; R11=Me)

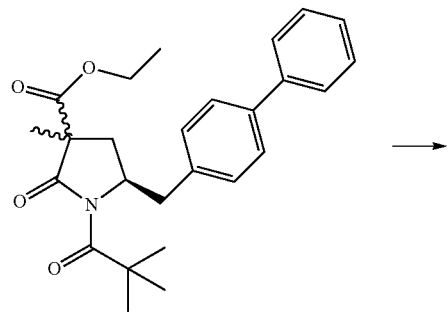

44 mg (3R/S, 5R)-5-Biphenyl-4-ylmethyl-3-methyl-2-oxo-pyrrolidine-3-carboxylic acid (R1=H; R10=OH; R11=Me) [66:34 mixture of C3-stereoisomers] are added to 10 ml toluene. 119 μl Triethylamine are added and the resulting mixture warmed to 60° C. 52 μl Pivaloyl chloride are added and the mixture is stirred for 4 h. The mixture is then cooled to room temperature. 250 mg Citric acid in water (5 ml) is added and the phases are separated. The organic phase is washed with water, dried (MgSO$_4$) and concentrated in vacuo to give (3R,5R)-5-Biphenyl-4-ylmethyl-1-(2,2-dimethylpropionyl)-3-methyl-2-oxo-pyrrolidine-3-carboxylic acid (R1=Piv; R10=OH; R11=Me) and (3S,5R)-5-Biphenyl-4-yl methyl-1-(2,2-dimethylpropionyl)-3-methyl-2-oxo-pyrrolidine-3-carboxylic acid (R1=Piv; R10=OH; R11=Me). According to HNMR analysis the ratio of C3 diastereoisomers is 65:35. Identity of major diastereomer not determined. $^1$H NMR (CDCl$_3$) [Mixture of stereoisomers]: 1.19 (9H), 1.21 (3H), 1.73-1.91 (1H), 2.23 (1H), 2.50 (2H), 3.12-3.33 (1H), 4.45-4.60 (1H), 7.19 (1H), 7.27 (2H), 7.37 (2H), 7.46 (4H).

Example 56

(3R,5S)-5-biphenyl-4-ylmethyl-1-(2,2-dimethylpropionyl)-3-methylpyrrolidin-2-one (2-a, R1=pivaloyl) and (3S,5S)-5-biphenyl-4-ylmethyl-1-(2,2-dimethylpropionyl)-3-methylpyrrolidin-2-one (2-b, R1=pivaloyl)

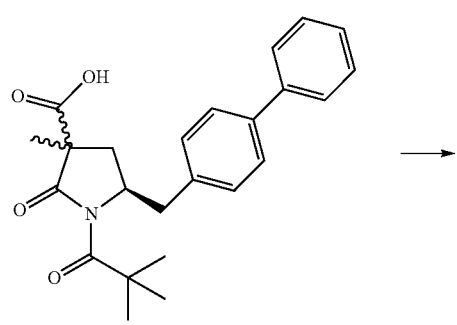

63 mg (3R/S, 5R)-5-Biphenyl-4-ylmethyl-1-(2,2-dimethylpropionyl)-3-methyl-2-oxo-pyrrolidine-3-carboxylic acid (R1=Piv; R10=OH; R11=Me) [65:35. ratio of C3 isomers] is added to 25 ml toluene. The resulting mixture is heated to reflux and stirred for 16 h. The mixture is then cooled to room temperature and washed successively with 10 ml aqueous sodium hydrogen carbonate, brine and water. The organic phase is dried (MgSO$_4$) and concentrated in vacuo to afford (3R,5S)-5-biphenyl-4-ylmethyl-1-(2,2-dimethylpropionyl)-3-methylpyrrolidin-2-one (2-a, R1=pivaloyl) and (3S,5S)-5-biphenyl-4-ylmethyl-1-(2,2-dimethylpropionyl)-3-methylpyrrolidin-2-one (2-b, R1=pivaloyl) as a 55:45 diastereomer mixture, respectively, according to the $^1$H NMR spectrum.

Example 57

(3R,5S)-5-biphenyl-4-ylmethyl-3-methylpyrrolidin-2-one (2-a, R1=H) and (3S,5S)-5-biphenyl-4-ylmethyl-3-methylpyrrolidin-2-one (2-b, R1=H)

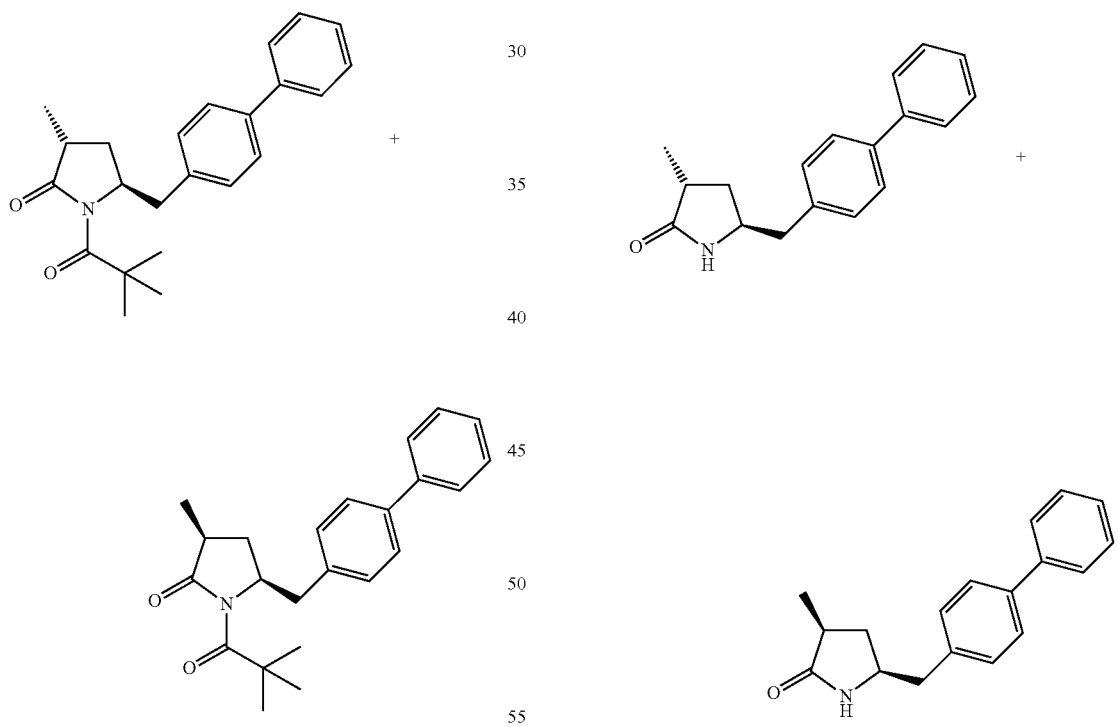

15 mg (3R/S, 5R)-5-Biphenyl-4-ylmethyl-3-methyl-2-oxo-pyrrolidine-3-carboxylic acid (R1=H; R10=OH; R11=Me) [66:34 mixture of C3-stereoisomers] is added to 25 ml toluene. The resulting mixture is heated to reflux and stirred for 16 h. The mixture is then cooled to room temperature and washed successively with 10 ml aqueous sodium hydrogen carbonate, brine and water. The organic phase is dried (MgSO$_4$) and concentrated in vacuo to afford (3R,5S)-5-biphenyl-4-ylmethyl-3-methylpyrrolidin-2-one (2-a, R1=H) and (3S,5S)-5-biphenyl-4-ylmethyl-3-methylpyrroli-

Example 58

1-Benzyl-5-[1-biphenyl-4-yl-meth-(E/Z)-ylidene]-1,5-dihydro-pyrrol-2-one

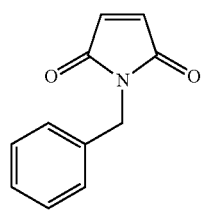 

3.55 g N-Benzylmaleimide is added to 35 ml THF and the mixture is then cooled to 0° C. A solution of 4-methylbiphenylmagnesium chloride in THF (5.6 g, 0.69 M) is then added over 30 min. The subsequent mixture is then stirred for 1.5 h at room temperature. Saturated ammonium chloride solution (50 ml) is then added and the mixture stirred for 20 min. The phases are separated and the aqueous phase is extracted with toluene. The combined organic phases are washed with water then brine and then concentrated in vacuo. The residue is then taken up in dichloromethane (35 ml). Trifluoroacetic acid is then added over 5 min and the mixture stirred for 3 h at room temperature. Mixture is then concentrated in vacuo. Toluene (50 ml) and saturated sodium hydrogen carbonate solution (50 ml) are added and the phases are separated. The organic phase is washed with water, then concentrated in vacuo. Methanol (2 ml) is added to the residue and heated to reflux whereby a hot filtration is performed. The filtrate is concentrated in vacuo to afford 1-Benzyl-5-[1-biphenyl-4-yl-meth-(E/Z)-ylidene]-1,5-dihydro-pyrrol-2-one. $^1$H NMR (DMSO): 4.96 (2H), 6.50 (1H), 6.70 (1H), 7.26-7.76 (15H).

Example 59

1-Benzyl-5-biphenyl-4-ylmethyl-pyrrolidin-2-one

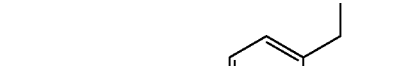

300 mg 1-Benzyl-5-[1-biphenyl-4-yl-meth-(E/Z)-ylidene]-pyrrolidin-2-one is added to ethanol (3 ml) at room temperature. 10% Pd/C, 50% water wet (30 mg) is added and a blanket of hydrogen gas applied to the vessel. The resulting mixture is stirred for 72 h at room temperature. The catalyst is removed by filtration and the filtrate concentrated in vacuo, to afford 1-Benzyl-5-biphenyl-4-ylmethyl-pyrrolidin-2-one. $^1$H NMR (DMSO): 1.74 (1H), 1.86 (1H), 2.16 (2H), 2.63 (1H), 3.02 (1H), 3.63 (1H), 4.21 (1H), 4.82 (1H), 7.23 (2H), 7.30 (3H), 7.35 (3H), 7.45 (2H), 7.57 (2H), 7.64 (2H).

Example 60

1-Benzyl-5-biphenyl-4-ylmethyl-pyrrolidin-2-one

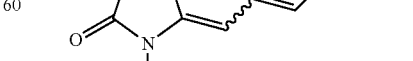

-continued

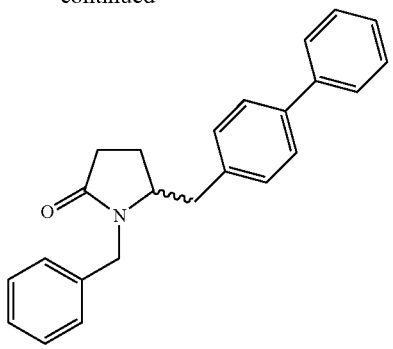

50 mg 1-Benzyl-5-[1-biphenyl-4-yl-meth-(E/Z)-ylidene]-1,5-dihydro-pyrrol-2-one is added to methanol (1.5 ml) at room temperature. 10% Pd/C, 50% water wet (15 mg) is added and a blanket of hydrogen gas applied to the vessel. The resulting mixture is stirred for 1 h at room temperature. The catalyst is removed by filtration and the filtrate concentrated in vacuo, to afford 1-Benzyl-5-biphenyl-4-ylmethyl-pyrrolidin-2-one. Spectroscopic data reported in Example 59.

Example 61

(3R,5S)-5-biphenyl-4-ylmethyl-1-(2,2-dimethylpropionyl)-3-methylpyrrolidin-2-one (2-a, R1=pivaloyl) and (3S,5S)-5-biphenyl-4-ylmethyl-1-(2,2-dimethylpropionyl)-3-methylpyrrolidin-2-one (2-a, R1=pivaloyl)

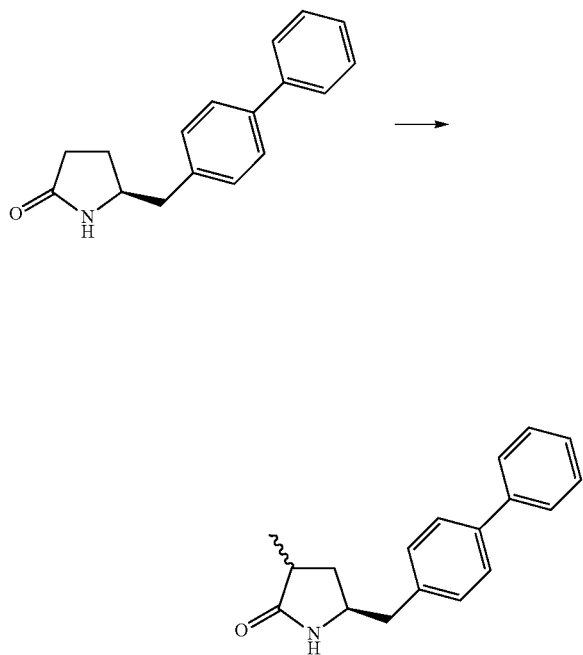

250 mg (S)-5-biphenyl-4-ylmethylpyrrolidin-2-one (1-a, R1=H) is added to THF (4 ml). The resulting mixture is then cooled to −78° C. 1.68 ml sec-butyllithium (1.3 M in cyclohexane) is then added and the resulting mixture is stirred for 0.5 h. 68 μl Methyl iodide are then added and the mixture stirred for 2 h at −78° C. Saturated ammonium chloride solution (5 ml), water (3 ml) and ethyl acetate (5 ml) are added and the mixture warmed to room temperature. The phases are separated. The organic phase is washed with brine solution, separated, dried (MgSO$_4$) and concentrated in vacuo to afford (3R,5S)-5-biphenyl-4-ylmethyl-1-(2,2-dimethylpropionyl)-3-methylpyrrolidin-2-one (2-a, R1=pivaloyl) and (3S,5S)-5-biphenyl-4-ylmethyl-1-(2,2-dimethylpropionyl)-3-methylpyrrolidin-2-one (2-a, R1=pivaloyl) as mixture (2-a) to (2-b) in a 20:80 ratio, as determined from $^1$H NMR. Spectroscopic data for (2-a, R1=H) as in Example 6. Spectroscopic data for (2-b, R1=H) as in Example 47.

The invention claimed is:
1. A compound selected from the group consisting of
a) a compound according to formula (2), or tautomer, or salt thereof,

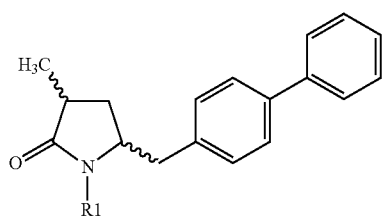

(2)

wherein R1 is hydrogen or a nitrogen protecting group,
b) a compound according to formula (13), or tautomer, or salt thereof,

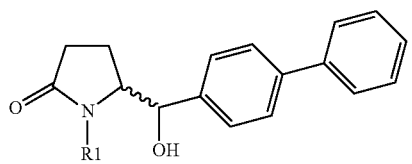

(13)

wherein R1 is hydrogen or a nitrogen protecting group,
c) a compound according to formula (15), or salt thereof,

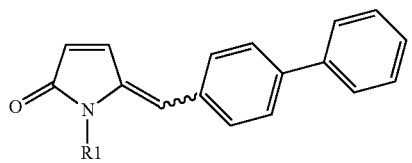

(15)

wherein R1 is hydrogen or a nitrogen protecting group,
d) a compound according to formula (16), or salt thereof,

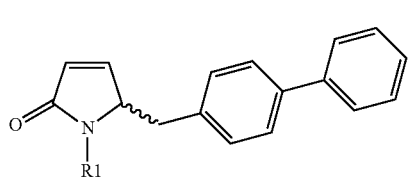

(16)

wherein R1 is hydrogen or a nitrogen protecting group, e) a compound according to formula (20), or salt thereof,

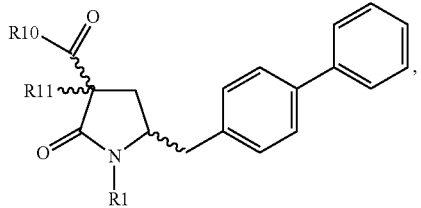
(20)

wherein R1 is hydrogen or a nitrogen protecting group, R10 is a group which can be saponified and/or decarboxylated and R11 is hydrogen or methyl f) a compound according to formula (21), or tautomer, or salt thereof,

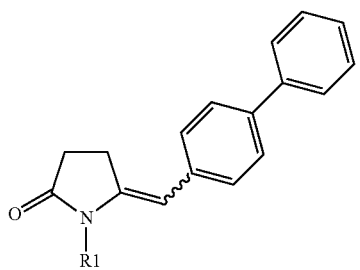
(21)

wherein R1 is hydrogen or a nitrogen protecting group, and g) a compound according to formula (22), or tautomer, or salt thereof,

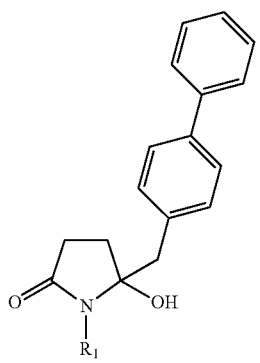
(22)

wherein R1 is hydrogen or a nitrogen protecting group.

2. A compound according to claim 1, wherein the compound of formula (2) has a configuration according to formula (2-a), or tautomer, or salt thereof,

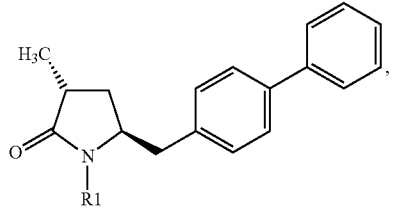
(2-a)

the compound of formula (13) has a configuration according to formula (13-a), or tautomer thereof,

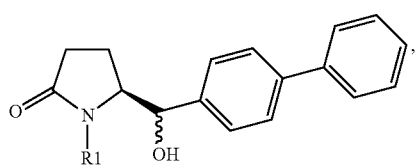
(13-a)

the compound of formula (16) has a configuration according to formula (16-a)

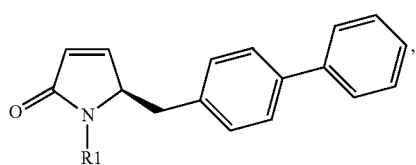
(16-a)

and the compound of formula (20) has a configuration according to formula (20-a)

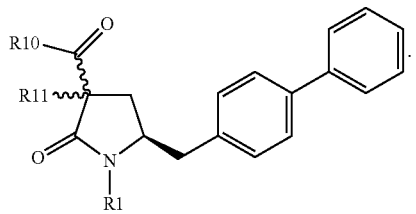
(20-a)

3. A compound according to claim 1 wherein the compound according to formula (2), or tautomer, or salt thereof, is in crystalline form.

4. A compound according to claim 2 wherein the compound according to formula (2-a), or tautomer, or salt thereof, is in crystalline form.

5. A compound according to claim 1, wherein in the compound of formula (2-a) R1 is hydrogen or a nitrogen protecting group selected from pivaloyl and t-butyloxycarbonyl (BOC).

6. A process for producing a compound according to formula (3) or a salt thereof

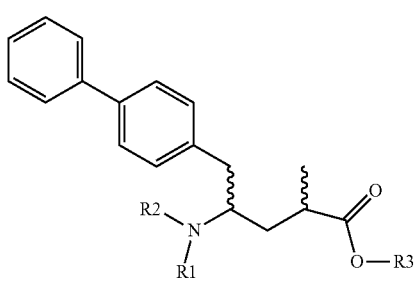
(3)

comprising reacting a compound according to formula (2), or tautomer, or salt thereof,

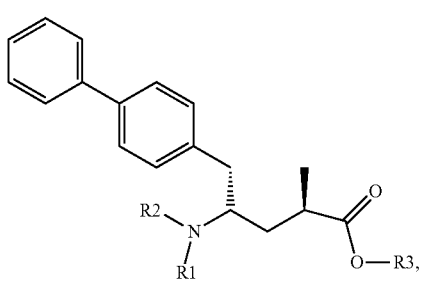
(2)

with a ring opening agent,
wherein in the above formulae R1 and R2 are independently, of each other, hydrogen or a nitrogen protecting group and R3 is hydrogen or alkyl.

7. A process according to claim 6 characterized in that a compound having a configuration according to formula (3-a) or a salt thereof is obtained (3-a)

wherein R1 and R2 are independently, of each other, hydrogen or a nitrogen protecting group and R3 is hydrogen or alkyl.

8. A process according to claim 6, wherein the compound of formula (2) is prepared by a process comprising methylating a compound according to formula (1), or tautomer, or salt thereof,

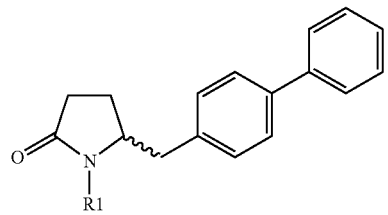
(1)

wherein R1 is hydrogen or a nitrogen protecting group.

9. A process according to claim 8, wherein
the compound of formula (1) has a configuration of formula (1-a), or tautomer, or salt thereof,

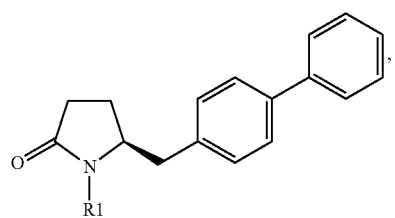
(1-a)

and
the compound of formula (2) has a configuration according to formula (2-a)

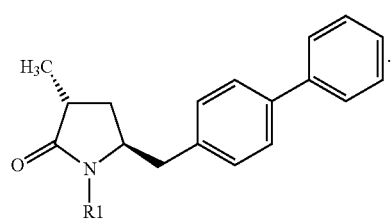
(2-a)

10. A process according to claim 8, wherein the methylating process comprises a) treating the compound of formula (1), or tautomer thereof, or salt thereof, with a base and a methylating reagent, or b) a process comprising i) treating the compound of formula (1), or tautomer thereof, or salt thereof, first with a base and then with a compound of the formula $YCO_2R$, wherein Y is halogen or —OR' and wherein R and R' are independently selected from alkyl, aryl and arylalkyl, to obtain a compound of formula (20), or salt thereof,

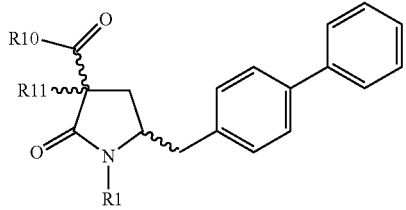

(20)

wherein R1 is hydrogen or a nitrogen protecting group, R11 is hydrogen and R10 is OR wherein R is alkyl, aryl or arylalkyl;

ii) reacting the resulting compound of formula (20) with a base and a methylating reagent to obtain a compound of formula (20), or salt thereof, wherein R1 is hydrogen or a nitrogen protecting group, R11 is methyl and R10 is OR wherein R is alkyl, aryl or arylalkyl;

iii) optionally, treating the compound of formula (20) wherein R1 is hydrogen or a nitrogen protecting group, R11 is methyl and R10 is OR wherein R is alkyl, aryl or arylalkyl, with a saponification reagent, to obtain a compound of formula (20), or salt thereof, wherein R1 is hydrogen or a nitrogen protecting group, R11 is methyl and R10 is OH; and iv) treating the compound obtained in step (b) or (c) under decarboxylation conditions to obtain the compound of formula (2).

11. A process according to claim 10, wherein the compound of formula (20) has a configuration of formula (20-a)

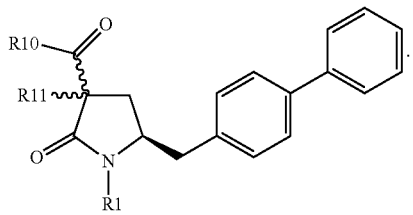

(20-a)

12. A process according to claim 8, wherein the compound of formula (1) has a configuration of formula (1-a), or tautomer, or salt thereof,

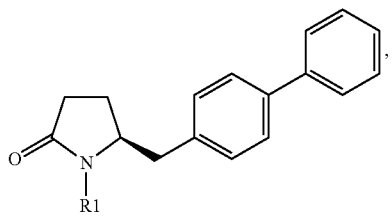

(1-a)

and wherein the compound according to formula (2) is produced in a ratio of diastereomers (2-a) to (2-b)

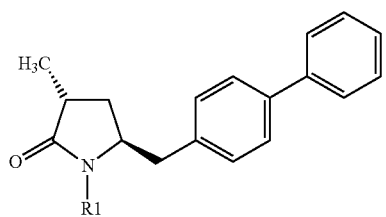

(2-a)

(2-b)

of at least 60:40.

13. A process according to claim 6, wherein R1 and R2 are hydrogen and R3 is an ethyl group.

14. A process according to claim 6, wherein the obtained compound of formula (3)

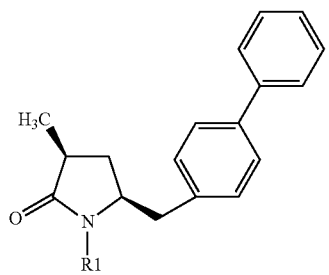

(3)

wherein R1 and R2 are independently, of each other, hydrogen or a nitrogen protecting group and R3 is hydrogen or alkyl, is further reacted to produce a compound according to formula (18) or a salt thereof

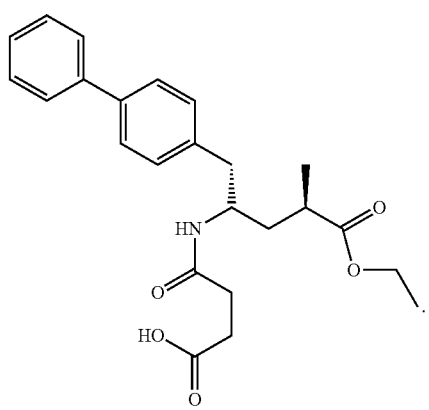

(18)

15. A process according to claim 14, wherein the compound of formula (3) has a configuration of formula (3-a)
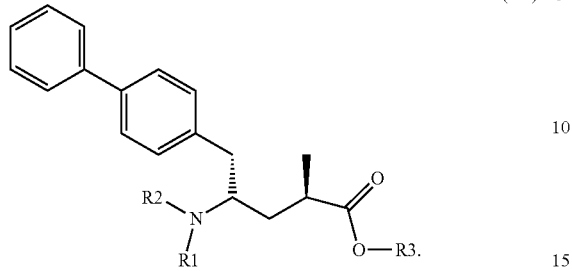
* * * * *